(12) United States Patent
Chatterjee et al.

(10) Patent No.: US 10,717,975 B2
(45) Date of Patent: Jul. 21, 2020

(54) UNIVERSAL PLATFORM FOR GENETIC CODE EXPANSION

(71) Applicant: Trustees of Boston College, Chestnut Hill, MA (US)

(72) Inventors: Abhishek Chatterjee, Brookline, MA (US); James Italia, Brighton, MA (US)

(73) Assignee: TRUSTEES OF BOSTON COLLEGE, Chestnut Hill, MA (US)

( * ) Notice: Subject to any disclaimer, the term of this patent is extended or adjusted under 35 U.S.C. 154(b) by 40 days.

(21) Appl. No.: 15/609,900

(22) Filed: May 31, 2017

(65) Prior Publication Data

US 2017/0349891 A1 Dec. 7, 2017

Related U.S. Application Data

(60) Provisional application No. 62/345,308, filed on Jun. 3, 2016.

(51) Int. Cl.
  *C12N 9/00* (2006.01)
  *C12P 21/00* (2006.01)

(52) U.S. Cl.
  CPC .......... *C12N 9/93* (2013.01); *C12P 21/00* (2013.01); *C12Y 601/01002* (2013.01)

(58) Field of Classification Search
  None
  See application file for complete search history.

(56) References Cited

PUBLICATIONS

Ngo et al. in The Protein Folding Problem and Tertiary Structure Prediction, 1994, Merz et al. (ed.), Birkhauser, Boston, MA, pp. 433 and 492-495.*
Anderson, J.C. et al., "An Expanded Genetic Code with a Functional Quadruplet Codon," Proceedings of the National Academy of Sciences, vol. 101, No. 20, pp. 7566-7571 (2004). Six pages.
Antonczak, A.K. et al., "Importance of Single Molecular Determinants in the Fidelity of Expanded Genetic Codes," Proceedings of the National Academy of Sciences, vol. 108, No. 4, pp. 1320-1325 (2011). Six pages.
Chatterjee, A. et al., "A Trytophanyl-tRNA Synthetase/tRNA Pair for Unnatural Amino Acid Mutagenesis in *E. coli*," Angewandte Chemistry International Edition, vol. 52, pp. 5106-5109, 2013. Ten pages.
Chatterjee, A. et al., "A Versatile Platform for Single- and Multiple-Unnatural Amino Acid Mutagenesis in *Escherichia coli*," Biochemistry, vol. 52, No. 10, pp. 1828-1837 (2013). Twenty-three pages.
Chatterjee, A. et al., "Efficient Viral Delivery System for Unnatural Amino Acid Mutagenesis in Mammalian Cells," Proceedings of the National Academy of Sciences, vol. 110, No. 29, pp. 11803-11808 (2013). Six pages.
Chatterjee, A. et al., "Evolution of Multiple, Mutually Orthogonal prolyl-tRNA synthetase/tRNA Pairs for Unnatural Amino Acid Mutagenesis in *Escherichia coli*," Proceedings of the National Academy of Sciences, vol. 109, No. 37, pp. 14841-14846 (2012). Six pages.
Chin, J.W. et al., "An Expanded Eurkaryotic Genetic Code," Science, vol. 301, pp. 964-967 (2003). Five pages.
Chin, J.W., Expanding and Reprogramming the Genetic Code of Cells and Animals. Annual Review of Biochemistry, vol. 83, pp. 379-408 (2014). Thirty-four pages.
Cooley, R.B. et al., "Gleaning Unexpected Fruits from Hard-Won Synthetases: Probing Principles of Permissivity in Non-Canonical Amino Acid-tRNA Synthetases," ChemBioChem, vol. 15, No. 12, pp. 1810-1819 (2014). Twenty-four pages.
Dumas, A. et al., "Designing Logical Codon Reassignment—Expanding the Chemistry in Biology," Chemical Science, vol. 6, pp. 50-69 (2015). Twenty pages.
Ellefson, J.W. et al., "Directed Evolution of Genetic Parts and Circuits by Compartmentalized Partnered Replication," Nature Biotechnology, vol. 32, pp. 97-101 (2014). Eight pages.
Guo, J. et al., "Evolution of Amber Suppressor tRNAs for Efficient Bacterial Production of Unnatural Amino Acid-Containing Proteins," Angewandte Chemistry International Edition, vol. 48, pp. 9148-9151 (2009). Ten pages.
Iraha, F. et al., "Functional Replacement of the Endogenous tyrosyl-tRNA Synthetase-tRNATyr Pair by the Archaeal Tyrosine Pair in *Escherichia coli* for Genetic Code Expansion," Nucleic Acids Research, vol. 38, No. 11, pp. 3682-3691 (2010). Ten pages.
Italia, J.S. et al., "An Orthogonalized Platform for Genetic Code Expansion in Both Bacteria and Eukaryotes," Nature Chemical Biology, vol. 13, pp. 446-453, Apr. 2017, and Supplemental Information, pp. S1-S18. Twenty-six pages.
Jahn, M. et al., "Anticodon and Acceptor Stem Nucleotides in tRNA(Gln) Are Major Recognition Elements for *E. coli* glutaminyl-tRNA Synthetase," Nature, vol. 352, pp. 258-260 (1991).
Kopelowitz, J. et al., "Influence of Codon Context on UGA Suppression and Readthrough," Journal of Molecular Biology, vol. 225, pp. 261-269 (1992).
Li, M. et al., "An Efficient Synthesis of 5-azidotryptophan," Tetrahedron Letters, vol. 35, No. 34, pp. 6255-6258 (1994).
Liu, C., et al., "Adding New Chemistries to the Genetic Code," Annual Review of Biochemistry, vol. 79, pp. 413-444 2010. Thirty-five pages.
Melancon, C.E. et al., "One Plasmid Selection System for the Rapid Evolution of Aminoacyl-tRNA Synthetases," Bioorganic Medical Chemistry Letters, vol. 19, No. 14, pp. 3845-3847 (2009). Six pages.
Neumann, H. et al., "Encoding Multiple Unnatural Amino Acids via Evolution of a Quadruplet-Decoding Ribosome," Nature, vol. 464, pp. 441-444 (2010). Five pages.

(Continued)

*Primary Examiner* — Richard G Hutson
(74) *Attorney, Agent, or Firm* — HoustonHogle LLP

(57) ABSTRACT

Methods and compositions are described for selecting and identifying orthogonal aminoacyl synthetase-tRNA pairs and their use to incorporate unnatural amino acids in a site-specific manner in proteins. Specifically described is a novel *E. coli* tyrptophanyl synthetase-tRNA pair that functions as both an opal and amber suppressor and that incorporates tryptophan analogs into proteins.

24 Claims, 47 Drawing Sheets
(38 of 47 Drawing Sheet(s) Filed in Color)

Specification includes a Sequence Listing.

(56) References Cited

PUBLICATIONS

O'Donoghue, P. et al., "Near-Cognate Suppression of Amber, Opal and Quadruplet Codons Competes with aminoacyl-tRNAPyl for Genetic Code Expansion," Federation of European Biochemical Societies Letters, vol. 586, pp. 3931-3937 (2012). Seven pages.

Prather, N.E. et al., "Primary Structure of an Unusual Glycine tRNA UGA Suppressor," Nucleic Acids Research, vol. 9, No. 23, pp. 6421-6428 (1981). Eight pages.

Raftery, L.A. et al., "Defined Set of Cloned Termination Suppressors: In Vivo Activity of Isogenetic UAG, UAA, and UGA Suppressor tRNAs," Journal of Bacteriology, vol. 158, No. 3, pp. 849-859 (1984). Eleven pages.

Rogers, M.J. et al., "Switching tRNA(Gln) Identity from Glutamine to Tryptophan," Proceedings of the National Academy of Sciences, vol. 89, pp. 3463-3467 (1992). Five pages.

Santoro, S.W. et al., "An Efficient System for the Evolution of Aminoacyl-tRNA Synthetase Specificity," Nature Biotechnology, vol. 20, pp. 1044-1048 (2002). Six pages.

Soll, L. et al., "Recessive Lethal Nonsense Suppressor in *Escherichia coli* which Inserts Glutamine," Nature, vol. 223, pp. 1340-1342 (1969). Three pages.

Syn, C.K. et al., "A Scalable Protocol for the Isolation of Large-Sized Genomic DNA within an Hour from Several Bacteria," Analytical Biochemistry, vol. 278, pp. 86-90 (2000). Five pages.

Wan, W. et al., "A Facile System for Genetic Incorporation of Two Different Noncanonical Amino Acids into One Protein in *Escherichia coli*," Angewandte Chemie International Edition, vol. 49, pp. 3211-3214 (2010). Four pages.

Wan, W. et al., "Pyrrolysyl-tRNA Synthetase: An Ordinary Enzyme but an Outstanding Genetic Code Expansion Tool," Biochimica et Biophysica Acta, vol. 1844, No. 6, pp. 1059-1070 (2014). Thirty-two pages.

Wang, H.H. et al., "Programming Cells by Multiplex Genome Engineering and Accelerated Evolution," Nature, vol. 460, No. 7257, pp. 894-898 (2009). Fourteen pages.

Wang, L. et al., "Expanding the Genetic Code of *Escherichia coil*," Science, vol. 292, pp. 498-500 (2001). Four pages.

Warming, S. et al., "Simple and Highly Efficient BAC Recombineering Using galK Selection," Nucleic Acids Research, vol. 33, No. 4, e36 (2005). Twelve pages.

Xiao, H. et al., "Genetic Incorporation of Multiple Unnatural Amino Acids into Proteins in Mammalian Cells," Angewandte Chemistry International Edition, vol. 52, pp. 14080-14083 (2013). Four pages.

Young, D.D. et al., "An Evolved aminoacyl-tRNA Synthetase with Atypical Polysubstrate Specificity," Biochemistry, vol. 50, pp. 1894-1900 (2011). Seven pages.

Young, T.S. et al., "An Enhanced System for Unnatural Amino Acid Mutagenesis in *E. coli*," Journal of Molecular Biology, vol. 395, pp. 361-374 (2010). Fourteen pages.

Zhang, Z. et al., "Selective Incorporation of 5-hydroxytryptophan into Proteins in Mammalian Cells," Proceedings of the National Academy of Sciences, vol. 101, No. 24, pp. 8882-8887 (2004). Six pages.

\* cited by examiner

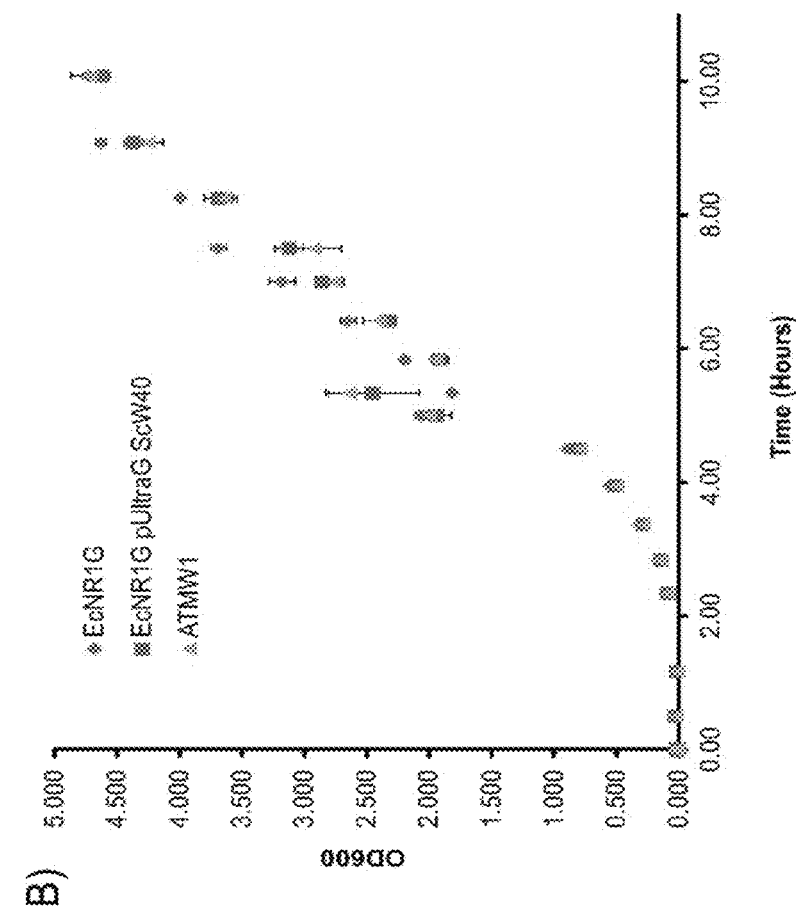
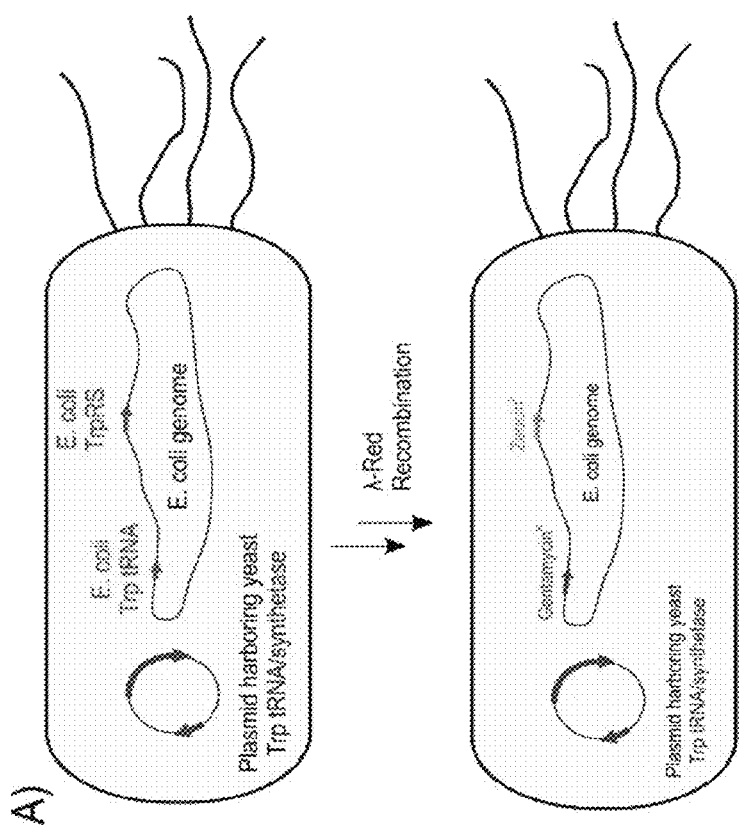
Figure 2B
Figure 2A

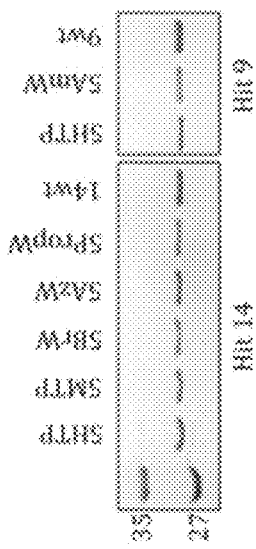
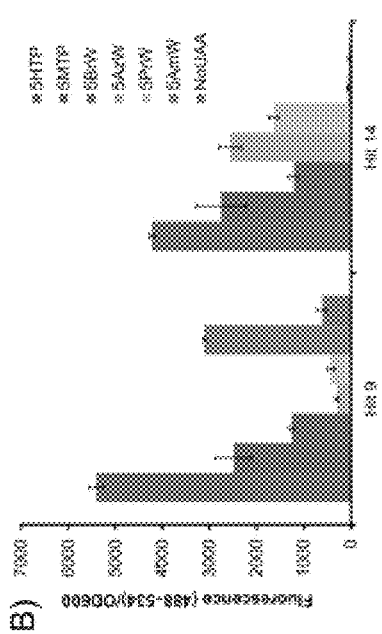
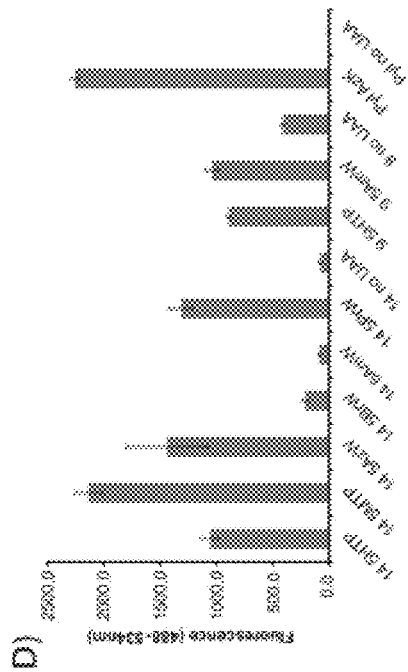
Figure 4C
Figure 4B
Figure 4D

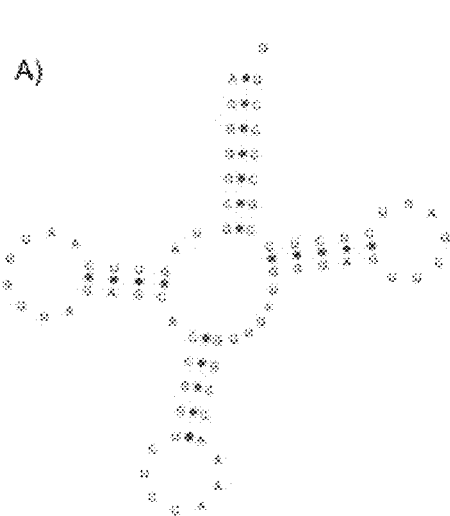 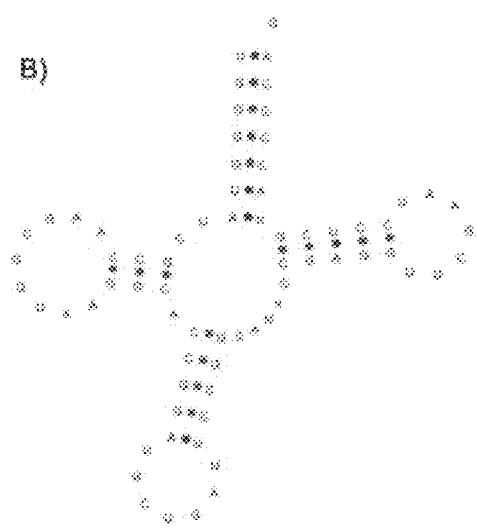
Figure 10A  Figure 10B
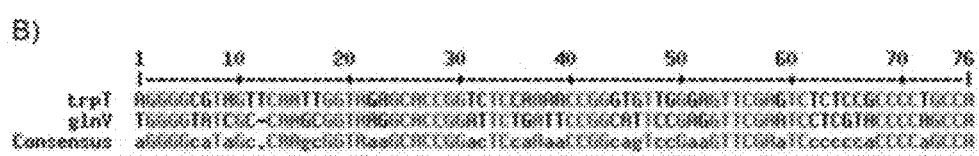
Figure 10C

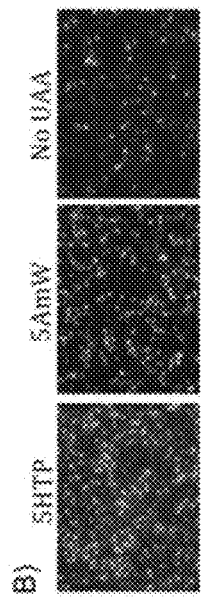
Figure 11B
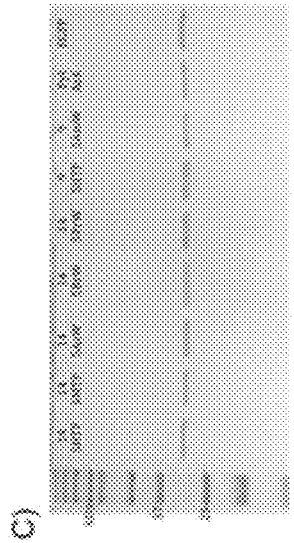
Figure 11D
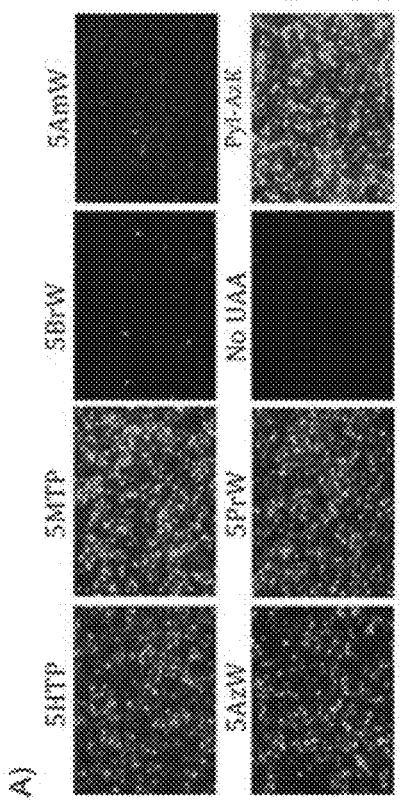
Figure 11A
Figure 11C

*trpS::ZeoR PCR cassette*
EM-7 promoter (red); ZeoR (green); CYC1 terminator (blue); TrpRS flanking homology (black)
ATCAGTCTATAAATGACCTTCTGCCCGCATTAGGGCTTCCGCATAGCGAAAATCAGGAATCGAAA
AAGGTGTTGACAATTAATCATCGGCATAGTATATTGGCATAGTATAATACGACAAGGTGAGGAA
CTAAACCATGGCCAAGCTGACCAGTGCCGTTCCGGTGCTCACCGCGCGCGACGTCGCCGGAGCGG
TCGAGTTCTGGACCGACCGGCTCGGGTTCTCCCGGGACTTCGTGGAGGACGACTTCGCCGGTGTG
GTCCGGGACGACGTGACCCTGTTCATCAGCGCGGTCCAGGACCAGGTGGTGCCGGACAACACCCT
GGCCTGGGTGTGGGTGCGCGGCCTGGACGAGCTGTACGCCGAGTGGTCGGAGGTCGTGTCCACGA
ACTTCCGGGACGCCTCCGGGCCGGCCATGACCGAGATCGGCGAGCAGCCGTGGGGCGGGAGTTC
GCCCTGCGCGACCCGGCCGGCAACTGCGTGCACTTCGTGGCCGAGGAGCAGGACTGACACGTCCG
ACGGCGGCCCACGGGTCCCAGGCCTCGGAGATCCGTCCCCTTTTCCTTTGTCGATATCATGTAA
TTAGTTATGTCACGCTTACATTCACGCCCTCCCCCACATCCGCTCTAACCGAAAAGGAAGGAGT
TAGACAACCTGAAGTCTAGGTCGCTATTTATTTTTTTATAGTTATGTTAGTATTAAGAACGTTA
TTTATATTTCAAATTTTCTTTTTTTTCTGTACAGACGCGTGTACGCATGTAACATTATACTGAA
AACCTTGCTTGAGAAGGTTTTGGGACGCTCGAAGGCTTTAATTTGCAAGCTTTCACTATTGCTGG
CAAATTGCGCTTTGTTCATGCCGGATGCGGCGTGAACGCCTTATCCGGCCTACA

Figure 12A

*trpT::GentR PCR cassette*
GentR (green); trpT flanking homology (red)
CAGTCGGTTAGAATACCTGCCTGTCACGCAGGGGGTCGCGGGTTCGAGTCCCGTCCGTTCCGCCA
CCCTAATTACGCACACCGTGGAAACGGATGAAGGCACGAACCCAGTTGACATAAGCCTGTTCGGT
TCGTAAACTGTAATGCAAGTAGCGTATGCGCTCACGCAACTGGTCCAGAACCTTGACCGAACGCA
GCGGTGGTAACGGCGCAGTGGCGGTTTTCATGGCTTGTTATGACTGTTTTTTGTACAGTCTATG
CCTCGGGCATCCAAGCAGCAAGCGCGTTACGCCGTGGGTCGATGTTTGATGTTATGGAGCAGCAA
CGATGTTACGCAGCAGCAACGATGTTACGCAGCAGGGCAGTCGCCCTAAAACAAAGTTAGGTGGC
TCAAGTATGGGCATCATTCGCACATGTAGGCTCGGCCCTGACCAAGTCAAATCCATGCGGGCTGC
TCTTCATCTTTTCGGTCGTGAGTTCGGAGACGTAGCCACCTACTCCCAACATCAGCCGGACTCCG
ATTACCTCGGGAACTTGCTCCGTAGTAAGACATTCATCGCGCTTGCTGCCTTCGACCAAGAAGCG
GTTGTTGGCGCTCTCGCGGCTTACGTTCTGCCCAGGTTTGAGCAGCCGCGTAGTGAGATCTATAT
CTATGATCTCGCAGTCTCCGGCGAGCACCGGAGGCAGGGCATTGCCACCGCGCTCATCAATCTCC
TCAAGCATGAGGCCAACGCGCTTGGTGCTTATGTGATCTACGTGCAAGCAGATTACGGTGACGAT
CCCGCAGTGGCTCTCTATACAAAGTTGGGCATACGGGAAGAAGTGATGCACTTTGATATCGACCC
AAGTACCGCCACCTAACAATTCGTTCAAGCCGAGATCGGCTTCCCGGGAAATCATCCTTAGCGAA
AGCTAAGGATTTTTTTTATCTGAAATAACCCTCTCCGAAGTAAATCCTTCTACCG

Figure 12B

λ-RED::galK PCR cassette
galK (green); galK promoter (blue); lambda deletion homology (red)
GCTATGAAATAGAAAAATGAATCCGTTGAAGCCTGCTTTTTTATACTAACTTGAGCGAAACGGG
AAGCCTGTTGACAATTAATCATCGGCAtagtatatcggcatagtataatacgacaaggtgaggaactaaacccagga
ggcagatcatgagtctgaaagaaaaaacacaatctctgtttgccaacgcatttggctaccctgccactcacaccattcaggcgcctgg
ccgcgtgaatttgattggtgaacacaccgactacaacgacggtttcgttctgccctgcgcgattgattatcaaaccgtgatcagttgtg
caccacgcgatgaccgtaaagttcgcgtgatggcagccgattatgaaaatcagctcgacgagttttccctcgatgcgcccattgtcgc
acatgaaaactatcaatgggctaactacgttcgtggcggtgaaacatctgcaactgcgtaacaacagcttcggcggcgtggacat
ggtgatcagcggcaatgtgccgcagggtgccggggttaagttcttccgcttcactggaagtcgcggtcggaaccgtattgcagcagctt
tatcatctgccgctggacggcgcacaaatcgcgcttaacggtcaggaagcagaaaaccagtttgtaggctgtaactgcgggatcatg
gatcagctaattccgcgctcggcaagaaagatcatgccttgctgatcgattgccgctcactggggaccaaagcagtttccatgccca
aaggtgtggctgtcgtcatcatcaacagtaacttcaaacgtaccctggttggcagcgaatacaacacccgtcgtgaacagtgcgaaa
ccggtgcgcgtttcttccagcagccagccctgcgtgatgtcaccattgaagagttcaacgctgttgcgcatgaactggacccgatcgt
ggcaaaacgcgtgcgtcatatactgactgaaaacgcccgcaccgttgaagctgccagcgcgctggagcaaggcgacctgaaacgt
atgggcgagttgatggcggagtctcatgcctctatgcgcgatgatttcgaaatcaccgtgccgcaaattgacactctggtagaaatcg
tcaaagctgtgattggcgacaaaggtggcgtacgcatgaccggcggcggatttggcggctgtatcgtcgcgctgatcccggaagag
ctggtgcctgccgtacagcaagctgtcgctgaacaatatgaagcaaaaacaggtattaaagagacttttacgtttgtaaaccatcac
AAGGAGCAGGACAGTGCTGAATATTACAACGCGGCAGCATTATGAGCTGGCAGGAGAAAATCAA
CGCGGC

Figure 12C

```
GGtaattccgcttcgcaacatgtgagcaccggtttattgactacAggaagcagtgtgaccgtgtgcttctcaaatgcctgaggccag
tttgctcaggctctccccgtggaggtaataattgacgatatgatcagtgcacggctaactaagcggcctgctgactttctcgccgatca
aaaggcattttgctattaagggattgacgagggcgtatctgcgcagtaagatgcgccccgcattGAAgcGGTGGCTCAAgGG
TAGAGCTggcgcCTCcAAAgcgcctGGtTGCAGGTTCAAgTCCTGcCCgtTTCACCAaattcgaaaagcctgct
caacgagcaggcttttttgcatgctcgagcagctcagggtcgaatttgCCATGGcggccACCAGGTacCACCGGCGcctca
ggcatttgagaagcacacggtcacactgcttccggtagtcaataaaccggtaaaccagcaatagacataagcggctatttaacgac
cctgccctgaaccgacgaccgggtcatcgtggccggatcttgcggcccctcggcttgaacgaattgttagacattatttgccgactac
cttggtgatctcgcctttcacgtagtggacaaattcttccaactgatctgcgcgcgaggccaagcgatcttcttcttgtccaagataagc
ctgtctagcttcaagtatgacgggctgatactgggccggcaggcgctccattgcccagtcggcagcgacatccttcggcgcgatttg
ccggttactgcgctgtaccaaatgcgggacaacgtaagcactacatttcgctcatcgccagcccagtcgggcggcgagttccatagc
gttaaggtttcatttagcgcctcaaatagatcctgttcaggaaccggatcaaagagttcctccgccgctggacctaccaaggcaacgc
tatgttctcttgcttttgtcagcaagatagccagatcaatgtcgatcgtggctggctcgaagatacctgcaagaatgtcattgcgctgc
cattctccaaattgcagttcgcgcttagctggataacgccacggaatgatgtcgtcgtgcacaacaatggtgacttctacagcgcgga
gaatctcgctctctccaggggaagccgaagtttccaaaaggtcgttgatcaaagctcgccgcgttgtttcatcaagccttacggtcac
cgtaaccagcaaatcaatatcactgtgtggcttcaggccgccatccactgcggagccgtacaaatgtacggccagcaacgtcggtc
gagatggcgctcgatgacgccaactacctctgatagttgagtcgatacttcggcgatcaccgcttccctcatactcttccttttcaata
ttattgaagcatttatcagggttattgtctcatgagcggatacatatttgaatgtatttagaaaaataaacaaatagctagctcactcgg
tcgctacgctccgggcgtgagactgcggcgggcgctgcggacacatacaaagttacccacagattccgtggataagcagggacta
acatgtgaggcaaaacagcagggccgcgccggtggcgttttccataggctccgccctcctgccagagttcacataaacagacgctt
ttccggtgcatctgtgggagccgtgaggctcaaccatgaatctgacagtacgggcgaaacccgacaggacttaaagatccccaccg
ttttccggcgggtcgctccctcttgcgctctcctgttccgaccctgccgtttaccggatacctgttccgcctttctcccttacgggaagtgt
ggcgctttctcatagctcacacactggtatctcggctcggtgtaggtcgttcgctccaagctgggctgtaagcaagaactccccgttca
gcccgactgctgcgccttatccggtaactgttcacttgagtccaacccggaaaagcacggtaaaacgccactggcagcagccattgg
taactgggagttcgcagaggatttgtttagctaaacacgcggttgctcttgaagtgtgcgccaaagtccggctacactggaaggaca
gatttggttgctgtgctctgcgaaagccagttaccacggttaagcagttccccaactgacttaaccttcgatcaaaccacctccccagg
tggttttttcgtttacagggcaaaagattacgcgcagaaaaaaggatctcaagaagatcctttgatcttttctactgaaccgctctag
agtcatcaatcatccccataatccttgttagattatcaattttaaaaaactaacagttgtcagcctgtcccgctttaatatcatacgccgt
tatacgttgtttacgctttAaggagGCGGCCGCATGAGCAACGACGAAACTGTAGAGAAAGTCACCCAACAA
GTGTCGGAACTAAAAAGCACAGATGTTAAAGAGCAAGTAGTTACACCTTGGGATGTGGAAGGTG
GGGTTGATGAACAAGGTAGAGCCCAAAATATTGATTACGACAAATTGATCAAACAATTCGGTAC
TAAGCCGGTCAACGAAGAAACCCTGAAGAGATTCAAGCAAGTGACGGGTCGTGAACCACATCAT
TTTTTGCGTAAGGGATTGTTTTTCAGTGAGCGTGACTTCACTAAAATATTAGACCTTTACGAAC
AAGGCAAACCATTTTTCCTATACACTGGTAGAGGTCCTTCGAGCGATTCTATGCACTTGGGTCAT
ATGATCCCTTTTGTCTTCACCAAATGGTTACAGGAAGTGTTTGACGTACCATTAGTCATAGAGTT
GACAGATGACGAAAAATTTTTATTCAAACACAAGTTGACCATCAATGACGTTAAGAATTTTGCC
CGTGAAAATGCCAAGGATATCATTGCTGTTGGCTTTGACCCAAAGAACACCTTTATCTTTTCTGA
TTTGCAATACATGGGTGGTGCATTTTACGAAACTGTAGTAAGAGTTTCCAGACAAATTACAGGA
TCCACTGCAAAGGCTGTTTTCGGGTTTAATGACTCCGACTGTATTGGTAAGTTCCATTTTGCCTC
GATTCAAATTGCTACCGCATTCCCAAGCTCATTTCCTAATGTGTTAGGCTTGCCTGATAAGACAC
CATGTTTGATTCCATGTGCAATTGACCAAGATCCATATTTCAGAGTTTGTAGGGATGTCGCGGAT
AAATTGAAGTACTCCAAACCTGCTTTGCTTCATTCCAGATTCTTTCCAGCTTTGCAAGGTTCCAC
GACCAAAATGTCAGCCTCTGATGATACCACTGCCATTTTCATGACCGATACACCAAAGCAAATTC
AAAAGAAAATTAACAAGTACGCATTCAGCGGTGGTCAAGTGTCCGCCGACCTACATAGAGAATT
AGGTGGTAATCCCGATGTCGATGTTGCATACCAATACTTGTCATTTTTCAAGGATGACGATGTTT
TCTTGAAGGAATGCTATGACAAATATAAGTCCGGTGAATTACTATCAGGTGAAATGAAGAAACT
GTGTATCGAGACTCTGCAAGAATTCGTTAAGGCGTTCCAGGAACGCAGAGCTCAGGTGGACGAA
GAGACCTTGGACAAATTCATGGTCCCACATAAGTTGGTTTGGGCGAAAAGGAAAGACTTGTCG
CACCTAAGCCAAAAACTAAGCAAGAAAAGAAGTAAGCGGCCGCtttcaaacgctaaattgcctgatgcgctac
gcttatcaggcctacatgatctctgcaatatattgagtttgcgtgcttttgtaggccggataaggcgttcacgccgcatccgcaagaa
acagcaaacaatccaaaacgccgcgttcagcggcgttttttctgcttttcttcgcgaattaattccgcttcgcaacatgtgagcaccgg
tttattgactacctgca
```

Figure 13B pRepAC-EcWtR-TAG gccctccggctggctggtttattgctgataaatctggagccggtgagcgtgggtctcgcggtatcattgcagcactggggccagatg
gtaagccctcccgtatcgtagttatctacacgacggggagtcaggcaactatggatgaacgaaatagacagatcgctgagataggt
gcctcactgattaagcattggtaactgtcagaccaagtttactcatatatactttagattgatttaaaacttcattttttaatttaaaagga
tctaggtgaagatcctttttgataatctcatgaccaaaatcccttaacgtgagttttcgttccactgagcgtcagaccccttaataagat
gatcttcttgagatcgttttggtctgcgcgtaatctcttgctctgaaaacgaaaaaaccgccttgcagggcggttttttcgaaggttctct
gagctaccaactctttgaaccgaggtaactggcttggaggagcgcagtcaccaaaacttgtcctttcagtttagccttaaccggcgca
tgacttcaagactaactcctctaaatcaattaccagtggctgctgccagtggtgcttttgcatgtctttccgggttggactcaagacgat
agttaccggataaggcgcagcggtcggactgaacggggggttcgtgcatacagtccagcttggagcgaactgcctacccggaactg
agtgtcaggcgtggaatgagacaaacgcggccataacagcggaatgacaccggtaaaccgaaaggcaggaacaggagagcgca
cgagggagccgccagggggaaacgcctggtatctttatagtcctgtcgggtttcgccaccactgatttgagcgtcagatttcgtgatg
cttgtcaggggggcggagcctatggaaaaacggctttgccgcggccctctcacttccctgttaagtatcttcctggcatcttccaggaa
atctccgccccgttcgtaagccatttccgctcgccgcagtcgaacgaccgagcgtagcgagtcagtgagcgaggaagcggaatatat
cctgtatcacatattctgctgacgcaccggtgcagccttttttctcctgccacatgaagcacttcactgacaccctcatcagtgccaaca
tagtaagccagtatacactccgctagcgctgatgtccggcggtgcttttgccgttacgcaccacccgtcagtagctgaacaggagg
gacagctgatagaaacagaagccactggagcacctcaaaaacaccatcatacactaaatcagtaagttggcagcatcacccgacg
cactttgcgccgaataaatacctgtgacggaagatcacttcgcagaataaataaatcctggtgtccctgttgataccgggaagccctg
ggccaacttttggcgaaaatgagacgttgatcggcacgtaagaggttccaactttcaccataatgaaataagatcactaccgggcgt
atttttttgagttatcgagattttcaggagctaaggaagctaaaatggagaaaaaatcactggatataccaccgttgatatatcccaa
tggcatcgtaaagaacatttgaggcatttcagtcagttgctcaatgtacctataaccagaccgttcagctggatattacggcctttta
aagacgtgaaagaaaataagcacaagtttatccggcctttattcacattcttgcccgcctgatgaatgctcatccggaattccgtat
ggcaatgaaagacggtgagctggtgatatgggatagtgttcacccttgttacaccgttttccatgagcaaactgaaacgttttcatcgc
tctggagtgaataccactaggatttccggcagtttctacacatatattcgcaagatgtggcgtgttacggtgaaaacctggcctatttc
cctaaagggtttattgagaatatgtttttcgtctcagccaatccctgggtgagtttcaccagttttgatttaaacgtggccaatatggac
aacttcttcgccccgttttcaccatgggcaaatattatacgcaaggcgacaaggtgctgatgccgctggcgattcaggttcatcatgc
cgtttgtgatggcttccatgtcggcagaatgcttaatgaattacaacagtactgcgatgagtggaggcggggcgtaatttttttaag
gcagttattggtgcccttaaacgcctggttgctacgcctgaataagtgataataagcggatgaatggcagaaattcgaaagcaaatt
cgacccggtcgtcggttcagggcagggtcgttaaatagccgcttatgtctattgctggtttaccggtttattgactaccggaagcagtg
tgaccgtgtgcttctcaaatgcctgaggccagtttgctcaggctctccccgtggaggtaataattgacgatatgatcatttattctgcct
cccagagcatgataaaaacggttagcgcttcgttaatacagatgtaggtgttccacagggtagccagcagcatcctgcgatgcagat
ccggaacataatggACTAGTgcgcttgtttcggcgggactgttgtaactcagaataagaaatgaggccgctcatggcgttctgttg
cccgtctcactggtgaaaagaaaaacaaccctggcgccgcttctttgagcgaacgatcaaaaataagtggcgccccatcaaaaaaa
tattctcaacataaaaaactttgtgtaatacttgtaacgctGAATTCAGGGGCGTAGTTCAATTGGTAGAGCACCG
GTCTctaAAACCGGGTGtTGGGAGTTCGAGTCTCTCCGCCCCTGCCACTGCAGATccttagcgaaagcta

Figure 14B aggattttttttaagcttggcactggccgtcgttttacaacgtcgtgactgggaaaaccctggcgttacccaacttaatcgccttgcagc
acatcccccttcgccagttgagcaccgccgccgcaaggaatggtGaattcaggaTCTAAGGAGcccgagatgcgccgcgtgc
ggctgctggagatggcggacgcgatggatatgttctgccaagggttggtttgcgcattcacagttctccgcaagaattgattggctcc
aattcttggagtggtgaatccgttagcgaggtgccgccggcttccattcaggtcgaggtggcccggctccatgcaccgcgacgcaac
gcggggaggcagacaaggtatagggcggcgcctacaatccatgccaacccgttccatgtgctcgccgaggcggcataaatcgccgt
gacgatcagcggtccaatgatcgaagttaggctggtaagagccgcgagcgatccttgaagctgtccctgatggtcgtcatctacctg
cctggacagcatggcctgcaacgcgggcatcccgatgccgccggaagcgagaagaatcataatggggaaggccatccagcctcgc
gtcgcgaacgccagcaagacgtagcccagcgcgtcggccgccatgccggcgataatggcctgcttctcgccgaaacgtttggtggc
gggaccagtgacgaaggcttgagcgagggcgtgcaagattccgaataccgcaagcgacaggccgatcatcgtcgcgctccagcga
aagcggtcctcgccgaaaaatgacccagagcgctgccggcacctgtcctacgagttgcatgataaagaagacagtcataagtgcggc
gacgatagtcatgccccgcgcccaccggaaggagctgactgggttgaaggctctcaagggcatcggtcgacgctctcccttatgcga
ctcctgcattaggaagcagcccagtagtaggttgaggccgttgagcaccgccgccgcaaggaatggtgcatgcaaggagatggcg
cccaacagtccccggccacggggcctgccaccatacccacgccgaaacaagcgctcatgagcccgaagtggcgagcccgatctt
ccccatcggtgatgtcggcgatataggcgccagcaaccgcacctgtggcgccggtgatgccggccacgatgcgtccggcgtagagg
atccacaggacgggtgtggtcgccatgatcgcgtagtcgatagtggctccaagtagcgaagcgagcaggactgggcggcggccaa
agcggtcggacagtgctccgagaacgggtgcgcatagaaattgcatcaacgcatatagcgctagcagcacgccatagtgactggc
gatgctgtcggaatggacgatatcccgcaagaggcccggcagtaccggcataaccaagctatgcctacagcatccagggtgacg
gtgccgaggatgacgatgagcgcattgttagatttcatacacggtgcctgactgcgttagcaatttaactgtgataaactaccgcatta
aagcttatcgatgataagctgtcaaacatgagaattacaacttatatcgtatggggctgacttcaggtgctacattgctcaaagatgc
agggtaaaagctaaccgcatctttaccgacaaggcatccggcagttcaacagatcgggaagggctggatttgctgaggatgaagg
tggaggaaggtgatgtcattctggtgaagaagctcgaccgtcttggccgcgacaccgccgacatgatccaactgataaaagagtttg
atgctcagggtgtagcggttcggtttattgacgacgggatcagtaccgacggtgatatggggcaaatggtggtcaccatcctgtcggc
tgtggcacaggctgaacgccggaggatcctccgggccgttgcttcgcaacgttcaaatccgctcccggcggatttgtcctactcagga
gagcgttcaccgacaaacaacagataaaacgaaaggcccagtctttcgactgagcctttcgttttatttgatgcctggcagttccctac
tctcgcatggggagaccccacactaccatcggcgctacggcgtttcacttctgagttcggcatggggtcaggtgggaccaccgcgct
actgccgccaggcaaattctgttttatcagaccgcttctgcgttctgatttaatctgtatcaggctgaaaatcttctctcatccgacgtct
taggcgaaggcgaagtccgactctaagatgtcacggaggttcaagttacctttagccggaagtgctggcattttgtccaattgagact
cgtgcaactggtcagcgaactggtcgtagaaatcagccagtacatcacaagactcatatgtgtcaaccatagtttcgcgcactgcttt
gaacaggtkcgcagcgtcagccggaatggtaccgaaggagtcgtgaatcagtgcaaaagattcgattccgtacttctcgtgtgccca
cactacagtcttacgaaggtggctaccgtcttggctgtgtacaaagttaggagcgataccagactcctgtttgtgtgcatcaatctcgc
tatctttgttggtgttaatggtaggctgtaagcggaactgaccgaggaacatcaggttcaagcgcgtctgaataggcttcttgtattcct
gccacacagggaaaccatcaggagttaccaatgcacagcgcaacgcttgcgaagaatctctccagtcttccttatctttgacctcagc
agccagcagcttagcagcagacttaagccagttcattgcttcaaccgcagctaccaccgtcacgctcacagattcccaaatcagctta
gccatgtatccagcagcctgattcggctgagtgaacatcagacccttgccggaatcaatagctggctgaatggtatcttccagcactt
gttgacggaagccgaactcttggaccgtaagccagcgtcatgactgaacgcttagtcacactgcgagtaacaccgtaagccagcc
attgaccagccagtgccttagtgcccagcttgactttctcagagatttcaccagtgttctcatcggtcacggtaactacttcgttatcgg
tccattgattgcgtctgcttgtagaatctcgttgacttcttagcaacaatcccgtagatgtcctgaacggttcactaggaagcaagt
taaccgcgcgaccacctacctcatccggagcatcgcggagaagtgctggatgccagagcaagacccgtcaaacgccagcggaag
ggagcagttatagctcaggccgtggtgctgtacccagcgtactcaaagcagaacgcaaggaagcagaacggagaatcttgctca
gcccaccaagtgttctccagtggagacttagcgcaagccatgatgttctcgtggttttcctcaatgaacttgatgcgctcagggaacg
gaaccttatcgacacccgcacagtttgcaccgtggattttcagccagtagtaaccttcttaccgattggtttacctttcgccagcgtaa
gcagtccttggtcatatcgttaccttgcgggtgaacattgacacagcgtaaacacgaccgcgccagtccatgttgtaagggaacca
gatggccttatggttagcaaacttattggcttgctcaagcatgaactcaaggctgatacggcgagacttgcgagccttgtccttgcggt
acacagcagcggcagcacgtttccacgcggtgagagcctcaggattcatgtcgatgtcttccggtttcatcgggagttcttcacgctc
aatcgcagggatgtcctcgaccggacaatgcttccacttggtgattacgttggcgaccgctaggacttcttgttgattttccatgcggt
gttttgcgcaatgttaatcgctttgtacacctcaggcatgtaaacgtcttcgtagcgcatcagtgcttcttactgtgagtacgcaccag

```
cgccagaggacgacgaccgttagcccaatagccaccaccagtaatgccagtccacggcttaggaggaactacgcaaggttggaac
atcggagagatgccagccagcgcacctgcacgggttgcgatagcctcagcgtattcaggtgcgagttcgatagtctcagagtctga
cctactacgccagcattttggcggtgtaagctaaccattccggttgactcaatgagcatctcgatgcagcgtactcctacatgaataga
gtcttccttatgccacgaagaccacgcctcgccaccgagtagacccttagagagcatgtcagcctcgacaacttgcataaatgctttc
ttgtagacgtgccctacgcgcttgttgagttgttcctcaacgttttcttgaagtgcttagcttcaaggtcacggatacgaccgaagcga
gcctcgtcctcaatggcccgaccgattgcgcttgctacagcctgaacggttgtattgtcagcactggttaggcaagccagagtggtctt
aatggtgatgtacgctacggcttccggcttgatttcctacaggaactggaaggctgtcgggcgcttgccgcgcttagctttcacttcct
caaccagtcgttgatgcgtgcaatcatcttaggagtagggtagtgatgagaggcttggcggcagcgttatccgcaacctcaccag
ctttaagttgacgctcaaacatcttgcggaagcgtgcttcacccatctcgtaagactcatgctcaagggccaactgttcgcgagctaa
acgctcaccgtaatggtcagccagagtgttgaacgggatagcagccagttcgatgtcagagaagtcgtcttagcaatgttaatggt
attctagtgcacggtaatcatggtcatggttaattcctcctgttagcccaaaaaacgggtatggagaaacagtagagagttgcgataa
aaagcgtcaggtaggatccgctaatcttatggataaaaatgctatggcatagcaaagtgtgacgccgtgcaaataatcaatgtggac
ttttctgccgtgattatagacacttttgttacgcgttttttgtcatggctttggtcccgctttgttacagaatgcttttaataagcggggttac
cggtttggttagcgagaagagccagtaaaagacgcagtgacggcaatgtctgatgcaatatggacaattggtttcttctctgaatggc
gggagtatgaaaagtatggctgaagcgcaaaatgatccctgctgccgggatactcgtttaatgcccatctggtggcgggtttaacg
ccgattgaggccaacggttatctcgatttttttatcgaccgaccgctgggaatgaaaggttatattctcaatctcaccattcgcggtcag
ggggtggtgaaaaatcagggacgagaatttgtttgccgaccgggtgatattttgctgttcccgccaggagagattcatcactacggtc
gtcatccggaggctcgcgaatggtatcaccagtgggtttactttcgtccgcgcgcctactggcatgaatggcttaactggccgtcaat
atttgccaatacggggttctttcgcccggatgaagcgcaccagccgcatttcagcgacctgtttgggcaaatcattaacgccgggcaa
ggggaagggcgctattcggagctgctggcgataaatctgcttgagcaattgttactgcggcgcatggaagcgattaacgagtcgctc
catccaccgatggataatcgggtacgcgaggcttgtcagtacatcagcgatcacctggcagacagcaattttgatatcgccagcgtc
gcacagcatgtttgcttgtcgccgtcgcgtctgtcacatcttttccgccagcagttagggattagcgtcttaagctggcgcgaggacca
acgtatcagccaggcgaagctgcttttgagcaccacccggatgcctatcgccaccgtcggtcgcaatgttggttttgacgatcaactc
tatttctcgcgggtatttaaaaaatgcaccggggccagcccgagcgagttccgtgccggttgtgaagaaaaagtgaatgatgtagcc
gtcaagttgtcataattggtaacgaatcagacaattgacggcttgacggagtagcatagggtttgcagaatccctgcttcgtccatttg
acaggcacattatgcatgccgcttcgccttcgcgcgcgaattgatctgctgcctcgcgcgtttcggtgatgacggtgaaaacctctga
cacatgcagctcccggagacggtcacagcctgcagcaaaaaaccctcaagacccgtttagaggccccaaggggttatgctagtta
ttgctcagcggtggcagcagccaactcagcttcctttcgggctttgttatttgtagagctcatccatgccatgtgtaatcccagcagcag
ttacaaactcaagaaggaccatgtggtcacgcttttcgttgggatctttcgaaagggcagattgtgtcgacaggtaatggttgtctggt
aaaaggacagggccatcgccaattggagtattttgttgataatggtctgctagttgaacggatccatcttcaatgttgtggcgaatttt
gaagttagctttgattccattctttgtttgtctgccgtgatgtatacattgtgtgagttatagttgtactcgagtttgtgtccgagaatgt
tccatcttctttaaaatcaataccttttaactcgatacgattaacaagggtatcaccttcaaacttgacttcagcacgcgtcttgtagttc
ccgtcatcttgaaagatatagtgcgttcctgtacataaccttcgggcatggcactcttgaaaaagtcatgccgtttcatatgatccgg
ataacgggaaaagcattgaacaccataagagaaagtagtgacaagtgttggccatggaacaggtagttttccagtagtgcaaataa
atttaagggtaagttttccgtatgttgcatcaccttcaccctctccactgacagaaaatttgtgcccattaacatcaccatctaattcaac
aagaattgggacaactccagtgaaaagttcttctcctttactcatatgtatatctccttcttaaagttaaacaaaattatttctagaggg
aaaccgttgtggtctccctatagtgagtcgtattaatttcgcgggatcg
```

Figure 14B cont.

cgcgtccgccatctccagcagccgcacgcggcgcatcttgggctccttgcatgcaccattccttgcggcggcggtgctcaacggcctc
aacctactactgggctgcttcctaatgcaggagtcgcataagggagagcgtctggcgaaaggggggatgtgctgcaaggcgattaag
ttgggtaacgccagggttttccagtcacgacgttgtaaaacgacggccagtgccaagcttaaaaaaaatccttagctttcgctaagg
atcaTATGCCTAGGTGGCAGGGGCGGAGAGACTCGAACTCCCAaCACCCGGTTTTGAAGACCGGTG
CTCTACCAATTGAACTACGCCCCTGAATTCagcgttacaagtattacacaaagttttttatgttgagaatattttttga
tggggcgccacttatttttgatcgttcgctcaaagaagcggcgccagggttgttttcttttcaccagtgagacgggcaacagaacGG
TACCtctagacaattggtgcacttcaaaaatcgatgagctgttgacaattaatcatcgaactagtgttgataccgggaagccctggg
ccaacttttggcgaaaatgagacgttgatcggcacgtaagaggttccaactttcaccataatgaaataagatcactaccgggcgtatt
ttttgagttatcgagattttcaggagctaaggaagctaaaatggagaaaaaatcactggatataccaccgttgatatatccaatgg
catcgtaaagaacatttgaggcatttcagtcagttgctcaatgtacctataaccagaccgttcagctggatattacggcctttttaaag
accgtaaagaaaataagcacaagttttatccggcctttattcacattcttgcccgcctgatgaatgctcatccggaattccgtatggc
aatgaaagacggtgagctggtgatatgggatagtgttcaccctgttacaccgttttccatgagTGATctgaaacgttttcatcgctc
tggagtgaataccacgacgatttccggcagtttctacacatatattcgcaagatgtggcgtgttacggtgaaaacctggcctattccc
taaagggttattgagaatatgtttttcgtctcagccaatccctgggtgagtttcaccagttttgatttaaacgtggccaatatggacaa
cttcttcgcccccgttttcaccatgggcaaatattatacgcaaggcgacaaggtgctgatgccgctggcgattcaggttcatcatgccg
tTtgtgatggcttccatgtcggcagaatgcttaatgaattacaacagtactgcgatggagtggcagggcggggcgtaatttttttaagg
cagttattggtgcccttaaacgcctggttgctacgcctgaataagtgataataagcggatgaatggcagaaatTCGCTGCAgcag
catcaaagttctggtgctggtagctgcgccagaaggtatcgctgcgctggaaaaagcgcacccggacgtcgaactgtataccgcatc
gattgatcagggactgaacgagcacggatacattattccgggcctcggcgatgccggtgacaaaatctttggtacgaaataaagaat
tcgaagcttgggcccgaacaaaaactcatctcagaagaggatctgaatagcgccgtcgaccatcaccatcatcatcattgagtttaa
acgacgtccagcttggctgttttggcggatgagagaagattttcagcctgatacagattaaatcagaacgcagaagcggtctgataa
aacagaatttgcctggcggcagtagcgcggtggtcccacctgacccatgccgaactcagaagtgaaacgccgtagcgccgatggt
agtgtgaggcctccatgcgagagtagggaactgccaggcatcaaataaaacgaaaggctcagtcgaaagactgggcctttcgttt
tatctgttgtttgtcggtgaacgatatctgcttttcttcggatccctcgagagatctccatgggctagcggagtgtatactggcttactat
gttggcactgatgagggtgtcagtgaagtgcttcatgtggcaggagaaaaaaggctgcaccggtgcgtcagcagaatatgtgatac
aggatatattccgcttcctcgctcactgactcgctacgctcggtcgttcgactgcggcgagcggaaatggcttacgaacggggcgga
gatttcctggaagatgccaggaagatacttaacagggaagtgagagggccgcggcaaagccgttttttccataggctccgccccctg
acaagcatcacgaaatctgacgctcaaatcagtggtggcgaaacccgacaggactataaagataccaggcgtttccccctggcggc
tccctcgtgcgctctcctgttcctgcctttcggtttaccggtgtcattccgctgttatggccgcgtttgtctcattccacgcctgacactca
gttccgggtaggcagttcgctccaagctggactgtatgcacgaaccccccgttcagtccgaccgctgcgccttatccggtaactatcg
tcttgagtccaacccggaaagacatgcaaaagcaccactggcagcagccactggtaattgatttagaggagttagtcttgaagtcat
gcgccggttaaggctaaactgaaaggacaagttttggtgactgcgctcctccaagccagttacctcggttcaaagagttggtagctca
gagaaccttcgaaaaaccgccctgcaaggcggttttttcgttttcagagcaagagattacgcgcagaccaaaacgatctcaagaag

Figure 15B atcatcttattaaggggtctgacgcacatgtaatgtagcacctgaagtcagccccatacgatataagttgtaattctcatgtttgacag
cttatcatcgataagctttaatgcggtagtttatcacagttaaattgctaacgcagtcaggcaccgtgtatgaaatctaacaatgcgct
catcgtcatcctcggcaccgtcaccctggatgctgtaggcataggcttggttatgccggtactgccgggcctcttgcgggatatcgtc
attccgacagcatcgccagtcactatggcgtgctgctagcgctatatgcgttgatgcaatttctatgcgcacccgttctcggagcactg
tccgaccgctttggccgccgcccagtcctgctcgcttcgctacttggagccactatcgactacgcgatcatggcgaccacacccgtcc
gtggattctctacgccggacgcatcgtggccggcatcaccggcgccacaggtgcggttgctggcgcctatatcgccgacatcaccga
tggggaagatcgggctcgccacttcgggctcatgagcgcttgtttcggcgtgggtatggtggcaggccccgtggccgggggactgtt
gggcgccatctccttgcatgcaccattccttgcggcggcggtgctcaacggcctcaacctactactgggctgcttcctaatgcaggag
tcgcataagggagagcgtcgaccgatgcccttgagagccttcaacccagtcagctccttccggtgggcgcggggcatgactatcgt
gccgcacttatgactgtcttctttatcatgcaactcgtaggacaggtgccggcagcgctctgggtcattttcggcgaggaccgctttcg
ctggagcgcgacgatgatcggcctgtcgcttgcggtattcggaatcttgcacgccctcgctcaagccttcgtcactggtcccgccacc
aaacgtttcggcgagaagcaggccattatcgccggcatggcggccgacgcgctgggctacgtcttgctggcgttcgcgacgcgagg
ctggatggccttccccattatgattcttctcgcttccggcggcatcgggatgcccgcgttgcaggccatgctgtccaggcaggtagat
acgaccatcagggacagcttcaaggatcgctcgcggctcttaccagcctaacttcgatcattggaccgctgatcgtcacggcgattta
tgccgcctcggcgagcacatggaacgggttggcatggattgtaggcgccgccctataccttgtctgcctccccgcgttgcgtcgcgg
gcatggagccgggccacctcgacctgaatggaagccggcggcacctcgctaacggattcaccactccaagaattggagccaatca
attcttgcggagaactgtgaatgcgcaaaccaacccttggcagaacatatccat pRepJI-EcW cgcgtccgccatctccagcagccgcacgcggcgcatcttgggctccttgcatgcaccattccttgcggcggcggtgctcaacggcctc
aacctactactgggctgcttcctaatgcaggagtcgcataagggagagcgtctggcgaaaggggatgtgctgcaaggcgattaag
ttgggtaacgccagggttttcccagtcacgacgttgtaaaacgacggccagtgccaagcttaaaaaaaatccttagctttcgctaagg
atcaTATGCCTAGGTGGCAGGGGCGGAGAGACTCGAACTCCCAaCACCCGGTTTTGAAGACCGGTG
CTCTACCAATTGAACTACGCCCCTGAATTCagcgttacaagtattacacaaagttttttatgttgagaatattttttga
tggggcgccacttatttttgatcgttcgctcaaagaagcggcgccagggttgtttttcttttcaccagtgagacgggcaacagaacGG
TACctctagacaattggtgcacttcaaaaatcgatgagctgttgacaattaatcatcgaactagtgttgataccgggaagccctggg
ccaacttttggcgaaaatgagacgttgatcggcacgtaagaggttccaactttcaccataatgaaataagatcactaccgggcgtatt
ttttgagttatcgagattttcaggagctaaggaagctaaaatggagaaaaaatcactggatataccaccgttgatatatcccaatgg
catcgtaaagaacatttgaggcatttcagtcagttgctcaatgtacctataaccagaccgttcagctggatattacggcctttttaaag
accgtaaagaaaataagcacaagttttatccggcctttattcacattcttgcccgcctgatgaatgctcatccggaattccgtatggc
aatgaaagacggtgagctggtgatatgggatagtgttcacccttgttacaccgttttccatgagTGATctgaaacgttttcatcgctc
tggagtgaataccacgacgatttccggcagtttctacacatatattgcaagatgtggcgtgttacggtgaaaacctggcctatttccc
taaagggtttattgagaatatgtttttcgtctcagccaatccctgggtgagtttcaccagttttgatttaaacgtggccaatatggacaa
cttcttcgccccgttttcaccatgggcaaatattatacgcaaggcgacaaggtgctgatgccgctggcgattcaggttcatcatgccg

gatatcgccagcgtcgcacagcatgtttgcttgtcgccgtcgcgtctgtcacatctttccgccagcagttagggattagcgtcttaagc
tggcgcgaggaccaacgtatcagccaggcgaagctgctttgagcaccacccggatgcctatcgccaccgtcggtcgcaatgttggt
tttgacgatcaactctatttctcgcgggtatttaaaaaatgcaccggggccagcccgagcgagttccgtgccggttgtgaagaaaaa
gtgaatgatgtagccgtcaagttgtcataattggtaacgaatcagacaattgacggcttgacggagtagcatagggtttgcagaatc
cctgcttcgtccatttgacaggcacattatgcatgccgcttcgccttcgcgcgcgaattgatctgctgcctcgcgcgtttcggtgatgac
ggtgaaaacctctgacacatgcagctcccggagacggtcacagcctgcagcaaaaaacccctcaagacccgtttagaggccccaa
ggggttatgctagttattgctcagcggtggcagcagccaactcagcttcctttcgggctttgttatttgtagagctcatccatgccatgt
gtaatccagcagcagttacaaactcaagaaggaccatgtggtcacgcttttcgttgggatcttcgaaagggcagattgtgtcgaca
ggtaatggttgtctggtaaaaggacagggccatcgccaattggagtattttgttgataatggtctgctagttgaacggatccatcttca
atgttgtggcgaattttgaagttagctttgattccattcttttgtttgtctgccgtgatgtatacattgtgtgagttatagttgtactcgagt
ttgtgtccgagaatgtttccatcttctttaaaatcaatacctttaactcgatacgattaacaagggtatcaccttcaaacttgacttcag
cacgcgtcttgtagttcccgtcatctttgaaagatatagtgcgttcctgtacataaccttcgggcatggcactcttgaaaaagtcatgcc
gtttcatatgatccggataacgggaaaagcattgaacaccataagagaaagtagtgacaagtgttggccatggaacaggtagttttc
cagtagtgcaaataaatttaagggtaagttttccgtatgttgcatcaccttcaccctctccactgacagaaatttgtgcccattaacat
caccatctaattcaacaagaattgggacaactccagtgaaaagttcttctcctttactcatatgtatatctccttcttaaagttaaacaa
aattatttctagagggaaaccgttgtggtctccctatagtgagtcgtattaatttcgcgggatcggcccttccggctggctggtttattg
ctgataaatctggagccggtgagcgtgggtctcgcggtatcattgcagcactggggccagatggtaagccctcccgtagcggccgcc
ctgcagcagcatcaaagttctggtgctggtagctgcgccagaaggtatcgctgcgctggaaaaagcgcacccggacgtcgaactgt
ataccgcatcgattgatcagggactgaacgagcacggatacattattccgggcctcggcgatgccggtgacaaaatctttggtacga
aataaagaattcgaagcttgggcccgaacaaaaactcatctcagaagaggatctgaatagcgccgtcgaccatcaccatcatcatc
attgagtttaaacgacgtccagcttggctgttttggcggatgagagaagattttcagcctgatacagattaaatcagaacgcagaagc
ggtctgataaaacagaatttgcctggcggcagtagcgcggtggtcccacctgaccccatgccgaactcagaagtgaaacgccgtag
cgccgatggtagtgtgaggcctcccatgcgagagtagggaactgccaggcatcaaataaaacgaaaggctcagtcgaaagactgg
gcctttcgttttatctgttgtttgtcggtgaacgatatctgcttttcttcggatccctcgagagatctccatgggctagcggagtgtatact
ggcttactatgttggcactgatgagggtgtcagtgaagtgcttcatgtggcaggagaaaaaaggctgcaccggtgcgtcagcagaat
atgtgatacaggatatattccgcttcctcgctcactgactcgctacgctcggtcgttcgactgcggcgagcggaaatggcttacgaac
ggggcggagatttcctggaagatgccaggaagatacttaacagggaagtgagagggccgcggcaaagccgttttccataggctcc
gccccctgacaagcatcacgaaatctgacgctcaaatcagtggtggcgaaacccgacaggactataaagataccaggcgtttccc
cctggcggctccctcgtgcgctctcctgttcctgcctttcggtttaccggtgtcattccgctgttatggccgcgtttgtctcattccacgcc
tgacactcagttccgggtaggcagttcgctccaagctggactgtatgcacgaaccccccgttcagtccgaccgctgcgccttatccgg
taactatcgtcttgagtccaacccggaaagacatgcaaaagcaccactggcagcagccactggtaattgatttagaggagttagtctt
gaagtcatgcgccggttaaggctaaactgaaaggacaagttttggtgactgcgctcctccaagccagttacctcggttcaaagagtt
ggtagctcagagaaccttcgaaaaaccgccctgcaaggcggttttttcgttttcagagcaagagattacgcgcagaccaaaacgatc
tcaagaagatcatcttattaaggggtctgacgcacatgtaatgtagcacctgaagtcagccccatacgatataagttgtaattctcatg
tttgacagcttatcatcgataagctttaatgcggtagtttatcacagttaaattgctaacgcagtcaggcaccgtgtatgaaatctaac
aatgcgctcatcgtcatcctcggcaccgtcaccctggatgctgtaggcataggcttggttatgccggtactgccgggcctcttgcggg
atatcgtccattccgacagcatcgccagtcactatggcgtgctgctagcgctatatgcgttgatgcaatttctatgcgcacccgttctcg
gagcactgtccgaccgctttggccgccgcccagtcctgctcgcttcgctacttggagccactatcgactacgcgatcatggcgaccac
acccgtcctgtggattctctacgccggacgcatcgtggccggcatcaccggcgccacaggtgcggttgctggcgcctatatcgccga
catcaccgatggggaagatcgggctcgccacttcgggctcatgagcgcttgtttcggcgtgggtatggtggcaggccccgtggccgg
gggactgttgggcgccatctccttgcatgcaccattccttgcggcggcggtgctcaacggcctcaacctactactgggctgcttcctaa
tgcaggagtcgcataagggagagcgtcgaccgatgcccttgagagccttcaacccagtcagctccttccggtgggcgcggggcatg
actatcgtcgccgcacttatgactgtcttctttatcatgcaactcgtaggacaggtgccggcagcgctctgggtcattttcggcgagga
ccgctttcgctggagcgcgacgatgatcggcctgtcgcttgcggtattcggaatcttgcacgccctcgctcaagccttcgtcactggtc
ccgccaccaaacgtttcggcgagaagcaggccattatcgccggcatggcggccgacgcgctgggctacgtcttgctggcgttcgcg
acgcgaggctggatggccttccccattatgattcttctcgcttccggcggcatcgggatgcccgcgttgcaggccatgctgtccaggc aggtagatgacgaccatcagggacagcttcaaggatcgctcgcggctcttaccagcctaacttcgatcattggaccgctgatcgtca
cggcgatttatgccgcctcggcgagcacatggaacgggttggcatggattgtaggcgccgccctataccttgtctgcctccccgcgtt
gcgtcgcggtgcatggagccgggccacctcgacctgaatggaagccggcggcacctcgctaacggattcaccactccaagaattgg
agccaatcaattcttgcggagaactgtgaatgcgcaaaccaacccttggcagaacatatccat
pNegj2-EcW

Figure 16B cont.

gggtggtgcgtaacggcaaaagcaccgccggacatcagcgctagcggagtgtatactggcttactatgttggcactgatgagggtgt
cagtgaagtgcttcatgtggcaggagaaaaaaggctgcaccggtgcgtcagcagaatatgtgatacaggatatattccgcttcctcg
ctcactgactcgctacgctcggtcgttcgactgcggcgagcggaaatggcttacgaacggggcggagatttcctggaagatgccag
gaagatacttaacagggaagtgagagggccgcggcaaagccgttttttccataggctccgcccccctgacaagcatcacgaaatctg
acgctcaaatcagtggtggcgaaacccgacaggactataaagataccaggcgtttcccctggcggctccctcgtgcgctctcctgtt
cctgcctttcggtttaccggtgtcattccgctgttatggccgcgtttgtctcattccacgcctgacactcagttccgggtaggcagttcgc
tccaagctggactgtatgcacgaaccccccgttcagtccgaccgctgcgccttatccggtaactatcgtcttgagtccaacccggaaa
gacatgcaaaagcaccactggcagcagccactggtaattgatttagaggagttagtcttgaagtcatgcgccggttaaggctaaact
gaaaggacaagttttggtgactgcgctcctccaagccagttacctcggttcaaagagttggtagctcagagaaccttcgaaaaaccg
ccctgcaaggcggttttttcgttttcagagcaagagattacgcgcagaccaaaacgatctcaagaagatcatcttattaatcagataa
aatatttctagatttcagtgcaatttatctcttcaaatgtagcacctgaagtcagccccatacgatataagttgtaattctcatgtttgac
agcttatcatcgataagcttgcaatttatctcttcaaatgtagcacctgaagtcagccccatacgatataagttgtaattctcatgttagt
catgccccgcgcccaccggaaggagctgactgggttgaaggctctcaagggcatcggtcgagatcccggtgcctaatgagtgagct
aacttacattaattgcgttgcgctcactgcccgctttccagtcgggaaacctgtcgtgccagctgcattaatgaatcggccaacgcgc
ggggagaggcggtttgcgtattgggcgccagggtggtttttctttcaccagtgagacgggcaacagctgattgcccttcaccgcctg
gccctgagagagttgcagcaagcggtccacgctggtttgccccagcaggcgaaaatcctgtttgatggtggttaacggcgggatata
acatgagctgtcttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacgcagacgcg
ccgagacagaacttaatgggcccgctaacagcgcgatttgctggtgacccaatgcgaccagatgctccacgcccagtcgcgtaccgt
cttcatgggagaaaataatactgttgatgggtgtctggtcagagacatcaagaaataacgccggaacattagtgcaggcagcttcca
cagcaatggcatcctggtcatccagcggatagttaatgatcagcccactgacgcgttgcgcgagaagattgtgcaccgccgctttac
aggcttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgccgccagttgttgtgccacgcggttgg gaatgtaattcagctccgccatcgccgcttccacttttttcccgcgttttcgcagaaacgtggctggcctggttcaccacgcgggaaacg
gtctgataagagacaccggcatactctgcgacatcgtataacgttactggttttcacattcaccaccctgaattgactctcttccgggcg
ctatcatgccataccgcgaaaggttttgcgccattcgatggtgtccgggatctcgacgctctcccttatgcgactcctgcattaggctca
ctataggggaattgtgagcggataacaattcccctctagagtttgacagcattatcatcgatctcgagaaatcataaaaaatttatttg
ctttgtgagcggataacaattataatagattcaattgtgagcggataacaatttcacacagaattcattaaagaggagaaattacatA
TGAGCAAAGGAGAAGAACTTTTCACTGGAGTTGTCCCAATTCTTGTTGAATTAGATGGTGATGT
TAATGGGCACAAATTTTCTGTCCGTGGAGAGGGTGAAGGTGATGCTACAAACGGAAAACTCACC
CTTAAATTTATTTGCACTACTGGAAAACTACCTGTTCCGTGGCCAACACTTGTCACTACTCTGAC
CTATGGTGTTCAATGCTTTTCCCGTTATCCGGATCACATGAAACGGCATGACTTTTTCAAGAGTG
CCATGCCCGAAGGTTATGTACAGGAACGCACTATATCTTTCAAAGATGACGGGACCTACAAGACG
CGTGCTGAAGTCAAGTTTGAAGGTGATACCCTTGTTAATCGTATCGAGTTAAAGGGTATTGATT
TTAAAGAAGATGGAAACATTCTTGGACACAAACTCGAGTACAACTTTAACTCACACAATGTATA
GATCACGGCAGACAAACAAAAGAATGGAATCAAAGCTAACTTCAAAATTCGCCACAACGTTGAA
GATGGTTCCGTTCAACTAGCAGACCATTATCAACAAAATACTCCAATTGGCGATGGCCCTGTCCT
TTTACCAGACAACCATTACCTGTCGACACAATCTGTCCTTTCGAAAGATCCCAACGAAAAGCGTG
ACCACATGGTCCTTCTTGAGTTTGTAACTGCTGCTGGGATTACACATGGCATGGATGAGCTCTAC
AAAGGATCCCACCACCACCACCACCACTAAaagcttaattagctgagcttggactcctgttgatagatccagtaatga
cctcagaactccatctggatttgttcagaacgctcggttgccgccgggcgttttttattggtgagaatccaagctagcttggcgCTGC
Agtgtgcttctcaaatgcctgaggccagtttgctcaggctctccccgtggaggtaataattgacgatatgatcagtgcacggctaact
aagcggcctgctgacttctcgccgatcaaaaggcattttgctattaagggattgacgagggcgTATCTgcgcagtaagatgcgc
cccgcatttAGGGGCGTAGTTCAATTGGTAGAGCACCGGTCTCtAAAACCGGGTGtTGGGAGTTCGAG
TCTCTCCGCCCCTGCCAAATTCGAAAAGCCTGCTCAACGAGCAGGCTTTTTTGCATGCTCGAGCA
GCTCAGGGTCGAATTTGCTTTCGAatttctgccattcatccgcttattatcacttattcaggcgtagcaaccaggcgtttaa
gggcaccaataactgccttaaaaaaattacgccccgccctgccactcatcgcagtactgttgtaattcattaagcattctgccgacatg
gaagccatcacaAacggcatgatgaacctgaatcgccagcggcatcagcaccttgtcgccttgcgtataatatttgcccatggtgaa
aacgggggcgaagaagttgtccatattggccacgtttaaatcaaaactggtgaaactcacccagggattggctgagacgaaaaaca
tattctcaataaacccttagggaaataggccaggttttcaccgtaacacgccacatcttgcgaatatatgtgtagaaactgccggaa
atcgtcgtggtattcactccagagcgatgaaaacgtttcagtttgctcatggaaaacggtgtaacaagggtgaacactatcccatatc
accagctcaccgtctttcattgccatacggaattccggatgagcattcatcaggcgggcaagaatgtgaataaaggccggataaaac
ttgtgcttattttctttacggtctttaaaaaggccgtaatatccagctgaacggtctggttataggtacattgagcaactgactgaaat
gcctcaaaatgttctttacgatgccattgggatatatcaacggtggtatatccagtgatttttttctccattttagcttccttagctcctga
aaatctcgataactcaaaaaatacgcccggtagtgatcttatttcattatggtgaaagttggaacctcttacgtgccgatcaacgtctc
attttcgccaaaagttggcccagggcttcccggtatcaacagggacaccaggatttatttattctgcgaagtgatcttccgtcacaggt
atttattcggcgcaaagtgcgtcgggtgatgctgccaacttactgatttagtgtatgatggtgttttgaggtgctccagtggcttctgtt
tctatcagctgtccctcctgttcagctactgacg

Figure 17B cont.

gggtggtgcgtaacggcaaaagcaccgccggacatcagcgctagcggagtgtatactggcttactatgttggcactgatgagggtgt
cagtgaagtgcttcatgtggcaggagaaaaaaggctgcaccggtgcgtcagcagaatatgtgatacaggatatattccgcttcctcg
ctcactgactcgctacgctcggtcgttcgactgcggcgagcggaaatggcttacgaacggggcggagatttcctggaagatgccag
gaagatacttaacagggaagtgagagggccgcggcaaagccgttttccataggctccgcccccctgacaagcatcacgaaatctg
acgctcaaatcagtggtggcgaaacccgacaggactataaagataccaggcgtttccccctggcggctccctcgtgcgctctcctgtt
cctgcctttcggtttaccggtgtcattccgctgttatggccgcgtttgtctcattccacgcctgacactcagttccggggtaggcagttcgc
tccaagctggactgtatgcacgaaccccccgttcagtccgaccgctgcgccttatccggtaactatcgtcttgagtccaacccggaaa
gacatgcaaaagcaccactggcagcagccactggtaattgatttagaggagttagtcttgaagtcatgcgccggttaaggctaaact
gaaaggacaagttttggtgactgcgctcctccaagccagttacctcggttcaaagagttggtagctcagagaacrttcgaaaaaccg
ccctgcaaggcggttttttcgttttcagagcaagagattacgcgcagaccaaaacgatctcaagaagatcatcttattaatcagataa
aatatttctagatttcagtgcaatttatctcttcaaatgtagcacctgaagtcagccccatacgatataagttgtaattctcatgtttgac
agcttatcatcgataagcttgcaatttatctcttcaaatgtagcacctgaagtcagccccatacgatataagttgtaattctcatgttagt
catgccccgcgcccaccggaaggagctgactgggttgaaggctctcaagggcatcggtcgagatcccggtgcctaatgagtgagct
aacttacattaattgcgttgcgctcactgcccgctttccagtcgggaaacctgtcgtgccagctgcattaatgaatcggccaacgcgc
ggggagaggcggtttgcgtattgggcgccagggtggttttctttcaccagtgagacgggcaacagctgattgcccttcaccgcctg
gccctgagagagttgcagcaagcggtccacgctggtttgccccagcaggcgaaaatcctgtttgatggtggttaacggcgggatata
acatgagctgtcttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacgcagacgcg
ccgagacagaacttaatgggcccgctaacagcgcgatttgctggtgacccaatgcgaccagatgctccacgcccagtcgcgtaccgt
cttcatgggagaaaataatactgttgatgggtgtctggtcagagacatcaagaaataacgccggaacattagtgcaggcagcttcca
cagcaatggcatcctggtcatccagcggatagttaatgatcagcccactgacgcgttgcgcgagaagattgtgcaccgccgctttac
aggcttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgccacgcggttgg
gaatgtaattcagctccgccatcgccgcttccacttttcccgcgttttcgcagaaacgtggctggcctggttcaccacgcgggaaacg
gtctgataagagacaccggcatactctgcgacatcgtataacgttactggtttcacattcaccaccctgaattgactctcttccgggcg
ctatcatgccataccgcgaaaggttttgcgccattcgatggtgtccgggatctcgacgctctcccttatgcgactcctgcattaggctca
ctataggggaattgtgagcggataacaattcccctctagagtttgacagcattGtcatcgatctcgagaaatcataaaaaatttatttg
ctttgtgagcggataacaattataatagattcaattgtgagcggataacaatttcacacagaattcattaaagaggagaaattacatA
TGAGCAAAGGAGAAGAACTTTTCACTGGAGTTGTCCCAATTCTTGTTGAATTAGATGGTGATGT
TAATGGGCACAAATTTTCTGTCCGTGGAGAGGGTGAAGGTGATGCTACAAACGGAAAACTCACC
CTTAAATTTATTTGCACTACTGGAAAACTACCTGTTCCGTGGCCAACACTTGTCACTACTCTGAC
CTatGGTGTTCAATGCTTTTCCCGTTATCCGGATCACATGAAACGGCATGACTTTTTCAAGAGTGC
CATGCCCGAAGGTTATGTACAGGAACGCACTATATCTTTCAAAGATGACGGGACCTACAAGACGC

Figure 18B

GTGCTGAAGTCAAGTTTGAAGGTGATACCCTTGTTAATCGTATCGAGTTAAAGGGTATTGATTT
TAAAGAAGATGGAAACATTCTTGGACACAAACTCGAGTACAACTTTAACTCACACAATGTATgaA
TCACGGCAGACAAACAAAAGAATGGAATCAAAGCTAACTTCAAAATTCGCCACAACGTTGAAGA
TGGTTCCGTTCAACTAGCAGACCATTATCAACAAAATACTCCAATTGGCGATGGCCCTGTCCTTT
TACCAGACAACCATTACCTGTCGACACAATCTGTCCTTTCGAAAGATCCCAACGAAAAGCGTGAC
CACATGGTCCTTCTTGAGTTTGTAACTGCTGCTGGGATTACACATGGCATGGATGAGCTCTACAA
AGGATCCACCACCACCACCACCACTAAaagcttaattagctgagcttggactcctgttgatagatccagtaatgacct
cagaactccatctggatttgttcagaacgctcggttgccgccgggcgttttttattggtgagaatccaagctagcttggcgCTGCAgt
gtgcttctcaaatgcctgaggccagtttgctcaggctctccccgtggaggtaataattgacgatatgatcagtgcacggctaactaag
cggcctgctgactttctcgccgatcaaaaggcattttgctattaagggattgacgagggcgTATCTgcgcagtaagatgcgcccg
catttAGGGGCGTAGTTCAATTGGTAGAGCACCGGTCTTCAAAACCGGGTGtTGGGAGTTCGAGTCT
CTCCGCCCCTGCCAAATTCGAAAAGCCTGCTCAACGAGCAGGCTTTTTTGCATGCTCGAGCAGCT
CAGGGTCGAATTTGCTTTCGAatttctgccattcatccgcttattatcacttattcaggcgtagcaaccaggcgtttaaggg
caccaataactgccttaaaaaaattacgccccgccctgccactcatcgcagtactgttgtaattcattaagcattctgccgacatggaa
gccatcacaAacggcatgatgaacctgaatcgccagcggcatcagcaccttgtcgccttgcgtataatatttgcccatggtgaaaac
gggggcgaagaagttgtccatattggccacgtttaaatcaaaactggtgaaactcacccagggattggctgagacgaaaaacatat
tctcaataaaccctttagggaaataggccaggttttcaccgtaacacgccacatcttgcgaatatatgtgtagaaactgccggaaatc
gtcgtggtattcactccagagcgatgaaaacgtttcagtttgctcatggaaaacggtgtaacaagggtgaacactatcccatatcacc
agctcaccgtctttcattgccatacggaattccggatgagcattcatcaggcgggcaagaatgtgaataaaggccggataaaacttg
tgcttatttttctttacggtctttaaaaaggccgtaatatccagctgaacggtctggttataggtacattgagcaactgactgaaatgcc
tcaaaatgttcttacgatgccattgggatatatcaacggtggtatatccagtgatttttttctccattttagcttccttagctcctgaaaa
tctcgataactcaaaaaatacgcccggtagtgatcttatttcattatggtgaaagttggaacctcttacgtgccgatcaacgtctcattt
tcgccaaaagttggcccagggcttcccggtatcaacagggacaccaggatttatttattctgcgaagtgatcttccgtcacaggtattt
attcggcgcaaagtgcgtcgggtgatgctgccaacttactgatttagtgtatgatggtgttttgaggtgctccagtggcttctgtttcta
tcagctgtccctcctgttcagctactgacg

Figure 18B cont.

gggtggtgcgtaacggcaaaagcaccgccggacatcagcgctagcggagtgtatactggcttactatgttggcactgatgagggtgt
cagtgaagtgcttcatgtggcaggagaaaaaaggctgcaccggtgcgtcagcagaatatgtgatacaggatatattccgcttcctcg
ctcactgactcgctacgctcggtcgttcgactgcggcgagcggaaatggcttacgaacggggcggagatttcctggaagatgccag
gaagatacttaacagggaagtgagagggccgcggcaaagccgttttttccataggctccgccccctgacaagcatcacgaaatctg
acgctcaaatcagtggtggcgaaacccgacaggactataaagataccaggcgtttccccctggcggctccctcgtgcgctctcctgtt
cctgcctttcggtttaccggtgtcattccgctgttatggccgcgtttgtctcattccacgcctgacactcagttccgggtaggcagttcgc
tccaagctggactgtatgcacgaaccccccgttcagtccgaccgctgcgccttatccggtaactatcgtcttgagtccaacccggaaa
gacatgcaaaagcaccactggcagcagccactggtaattgatttagaggagttagtcttgaagtcatgcgccggttaaggctaaact
gaaaggacaagttttggtgactgcgctcctccaagccagttacctcggttcaaagagttggtagctcagagaaccttcgaaaaacg
ccctgcaaggcggttttttcgttttcagagcaagagattacgcgcagaccaaaacgatctcaagaagatcatcttattaatcagataa
aatatttctagatttcagtgcaatttatctcttcaaatgtagcacctgaagtcagccccatacgatataagttgtaattctcatgtttgac
agcttatcatcgataagcttgcaatttatctcttcaaatgtagcacctgaagtcagccccatacgatataagttgtaattctcatgttagt
catgccccgcgcccaccggaaggagctgactgggttgaaggctctcaagggcatcggtcgagatcccggtgcctaatgagtgagct
aacttacattaattgcgttgcgctcactgcccgctttccagtcgggaaacctgtcgtgccagctgcattaatgaatcggccaacgcgc
ggggagaggcggtttgcgtattgggcgccagggtggtttttctttcaccagtgagacgggcaacagctgattgcccttcaccgcctg
gccctgagagagttgcagcaagcggtccacgctggtttgccccagcaggcgaaaatcctgtttgatggtggttaacggcgggatata
acatgagctgtcttcggtatcgtcgtatcccactaccgagatgtccgcaccaacgcgcagcccggactcggtaatggcgcgcattgc
gcccagcgccatctgatcgttggcaaccagcatcgcagtgggaacgatgccctcattcagcatttgcatggtttgttgaaaaccggac
atggcactccagtcgccttcccgttccgctatcggctgaatttgattgcgagtgagatatttatgccagccagccagacgcagacgcg

Figure 19 ccgagacagaacttaatgggcccgctaacagcgcgatttgctggtgacccaatgcgaccagatgctccacgcccagtcgcgtaccgt
cttcatgggagaaaataatactgttgatgggtgtctggtcagagacatcaagaaataacgccggaacattagtgcaggcagcttcca
cagcaatggcatcctggtcatccagcggatagttaatgatcagcccactgacgcgttgcgcgagaagattgtgcaccgccgctttac
aggcttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgccacgcggttgg
gaatgtaattcagctccgccatcgccgcttccacttttttcccgcgttttcgcagaaacgtggctggcctggttcaccacgcgggaaacg
gtctgataagagacaccggcatactctgcgacatcgtataacgttactggtttcacattcaccacccctgaattgactctcttccgggcg
ctatcatgccataccgcgaaaggttttgcgccattcgatggtgtccgggatctcgacgctctcccttatgcgactcctgcattaggGA
GCTGTTGACAATTAATCATCGGCTCGTATAATGTGTGGAATTGTGAGCGGATAACAATTTCACAa
AGGAggtGCggccgcatgactaagcccatcgttttGCTggcgcacagccctcaggtgaattgaccattggtaactacatgggtg
cgctgcgtcagtgggtaaacatgcaggatgactaccattgcatttactgtatcgttgaccaacacgcgatcaccgtgcgccaggatgc
acagaagctgcgtaaagcgacgctggatacgctggccttgtatctggcttgtggtatcgatcctgagaaaagcaccattttttgttcagt
cccacgtgccggaacatgcacagttaggctgggcactgaactgctatacctacttcggcgaactgagtcgcatgacgcagtttaaag
ataaatctgcgcgttatgccgagaacatcaacgctggtctgtttgactatccggtgctgatggcagcggacatcctgctgtatcaaact
aatctgGGTCCTTGTggtgaagaccagaaacagcacctcgaactgagccgcgatattgcccagcgtttcaacgcgctgtatggc
gagatctttaaggtgccggagccgtttattccgaaatctggcgcgcgcgtaatgtcgctgctggagccgaccaagaagatgtccaag
tctgacgataatcgcaataacgttatcggcctgctggaagatccgaaatcggtagtgaagaaaatcaaacgtgcggtcactgactcc
gacgagccgccggtagttcgctacgatgtgcagaacaaagcgggcgtttccaacctgttggatatcctttcagcggtaacgggccag
agcatcccagaactggaaaaacagttcgaaggcaagatgtatggtcatctgaaaggtgaagtggctgatgccgtttccggtatgctg
actgaattgcaggaacgctatcaccgtttccgcaacgatgaagccttcctgcaacaggtgatgaaagatggcgcggaaaaagccag
cgcgcacgcttcccgtacgctaaaagcggtgtacgaagcgattggttttgtggcgaagccgtaagcGGCCGcgtttaaacggtctc
cagcttggctgttttggcggatgagagaagattttcagcctgatacagattaaatcagaacgcagaagcggtctgataaaacagaat
ttgcctggcggcagtagcgcggtggtcccacctgacccatgccgaactcagaagtgaaacgccgtagcgccgatggtagtgtggg
gtctccccatgcgagagtagggaactgccaggcatcaaataaaacgaaaggctcagtcgaaagactgggccttgtttgtgagctcc
cggtcatcaatcatccccataatccttgttagCCTGCAgtgtgcttctcaaatgcctgaggccagtttgctcaggctctccccgtgga
ggtaataattgacgatatgatcagtgcacggctaactaagcggcctgctgactttctcgccgatcaaaaggcattttgctattaaggg
attgacgagggcgTATCTgcgcagtaagatgcgccccgcatttAGGGGCGTAGTTCAATTGGTAGAGCACCGGT
CTTCAAAACCGGGTGtTGGGAGTTCGAGTCTCTCCGCCCCTGCCAAATTCGAAAAGCCTGCTCAAC
GAGCAGGCTTTTTTGCATGctcgagcagctcagggtcgaatttgCtttcgaatttctgccattcatccgcttattatcacttat
tcaggcgtagcaaccaggcgtttaagggcaccaataactgccttaaaaaaattacgccccgccctgccactcatcgcagtactgttgt
aattcattaagcattctgccgacatggaagccatcacaAacggcatgatgaacctgaatcgccagcggcatcagcaccttgtcgcct
tgcgtataatatttgcccatggtgaaaacgggggcgaagaagttgtccatattggccacgtttaaatcaaaactggtgaaactcaccc
agggattggctgagacgaaaaacatattctcaataaacccttlagggaaataggccaggttttcaccgtaacacgccacatcttgcg
aatatatgtgtagaaactgccggaaatcgtcgtggtattcactccagagcgatgaaaacgtttcagtttgctcatggaaaacggtgta
acaagggtgaacactatccatatcaccagctcaccgtctttcattgccatacggaattccggatgagcattcatcaggcgggcaag
aatgtgaataaaggccggataaaacttgtgcttattttctttacggtctttaaaaaggccgtaatatccagctgaacggtctggttata
ggtacattgagcaactgactgaaatgcctcaaaatgttctttacgatgccattgggatatatcaacggtggtatatccagtgattttttt
ctccattttagcttccttagctcctgaaaatctcgataactcaaaaaatacgcccggtagtgatcttatttcattatggtgaaagttgga
acctcttacgtgccgatcaacgtctcattttcgccaaaagttggcccagggcttcccggtatcaacagggacaccaggattttatttatt
ctgcgaagtgatcttccgtcacaggtatttattcggcgcaaagtgcgtcgggtgatgctgccaacttactgatttagtgtatgatggtgt
ttttgaggtgctccagtggcttctgtttctatcagctgtccctcctgttcagctactgacg

Figure 19 cont.

ATGACTAAGCCCATCGTTTTTgctGGCGCACAGCCCTCAGGTGAATTGACCATTGGTAAGTACATG
GGTGCGCTGCGTCAGTGGGTAAACATGCAGGATGACTACCATTGCATTTACTGTATCGTTGACCA
ACACGCGATCACCGTGCGCCAGGATGCACAGAAGCTGCGTAAAGCGACGCTGGATACGCTGGCCT
TGTATCTGGCTTGTGGTATCGATCCTGAGAAAAGCACCATTTTTGTTCAGTCCCACGTGCCGGAA
CATGCACAGTTAGGCTGGGCACTGAACTGCTATACCTACTTCGGCGAACTGAGTCGCATGACGCA
GTTTAAAGATAAATCTGCGCGTTATGCCGAGAACATCAACGCTGGTCTGTTTGACTATCCGGTGC
TGATGGCAGCGGACATCCTGCTGTATCAAACTAATCTGagtcctgctGGTGAAGACCAGAAACAGCA
CCTCGAACTGAGCCGCGATATTGCCCAGCGTTTCAACGCGCTGTATGGCGAGATCTTTAAGGTGC
CGGAGCCGTTTATTCCGAAATCTGGCGCGCGTAATGTCGCTGCTGGAGCCGACCAAGAAGATG
TCCAAGTCTGACGATAATCGCAATAACGTTATCGGCCTGCTGGAAGATCCGAAATCGGTAGTGA
AGAAAATCAAACGTGCGGTCACTGACTCCGACGAGCCGCCGGTAGTTCGCTACGATGTGCAGAAC
AAAGCGGGCGTTTCCAACCTGTTGGATATCCTTTCAGCGGTAACGGGCCAGAGCATCCCAGAACT
GGAAAAACAGTTCGAAGGCAAGATGTATGGTCATCTGAAAGGTGAAGTGGCTGATGCCGTTTCC
GGTATGCTGACTGAATTGCAGGAACGCTATCACCGTTTCCGCAACGATGAAGCCTTCCTGCAACA
GGTGATGAAAGATGGCGCGGAAAAAGCCAGCGCGCACGCTTCCCGTACGCTAAAAGCGGTGTACG
AAGCGATTGGTTTTGTGGCGAAGCCGTAA

Figure 20 pBK-EcWRS cttttgctgagttgaaggatccGCGGCCGCtcgggttgtcagcctgtcccgcttataagatcatacgccgttatacgttgtttacgct
ttgaggaatcccaTATGatgactaagcccatcgttttagtggcgcacagccctcaggtgaattgaccattggtaactacatgggtg
cgctgcgtcagtgggtaaacatgcaggatgactaccattgcatttactgtatcgttgaccaacacgcgatcaccgtgcgccaggatgc
acagaagctgcgtaaagcgacgctggatacgctggccttgtatctggcttgtggtatcgatcctgagaaaagcaccatttttgttcagt
cccacgtgccggaacatgcacagttaggctgggcactgaactgctatacctacttcggcgaactgagtcgcatgacgcagtttaaag
ataaatctgcgcgttatgccgagaacatcaacgctggtctgtttgactatccggtgctgatggcagcggacatcctgctgtatcaaact
aatctggtaccggtgggtgaagaccagaaacagcacctcgaactgagccgcgatattgcccagcgtttcaacgcgctgtatggcga
gatctttaaggtgccggagccgtttattccgaaatctggcgcgcgcgtaatgtcgctgctggagccgaccaagaagatgtccaagtct
gacgataatcgcaataacgttatcggcctgctggaagatccgaaatcggtagtgaagaaaatcaaacgtgcggtcactgactccga
cgagccgccggtagttcgctacgatgtgcagaacaaagcgggcgtttccaacctgttggatatcctttcagcggtaacgggccagag
catcccagaactggaaaaacagttcgaaggcaagatgtatggtcatctgaaaggtgaagtggctgatgccgtttccggtatgctgac
tgaattgcaggaacgctatcaccgtttccgcaacgatgaagccttcctgcaacaggtgatgaaagatggcgcggaaaaagccagcg
cgcacgcttcccgtacgctaaaagcggtgtacgaagcgattggttttgtggcgaagccgtaaCTGCAgtttcaaacgctaaattgc
ctgatgcgctacgcttatcaggcctacatgatctctgcaatatattgagtttgcgtgcttttgtaggccggataaggcgttcacgccgca
tccggcaagaaacagcaaacaatccaaaacgccgcgttcagcggcgttttttctgcttttcttcgcgaattaattccgcttcgcacatg
tgagcaaaaggccagcaaaaggccaggaaccgtaaaaaggccgcgttgctggcgtttttccataggctccgcccccctgacgagca
tcacaaaaatcgacgctcaagtcagaggtggcgaaacccgacaggactataaagataccaggcgtttccccctggaagctccctcg
tgcgctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgccttatcc
ggtaactatcgtcttgagtccaacccggtaagacacgacttatcgccactggcagcagccactggtaacaggattagcagagcgag
gtatgtaggcggtgctacagagttcttgaagtggtggcctaactacggctacactagaaggacagtatttggtatctgcgctctgctg
aagccagttaccttcggaaaaagagttggtagctcttgatccggcaaacaaaccaccgctggtagcggtggtttttttgtttgcaagc
agcagattacgcgcagaaaaaaaggatctcaagaagatcctttgatcttttctacggggtctgacgctcagtggaacgaaaactcac
gttaagggattttggtcatgaacaataaaactgtctgcttacataaacagtaatacaagggggtgttatgagccatattcaacgggaaa
cgtcttgctcgaggccgcgattaaattccaacatggatgctgatttatatgggtataaatgggctcgcgataatgtcgggcaatcagg
tgcgacaatctatcgattgtatgggaagcccgatgcgccagagttgtttctgaaacatggcaaaggtagcgttgccaatgatgttaca
gatgagatggtcagactaaactggctgacggaatttatgcctcttccgaccatcaagcatttttatccgtactcctgatgatgcatggtt
actcaccactgcgatccccgggaaaacagcattccaggtattagaagaatatcctgattcaggtgaaaatattgttgatgcgctggca
gtgttcctgcgccggttgcattcgattcctgtttgtaattgtccttttaacagcgatcgcgtatttcgtctcgctcaggcgcaatcacgaa
tgaataacggtttggttgatgcgagtgattttgatgacgagcgtaatggctggcctgttgaacaagtctggaaagaaatgcataagct
tttgccattctcaccggattcagtcgtcactcatggtgatttctcacttgataaccttatttttgacgaggggaaattaataggttgtattg
atgttggacgagtcggaatcgcagaccgataccaggatcttgccatcctatggaactgcctcggtgagttttctccttcattacagaaa
cggctttttcaaaaatatggtattgataatcctgatatgaataaattgcagtttcatttgatgctcgatgagttttttctaatcagaattggt
taattggttgtaacactggcagagcattacgctgacttgacgggacggcggctttgttgaataaatcgaa

Figure 21B

Atgactaagcccatcgttttttgctggcgcacagccctcaggtgaattgaccattggtaactacatgggtgcgctgcgtcagtgggtaa
acatgcaggatgactaccattgcatttactgtatcgttgaccaacacgcgatcaccgtgcgccaggatgcacagaagctgcgtaaag
cgacgctggatacgctggccttgtatctggcttgtggtatcgatcctgagaaaagcaccattttttgttcagtcccacgtgccggaacat
gcacagttaggctgggcactgaactgctatacctacttcggcgaactgagtcgcatgacgcagtttaaagataaatctgcgcgttatg
ccgagaacatcaacgctggtctgtttgactatccggtgctgatggcagcggacatcctgctgtatcaaactaatctgggtccttgtggt
gaagaccagaaacagcacctcgaactgagccgcgatattgcccagcgtttcaacgcgctgtatggcgagatctttaaggtgccgga
gccgtttattccgaaatctggcgcgcgcgtaatgtcgctgctggagccgaccaagaagatgtccaagtctgacgataatcgcaataa
cgttatcggcctgctggaagatccgaaatcggtagtgaagaaaatcaaacgtgcggtcactgactccgacgagccgcggtagttc
gctacgatgtgcagaacaaagcgggcgtttccaacctgttggatatcctttcagcggtaacgggccagagcatcccagaactggaa
aaacagttcgaaggcaagatgtatggtcatctgaaaggtgaagtggctgatgccgtttccggtatgctgactgaattgcaggaacgc
tatcaccgtttccgcaacgatgaagccttcctgcaacaggtgatgaaagatggcgcggaaaaagccagcgcgcacgcttcccgtac
gctaaaagcggtgtacgaagcgattggttttgtggcgaagccgtaa

Figure 22

ATGACTAAGCCCATCGTTTTTgctGGCGCACAGCCCTCAGGTGAATTGACCATTGGTAACTACATG
GGTGCGCTGCGTCAGTGGGTAAACATGCAGGATGACTACCATTGCATTTACTGTATCGTTGACCA
ACACGCGATCACCGTGCGCCAGGATGCACAGAAGCTGCGTAAAGCGACGCTGGATACGCTGGCCT
TGTATCTGGCTTGTGGTATCGATCCTGAGAAAAGCACCATTTTTGTTCAGTCCCACGTGCCGGAA
CATGCACAGTTAGGCTGGGCACTGAACTGCTATACCTACTTCGGCGAACTGAGTCGCATGACGCA
GTTTAAAGATAAATCTGCGCGTTATGCCGAGAACATCAACGCTGGTCTGTTTGACTATCCGGTGC
TGATGGCAGCGGACATCCTGCTGTATCAAACTAATCTGagtcctgctGGTGAAGACCAGAAACAGCA
CCTCGAACTGAGCCGCGATATTGCCCAGCGTTTCAACGCGCTGTATGGCGAGATCTTTAAGGTGC
CGGAGCCGTTTATTCCGAAATCTGGCGCGCGCGTAATGTCGCTGCTGGAGCCGACCAAGAAGATG
TCCAAGTCTGACGATAATCGCAATAACGTTATCGGCCTGCTGGAAGATCCGAAATCGGTAGTGA
AGAAAATCAAACGTGCGGTCACTGACTCCGACGAGCCGCCGGTAGTTCGCTACGATGTGCAGAAC
AAAGCGGGCGTTTCCAACCTGTTGGATATCCTTTCAGCGGTAACGGGCCAGAGCATCCCAGAACT
GGAAAAACAGTTCGAAGGCAAGATGTATGGTCATCTGAAAGGTGAAGTGGCTGATGCCGTTTCC
GGTATGCTGACTGAATTGCAGGAACGCTATCACCGTTTCCGCAACGATGAAGCCTTCCTGCAACA
GGTGATGAAAGATGGCGCGGAAAAAGCCAGCGCGCACGCTTCCCGTACGCTAAAAGCGGTGTACG
AAGCGATTGGTTTTGTGGCGAAGCCGTAA

Figure 23 ttctctgtcacagaatgaaaattttctgtcatctcttcgttattaatgtttgtaattgactgaatatcaacgcttatttgcagcctgaatg
gcgaatgggacgcgccctgtagcggcgcattaagcgcggcgggtgtggtggttacgcgcagcgtgaccgctacacttgccagcgcc
ctagcgccgctcctttcgctttcttcccttcctttctcgccacgttcgccggctttccccgtcaagctctaaatcgggggctcccttagg
gttccgatttagtgctttacggcacctcgaccccaaaaaacttgattagggtgatggttcacgtagtgggccatcgccctgatagacg
gtttttcgccctttgacgttggagtccacgttctttaatagtggactcttgttccaaactggaacaacactcaaccctatctcggtctatt
cttttgatttataagggattttgccgatttcggcctattggttaaaaaatgagctgatttaacaaaaatttaacgcgaattttaacaaaa
tattaacgtttacaatttcaggtggcacttttcggggaaatgtgcgcggaacccctatttgtttatttttctaaatacattcaaatatgtat
ccgctcatgagacaataaccctgataaatgcttcaataatattgaaaaaggaagagtatggcgtagagtattcaacatttccgtgtcg
cccttattccctttttttgcggcattttgccttcctgtttttgctcacccagaaacgctggtgaaagtaaaagatgctgaagatcagttggg
tgcacgagtgggttacatcgaactggatctcaacagcggtaagatccttgagagttttcgccccgaagaacgttttccaatgatgagc
acttttaaagttctgctatgtggcgcggtattatcccgtattgacgccgggcaagagcaactcggtcgccgcatacactattctcagaa
tgacttggttgagtactcaccagtcacagaaaagcatcttacggatggcatgacagtaagagaattatgcagtgctgccataaccat
gagtgataacactgcggccaacttacttctgacaacgatcggaggaccgaaggagctaaccgcttttttgcacaacatgggggatca
tgtaactcgccttgatcgttgggaaccggagctgaatgaagccataccaaacgacgagcgtgacaccacgatgcctgtagcaatgg
caacaacgttgcgcaaactattaactggcgaactacttactctagcttcccggcaacaattaatagactggatggaggcggataaag
ttgcaggaccacttctgcgctcggcccttccggctggctggtttattgctgataaatctggagccggtgagcgtgggtctcgcggtatc

Figure 24B attgcagcactggggccagatggtaagccctcccgtatcgtagttatctacacgacggggagtcaggcaactatggatgaacgaaat
agacagatcgctgagataggtgcctcactgattaagcattggtaactgtcagaccaagtttactcatatatactttagattgatttaaa
acttcatttttaatttaaaaggatctaggtgaagatccttttttgataatctcatgaccaaaatcccttaacgtgagttttcgttccactga
gcgtcagaccccgtagaaaagatcaaaggatcttcttgagatccttttttctgcgcgtaatctgctgcttgcaaacaaaaaaaccac
cgctaccagcggtggtttgtttgccggatcaagagctaccaactcttttccgaaggtaactggcttcagcagagcgcagataccaaa
tactgtccttctagtgtagccgtagttaggccaccacttcaagaactctgtagcaccgcctacatacctcgctctgctaatcctgttacc
agtggctgctgccagtggcgataagtcgtgtcttaccgggttggactcaagacgatagttaccggataaggcgcagcggtcgggctg
aacgggggggttcgtgcacacagcccagcttggagcgaacgacctacaccgaactgagatacctacagcgtgagcattgagaaagc
gccacgcttcccgaagggagaaaggcggacaggtatccggtaagcggcagggtcggaacaggagagcgcacgagggagcttcc
agggggaaacgcctggtatctttatagtcctgtcgggtttcgccacctctgacttgagcgtcgatttttgtgatgctcgtcaggggggc
ggagcctatggaaaaacgccagcaacgcggcctttttacggttcctggccttttgctggccttttgctcacatgttctttcctgcgttatc
ccctgattctgtggataaccgtattaccgcctttgagtgagctgataccgctcgccgcagccgaacgaccgagcgcagcgagtcagt
gagcgaggaagcggaagagcgcctgatgcggtattttctccttacgcatctgtgcggtatttcacaccgcagaccagccgcgtaacc
tggcaaaatcggttacggttgagtaataaatggatgccctgcgtaagcgggtgtgggcggacaataaagtcttaaactgaacaaaa
tagatctaaactatgacaataaagtcttaaactagacagaatagttgtaaactgaaatcagtccagttatgctgtgaaaaagcatact
ggacttttgttatggctaaagcaaactcttcattttctgaagtgcaaattgcccgtcgtattaaagaggggcgtggccaagggcatggt
aaagactatattcgcggcgttgtgacaatttaccgaacaactccgcggccgggaagccgatctcggcttgaacgaattgttaggtgg
cggtacttgggtcgatatcaaagtgcatcacttcttcccgtatgcccaactttgtatagagagccactgcgggatcgtcaccgtaatct
gcttgcacgtagatcacataagcaccaagcgcgttggcctcatgcttgaggagattgatgagcgcggtggcaatgccctgcctccgg
tgctcgccggagactgcgagatcatagatatagatctcactacgcggctgctcaaacctgggcagaacgtaagccgcgagagcgcc
aacaaccgcttcttggtcgaaggcagcaagcgcgatgaatgtcttactacggagcaagttcccgaggtaatcggagtccggctgatg
ttgggagtaggtggctacgtctccgaactcacgaccgaaaagatcaagagcagcccgcatggatttgacttggtcagggccgagcc
tacatgtgcgaatgatgcccatacttgagccacctaactttgttttagggcgactgccctgctgcgtaacatcgttgctgctgcgtaac
atcgttgctgctccataacatcaaacatcgacccacggcgtaacgcgcttgctgcttggatgcccgaggcatagactgtacaaaaaa
acagtcataacaagccatgaaaaccgccactgcgccgttaccaccgctgcgttcggtcaaggttctggaccagttgcgtgagcgcat
acgctacttgcattacagtttacgaaccgaacaggcttatgtcaactgggttcgtgccttcatccgtttccacggtgtgcgtcacccgg
caaccttgggcagcagcgaagtcgaggcatttctgtcctggctggcgaacgagcgcaaggtttcggtctccacgcatcgtcaggcat
tggcggccttgctgttcttctacggcaaggtgctgtgcacggatctgccctggcttcaggagatcggtagacctcggccgtcgcggcg
cttgccggtggtgctgaccccggatgaagtggttcgcatcctcggttttctggaaggcgagcatcgtttgttcgcccaggactctagct
atagttctagtggttggctacgtacccgtagtggctatggcagggcttgcgcttaatgcgccgctacagggcgcgtggggataccccc
tagagccccagctggttctttccgcctcagaagccatagagcccaccgcatccccagcatgcctgctattgtcttcccaatcctccccc
ttgctgtcctgccccacccccaccccccagaatagaatgacacctactcagacaatgcgatgcaatttcctcattttattaggaaagga
cagtgggagtggcaccttccagggtcaaggaaggcacggggggagggcaaacaacagatggctggcaactagaaggcacagtc
gaggctgatcagcgggtttaaacgggccctctagactcgagttaaagtcgacgcggggaggcggcccaaagggagatccgactcg
tctgagggcgaaggcgaagacgcggaagagggccgcagagccggcagcaggccgcgggaaggaaggtccgctggattgagggcc
gaagggacgtagcagaaggacgtcccgcgcagaatccaggtggcaacacaggcgagcagccaaggaaaggacgatgatttcccc
gacaacaccacggaattgtcagtgcccaacagccgagcccctgtccagcagcgggcaaggcaggcggcgatgagttccgccgtgg
caatagggaggggaaagcgaaagtcccggaaaggagctgacaggtggtggcaatgccccaaccagtgggggttgcgtcagcaa
acacagtgcacaccacgccacgttgcctgacaacgggccacaactcctcataaagagacagcaaccaggatttatacaaggagga
gaaaatgaaagcctatcgggaagcaatagcatgatacaaaggcattaaagcagcgtatccacatagcgtaaaaggagcaacata
gttaagaataccagtcaatctttcacaaattttgtaatccagaggttgattgtcgacttaacgcgttgaattcTCAATGGTGATG
GTGATGATGACCGGTATGCATATTCAGATCCTCTTCTGAGATGAGTTTTTGTTCGAAGGGCCCCT
TGTACAGCTCGTCCATGCCGAGAGTGATCCCGGCGGCGGTCACGAACTCCAGCAGGACCATGTGA
TCGCGCTTCTCGTTGGGGTCTTTGCTCAGGGCGGACTGGGTGCTCAGGTAGTGGTTGTCGGGCAG
CAGCACGGGGCCGTCGCCGATGGGGGTGTTCTGCTGGTAGTGGTCGGCGAGCTGCACGCTGCCGT
CCTCGATGTTGTGGCGGATCTTGAAGTTCACCTTGATGCCGTTCTTCTGCTTGTCGGCCATGATA

Figure 24B cont.

```
TAGACGTTGTGGCTGTTGTAGTTGTACTCCAGCTTGTGCCCCAGGATGTTGCCGTCCTCCTTGAA
GTCGATGCCCTTCAGCTCGATGCGGTTCACCAGGGTGTCGCCCTCGAACTTCACCTCGGCGCGGG
TCTTGTAGTTGCCGTCGTCCTTGAAGAAGATGGTGCGCTCCTGGACGTAGCCTTCGGGCATGGCG
GACTTGAAGAAGTCGTGCTGCTTCATGTGGTCGGGGTAGCGGCTGAAGCACTGCACGCCGTAgGT
CAGgGTGGTCACGAGGGTGGGCCAGGGCACGGGCAGCTTGCCGGTGGTGCAGATGAACTTCAGGG
TCAGCTTGCCctaAGTGGCATCGCCCTCGCCCTCGCCGGACACGCTGAACTTGTGGCCGTTTACGT
CGCCGTCCAGCTCGACCAGGATGGGCACCACCCCGGTGAACAGCTCCTCGCCCTTGCTCACCATgg
tggcggcGctagccagcttgggtctccctatagtgagtcgtattaatttcgataagccagtaagccagtaagcagtgggttctctagtt
agccagagagctctgcttatatagacctcccaccgtacacgcctaccgcccatttgcgtcaatggggcggagttgttacgacattttg
gaaagtcccgttgatttggtgccaaaacaaactcccattgacgtcaatggggtggagacttggaaatccccgtgagtcaaaccgct
atccacgcccattgatgtactgccaaaaccgcatcaccatggtaatagcgatgactaatacgtagatgtactgccaagtaggaaagt
cccataaggtcatgtactgggcataatgccaggcgggccatttaccgtcattgacgtcaatagggggcgtacttggcatatgatacac
ttgatgtactgccaagtgggcagtttaccgtaaatagtccacccattgacgtcaatgaaagtccctattggcgttactatgggaacat
acgtcattattgacgtcaatgggcggggtcgttgggcggtcagccaggcgggccatttaccgtaagttatgtaacgcggaactcca
tatatgggctatgaactaatgaccccgtaattgattactattaataactagtcaataatcaatgtcaacgcgtatatctggcccgtacat
cgcgaagcagcgcaaaacGGATCCtgcaggtatttGCGGCCGCggtccgtatactccggaatattaatagatcatggagata
attaaaatgataaccatctcgcaaataaaataagtatttttactgttttcgtaacagttttgtaataaaaaaacctataaatattccggatt
attcataccgtcccaccatcgggcgcgAACTCCTAAAAAACCGCCACCatgaagtgccttttgtacttagccttttttattcat
tggggtgaattgcaagttcaccatagttttccacacaaccaaaaaggaaactggaaaatgttcttctaattaccattattgcccgt
caagctcagatttaaattggcataatgacttaataggcacagccttacaagtcaaaatgcccaagagtcacaaggctattcaagcag
acggttggatgtgtcatgcttccaaatgggtcactacttgtgatttccgctggtatggaccgaagtatataacacattccatccgatcct
tcactccatctgtagaacaatgcaaggaaagcattgaacaaacgaaacaaggaacttggctgaatccaggcttccctcctcaaagtt
gtggatatgcaactgtgacggatgccgaagcagtgattgtccaggtgactcctccaccatgtgctggttgatgaatacacaggagaat
gggttgattcacagttcatcaacggaaaatgcagcaattacatatgccccactgtccataactctacaacctggcattctgactataa
ggtcaaagggctatgtgattctaacctcatttccatggacatcaccttcttctcagaggacggagagctatcatccctgggaaaggag
ggcacagggtcagaagtaactactttgcttatgaaactggaggcaaggcctgcaaaatgcaatactgcaagcattggggagtcag
actcccatcaggtgtctggttcgagatggctgataaggatctctttgctgcagccagattccctgaatgccagaagggtcaagtatct
ctgctccatctcagacctcagtggatgtaagtctaattcaggacgttgagaggatcttggattattccctctgccaagaaacctggagc
aaaatcagagcgggtcttccaatctctccagtggatctcagctatcttgctcctaaaaacccaggaaccggtcctgctttcaccataat
caatggtaccctaaaatactttgagaccagatacatcagagtcgatattgctgctccaatcctctcaagaatggtcggaatgatcagt
ggaactaccacagaaagggaactgtgggatgactgggcaccatatgaagacgtggaaattggacccaatggagttctgaggacca
gttcaggatataagtttcctttatacatgattggacatggtatgttggactccgatcttcatcttagctcaaaggctcaggtgttcgaac
atcctcacattcaagacgctgcttcgcaacttcctgatgatgagagtttattttttggtgatactgggctatccaaaaatccaatcgagc
ttgtagaaggttggttcagtagttggaaaagctctattgcctctttttttctttatcatagggttaatcattggactattcttggttctccga
gttggtatccatctttgcattaaattaaagcacaccaagaaaagacagatttatacagacatagagatgaaccgacttggaaagtga
taaggccaggccggccaagcttgtcgagaagtactagaggatcataatcagccataccacatttgtagaggttttacttgctttaaaa
aacctcccacacctcccctgaacctgaaacataaaatgaatgcaattgttgttgttaacttgtttattgcagcttataatggttacaaa
taaagcaatagcatcacaaatttcacaaataaagcattttttcactgcattctagttgtggtttgtccaaactcatcaatgtatcttatc
atgtctggatctgatcactgcttgagcCTAGGTCGGGCAGGAAGAGGGCCTATTTCCCATGATTCCTTCATA
TTTGCATATACGATACAAGGCTGTTAGAGAGATAATTAGAATTAATTTGACTGTAAACACAAAG
ATATTAGTACAAAATACGTGACGTAGAAAGTAATAATTTCTTGGGTAGTTTGCAGTTTTAAAAT
TATGTTTTAAAATGGACTATCATATGCTTACCGTAACTTGAAAGTATTTCGATTTCTTGGCTTTA
TATATCTTGTGGAAAGGACGAAACACCAGGGCGTAGTTCAATTGGTAGAGCACCGGTCTCtAAA
ACCGGGTGtTGGGAGTTCGAGTCTCTCCGCCCCTGCCATTTTTTgctaggctCAAgcagtgatctccgaacc
agataagtgaaatctagttccaaactattttgtcatttttaattttcgtattagcttacgacgctacacccagttccatctatttgtcact
cttccctaaataatccttaaaaactccatttccaccccctcccagttcccaactattttgtccgcccacagcggggcattttcttcctgtta
tgttttaatcaaacatcctgccaactccatgtgacaaaccgtcatcttcggctactt
```

Figure 24B cont.

```
ttctctgtcacagaatgaaaattttttctgtcatctcttcgttattaatgtttgtaattgactgaatatcaacgcttatttgcagcctgaatg
gcgaatgggacgcgccctgtagcggcgcattaagcgcggcgggtgtggtggttacgcgcagcgtgaccgctacacttgccagcgcc
ctagcgcccgctcctttcgctttcttccccttcctttctcgccacgttcgccggctttccccgtcaagctctaaatcgggggctcccttagg
gttccgatttagtgctttacggcacctcgaccccaaaaaacttgattagggtgatggttcacgtagtgggccatcgccctgatagacg
gtttttcgcccttttgacgttggagtccacgttctttaatagtggactcttgttccaaactggaacaacactcaaccctatctcggtctatt
cttttgatttataagggattttgccgatttcggcctattggttaaaaaatgagctgatttaacaaaaatttaacgcgaattttaacaaaa
tattaacgtttacaatttcaggtggcacttttcggggaaatgtgcgcggaacccctatttgtttatttttctaaatacattcaaatatgtat
ccgctcatgagacaataaccctgataaatgcttcaataatattgaaaaaggaagagtatgagtattcaacatttccgtgtcgcccttat
tccctttttttgcggcatttttgccttcctgtttttgctcacccagaaacgctggtgaaagtaaaagatgctgaagatcagttgggtgcacg
agtgggttacatcgaactggatctcaacagcggtaagatccttgagagttttcgccccgaagaacgttttccaatgatgagcacttta
aagttctgctatgtggcgcggtattatcccgtattgacgccgggcaagagcaactcggtcgccgcatacactattctcagaatgactt
ggttgagtactcaccagtcacagaaaagcatcttacggatggcatgacagtaagagaattatgcagtgctgccataaccatgagtga
taacactgcggccaacttacttctgacaacgatcggaggaccgaaggagctaaccgcttttttgcacaacatgggggatcatgtaac
tcgccttgatcgttgggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcggataaagttgcag
gaccacttctgcgctcggcccttccggctggctggtttattgctgataaatctggagccggtgagcgtgggtctcgcggtatcattgca
gcactggggccagatggtaagccctcccgtatcgtagttatctacacgacggggagtcaggcaactatggatgaacgaaatagaca
gatcgctgagataggtgcctcactgattaagcattggtaactgtcagaccaagtttactcatatatactttagattgatttaaaacttca
tttttaatttaaaaggatctaggtgaagatcctttttgataatctcatgaccaaaatcccttaacgtgagttttcgttccactgagcgtca
gaccccgtagaaaagatcaaaggatcttcttgagatcctttttttctgcgcgtaatctgctgcttgcaaacaaaaaaaccaccgctacc
agcggtggtttgtttgccggatcaagagctaccaactctttttccgaaggtaactggcttcagcagagcgcagataccaaatactgtc
cttctagtgtagccgtagttaggccaccacttcaagaactctgtagcaccgcctacatacctcgctctgctaatcctgttaccagtggct
gctgccagtggcgataagtcgtgtcttaccgggttggactcaagacgatagttaccggataaggcgcagcggtcgggctgaacggg
gggttcgtgcacacagcccagcttggagcgaacgacctacaccgaactgagatacctacagcgtgagcattgagaaagcgccacg
cttcccgaagggagaaaggcggacaggtatccggtaagcggcagggtcggaacaggagagcgcacgagggagcttccagggggg
```

Figure 25B aaacgcctggtatctttatagtcctgtcgggtttcgccacctctgacttgagcgtcgattttttgtgatgctcgtcagggggggcggagcct
atggaaaaacgccagcaacgcggccttttttacggttcctggccttttttgctggcctttttgctcacatgttctttcctgcgttatcccctgatt
ctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcagaccagccgcgtaacctggcaaa
atcggttacggttgagtaataaatggatgccctgcgtaagcgggtgtggcggacaataaagtcttaaactgaacaaaatagatcta
aactatgacaataaagtcttaaactagacagaatagttgtaaactgaaatcagtccagttatgctgtgaaaaagcatactggacttttt
gttatggctaaagcaaactcttcattttctgaagtgcaaattgcccgtcgtattaaagaggggcgtggccaagggcatggtaaagact
atattcgcggcgttgtgacaatttaccgaacaactccgcggccgggaagccgatctcggcttgaacgaattgttaggtggcggtactt
gggtcgatatcaaagtgcatcacttcttcccgtatgcccaactttgtatagagagccactgcgggatcgtcaccgtaatctgcttgcac
gtagatcacataagcaccaagcgcgttggcctcatgcttgaggagattgatgagcgcggtggcaatgccctgcctccggtgctcgcc
ggagactgcgagatcatagatatagatctcactacgcggctgctcaaacctgggcagaacgtaagccgcgagagcgccaacaacc
gcttcttggtcgaaggcagcaagcgcgatgaatgtcttactacggagcaagttcccgaggtaatcggagtccggctgatgttgggag
taggtggctacgtctccgaactcacgaccgaaaagatcaagagcagcccgcatggatttgacttggtcagggccgagcctacatgtg
cgaatgatgcccatacttgagccacctaactttgttttagggcgactgccctgctgcgtaacatcgttgctgctgcgtaacatcgttgct
gctccataacatcaaacatcgacccacggcgtaacgcgcttgctgcttggatgcccgaggcatagactgtacaaaaaaacagtcat
aacaagccatgaaaaccgccactgcgccgttaccaccgctgcgttcggtcaaggttctggaccagttgcgtgagcgcatacgctact
tgcattacagtttacgaaccgaacaggcttatgtcaactgggttcgtgccttcatccgtttccacggtgtgcgtcaccccggcaaccttg
ggcagcagcgaagtcgaggcatttctgtcctggctggcgaacgagcgcaaggtttcggtctccacgcatcgtcaggcattggcggcc
ttgctgttcttctacggcaaggtgctgtgcacggatctgccctggcttcaggagatcggtagacctcggccgtcgcggcgcttgccggt
ggtgctgaccccggatgaagtggttcgcatcctcggttttctggaaggcgagcatcgtttgttcgcccaggactctagctatagttcta
gtggttggctacgtacccgtagtggctatggcagggcttgcgcttaatgcgccgctacagggcgcgtggggatacccctagagccc
cagctggttctttccgcctcagaagccatagagcccaccgcatcccagcatgcctgctattgtcttcccaatcctccccccttgctgtcc
tgccccaccccaccccccagaatagaatgacacctactcagacaatgcgatgcaatttcctcattttattaggaaaggacagtggga
gtggcaccttccagggtcaaggaaggcacggggggagggcaaacaacagatggctggcaactagaaggcacagtcgaggctgat
cagcgggtttaaacgggccctctagactcgagttaaagtcgacgcggggaggcggcccaagggagatccgactcgtctgagggc
gaaggcgaagacgcggaagaggccgcagagccggcagcaggccgcggggaaggaaggtccgctggattgagggccgaagggac
gtagcagaaggacgtcccgcgcagaatccaggtggcaacacaggcgagcagccaaggaaaggacgatgatttccccgacaacac
cacggaattgtcagtgcccaacagccgagcccctgtccagcagcgggcaaggcaggcggcgatgagttccgccgtggcaataggg
agggggaaagcgaaagtcccggaaaggagctgacaggtggtggcaatgccccaaccagtgggggttgcgtcagcaaacacagtg
cacaccacgccacgttgcctgacaacgggccacaactcctcataaagagacagcaaccaggatttatacaaggaggagaaaatga
aagccatacgggaagcaatagcatgatacaaaggcattaaagcagcgtatccacatagcgtaaaaggagcaacatagttaagaat
accagtcaatctttcacaaattttgtaatccagaggttgattgtcgacttaacgcgttGaattCTTACGGCTTCGCCACAAAA
CCAATCGCTTCGTACACCGCTTTTAGCGTACGGGAAGCGTGCGCGCTGGCTTTTTCCGCGCCATC
TTTCATCACCTGTTGCAGGAAGGCTTCATCGTTGCGGAAACGGTGATAGCGTTCCTGCAATTCAG
TCAGCATACCGGAAACGGCATCAGCCACTTCACCTTTCAGATGACCATACATCTTGCCTTCGAAC
TGTTTTTCCAGTTCTGGGATGCTCTGGCCCGTTACCGCTGAAAGGATATCCAACAGGTTGGAAAC
GCCCGCTTTGTTCTGCACATCGTAGCGAACTACCGGCGGCTCGTCGGAGTCAGTGACCGCACGTT
TGATTTTCTTCACTACCGATTTCGGATCTTCCAGCAGGCCGATAACGTTATTGCGATTATCGTCA
GACTTGGACATCTTCTTGGTCGGCTCCAGCAGCGACATTACGCGCGCGCCAGATTTCGGAATAAA
CGGCTCCGGCACCTTAAAGATCTCGCCATACAGCGCGTTGAAACGCTGGGCAATATCGCGGCTCA
GTTCGAGGTGCTGTTTCTGGTCTTCACCCACCGGTACCAGATTAGTTTGATACAGCAGGATGTCC
GCTGCCATCAGCACCGGATAGTCAAACAGACCAGCGTTGATGTTCTCGGCATAACGCGCAGATTT
ATCTTTAAACTGCGTCATGCGACTCAGTTCGCCGAAGTAGGTATAGCAGTTCAGTGCCCAGCCTA
ACTGTGCATGTTCCGGCACGTGGGACTGAACAAAAATGGTGCTTTTCTCAGGATCGATACCACAA
GCCAGATACAAGGCCAGCCGTATCCAGCGTCGCTTTACGCAGCTTCTGTGCATCCTGGCGCACGGT
GATCGCGTGTTGGTCAACGATACAGTAAATGCAATGGTAGTCATCCTGCATGTTTACCCACTGAC

Figure 25B cont.

```
GCAGCGCACCCATGTAGTTACCAATGGTCAATTCACCTGAGGGCTGTGCGCCACTAAAAACGATG
GGCTTAGTCATgctagccagcttgggtctccctatagtgagtcgtattaatttcgataagccagtaagcagtgggttctctagtta
gccagagagctctgcttatatagacctcccaccgtacacgcctaccgcccatttgcgtcaatggggcggagttgttacgacattttgg
aaagtcccgttgattttggtgccaaaacaaactcccattgacgtcaatggggtggagacttggaaatcccgtgagtcaaaccgctat
ccacgcccattgatgtactgccaaaaccgcatcaccatggtaatagcgatgactaatacgtagatgtactgccaagtaggaaagtcc
cataaggtcatgtactgggcataatgccaggcgggccatttaccgtcattgacgtcaataggggggcgtacttggcatatgatacactt
gatgtactgccaagtgggcagtttaccgtaaatagtccacccattgacgtcaatggaaagtccctattggcgttactatgggaacata
cgtcattattgacgtcaatgggcgggggtcgttgggcggtcagccaggcgggccatttaccgtaagttatgtaacgcggaactccat
atatgggctatgaactaatgaccccgtaattgattactattaataactagtcaataatcaatgtcaacgcgtatatctggcccgtacat
cgcgaagcagcgcaaaacGGATCCtgcaggtatttGCGGCCGCggtccgtatactccggaatattaatagatcatggagata
attaaaatgataaccatctcgcaaataaataagtattttactgtttcgtaacagttttgtaataaaaaaacctataaatattccggatt
attcataccgtcccaccatcgggcgcgAACTCCTAAAAACCGCCACCatgaagtgccttttgtacttagccttttattcat
tggggtgaattgcaagttcaccatagttttccacacaaccaaaaaggaaactggaaaaatgttccttctaattaccattattgcccgt
caagctcagatttaaattggcataatgacttaataggcacagccttacaagtcaaaatgcccaagagtcacaaggctattcaagcag
acggttggatgtgtcatgcttccaaatgggtcactacttgtgatttccgctggtatggaccgaagtatataacacattccatccgatcct
tcactccatctgtagaacaatgcaaggaaagcattgaacaaacgaaacaaggaacttggctgaatccaggcttccctcctcaaagtt
gtggatatgcaactgtgacggatgccgaagcagtgattgtccaggtgactcctcaccatgtgctggttgatgaatacacaggagaat
gggttgattcacagttcatcaacggaaaatgcagcaattacatatgccccactgtccataactctacaacctggcattctgactataa
ggtcaaagggctatgtgattctaacctcatttccatggacatcaccttcttctcagaggacggagagctatcatccctgggaaaggag
ggcacagggttcagaagtaactactttgcttatgaaactggaggcaaggcctgcaaaatgcaatactgcaagcattggggagtcag
actcccatcaggtgtctggttcgagatggctgataaggatctctttgctgcagccagattccctgaatgcccagaagggtcaagtatct
ctgctccatctcagacctcagtggatgtaagtctaattcaggacgttgagaggatcttggattattccctctgccaagaaacctggagc
aaaatcagagcgggtcttccaatctctccagtggatctcagctatcttgctcctaaaaacccaggaaccggtcctgctttcaccataat
caatggtaccctaaaatactttgagaccagatacatcagagtcgatattgctgctccaatcctctcaagaatggtcggaatgatcagt
ggaactaccacagaaagggaactgtgggatgactgggcaccatatgaagacgtggaaattggacccaatggagttctgaggacca
gttcaggatataagtttcctttatacatgattggacatggtatgttggactccgatcttcatcttagctcaaaggctcaggtgttcgaac
atcctcacattcaagacgctgcttcgcaacttcctgatgatgagagtttattttttggtgatactgggctatccaaaaatccaatcgagc
ttgtagaaggttggttcagtagttggaaaagctctattgcctctttttttctttatcatagggttaatcattggactattcttggttctccga
gttggtatccatctttgcattaaattaaagcacaccaagaaaagacagatttatacagacatagagatgaaccgacttggaaagtga
taaggccaggccggccaagcttgtcgagaagtactagaggatcataatcagccataccacatttgtagaggttttacttgctttaaaa
aacctcccacacctccccctgaacctgaaacataaaatgaatgcaattgttgttgttaacttgttattgcagcttataatggttacaaa
taaagcaatagcatcacaaatttcacaaataaagcattttttcactgcattctagttgtggtttgtccaaactcatcaatgtatcttatc
atgtctggatctgatcactgcttgagcCTAGGTCGGGCAGGAAGAGGGCCTATTTCCCATGATTCCTTCATA
TTTGCATATACGATACAAGGCTGTTAGAGAGATAATTAGAATTAATTTGACTGTAAACACAAAG
ATATTAGTACAAAATACGTGACGTAGAAAGTAATAATTTCTTGGGTAGTTTGCAGTTTTAAAAT
TATGTTTTAAAATGGACTATCATATGCTTACCGTAACTTGAAAGTATTTCGATTTCTTGGCTTTA
TATATCTTGTGGAAAGGACGAAACACCAGGGGCGTAGTTCAATTGGTAGAGCACCGGTCTCtAAA
ACCGGGTGtTGGGAGTTCGAGTCTCTCCGCCCCTGCCATTTTTTgctagggctaggagatccgaaccagata
agtgaaatctagttccaaactattttgtcatttttaattttcgtattagcttacgacgctacacccagttcccatctatttgtcactcttcc
ctaaataatccttaaaaactccatttccaccctcccagttcccaactattttgtccgcccacagcggggcattttcttcctgttatgttt
ttaatcaaacatcctgccaactccatgtgacaaaccgtcatcttcggctacttt
```

UNIVERSAL PLATFORM FOR GENETIC CODE EXPANSION

RELATED APPLICATIONS

This application claims the benefit under 35 USC 119(e) of U.S. Provisional Application No. 62/345,308, filed on Jun. 3, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 30, 2017, is named 0342_0005US1_SL.txt and is 116,984 bytes in size.

FIELD OF THE INVENTION

The present invention is directed to a universal platform for genetic code expansion,

BACKGROUND OF THE INVENTION

The ability to site-specifically incorporate unnatural amino acids (UAAs) into a protein in living cells has emerged as a powerful method to probe and manipulate its structure and function. Central to this technology is an engineered tRNA/aminoacyl-tRNA synthetase (aaRS) pair that delivers a desired UAA in response to a nonsense or frameshift codon. Such UAA-specific tRNA/aaRS pair must not cross-react with its host counterparts (i.e., orthogonal) to maintain the fidelity of translation. To ensure the absence of such cross-reactivity, candidates for the development of UAA-specific orthogonal tRNA/aaRS pairs are imported into a host cell from a different domain of life harboring evolutionarily divergent translational components. Thus, genetic code expansion of bacteria relies upon tRNA/aaRS pairs of eukaryotic or archaeal origin, and the same in eukaryotic cell generally utilizes bacterial pairs (homology of archaeal tRNA/aaRS pairs to their eukaryotic counterparts generally precludes their use in eukaryotic cells). The use of two distinct sets of tRNA/aaRS pairs for genetic code expansion in eukaryotes and bacteria has led to a significant disadvantage: each desirable UAA must be separately genetically encoded using two separate platforms.

The archaebacteria derived pyrrolysyl (Pyl) tRNA/PylRS pair is a natural TAG suppressor, and is orthogonal in both bacteria and eukaryotes owing to its unique structural features. As a result, its adaptation for genetic code expansion has created a universal platform that can be used to incorporate UAAs into proteins expressed in both E. coli and eukaryotic cells. The universal pyrrolysyl platform has been particularly beneficial for eukaryotic genetic code expansion for the following reason. Two selection systems have been developed so far to enable the generation of UAA-specific aaRS variants that use E. coli or Saccharomyces cerevisiae (yeast) as selection hosts to enable the directed evolution of eukaryotic-archaeal or bacterial tRNA/aaRS pairs, respectively. Due to its facile nature, the E. coli based selection platform has been significantly more successful for genetically encoding new UAAs relative to its yeast counterpart. The Pyl-tRNA/PylRS pair offers a unique opportunity to genetically encode new UAAs into eukaryotic cells using the facile E. coli based selection system. The advantage of this strategy is evident from the fact that all new UAAs genetically encoded in eukaryotic cells in the last six years have utilized the Pyl-tRNA/PylRS pair.

Development of additional "universal" tRNA/aaRS pairs that share these unique advantages, but provide access to new active site topologies for genetically encoding structurally distinct UAAs inaccessible to the pyrrolysyl system, would significantly augment our ability to expand and diversify the UAA tool box that can be used both in bacterial and eukaryotic cells. Access to multiple mutually orthogonal tRNA/aaRS pairs—each of which enable the incorporation of a rich set of UAAs—will also be crucial to facilitate site-specific incorporation of multiple distinct UAAs into proteins. Prolonged natural evolution has crafted the unique Pyl-tRNA/aaRS pair from a phenylalanyl ancestor a feat challenging to replicate in the laboratory setting.

SUMMARY OF THE INVENTION

Genetic code expansion of a cell relies on an orthogonal tRNA/aminoacyl-tRNA synthetase pair that is imported into the host from a different domain of life. The current invention demonstrates the feasibility of expanding the genetic code of E. coli using its endogenous tryptophanyl-tRNA/TrpRS pair. This was made possible by first functionally replacing this endogenous pair with an E. coli-optimized counterpart from yeast, and then reintroducing the liberated E. coli-tRNATrp/TrpRS pair into the resulting strain as a nonsense suppressor, followed by its directed evolution to selectively charge several unnatural amino acids. The current invention demonstrates the ability of these engineered E. coli tRNATrp/TrpRS variants to drive efficient unnatural amino acid mutagenesis in mammalian cells. The current invention also provides a general strategy to develop "universal" tRNA/aaRS pairs that can be used for unnatural amino acid mutagenesis of proteins of interest expressed in both E. coli and eukaryotic cells. Methods and compositions are described herein for selecting and identifying orthogonal aminoacyl synthetase-tRNA pairs and their use to incorporate unnatural or atypical amino acids in a site-specific manner in a protein of interest. Specifically described is a novel E. coli tyrptophanyl RNA synthetase-tRNA pair that functions as a highly efficient opal (TGA) suppressor that incorporates tryptophan analogs into proteins.

Compositions are described herein, comprising a genetically-engineered bacterial or archeal tRNA synthetase (RS) that preferentially aminoacylates (e.g., charges), as compared to the endogenous RNA synthetase, tRNA with an unnatural amino acid. For example, described herein, is a composition comprising an E. coli tryptophanyl-tRNA synthetase (EcTrp-RS) wherein the EcTrp-RS preferentially aminoacylates an E. coli tryptophanyl tRNA (Ec-tRNA$^{Trp}$) with a tryptophan analog over the naturally-occurring tryptophan amino acid.

The tryptophanyl analog (also referred to herein as a derivative) is selected from the group consisting of: 5-azidotryptophan, 5-propargyloxytryptophan, 5-aminotryptophan, 5-methoxyttyptophan, 5-O-allyltryptophan or 5-bromotryptophan. These analogs are synthesized as described herein. Other tryptophan analogs suitable for use as described herein can be synthesized by one of skill in the art using known methods.

In particular, the current invention encompasses a composition comprising an E. coli tryptophanyl-tRNA synthetase (EcTrp-RS) wherein the EcTrp-RS comprises the amino acid sequence of E. coli published in the NCBI database for the K-12 E. coli strain (ncbi.nlm.nih.gov/protein/BAE77907.1) as represented herein by SEQ. ID NO:

91 (or a sequence having at least about 80%, about 85%, about 90%, about 95% or greater than about 95% sequence identity). The EcTrp-RS (or a homologous Trp-RS) is mutated at its active-sites to replace the serine at position 8 with alanine; the valine at position 144 is replaced with either serine, glycine or alanine; and the valine at position 146 is replaced with either alanine, isoleucine or cysteine. Polynucleotide sequences encoding this polypeptide are also encompassed herein.

Specifically encompassed by the present inventions are four EcTrp-RNA synthetases wherein the EcTrp-RS comprises the amino acid sequence SEQ ID NO: 91 wherein the EcTrp-RS is mutated (1) to replace the serine at position 8 with alanine; the valine at position 144 with serine; and the valine at position 146 with alanine; (2) wherein the EcTrp-RS comprises the amino acid sequence of SEQ ID NO: 91 wherein the EcTrp-RS is mutated to replace the serine at position 8 with alanine; the valine at position 144 glycine; and the valine at position 146 with isoleucine; (3) wherein the EcTrp-RS comprises the amino acid sequence of SEQ ID NO: 91 wherein the EcTrp-RS is mutated to replace the serine at position 8 with alanine; the valine at position 144 with alanine; and the valine at position 146 with alanine; and (4) wherein the EcTrp-RS comprises the amino acid sequence of SEQ ID NO: 91 wherein the EcTRP-RS is mutated to replace the serine at position 8 alanine; the valine at position 144 with glycine; and the valine at position 146 with cysteine.

The Trp-RNA synthetases encompassed by the present invention further include homologous bacteria-derived Trp-RNA synthetases with active-site residues substituted with mutations as described herein. Such homologous TrpRS genes can be identified by techniques known to those of skill in the art, for example by performing sequence identity/homology searches of TrpRS genetic sequence databases to identify TrpRS gene sequences with, for example, about 80% sequence identity; about 85% sequence identity; about 90% sequence identity; about 95% sequence identity or greater than about 95% sequence identity, which are substantially homologous, or highly homologous to the *E. coli* TrpRS described herein. A specific example of a homologous bacteria-derived TrpRS is the TrpRS from *G. stearothennophilus*. Such homologous Trp-RS genes suitable for use as described herein may contain sequence variation from the *E. coli* Trp-RS wherein such sequence variations do not affect the functionality (aminoacyl activity) of the RNA synthetase. Such nucleotide variations can also be defined as conservative sequence variations or substitutions. Also encompassed by the present invention are complementary polynucleotide sequences and polynucleotide sequences that hybridize under highly stringent conditions over substantially the entire length of the nucleotide sequence, as well as the polypeptides encoded by the polynucleotides.

The homologous bacteria-derived Trp-RS can be mutated at its active-site residues corresponding to Ser 8, Val 144 and Val 146 to, for example, replace the serine at position 8 with alanine; the valine at position 144 is replaced with either serine, glycine or alanine; and the valine at position 146 is replaced with either alanine, isoleucine or cysteine as described herein for the *E. coli* Trp-RS.

The present invention further encompasses tRNA compositions wherein the tRNA anti-codon loop is modified (e.g., mutated) to specifically bind to (e.g., recognize) an amber (UAG/TAG) or opal (UGA/TGA). In particular, the present invention encompasses compositions wherein the tRNA is the *E. coli* tyrptophanyl tRNA, or another homologous bacteria-derived tRNA, wherein the polynucleotide sequence comprises SEQ ID NO: 1 or SEQ ID NO: 3 (or with about 80%; about 85%; about 90%, about 95% or greater than about 95% sequence identity) with an anti-codon loop comprising a sequence that specifically binds to a selector sequence of an mRNA selected from the group consisting of an amber codon or an opal codon. Importantly, the tRNA EcTrp UCA described herein is a novel opal suppressor suitable for use in both genetically-engineered bacteria and eukaryotes.

It is important to note that the modified tRNA of *E. coli*, or a homologous bacteria-derived tRNA, can be combined with an RNA synthetase of another homologous bacteria-derived RNA synthetase to produce novel combinations for unnatural amino acid, e.g., tryptophan analog, incorporation into proteins. Additionally, a combination of two distinct Trp-RS/tRNA pairs can be combined. For example, the EcTrp-RS/tRNA pair described herein, as an opal (TGA) suppressor, can also be combined with other suitable tRNA/RS pairs (e.g., pyrrolysine which is an amber (TAG) suppressor, to site-specifically incorporate two distinct unnatural amino acids into polypeptide/proteins expressed in eukaryotic cells.

Also encompassed by the present invention are cells (either cultured in vitro or in vivo) comprising an orthogonal *E. coli* tryptophanyl tRNA synthetase (EcTrp-RS), wherein the EcTrp-RS preferentially aminoacylates an *E. coli* tryptophanyl tRNA with a tryptophan analog, and an orthogonal *E. coli* tryptophanyl tRNA (Ec-tRNA$^{Trp}$) as a pair. Importantly, the orthogonal TrpRS/tRNA pair) does not cross-react the cell's endogenous TrpRSARNA pair. Such cells comprise not only the RS/tRNA pairs described herein, but also all cellular components required for translation of polynucleotides into proteins, including translation system components such as, for example, ribosomes, endogenous tRNAs, translation enzymes, mRNA and amino acids.

The cells of the present invention can be any bacterial cell or eukaryotic cell suitable for use with the RNA synthetase:/tRNA pairs described herein. In particular, the cell can be a mammalian cell. In particular, the bacterial cell is a genetically-engineered *E. coli* cell, or a homologous/analogous bacterial cell. More specifically, the *E. coli* is the ATMW1 or BL21(DE3) strain of *E. coli* cell.

Also encompassed by the present invention are methods of producing a polypeptide/protein in a cell with one, or more, unnatural amino acids incorporated into the polypeptide/protein in a site-specific manner by one, or more of the RS/tRNA pairs described herein. Such proteins can be labeled or chemically modified for further post-translational site-specific modifications.

Specifically encompassed by the present invention is a method of incorporating tryptophan analogs at specified positions in a protein of interest expressed in the cell, the method comprising culturing the cell in a culture medium under conditions suitable for growth, wherein the cell comprises a nucleic acid that encodes a protein with one, or more, amber or opal selector codons, wherein the cell further comprises an Ec-tRNA$^{Trp}$ that recognizes the selector codon(s), and wherein the cell further comprises an EcTrp-RS that preferentially aminoacylates the Ec-tRNA$^{Trp}$ with a tryptophan analog. The cell culture medium containing the growing cells is then contacted with one, or more, tryptophan analogs under conditions suitable for incorporation of the one, or more, tryptophan analogs into the protein in response to the selector codon(s), thereby producing the protein with one, or more tryptophan analogs. The method specifically encompasses the use of the EcTrp-RS and the Ec-tRNA$^{Trp}$ pair described herein. Such tryptophan analogs can be selected from the group consisting of: 5-azidotryptophan, 5-propargyloxytryptophan, 5-aminotryptophan, 5-methoxytryptophan, 5-O-allyltryptophan, or 5-bromotryptophan, or other suitable tryptophan analogs.

Also encompassed by the present invention are methods of incorporating two, or more unnatural amino acids at specified positions in a polypeptide/protein expressed in a cell. In these methods the cell further comprises a second tRNA/RS pair that is orthogonal to the cell, wherein the second pair recognizes an amber selector codon in the protein, but does not cross-react with the first RS/tRNA pair (e.g., EcTrp-RS/tRNA$^{trp}$). The method is performed as above (or in a similar manner) wherein the protein expressed/produced contains one, or more tryptophan analogs and one, or more, distinct unnatural amino acid other than a tryptophan analog incorporated by the first RS/tRNA pair.

Further encompassed by the present invention are kits for producing a protein in a cell, wherein the protein comprises one, or more tryptophan analogs, the kit comprising a container containing a polynucleotide sequence encoding an Ec-tRNA$^{Trp}$ that recognizes an amber or opal selector codon(s) in a nucleic acid of interest in the cell and a container containing an EcTrp-RS that preferentially aminoacylates the Ec-tRNA$^{Trp}$ with a tryptophan analog. Such kits can further comprise one, or more, tryptophan analogs, or other components required for cellular translation such as buffers and/or culture media. The kits can further include instructions for using the components and producing the desired protein.

The present invention encompasses a genetically engineered E. coli bacterial strain having the genotype EcNR1 pUltraG-ScW40CCA trpS::ZeoR trpT::GentR ΔgalK λRED::galK. Procedures for producing such genetically-engineered bacteria are described herein, specifically for the ATMW1 bacterial strain. Also encompassed by the present invention are homologous bacterial strains where analogous genetic modifications are made to the bacteria resulting in a bacterial strain with substantially similar functionality as ATMW1, e.g., as a host for protein expression. Methods described herein for producing ATMW1 are suitable for use in producing homologous genetically-engineered bacteria with essentially the same genotype with substantially similar, or better functionality as ATMW1. In particular, the genetically engineered E. coli strains ATMW1 or BL21 (DE3) are encompassed by the present invention.

The present invention also encompasses methods of producing orthogonal aminoacyl synthetase-tRNA pairs for incorporating unnatural amino acids into specific sites in proteins (e.g., expanding the genetic code) expressed/produced in E. coli and mammalian cells. The methods include the first step of functionally replacing an endogenous aminoacyl synthetase-tRNA pair in an E. coli host cell with a counter-part aminoacyl synthetase-tRNA pair orthogonal to E. coli and mammalian cells, resulting in an altered translational machinery (ATM) E. coli and liberating the endogenous E. coli aminoacyl synthetase-tRNA pair, wherein the liberated E. coli aminoacyl synthetase-tRNA pair is orthogonal to the ATM E. coli and mammalian cells.

The next step is reintroducing the liberated E. coli aminoacyl synthetase-tRNA pair into the ATM E. coli cell as a nonsense suppressor under conditions suitable for genetically selecting and identifying a variant E. coli aminoacyl synthetase that preferentially aminoacylates a tRNA with an unnatural amino acid over a natural amino acid. These steps result in producing an orthogonal aminoacyl synthetase-tRNA pair for incorporating unnatural amino acids into specific sites in proteins produced in E. coli and mammalian cells. The genetically-engineered ATM E. coli can be either ATMW1 or BL21 (DE3).

The current invention is the first tryptophanyl tRNA/tryptophanyl-tRNA synthetase platform that enables genetic incorporation of tryptophan analogs in eukaryotic cells (i.e., mammalian cells). The same engineered tryptophanyl tRNA/tryptophanyl-tRNA synthetase pair enables incorporation of the aforementioned Trp analogs into proteins expressed in E. coli (engineered) and eukaryotic cells.

As described herein, an E. coli cell has been developed where the endogenous tryptophanyl tRNA/tryptophanyl-tRNA synthetase was functionally replaced with a counterpart from yeast. This enables the use of the liberated E. coli tryptophanyl tRNA/tryptophanyl-tRNA synthetase pair to drive the incorporation of unnatural amino acids in response to the TGA (opal) nonsense codon.

Also as described herein is the first reported incorporation of 5-azidotryptophan, 5-propargyltryptophan, 5-aminotryptophan, 5-methoxytryptophan, 5-allyltryptophan, and 5-bromotryptophan using engineered tryptophanyl tRNA/tryptophanyl-tRNA synthetase pairs derived from E. coli.

The current invention demonstrates features and advantages that will become apparent to one of ordinary skill in the art upon reading the attached Detailed Description.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. The patent or application file contains at least one drawing executed in color. Copies of this patent or patent application publication with color drawings(s) will be provided by the Office upon request and payment of the necessary fee. Of the drawings:

FIG. 2A-B shows (A) depiction of ATMW1 recombination containing Ec-TrpRS replaced with ZeoR, Ec-Trp tRNA replaced with GentR, and complementation plasmid pUltraG ScW40 CCA. (B) Growth rate comparison of ATMW1 to progenitor EcNR1 strain containing pUltraG.

FIG. 4A-D shows (A) Structures of additional tryptophan analogs used here. (B) Demonstration of polyspecificity associated with EcTrpRS-h9 and h14 using sfGFP-151-TGA expression assay. (C) SDS-PAGE of sfGFP-151-TGA containing various 5-position Trp residues. (D) Expression of EGFP-39-TAG reporter incorporating various UAAs in HEK293T cells using EcTrpRS(variant)/tRNAEcTrpCUA pair.

FIG. 10A-C show predicted (A) EcTrp-tRNACCA (trpT) SEQ ID NO: 1 and (B) EcGln-tRNACUG (glnV) structures SEQ ID NO:2. (C) shows the respective DNA sequences and homology alignment of tRNA sequences SEQ ID NOS:3-5.

FIG. 11A-D shows (A) EGFP39*-fluorescence images of EcWRS-h14 and (B) -h9 transfected HEK293T, as previously described. (C) SDS-PAGE of purified EGFP39* containing an UAA incorporated through the pacbac system expressing h14, h9, or the Pyl system, ( ) Yields of aforementioned purified EGP39*.

FIG. 12A-C show the sequences (SEQ ID NOS:75, 76 and 77 respectively) that are the ds DNA PCR products that were electroporated for recombination. Primers are listed in MM and primer list. Important features are mentioned prior to the sequence with color code in parenthesis.

FIG. 13A-B. FIG. 13A shows the plasmid map and FIG. 13B shows the plasmid sequence (SEQ ID NO: 78) for pUltra_ScW40$_{CCA}$. GFP is highlighted in green, CAT/Barnase is orange, T7 RNA polymerase in purple, tRNA in red and aaRS in blue unless otherwise specified.

FIG. 14A-B. FIG. 14A shows the plasmid map and FIG. 14B shows the plasmid sequence (SEQ ID NO: 79) for pRepAC-EcWtR-TAG.

FIG. 15A-B, FIG. 15A shows the plasmid map and FIG. 15B shows the plasmid sequence (SEQ ID NO:80) of pRep-Cm3J-98TGA-EcWtR.

Figure 16B:
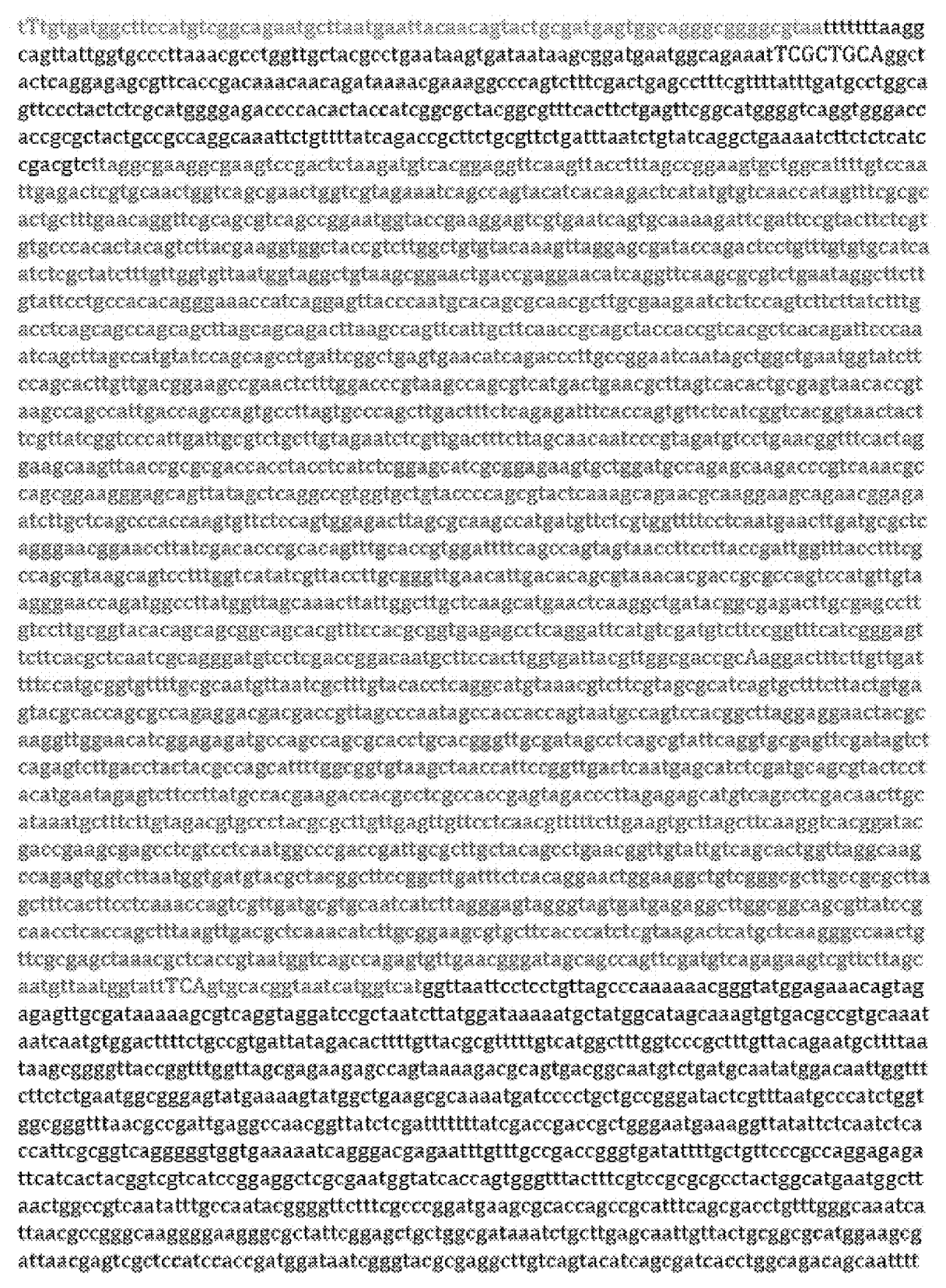

FIG. 16A-B. FIG. 16A shows the plasmid map and FIG. 16B shows the plasmid sequence (SEQ ID NO:81) of pRepJI-EcW.

FIG. 17A-B. FIG. 17A shows the plasmid map and FIG. 17B shows the plasmid sequence (SEQ ID NO: 82) of pEvolT5-EcW-sfGFP151TAG.

FIG. 18A-B. FIG. 18A shows the plasmid map and FIG. 18B shows the sequence (SEQ ID NO:83) of pEvolT5-EcW-sfGFP151TAG.

FIG. 19 shows the plasmid sequence (SEQ ID NO: 84) of pEvoltac-EcW-TGA-h14.

FIG. 20 shows the plasmid sequence (SEQ ID NO: 85) of the plasmid pEvoltac-EcW-TGA-h9. The sequence is identical to pEvoltac-EcW-TGA-h14 except for the V144-146 region. The h9 aaRS is listed with mutations in blue.

FIG. 21A-B. FIG. 21A shows the plasmid map and FIG. 21B shows the plasmid sequence (SEQ ID NO: 86) of pBK-EcWRS.

FIG. 22 shows the sequence (SEQ ID NO:87) of pRK-EcWRS-h14. The pBK sequence is the same as with EcWRS-h14 with mutations shown in blue.

FIG. 23 shows the sequence of pBK-EcWRS h-9 (SEQ ID NO:88). The pRK sequence is the same as with EcWRS-h9 with mutations shown in blue.

FIG. 24A-B. FIG. 24A shows the plasmid map and FIG. 24B shows the plasmid sequence (SEQ ID NO:89) of pAcBac1-EGFP39*-U6-EcWtR-TAG.

FIG. 25A-B. FIG. 25A shows the plasmid map and FIG. 25B shows the sequence (SEQ ID NO:90) of pAcBac1-TrpRS-U6EcWtR-TAG.

DETAILED DESCRIPTION OF THE PREFERRED EMBODIMENTS

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof.

Figure 1:
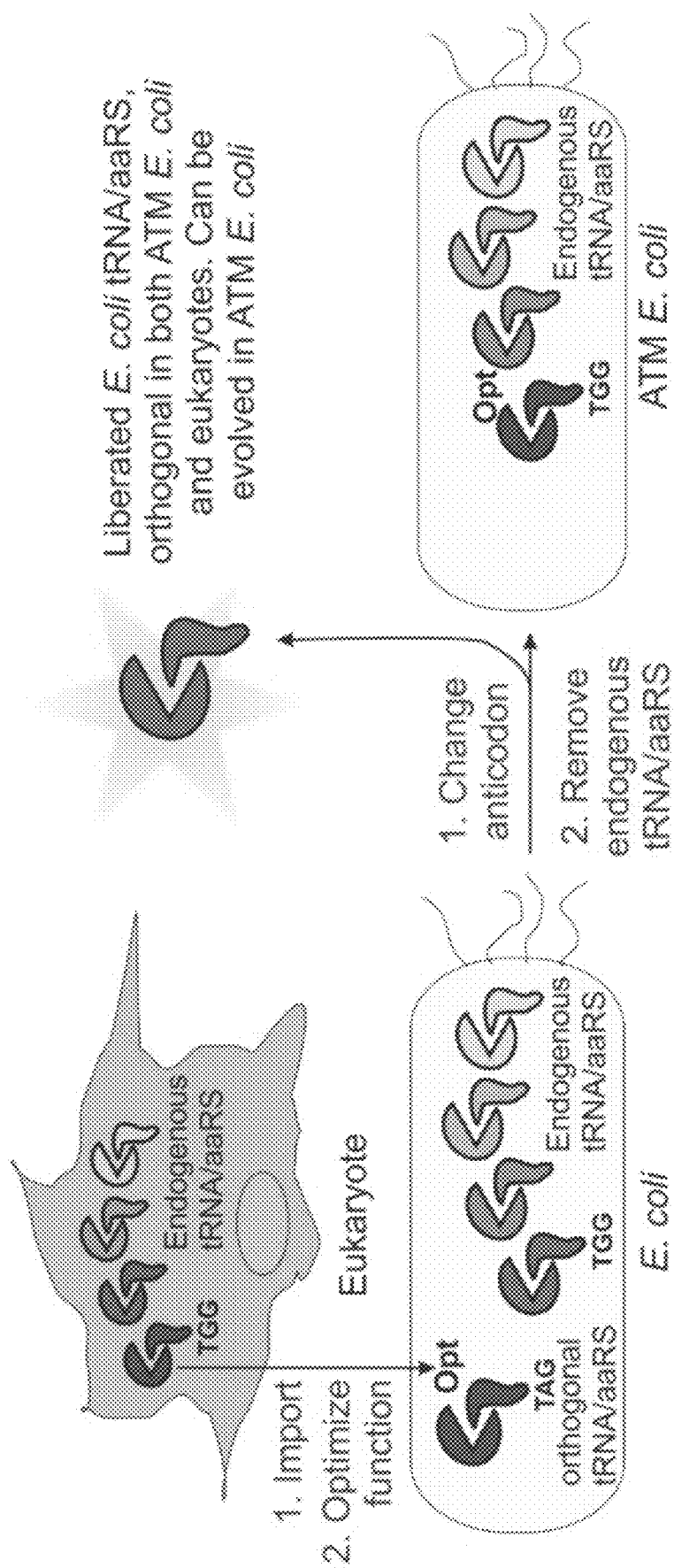
FIG. 1 shows an overview of the general strategy to create ATM E. coli strains.

The present disclosure provides a universal platform for genetic code expansion and involves a bacterial tryptophanyl-tRNA/tryptophanyl-tRNA synthetase pair for site-specific incorporation of tryptophan analogs into proteins expressed in E. Coli and eukaryotic cells. The current invention discloses an alternative strategy which takes advantage of an E. coli strain, where one of its native tRNA/aaRS pairs is functionally replaced with a eukaryotic/archaeal counterpart (FIG. 1). The "liberated" tRNA/aaRS pair can then be reintroduced in the resulting "altered translational machinery (ATM)" E. coli as a nonsense suppressor, and can be evolved to charge desirable UAAs. Owing to its bacterial origin, the same pair can also be directly used for eukaryotic genetic code expansion.

The feasibility of substituting a tRNA/aaRS pair in E. coli with an evolutionarily distant counterpart has previously been demonstrated. However, the resulting strains often exhibit growth defect, presumably due to the suboptimal interaction of the heterologous tRNA/aaRS with the translational apparatus of E. coli. Moreover, whether variants of the liberated tRNA/aaRS pair with altered substrate specificity can be developed using the corresponding ATM strain as the selection host remains unknown. Optimizing the performance of the substituting tRNA/aaRS pair in E. coli using directed evolution may allow it to functionally replace its endogenous counterpart more efficiently, circumventing the growth defect associated with such substitution. A number of heterologous tRNA/aaRS pairs have already been engineered for efficient suppression of nonsense codons in E. coli, providing a pool of potential candidates.

Figure 6:
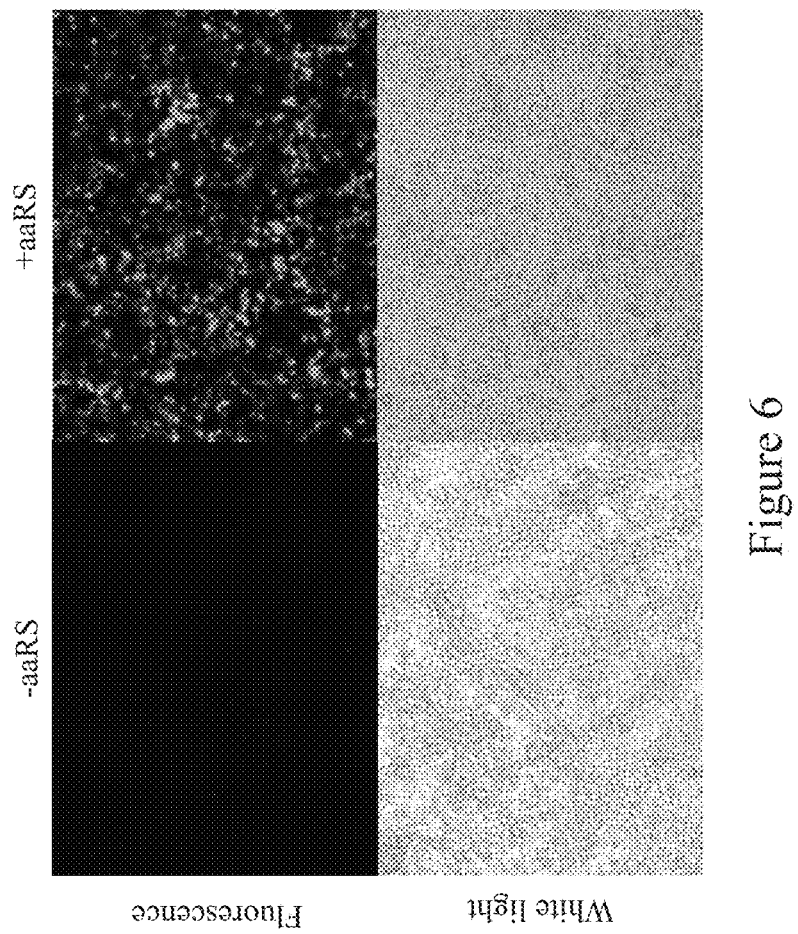
FIG. 6 shows EGFP39*-fluorescence and white light images demonstrating E. coli tRNATrpCUA orthogonality and Trp-aaRS activity in ITEK293T, imaged 24 hrs post-transfection with PEI-Max. pAcBac1 system previously described was used, with or without cognate aaRS.

The endogenous tryptophanyl (Trp)-tRNA/aaRS pair in E. coli was targeted for functional replacement with a eukaryotic/archaeal counterpart. A S. cerevisiae derived tryptophanyl-tRNA/TrpRS pair has already been optimized in E. coli for highly efficient nonsense suppression, providing a great candidate for substituting its endogenous counterpart. Additionally, the unique active site of TrpRS should enable the introduction of structurally novel UAAs in the eukaryotic, as well as the bacterial genetic code. To verify if the E. coli Trp-tRNA/aaRS pair is indeed suitable for eukaryotic genetic code expansion, HEK293T cells were co-expressed with the TAG-suppressing E. coli Trp-tRNA (tRNAEcTrpCUA) and an enhanced green fluorescent protein (EGFP) reporter harboring a stop codon at a permissive site (EGFP-39-TAG), with or without the cognate synthetase. Robust EGFP expression was only observed in the presence of the EcTrpRS (FIG. 6), suggesting that: 1) EcTrpRS/tRNAEcTrpCUA is capable of efficient TAG-suppression in eukaryotic cells, and 2) the pair is non-cross-reactive with its eukaryotic counterparts.

Figure 7B:
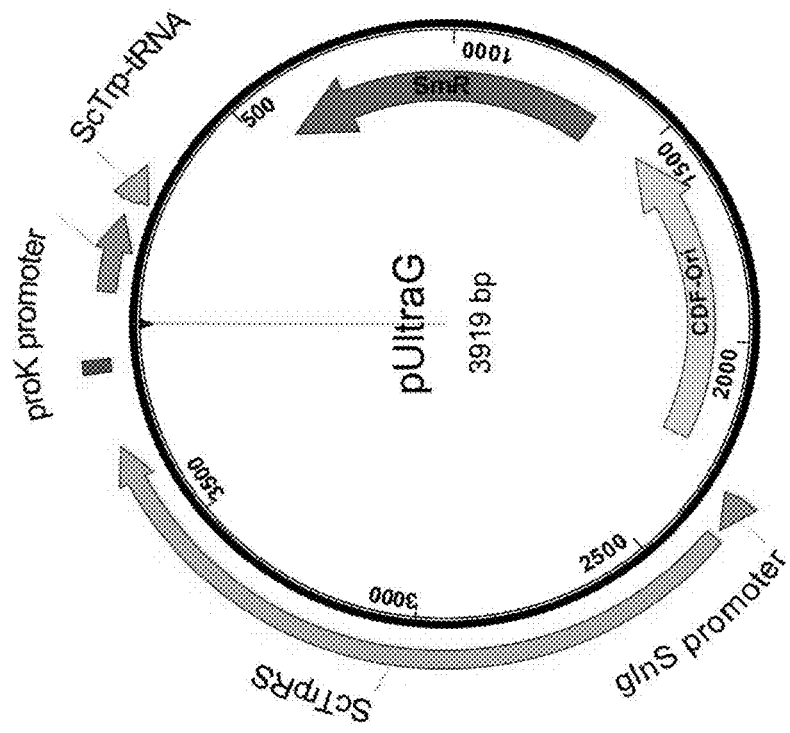
FIG. 7A-B shows the plasmid maps used to complement endogenous E. coli Trp-tRNA/aaRS removal. pUltraG ScW40 CCA contains a glnS' promoted wild-type E. coli TrpRS, prok promoted E. coli Trp-tRNA, CloDF13 origin of replication, and Spectinomycin resistance. pUltra is as previously reported.
Figure 7A:
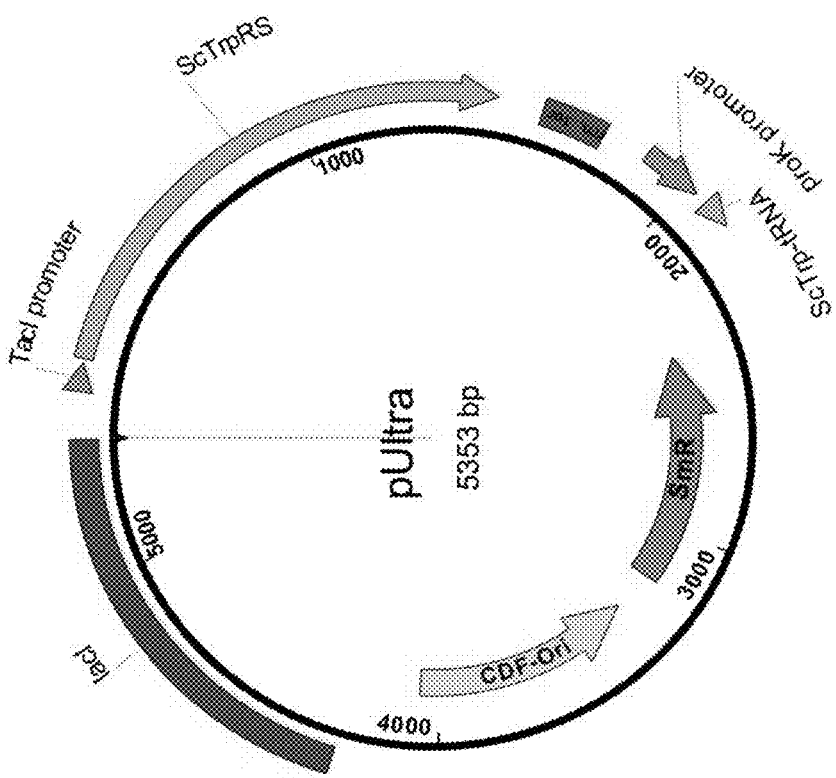
Figure 8A:
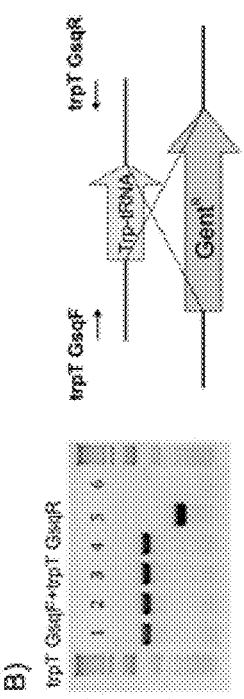
FIG. 8A-D shows Colony PCR assay for genomic recombination. (A) Ec-TrpRS replaced with zeoR screen. Left: Primers anneal 150 bp upstream and downstream from trpS location (Zeocin ~200 bp smaller than Ec-TrpRS). Middle: Forward primer anneals 150 bp upstream and an internal reverse primer anneals only to trpS. Right: Primers anneal directly to the N and C terminus of trpS. Lanes 1-6 are potential hits, lane 7 is EcNR1, and lane 8 is PBS. (B) Ec-Trp tRNA replaced with gentR screen. Primers anneal 150 bp upstream and downstream from the trpT genomic location. Successful hits will have a larger PCR product due to the increased gentamycin cassette. Lanes 1-4 are potential hits, lane 5 is EcNR1 pUG ScW40 trpS::zeoR prior to recombination, and lane 6 is PBS. (C) galK deletion screen: Primers anneal 150 bp upstream and downstream from the galK endogenous location. Successful hits will have a larger PCR product due to the increased gentamycin cassette. Lanes 1-8 are potential hits, lane 9 is EcNR1, lane 10 is C321, and lane 11 is PBS. (D) Genornic λ-Red replaced with galK screen—ATMW1. A: Forward primer anneals 150 bp upstream from the prophage and the reverse primer anneals only to galK. B: Primers anneal 150 bp upstream and downstream from the galK endogenous location. 1-4 are final ATMW1 hits, 5 is EcNR1, 6 is Top10, and 7 is PBS. Associated primer maps are depicted with each screen.
Figure 8B:
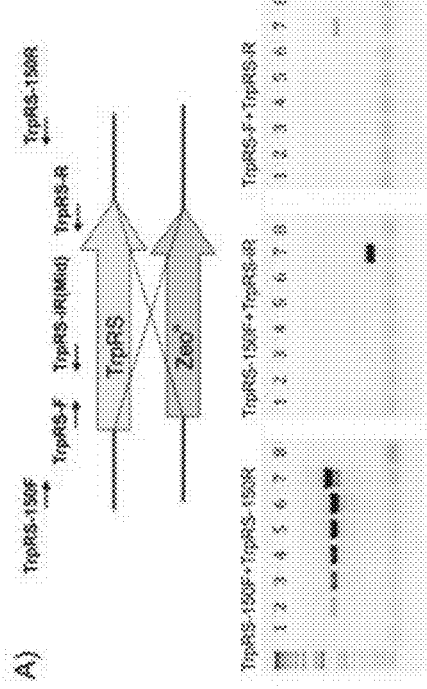
Figure 8C:
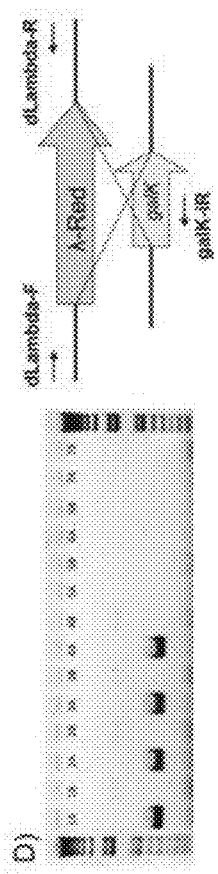
Figure 8D:
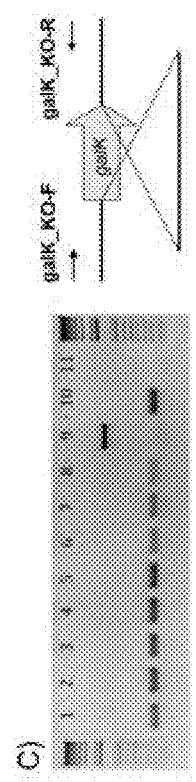

To allow the deletion of the endogenous tryptophanyl pair from the E. coli genome, a plasmid (pUltra-ScW40CCA) was first generated expressing the aforementioned engineered ScTrpRS/tRNAScTrpCCA pair derived from yeast (FIG. 7). It harbors a unique CloDF13 origin of replication to maintain compatibility with most commonly used plasmids. The K12-derived EcNR1 strain of E. coli, encoding a heat-inducible λ-Red recombination system, was used as the host. Attempts at replacing the trpS (encoding EcTrpRS) and trpT (encoding Trp-tRNA) genes from the EcNR1 genome using a zeocin and gentamycin selectable markers (FIG. 2A), respectively, were successful in the presence of the pUltra-ScW40CCA complementation plasmid (FIG. 8). Finally, the λ-prophage encoding the Red-recombination system was removed from the genome using a galactose-selectable galK marker, to provide a strain named ATMW1, with the following genotype: EcNR1 pUltraG-ScW40CCA trpS::ZeoR trpT::GentR. ΔgalK λRED::galK. The ATMW1 strain exhibited no observable growth defect when compared to its progenitor EcNR1, confirming efficient functional complementation by the engineered ScTrpRS/tRNA-ScTrpCCA pair (FIG. 2B).

Figure 9A:
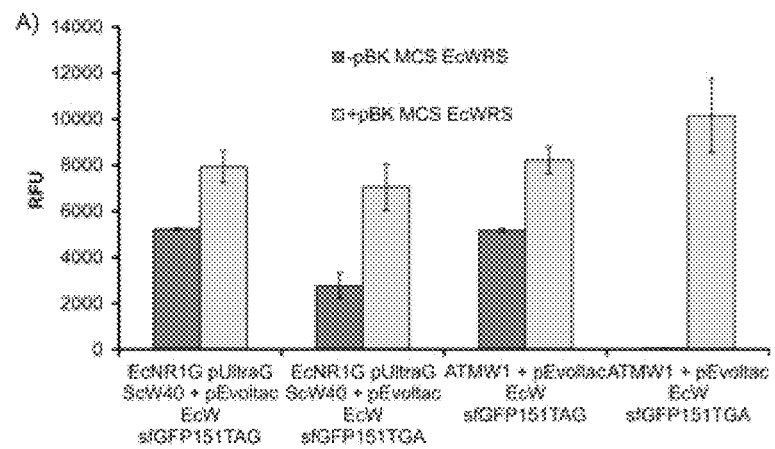
FIG. 9A-C shows (A) cross reactivity comparison with tRNAEcTrp CUA vs UCA via sfGFP151 assay. Strains were transformed with pEvolT5 EcW sfCFP151TAG or TGA, grown to 0.5 OD600 and induced with 1 mM IPTG. Fluorescence/OD600 was measured in a plate reader (488 ex, 534 em, 515CO). (B) LCMS of ATMW1 purified sfGFP151TAG+pBK MCS EcWRS (C) LCMS of ATMW1 purified sfGFP151TAG+pBK MCS EcWRS.
Figures 9B, 9C:
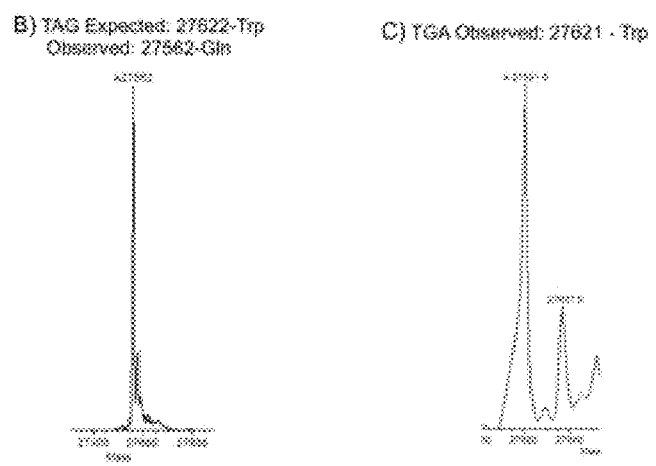
Figure 13A:
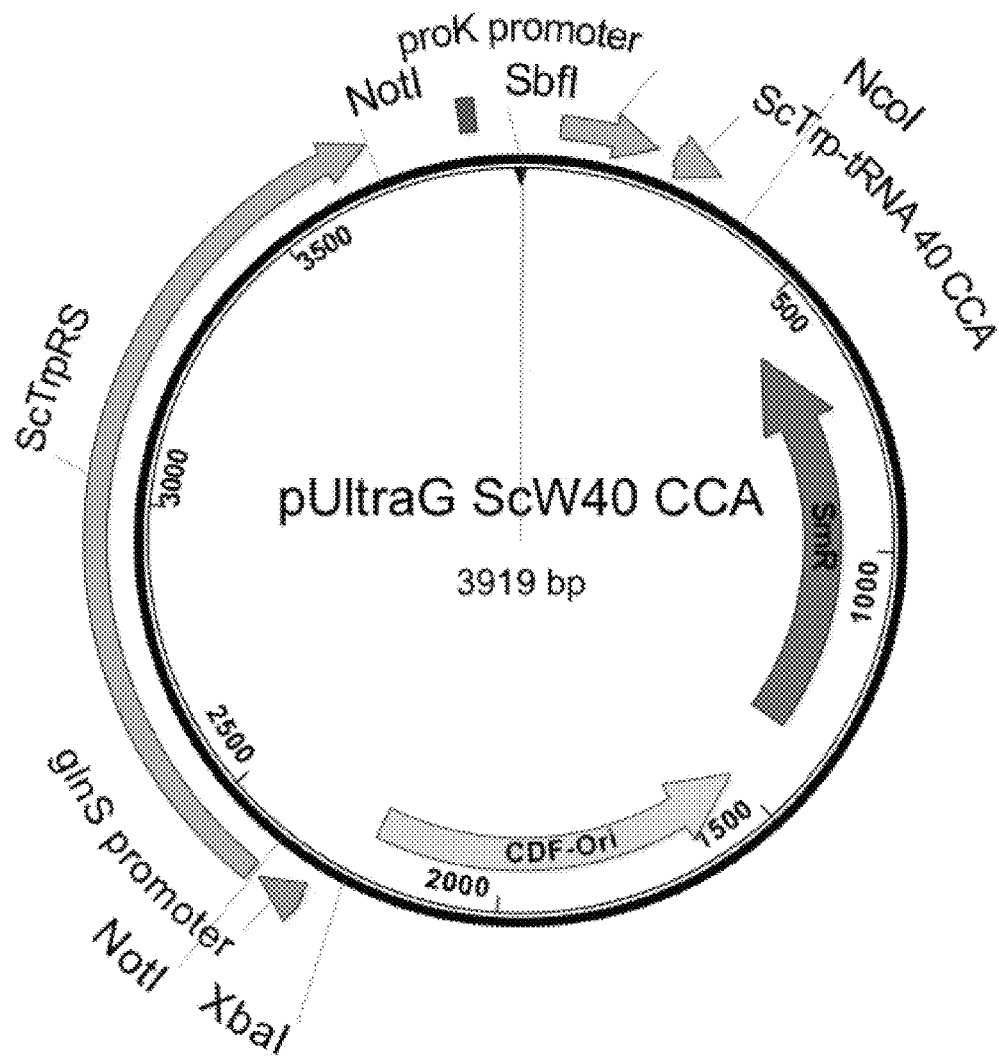
Figure 14A:
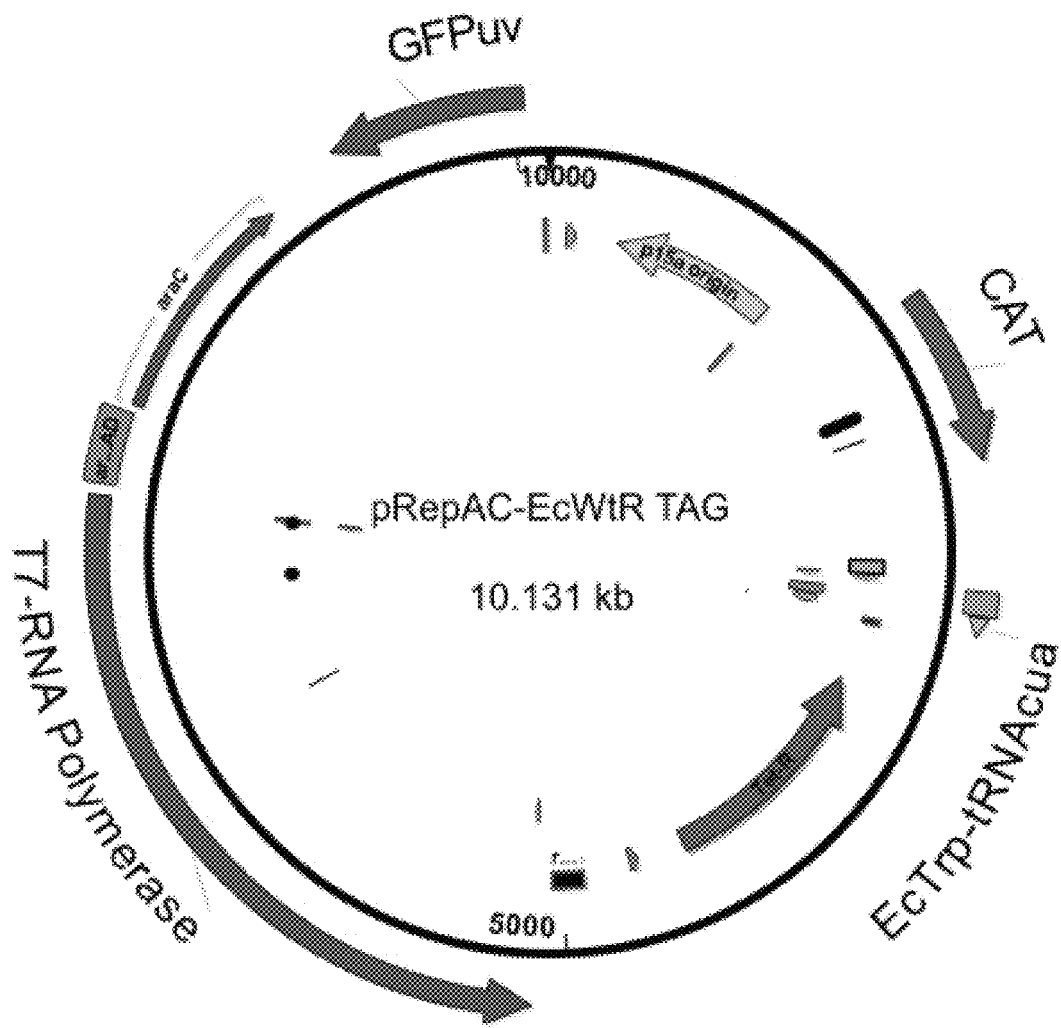
Figure 15A:
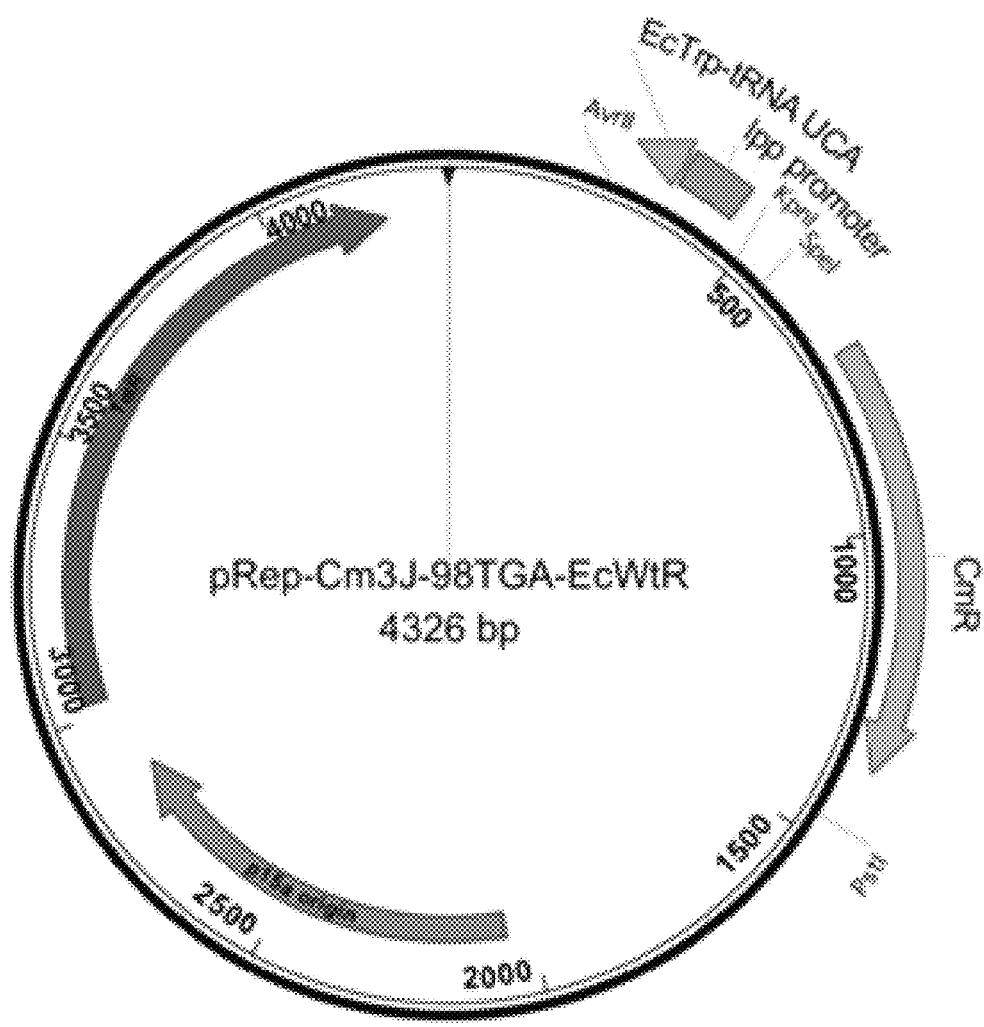
Figure 16A:
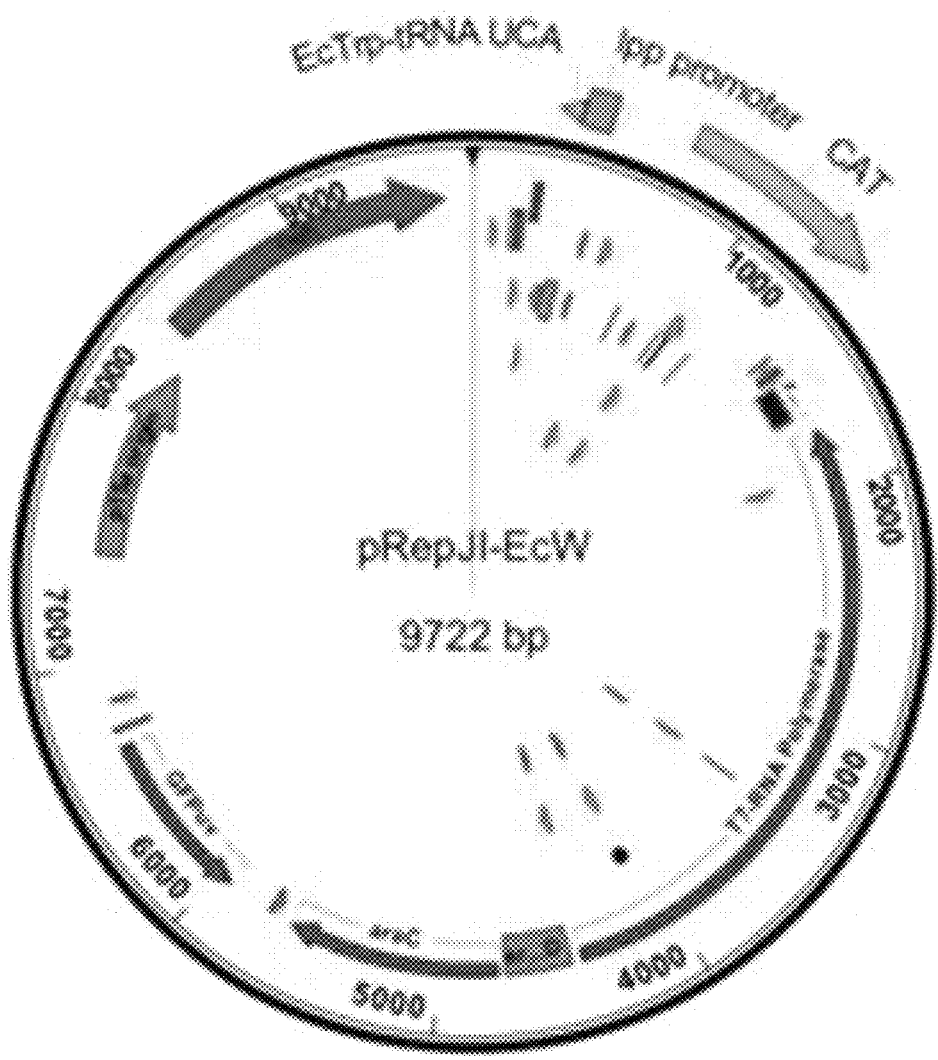
Figure 17A:
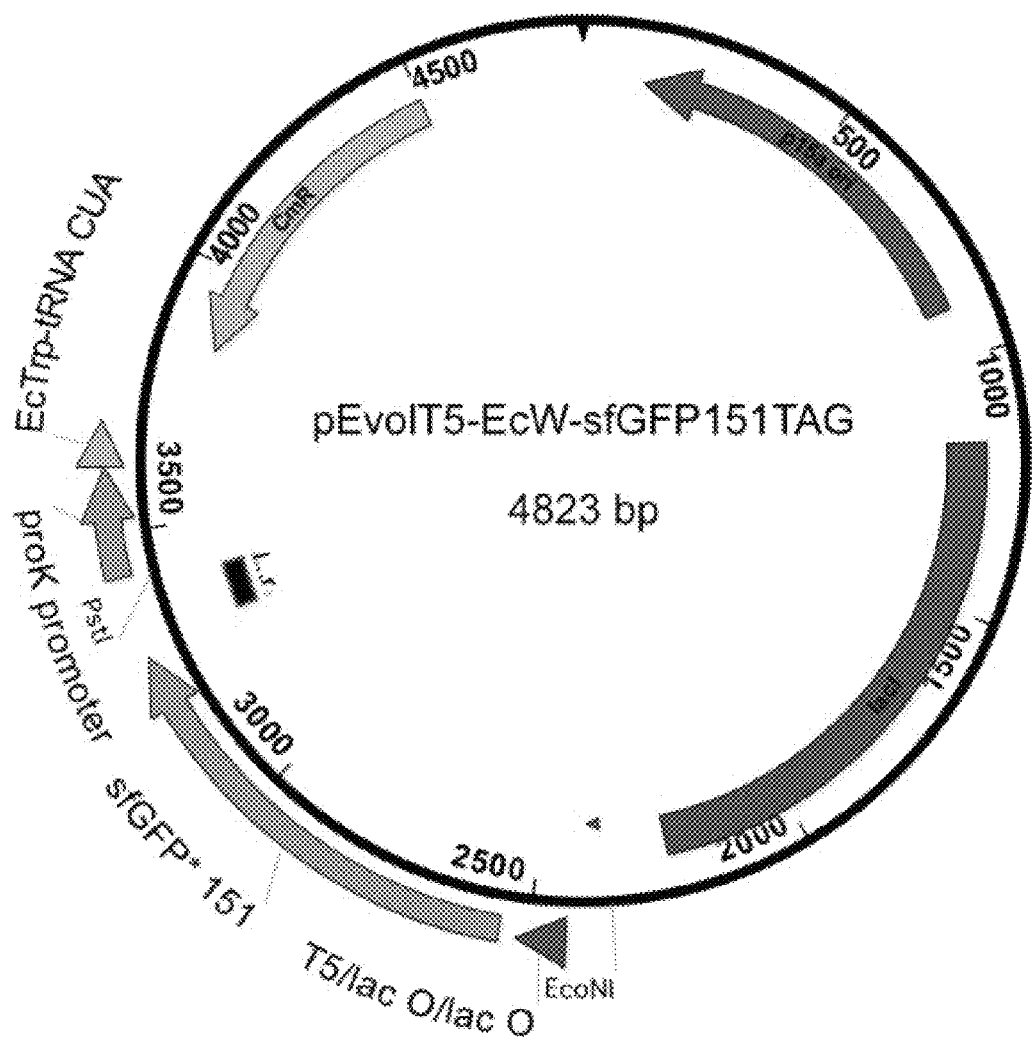
Figure 18A:
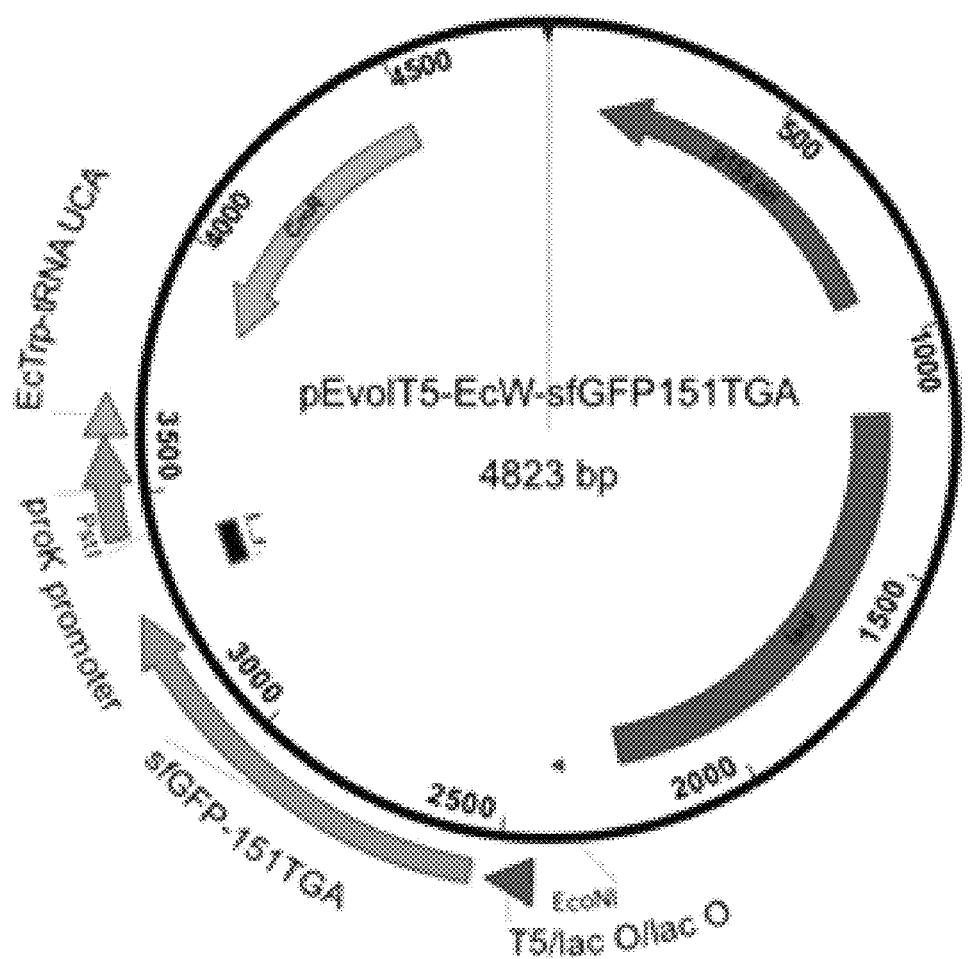
Figure 21A:
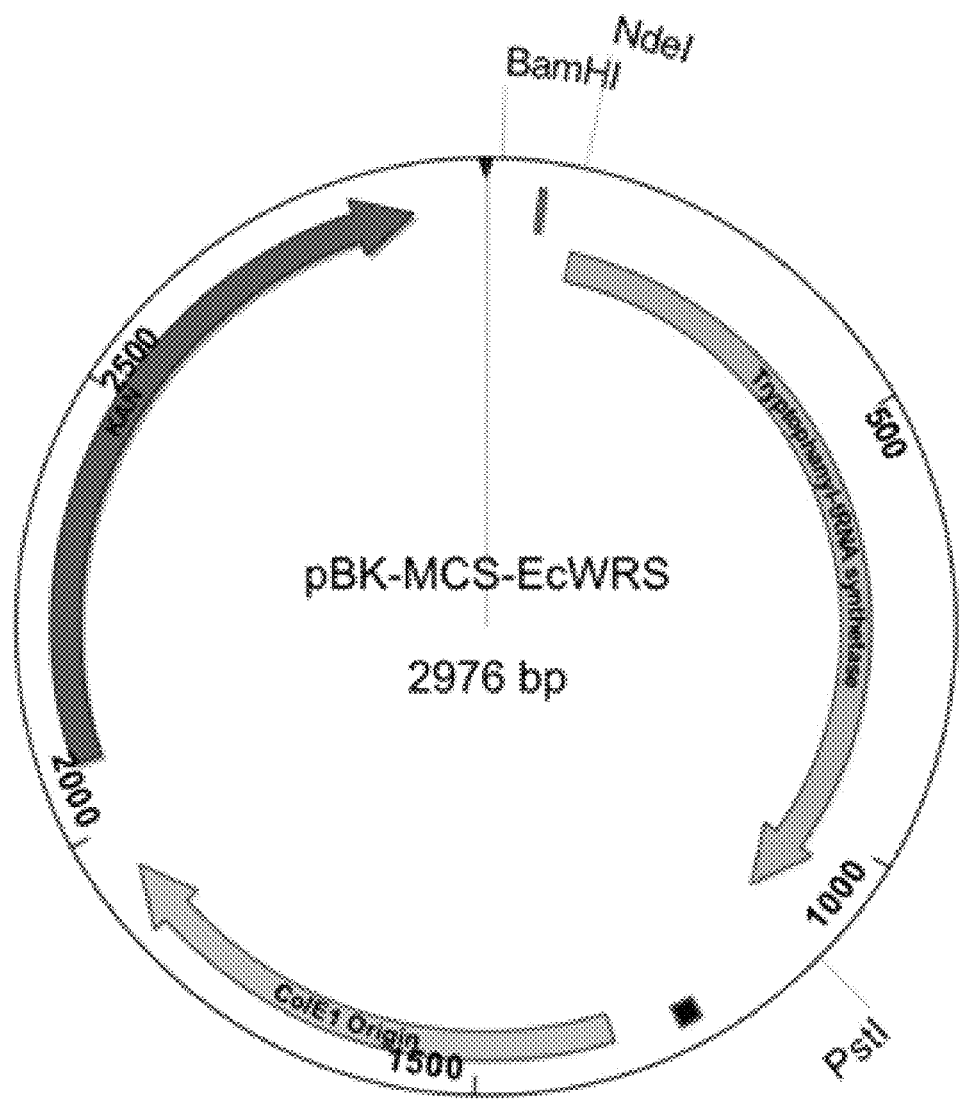
Figure 24A:
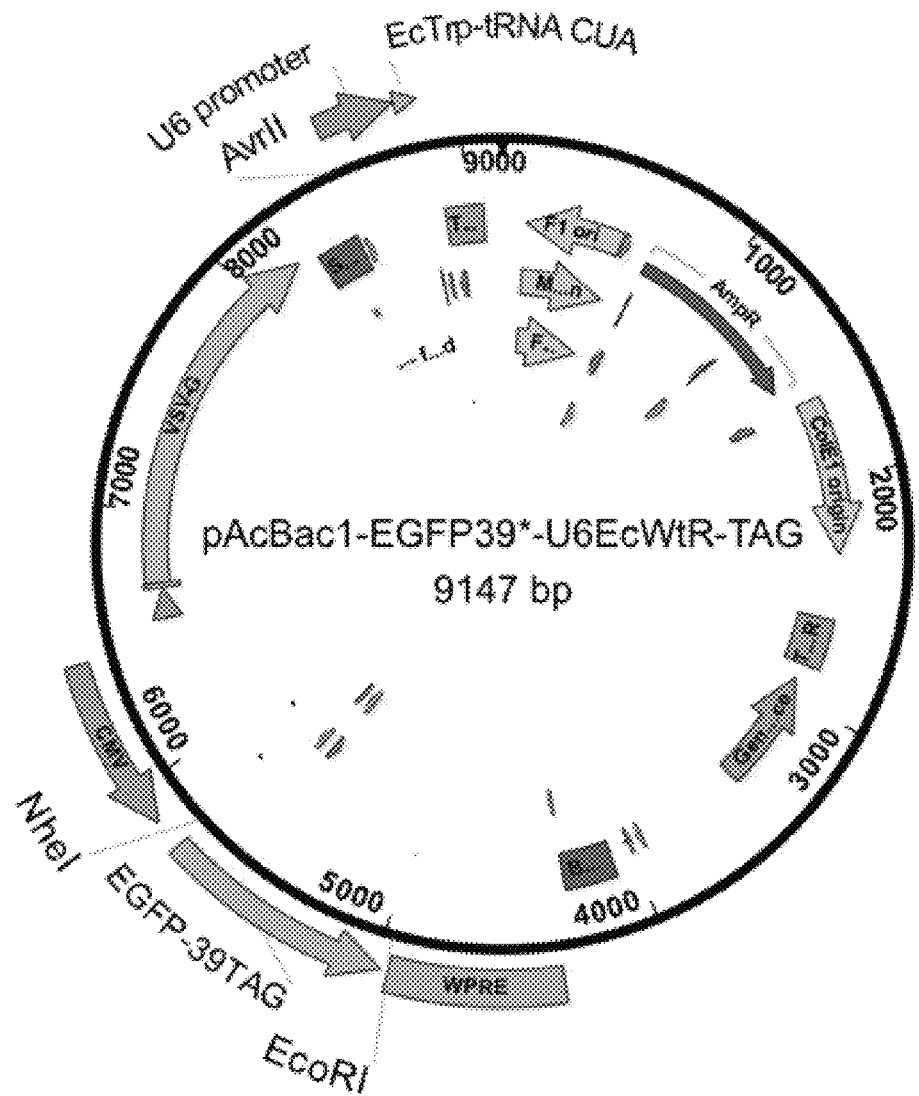
Figure 25A:
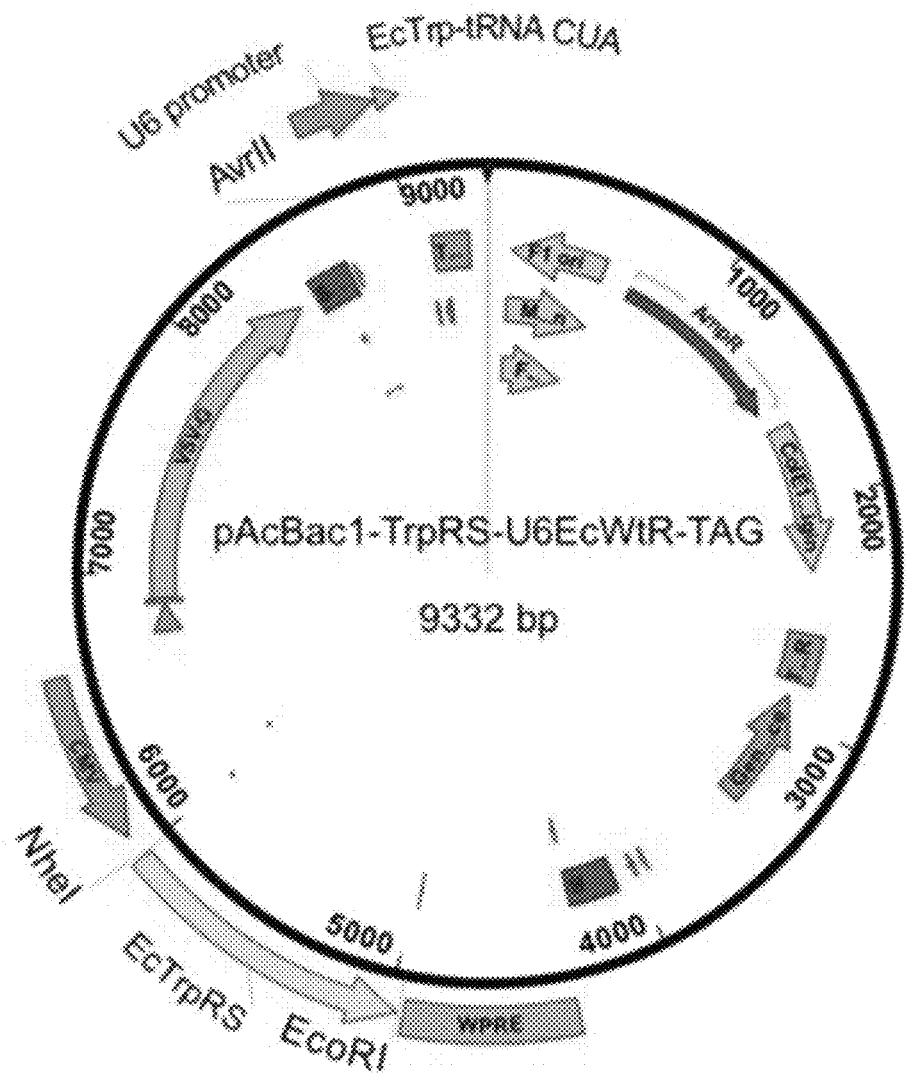

With A TMW1 in hand, the possibility of reintroducing the liberated EcTrpRS/tRNAEcTrp pair for TAG suppression into this strain as a TAG suppressor was investigated. Surprisingly, when the tRNAEcTrpCUA was expressed in ATMW1 along with a superfolder GFP reporter (sfGFP-151-TAG), robust protein expression was observed in the absence of EcTrpRS, indicating cross-reactivity of this tRNA with another E. coli aaRS (FIG. 9A). To identify the origin of this cross-reactivity, the reporter protein was isolated by Ni-NTA affinity purification, and subjected to mass-spectrometry analysis (whole protein, as well as tryptic digestion/MS), which identified the amino acid being charged in response to TAG as glutamine (FIG. 9B). Sequence alignment reveals remarkable homology between the tryptophanyl and glutaminyl tRNA of E. coli (FIG. 10). The middle U residue in the anticodon of EctRNAGlnCUG is a major identity element in its interaction with EcGlnRS. While the EctRNATrpCCA lacks this residue, enabling its distinction from EctRNAGln, it was inadvertently introduced in the TAG suppressor variant EctRNATrpCUA, leading to cross-reactivity with EcGlnRS.

Circumventing this issue is envisioned by generating a TGA suppressor EctRNATrpUCA that avoids introducing the middle U-residue in the anticodon. Unfortunately, termination at the TGA stop codon in E. coli is often "leaky" a result of non-specific suppression by the endogenous tryptophanyl tRNA making it a suboptimal choice for genetic code expansion. However, in the ATMW1 strain where the endogenous tryptophanyl pair was replaced with the yeast counterpart TGA did not exhibit such leaky behavior (FIG. 9A), suggesting the feasibility of its use for genetic code expansion with high fidelity. When the sfGFP-151-TGA reporter and EctRNATrpUCA were coexpressed in ATMW1, no reporter expression was observed unless the EcWRS was also present, confirming the non-cross-reactivity of EctRNATrpUCA in ATMW1 as well as the efficient opal suppression activity of the EcTrpRS/tRNAEcTrpUCA pair (FIG. 9A). MS analysis of the isolated protein further confirmed incorporation of tryptophan in response to TGA (FIG. 9C)

Figure 3A:
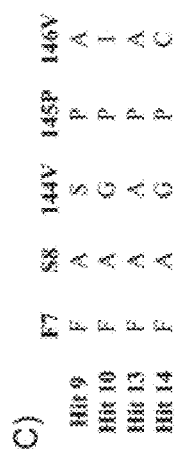
FIG. 3A-E shows (A) Geobacillus stearothermophilus TrpRS (PDB 1I6M) active site. (B) Structures of tryptophan and 5-hydroxytryptophan (5HTP). (C) Mutations associated with 5HP-specific EcTrpRS variants. (D) Expression of sfGFP-151-TGA using EcTrpRS hits 9, 10, 13, and 14 demonstrating 5HTP dependence. (E) SDS-PAGE analysis of sfGFP-151-TGA expression facilitated by various EcTrpRS variants in the presence or absence of added 5HTP.
Figure 3B:
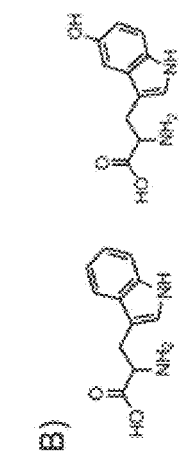

Establishment of an efficient, orthogonal opal suppressing EcTrpRS/tRNAEcTrpUCA pair in the ATMW1 E. coli opens up the possibility of altering its substrate specificity using the facile E. coli-based selection system. The existing reporter plasmids used for this double-sieved selection scheme, which enables either enrichment (positive selection) or depletion (negative selection) of aaRS variants based on their ability to charge its amber suppressing cognate tRNACUA, were mutated to generate variants that would allow selection based on opal suppression instead. Based on the crystal structure (FIG. 3A) of the highly homologous Geobacillus stearothermophilus TrpRS (PUB ID 116M), a library of 3.15×10⁶ EcTrpRS mutants was constructed by simultaneously randomizing Phe7(NBT), Ser8(NST), Val144(NNK), Pro145(NNK), Val146(NNK) residues using site-saturation mutagenesis, and covering the library using ~3×10⁷ unique transformants. These residues point at C4-C5-C6 of the indole ring of the substrate tryptophan. A first attempt at identifying a mutant from this library that selectively charges 5-hydroxytryptophan is shown (5HTP; FIG. 3B). This UAA was previously genetically encoded in bacteria using a yeast-derived tryptophanyl pair. A report claiming its incorporation in mammalian cells using a bacteria-derived tRNA/aaRS pair was recently refuted.

Figure 3C:
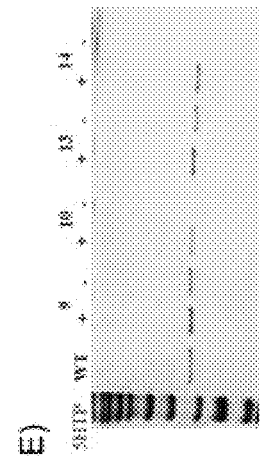
Figure 3D:
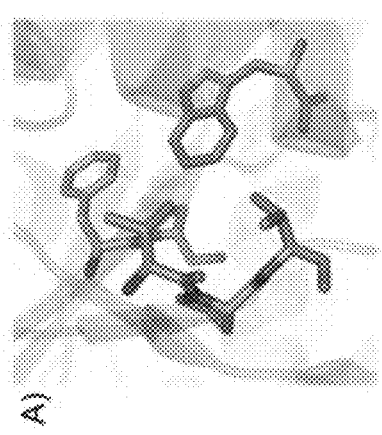
Figure 3E:
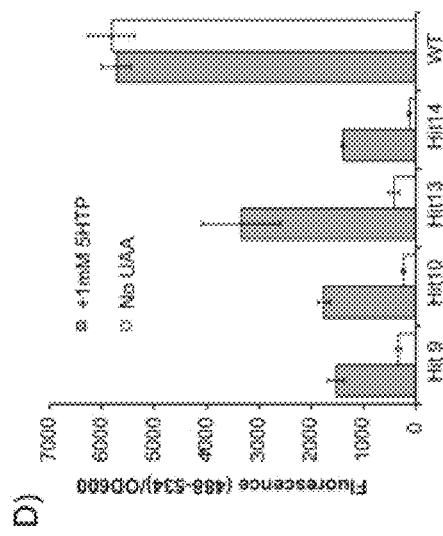

The aforementioned library of EcTrpRS variants was subjected to three rounds of selections (positive selection in the presence of 1 mM 5HTP, negative selection in the absence of the UAA, then another round of positive selection) in the ATMW1 strain, and 96 colonies from the surviving pool were individually screened for conditional survival under the positive selection conditions (40 chloramphenicol) in the presence of 5HTP. Sequence analysis of four of the most successful mutants show significant sequence-convergence, where Phe7 and Pro145 are conserved, Ser8 is mutated to Ala, Val144 changes to a small amino acid (Gly/Ser/Ala), and Val146 is mutated to different small/hydrophobic amino acids (FIG. 3C). Next the ability of these mutant EcTrpRS variants to drive the expression of a sfGFP-151-TGA reporter along with its cognate tRNAEcTrpUCA were evaluated. All mutants were able to facilitate efficient reporter expression in the presence of 1 mM 5HTP, but EcTrpRS-h14 exhibited the least background in the absence of the UAA (FIG. 3D, E). The reporter protein was isolated using a C-terminal (His)6 tag and MS analysis confirmed 5HTP incorporation (Table 1).

Figure 4A:
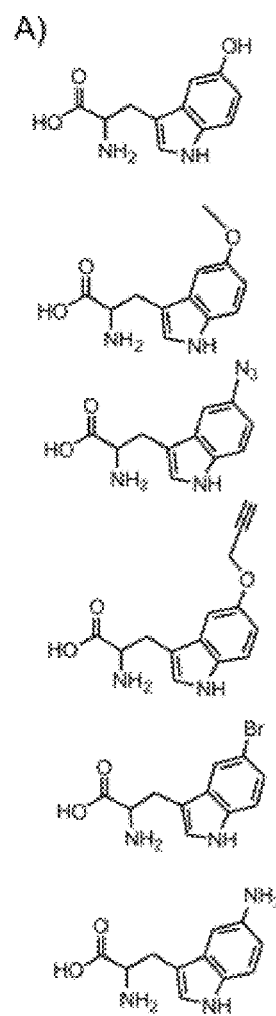
Figure 5B:
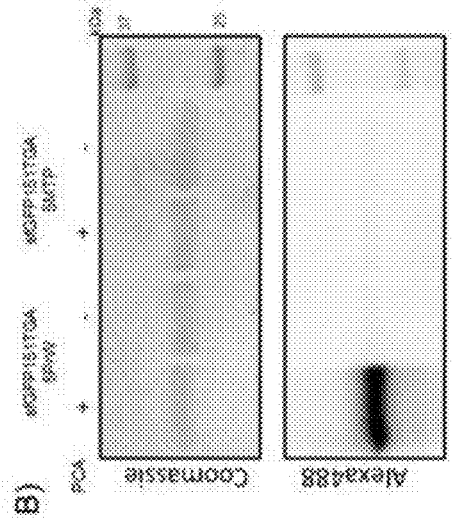
FIG. 5A-D shows (A) EGFP-39-TAG and sfGFP-151-TGA containing 5AzW or 5HTP were labeled with DBCO-Cy5 and imaged. (B) sfGFP151TGA containing 5PrW or 5MTP was labeled with Alexa488-PCA and imaged. (C) Structure of DBCO-Cy5. (D) Structure of Alexa488-PCA.
Figure 5D:
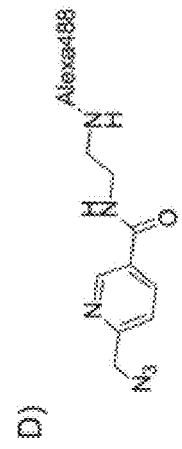
Figure 5A:
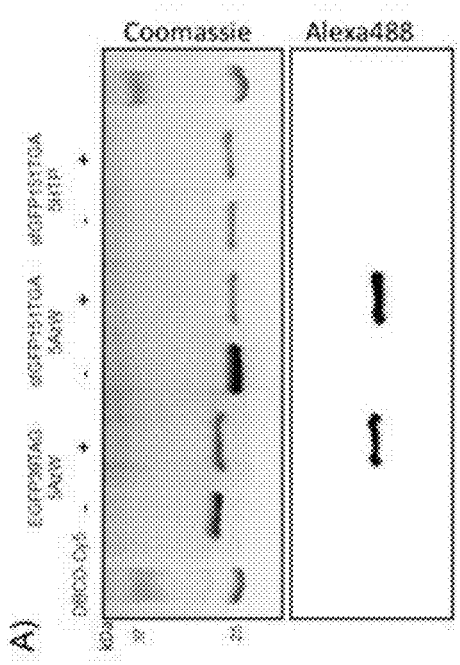
Figure 5C:
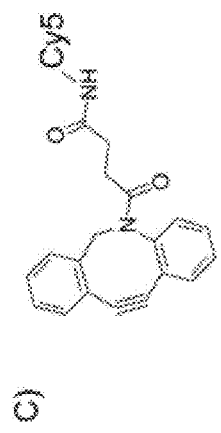

Table 1 below shows whole protein LCMS measurements.

sures the enhancement of sfGFP-151-TGA expression in the presence of a particular UAA, relative to a no-UAA control. EcTrpRS-h14 exhibited high polyspecificity towards four additional amino acids, whereas EcTrpRS-h9 also enabled the incorporation 5-aminotryptophan (FIG. 4B). In all cases, the reporter protein was isolated and characterized by MS analysis to confirm the incorporation of these UAAs (FIG. 4C, Table 1). To demonstrate the feasibility of the evolved EcTrpRS variants for UAA-incorporation into proteins in mammalian cells, EcTrpRS-h14 and h9 were cloned into the previously described pAcBac1 plasmid system together with its cognate tRNAEcTrpCUA, driven by CMV and U6 promoters, respectively, and this plasmid was co-transfected into HEK293T cells along with an EGFP-39-TAG reporter. Apart from 5-bromotryptophan, addition of all other UAAs led to robust reporter-expression relative to a no-UAA control (FIG. 4D). Expression levels were comparable with

| Reporter | UAA | aaRS | Expected mass | Observed mass | Note |
|---|---|---|---|---|---|
| sfGFP-151-TAG | None | None | No expr. | 27562 | pBK system in ATMW1 |
| sfGFP-151TAG | W | EcWRSwt | 27620 | 27562* | pBK/tac system in ATMW1 (Gln x-rxtive) |
| sfGFP-151-TGA | W | EcWRSwt | 27620 | 27621 | pBK/tac system in ATMW1 |
| sfGFP-151-TGA | 5HTP | Hit 14 | 27636 | 27637 | pBK/tac system in ATMW1 |
| sfGFP-151-TGA | 5MTP | Hit 14 | 27652 | 27652 | pBK/tac system in ATMW1 |
| sfGFP-151-TGA | 5BrW | Hit 14 | 27700 | 27699 | pBK/tac system in ATMW1 |
| sfGFP-151-TGA | 5AzW | Hit 14 | 27663 | 27660 | pBK/tac system in ATMW1 |
| sfGFP-151-TGA | 5PropW | Hit 14 | 27676 | 27674 | pBK/tac system in ATMW1 |
| sfGFP-151-TGA | 5HTP | Hit 9 | 27636 | 27637 | pBK/tac system in ATMW1 |
| sfGFP-151-TGA | 5AmW | Hit 9 | 27636 | 27635 | pBK/tac system in ATMW1 |
| EGFPwt | Y | None | 29683 | 29683 | Pacbac1 system in HEK293T |
| EGFP-39-TAG | BocK | MbPy1 | 29748 | 29748 | Pacbac1 system in HEK293T |
| EGFP-39-TAG | AzK | MbPy1 | 29761 | 29761 | Pacbac1 system in HEK293T |
| EGFP-39-TAG | W | EcWRSwt | 29707 | 29708 | Pacbac1 system in HEK293T |
| EGFP-39-TAG | 5HTP | Hit 14 | 29723 | 29724 | Pacbac1 system in HEK293T |
| EGFP-39-TAG | 5MTP | Hit 14 | 29736 | 29736 | Pacbac1 system in HEK293T |
| EGFP-39-TAG | 5BrW | Hit 14 | 29786 | 29785 | Pacbac1 system in HEK293T |
| EGFP-39-TAG | 5AzW | Hit 14 | 29748 | 29747 | Pacbac1 system in HEK293T |
| EGFP-39-TAG | 5PropW | Hit 14 | 29761 | 29760 | Pacbac1 system in HEK293T |
| EGFP-39-TAG | 5HTP | Hit 9 | 29723 | 29724 | Pacbac1 system in HEK293T |
| EGFP-39-TAG | 5AmW | Hit 9 | 29722 | 29721 | Pacbac1 system in HEK293T |
| sfGFP-151-TAG | 5AzW | Hit 14 | 28368 | 28366 | Labeled with DBCO-biotin |
| EGFP-39-TAG | 5AzW | Hit 14 | 30453 | 30453 | Labeled with DBCO-biotin |

Since the negative selection step in the aforementioned scheme only discriminates against natural amino acids, but not other UAAs, the isolated mutants are sometimes capable of polyspecificity: The ability to charge a number of structurally similar UAAs, while discriminating against the 20 canonical amino acids. The isolated EcTrpRS mutants were screened for polyspecificity towards other 5-substituted tryptophan derivatives (FIG. 4A), using an assay that meathose obtained with the well-established pyrrolysyl system for the same reporter. Incorporation of 5-azidotryptophan (5AzW) and 5-propargyloxytryptophan (5PrW) into proteins introduces unique azido- and alkyne-functionalities, respectively, that can be utilized for bioorthogonal conjugation reactions using Cu-mediated or Cu-free "click" chemistry. This was demonstrated by conjugating DBCO-Cy5 or Alexa Fluor 488 picolyl azide to the 5AzW or 5PrW residue in reporter proteins, using strain-promoted or Cu-dependent click conjugation, respectively (FIG. 5).

In conclusion, the present invention demonstrates here the feasibility of functionally replacing an endogenous tRNA/aaRS in *E. coli* with an *E. coli*-optimized counterpart from a different domain of life with no growth-penalty, and that the resulting strain can be used as a selection host for evolving variants of the liberated tRNA/aaRS pair for charging LAM. In addition to *E. coli*, these variants also enable genetic code expansion in eukaryotes. Since bacterial tRNA/aaRS pairs are generally orthogonal in eukaryotic cells, this approach holds the potential to provide additional "universal" tRNA/aaRS platforms. The present invention also introduces a new tryptophanyl-tRNA synthetase/tRNA platform, the utility of which was illustrated by introducing several new UAA additions to the genetic code of *E. coli* as well as eukaryotes, including 5AzW and 5PrW which enable selective bioconjugation reactions. Access to new universal tRNA/aaRS pairs will augment the structural diversity of genetically encoded UAA toolbox, and facilitate the development of powerful new technology involving simultaneous incorporation of multiple UAAs into a polypeptide in both *E. coli* and eukaryotes.

A number of tRNA/aminoacyl-tRNA synthetase (aaRS) pair has been developed to date to site specifically incorporate novel unnatural amino acids into proteins. The *E. coli* tryptophanyl-tRNA synthetase/tRNA pair developed in the present invention is unique and is a novel system because it can be used to incorporate new unnatural amino acids into proteins both in an engineered *E. coli* (the strain created where the endogenous tryptophanyl tRNA/aaRS pair was replaced with a counterpart from yeast) as well as in eukaryotic cells. This tRNA/aaRS pair has been engineered to enable site specific incorporation of six new unnatural tryptophan analogs into proteins expressed in both *E. coli* as well as eukaryotic cells.

The novel system described in the present invention has a number of potential applications. This includes site-specific bioconjugation using 5-azidotryptophan and 5-propargyltryptophan: These two unnatural amino acids can be incorporated into proteins expressed in both *E. coli* and eukaryotic cells (e.g., mammalian cells), and will allow site-specific bioconjugation using bioorthogonal azide-alkyne click reactions. This reaction can be used to site-specifically attach onto proteins a variety of entities such as drugs (for antibody-drug conjugation), attachment of biophysical probes (such as fluorophores, PET probe, etc.), polyethylene glycol (to improve pharmacokinetic properties of therapeutic proteins), onto recombinantly expressed proteins.

The same strategy can also be used to label the capsid proteins of human viruses, which can be subsequently labeled with either probes to study its infection process, or attach synthetic receptor binding agents that target specific cell-surface receptors to generate cell-specific viral vectors. The site-specific conjugation strategy can also be used to attach relevant proteins on surfaces (e.g, sensor chips, electrodes, etc.) with precise control over its orientation and site of attachment.

Another application involves 5-azidotryptophan, which is an aryl-azide, which upon irradiation forms a highly reactive nitrene intermediate. Its incorporation into proteins will allow light-induced capture of weak protein-protein interactions by the formation of a stable covalent linkage between the reactive nitrene intermediate and various residues from the interacting protein. This can be a powerful tool to interrogate weak or transient protein-protein interactions. Additionally tryptophan residues are frequently found at the interface of protein-protein interactions, making 5-azidotyrptophan an ideal candidate to capture such interactions.

The tryptophanyl-tRNA synthetase/tRNA pair of the present invention can be further engineered to incorporate new tryptophan analogs such as fluorinated-tryptophan (NMR as well as fluorescence probe), nitrated tryptophans (these residues form naturally as post-translational modifications, but their physiological relevance remain poorly characterized, since such modified proteins cannot be homogeneously produced; however, the ability to specifically charge these nitrated amino acid into specific sites of proteins using the technology of the present invention will circumvent this problem). The large active site of the tryptophanyl-tRNA synthetase can also be engineered to charge other unnatural amino acids with large side chains, such as fluorophores.

A variety of tryptophan analogs can be incorporated site-specifically into proteins expressed in *E. coli* or eukaryotic cells, enabling the study of the roles of functionally important tryptophan residues. 5-azidotryptophan, 5-propargytryptophan, which can be incorporated site-specifically into any protein expressed in bacteria or eukaryotic cells using our platform, will allow selective conjugation of various molecules to these proteins for applications such as PEGylation, generation of site-specific antibody-drug conjugates. 5-azidotryptophan which can be incorporated site-specifically into any protein expressed in bacteria or eukaryotic cells using the platform of the current invention, can be used as a photo-affinity probe to capture weak or transient protein-protein interactions within a living cell.

The present invention has many commercial applications and could be useful to manufacturers of research kits, and to companies pursuing antibody-drug conjugate or other protein modification (such as PEGylation). Without further elaboration, it is believed that one skilled in the art can, based on the above description, utilize the present invention to its fullest extent. The following specific embodiments and examples are, therefore, to be construed as merely illustrative, and not limitative of the remainder of the disclosure in any way whatsoever.

Without further elaboration, it is believed that one skilled in the art can, based on the above description, utilize the present invention to its fullest extent. The following specific embodiments and examples are, therefore, to be construed as merely illustrative, and not limitative of the remainder of the disclosure in any way whatsoever.

Materials and Methods

For cloning and plasmid propagation, the DH10b (Life Technologies) strain of *E. coli* was used. Polymerase chain reaction (PCR) was performed using the Phusion Hot Start II DNA polymerase (Fisher Scientific) using manufacturer's protocol. For purification of DNA (plasmid as well as PCR products, etc.) spin columns from Epoch Life Science were used. Restriction enzymes and T4 DNA ligase were obtained from New England BioLabs (NEB), DNA oligomers for PCR were purchased from Integrated DNA Technologies (IDT). Verification of cloned DNA by Sanger sequencing was performed by Eton Biosciences. Antibiotics, isopropyl β-D-1-thiogalactopyranoside (IPTG), and L-arabinose were purchased from Sigma-Aldrich or Fisher Scientific. Components of media were obtained from Fisher Scientific. Bacteria were grown on LB or M63 agar plates[17] and LB liquid medium with the following antibiotic concentrations unless otherwise mentioned: 95 µg/mL spectinomycin, 20 µg/mL chloramphenicol, and 100 µg/mL ampicillin, 30 µg/mL kanamycin, 15 µg/mL zeocin, 12 µg/mL tetracycline, 10 µg/mL gentamycin.

Sequences of the oligonucleotides used herein are shown in Table 2, below SEQ ID NOS: 6-74, respectively.

| SEQ ID NO: | | |
|---|---|---|
| 6 | TrpRS.Z.ab-F | ATCAGTCTATAAATGACCTTCTGCCCGCATTAGGGCTTCCGCATAGCGAAAATCAGGAATCGAAAAAGGTGTTGACAATTAATCATCGGC |
| 7 | TrpRS.Z.ab-R | TGTAGGCCGGATAAGGCGTTCACGCCGCATCCGGCATGAACAAAGCGCAATTTGCCAGCAATAGTGAAAGCTTGCAAATTAAAGCCTTCG |
| 8 | TrpRS150F | GTCGGCGACTCACGCAATGATATTCAGGCGGC |
| 9 | TrpRS150R | AGCGAGATGTGGAAACGGCGAGGCACTTCAC |
| 10 | Zeo-iR | CTGGTCCTGGACCGCGCTGATGAAC |
| 11 | TrpRS_sqiR | ATCCTGGCGCACGGTGATCGCGTGTTG |
| 12 | trpTKO.Gent-F | CAGTCGGTTAGAATACCTGCCTGTCACGCAGGGGGTCGCGGGTTCGAGTCCCGTCCGTTCCGCCACCCTAATTACGCACACCGTGGAAAC |
| 13 | trpTKO.Gent-R | CGGTAGAAGGATTTACTTCGGAGAGGGTTATTTCAGATAAAAAAAATCCTTAGCTTTCGCTAAGGATGATTTCCCGGGAAGCCGATCTCG |
| 14 | trpT GsqF | GGGGTCTCCCCATGCGAGAGTAGGGAAC |
| 15 | trpT GsqR | CCGTTGTCGATAGCACAACACTTTCACGGCC |
| 16 | galK.90 del | CGCGCAGTCAGCGATATCCATTTTCGCGAATCCGGAGTGTAAGAACGCGCAGTCAGCGATATCCATTTTCGCGAATCCGGAGTGTAAGAA |
| 17 | galK_KO_vert_F | TGGCAGAGACCCAGCG |
| 18 | galK_KO_verf_R | ACCCCAGTCCATCAGCG |
| 19 | dLambda.galK-F | GCTATGAAATAGAAAAATGAATCCGTTGAAGCCTGCTTTTTTATACTAACTTGAGCGAAACGGGAAGCCTGTTGACAATTAATCATCGGC |
| 20 | dlambda.galK dterm-R | GCCGCGTTGATTTTCTCCTGCCAGCTCATAATGCTGCCGCGTTGTAATATTCAGCACTGTCCTGCTCCTT |
| 21 | dlambda.sqF | GGTTTGATCAGAAGGACGTTGATCGGCGG |
| 22 | dlambda.sqR | TTCAGATACTGGCGATCATCCGCCACCAG |
| 23 | dLambda.sqiR | AGCCCATTGATAGTTTTCATGTGCGACAATGGGCG |
| 24 | EcWRS_mut7_8-F | GAATCCCATATGATGACTAAGCCCATCGTTNBTNSTGGCGCACAGCCCTCAGGTGAATTG |
| 25 | libEcWRS-NdeI-F | TACGCTTTGAGGAATCCCATATGATGACTAAGCCCATCG |
| 26 | EcWRS1_mut-VPViR | CAGATTAGTTTGATACAGCAGGATGTCCGCTGCCATC |
| 27 | EcWRS1_mut144-6_F | GATGGCAGCGGACATCCTGCTGTATCAAACTAATCTGnnknnknnkGGTGAAGACCAGAAACAGCACCTCGAACTGAGC |
| 28 | EcWRS_NcoI_PstI_termR | agcgtttgaaactgcagccatggtaccTTACGGCTTCGCCACAAAACCAATCGC |
| 29 | proK-F | GTTAGCCTGCAGGTAATTCCGCTTCGCAACATGTGAG |
| 30 | TrpH NcoI-R | GGCCGCCATGGCAAATTCGACCCTG |
| 31 | Trp40CCA-iR | GCAACCAGGCGCTTTGGAGGCGCCAGCTCTACCCTTGAG |
| 32 | Trp40CCA-iF | AGCTGGCGCCTCCAAAGCGCCTGGTTGCAGGTTC |
| 33 | SmR-R | CGCGCGCAGATCAGTTGGAAGAATTTGTCCACTACGTG |
| 34 | pNP-SpeI-F | ATAATGGACTAGTGCGCTTGTTTCGGC |
| 35 | pNP-BAB-R | CTCCTTAGATCTTCCTAGGTGGATCCACCATTCC |

-continued

| SEQ ID NO: | | |
|---|---|---|
| 36 | pEvol CmR SpeI-F | AATAATACTAGTGTTGATACCGGGAAGCCCTGG |
| 37 | pEvol_CmR PstI-R | AATAATCTGCAGCGAATTTCTGCCATTCATCCGCTTATTATCAC |
| 38 | CmR-TGA-7 | GCTAAGGAAGCTAAAATGGAGAAAAAAATCACTTGATATACCACCGTTGATATATCCCAATGGC |
| 39 | CmR-TGA-84 | GCAATGAAAGACGGTGAGCTGGTGTGATGGGATAGTGTTCACCCTTGTTACACC |
| 40 | CmR-TGAT-98 | CCCTTGTTACACCGTTTTCCATGAGTGATCTGAAACGTTTTCATCGCTCTGGAG |
| 41 | pRep-Kpnl-tR-F | AATAAtaggtaccGTTCTGTTGCCCGTCTCACTGGTG |
| 42 | pRep-EcWtR-NdeI/AvrII-R | AATAATAcatatgCCTAGGTGGCAGGGGCGGAGAGACTC |
| 43 | EcW-TGA-MSDM | GTTCAATTGGTAGAGCACCGGTCTTCAAAACCGGGTGTTGGGAGTTCGAG |
| 44 | T7F1 | CAGGTTCGCAGCGTCAGCCGGAATGGTACCG |
| 45 | T7R3 | GCGCCCGACAGCCTTCCAGTTCCTGTGAGAAATCAAGCCGGAAGCCGTAGCGTAC |
| 46 | T7F3 | GTACGCTACGGCTTCCGGCTTGATTTCTCACAGGAACTGGAAGGCTGTCGGGCGC |
| 47 | T7R4b | CCATGACCATGATTCACCGTGCACTGAAATACCATTAACATTGCTAAGAACG |
| 48 | T7F4 | CGTTCTTAGGAATGTTAATGGTATTTCAGTGCACGGTAATCATGGTCATGG |
| 49 | T7R5 | CGAAGGCGAAGCGGCATGCATAATGTGCCTGTCAAATGG |
| 50 | T7_mut-SbfI-F | AATAATcctgcaggCTACTCAGGAGAGCGTTCACCGAC |
| 51 | T7_mut-NotI/SbfI-R | AATAATCCTGCAGGGCGGCCGCTACGGGAGGGCTTACCATCTGG |
| 52 | Barnase MSDM 3 TGA | TTTAACTTTAAGAAGGAGATATACATATGGCATgaGTTATCAACACGTFFGACGGGGTTG |
| 53 | Barnase MSDM 45 TGA | GTGGCATCAAAAGGGAACCTTGCATGAGTCGCTCCGGGGAAAAGCATC |
| 54 | EcWtR-PstI-F | TTAGCCTGCAGTGTGCTFCTCAAATGCCTGAGGCCAGTFFGCTC |
| 55 | EcWtR-prok-oF | GCGCCCCGCATTTAGGGGCGTAGTTCAATTGGTAGAGCACCGGTC |
| 56 | EcWtR-proK-oR | ACTACGCCCCTAAATGCGGGGCGCATCTTACTGCGC |
| 57 | EcWtR-KpnI-R | ATATATGGTACCAAAAAATGGCAGGGGCGGAGAGACTCG |
| 58 | GFPflip-NotI-F+ | TCGATCCCGCGAAATTAATACGACTCACTATAG |
| 59 | sfGFP-T7 + lam-PstI-R | ATATACTGCAGCGCCAAGCTAGCTTGGATTCTCACCAATAAAAAACGC |
| 60 | MjYtR del F | TGGCAGGGGCGGAGAGACTCGAACTCC |
| 61 | MjYtR del oR | CGAGTCTCTCCGCCCCTGCCAAATTCGAAAAGCCTGCTAACGAGCAGG |
| 62 | EcWtR TGA MSDM | GTTCAATTGGTAGAGCACCGGTCTTCAAAACCGGGTGTTGGGAGTTCGAG |
| 63 | sfGFP (pEvol) TGA151 | CTCGAGTACAACTTTAACTCACACAATGTATGAATCACGGCAGACAAACAAAGAATGG |
| 64 | EcWRS1.FA.NotI-F | AATAATAgcggccgcATGACTAAGCCCATCGTTTTTGCTGGCGCAC |

-continued

| SEQ ID NO: | | |
|---|---|---|
| 65 | EcWRS-NotI-R | AATAATAgcggccgcTTACGGCTTCGCCACAAAACCAATCGC |
| 66 | pUltraII-tRsqR | GGTGCCCTTAAACGCCTGGTTGC |
| 67 | EcTrpRS-NdeI-F | AAtAAAcatatgATGACTAAGCCCATCGTTTTTAGTGGCGCAC |
| 68 | EcTrpRS-PstI-R | TTATTCTGCAGTTACGGCTTCGCCACAAAACCAATCGC |
| 69 | TrpRS-R EcoRI | TTATTATTGAATTCTTACGGCTTCGCCACAA |
| 70 | TrpRS-F-NheI | AATAAATGCTAGCATGACTAAGCCCATC |
| 71 | U6-R tRNAtrp* AvrII | AATTATTGCTAGCAAAAAATGGCAGGGGCG |
| 72 | tRNAtrp* Nhe-R | AATTATTGCTAGCAAAAAATGGCAGGGGCG |
| 73 | EcWRS_mamNheI-F | aataataGCTAGCgccaccATGACTAAGCCCATCGTT |
| 74 | EcWRS_mamEcoRI-R | AATAATAgaattcTTACGGCTTCGCCACAAAACCAATCGC |

Statistical methods. For all expression analysis (sfGFP in bacteria or EGFP in HEK293T cells), mean of three independent experiments were reported, and error bars represent standard deviation. For the growth rate analysis, each data point represent the mean O.D.600 of three independent cultures of the same strain (error bars represent S.D.). In our experience, a mean of three experiments provides adequate levels of accuracy for these experiments.

Strains, cell lines. The EcNR1 strain was a gift from Prof. George M. Church. The HEK293T cell-line was obtained from ATCC, and propagated without further confirmation. Cell lines are regularly monitored for Mycoplasma contamination. Even though HEK293T is listed under misidentified cell lines in ICLAC database, we used it for our expression analyses as a representative mammalian cell-line. Given the wide-spread use of this cell-line as a model mammalian expression host, and since our conclusions does not rely on its specific identity (beyond a representative mammalian cell-line), we believe that the use of this strain is justified.

Lambda-Red recombination. All strains were derived from EcNR1[16]. This strain contains temperature inducible lambda-recombinase genes (Exo, Beta, Gam) and a constitutive ampicillin resistance gene disrupting the bioA/bioB genomic locus. Strains were grown in 10 mL LB at 30+ C. to 0.5 $OD_{600}$ and then induced for 15 minutes in a 42° C. water bath (250 rpm). The cell pellet was then washed twice with 10 mL $ddH_2O$ by centrifuging at 4500×g. Cells were resuspended in residual $ddH_2O$ (~250 μL) and 50 μL aliquots were electroporated with 50 ng dsDNA or 2 μM 90 bp oligo containing 45-77 bp genomic homology, depending on the desired recombination. Electroporated cells were recovered for 1-6 hours and plated on either LB or minimal media. Single colonies from selection plates were re-streaked and subjected to colony PCR using KAPA-2G polymerase (Kapa Biosystems), following manufacturer's instructions, to verify desired recombination.

Building ATMW1. EcNR1 was transformed with pUltraG_ScW40$_{CCA}$. To remove the E. coli tryptophanyl-tRNA synthetase (trpS) from this strain, the gene encoding zeocin resistance (ShBle) driven by the EM-7 promoter and the CYC1 transcription terminator was PCR amplified using primers TrpR S.Z.a.b-F and TrpRS.Z.ab-R to generate the PCR product trpS::Zeo$^R$. 50 ng of the trpS::ZeoR PCR cassette was transformed in the recombination following the aforementioned protocol, and the resulting strains were plated on LB-Agar plates supplemented with Zeocin. The resulting colonies were screened via colony PCR using TrpRS150F+TrpRS150R, TrpRS150F⇌Zeo-iR, and TrpRS150F+TrpRS_sqiR, as well as sequencing these colony PCR products. This strain was named EZ4.

To replace the E. coli trp-tRNA$_{CCA}$ (trpT), the trpT::Gent$^R$PCR cassette was amplified using trpTKO.Gent-F and trpTKO.Gent-R (965 bp). 50 ng of trpT::Gent$^R$ PCR cassette was transformed into EZ4, induced as previously described. Resulting gentamycin resistant colonies were screened for the desired recombination using colony PCR primers trpT GsqF and trpT GsqR, as well as sequencing of the PCR product. The resulting strain was named EZG4.

2 μM 90 bp oligo, galK.90 del, was used to delete galK from the endogenous genomic location. Following transformation, cells were recovered for 6 hours, washed twice with M9 minimal media at 5000×g for 5 min and 100 μL of a $10^4$ dilution was plated on M63 minimal media supplemented with glycerol and 2-deoxygalactose to select for successful galK deletion. Colony PCR was used to verify the deletion of gall using galK_KO_verf-F/R. The resulting strain was named G4.

galK.PCR cassette was amplified containing the endogenous promoter dlambda.GalK-F and dlambda.galK dterm-R (1348 bp) and was used to remove the λ-RED genes from the G strain. Following transformation of 50 ng of this PCR product into strain G, successful insertion of the galK.PCR cassette into the λ-RED site was selected by plating the cells on M63 plates containing galactose as the sole carbon source for three days.[17] Surviving colonies were screened by colony PCR using dlambda.sqF with diambda.sqR or dLambda.sqiR for the desired deletion. This final strain was named ATMW1 (EcNR1 trpS::Zeo$^R$ trpT::Gent$^R$ ΔgalK λ-RED::galK.

Essentially the same procedure as described above for producing ATMW1 was used to produce BL21(DE3).

Growth Comparison. 5 mL starter cultures of EcNR1G, EcNR1G+FpUltraG_ScW40$_{CCA}$, and ATMW1 strains were grown for 16 hrs in LB with all strain-dependent antibiotics. For each strain, the starter culture was diluted to an initial OD600 of 0.01 in three identical cultures of 80 mL LB with no antibiotics and allowed to grow in 250 mL sterile Erlenmeyer flasks at 30° C., with shaking (250 rpm). Growth was monitored every 30 min by measuring $OD_{600}$ in a 10 mm cuvette.

Assessment of tRNA/aaRS activity using a chloramphenicol reporter. Overnight cultures of ATMW1 harboring pRepAC-EcW-TAG or pRepThEcW-TGA, with or without pBK-EcWRSwt, were diluted to an $OD_{600}$ of 0.1 and 3 µL was spot plated on LB agar plates supplemented with kanamycin (+pBK plates), spectinomycin, tetracycline, and varying chloramphenicol concentrations. Growth was analyzed after 48 hrs of incubation at 37° C.

Assessment of tRNA/aaRS activity using a sfGFP151 reporter. EcNR1 or ATMW1 harboring pEvol T5-EcW sfGFP151 (TAG or TGA) with or without pBK-EcWRSwt, pBK-EcWRS-h14, or pBK-EcWRS-h9 were grown overnight in LB. The starter cultures were diluted in LB supplemented with required antibiotics to 0.05 $OD_{600}$. Cultures were grown at 30° C. or 37° C. (30° C. when comparing to progenitor strain EcNR1) until 0.55 $OD_{600}$, at which point the sfGFP expression was induced with a final concentration of 1 mM IPTG. Unnatural amino acids (UAA) were added during induction to a final concentration of 1 mM. Cultures were grown for an additional 17-20 hours at 37° C. with shaking. To evaluate sfGFP expression, cells from 150 µL of the cultures were pelleted at 5000×g, resuspended in 150 µL PBS, and transferred to a 96-well clear-bottom assay plate. Fluorescence was measured by using a SpectraMAX MS (Molecular Devices) (Ex. 488 nm; Em. 534 nm). Fluorescence for each sample was normalized using its $OD_{600}$.

Protein purification. To maximize the yield of UAA-modified protein expression, a different plasmid combination was used: EcTrpRS-h14 and -h9 was cloned into a pEvoltac plasmid that expresses them from a strong tact promoter, while the tRNA$^{EcTrp}_{UCA}$ is expressed from the proK promoter. The sfGFP reporter gene (sfGFP-151-TGA or wild type sfGFP) was expressed from pET22b-T5lac plasmid driven by the strong t5.lac promoter. Overnight expression cultures were centrifuged and resuspended in lysis buffer: B-PER Bacterial Protein Extraction Reagent (Thermo Scientific)+1× Halt Protease Inhibitor Cocktail (Thermo Scientific)+0.01% Pierce Universal Nuclease (Thermo Scientific). After 30 min incubation at room temperature, the lysate was clarified by centrifuging at 22,000×g for 5 min. The C-terminally polyhistidine tagged soluble sfGFP in the supernatant was purified using a HisPur Ni-NTA resin (Thermo Scientific) following manufacturer's protocol. Protein purity was confirmed by SDS-PAGE and purified protein molecular weight was confirmed by ESI-MS (Agilent Technologies 1260 Inifinity ESI-TOF).

Construction of the EcWRS-5HTP pBK library. Overlap extension was used to introduce degenerate codons, creating the five-residue tryptophanyl tRNA-synthetase library pBK-EcWRS1.5 (786,432 diversity): F7-NBT, S8-NST, V144-NNK, P145-NST, V146-NNK. Using Illusion HSII (Fisher Scientific) and manufacturer's protocol, EcWRS1_mut7-8-F+EcWRS1_mut-VPViR and EcWRS1_mut144-6_F+EcWRS_NcoI_PstI_termR were used to PCR amplify the N-term and C-term of the EcWRS PCR product, respectively. The N-term and C-term PCR products were joined together by overlap extension PCR using the following terminal primers: libEcWRS-NdeI-F and EcWRS_NcoI_PstI_termR. These inserts were digested with NdeI/NcoI (NEB) and ligated by T4 DNA Ligase (NEB) into pBK vector cut with the same restriction enzymes. The ligation mixture was ethanol precipitated with Yeast-tRNA (Ambion) and transformed into electrocompetent DR10b cells. The library was covered using ~$10^7$ distinct colony forming units.

Selection for Synthetase Charging 5HTP. ATMW1 was co-transformed with the pBK-EcWRS1.5b library and the positive selection reporter plasmid pRepJI EcW TGA. The reporter plasmid harbors a lpp-promoted E. coli tRNA$^{Tr}_{PUCA}$, a CAT reporter modified to contain TGA codons (Q98TGA), an arabinose-inducible T7 RNA polymerase harboring two TGA nonsense codons (at positions 8 and 114), and a wild-type GFPuv reporter expressed from a t7 promoter. Suppression of CAT leads to chloramphenicol resistance, and suppression of T7 RNA polymerase drives expression of a t7-promoted GFPuv, 9.2×$10^7$cfu (colony forming units) were plated on LB+0.5× Spec/0.5× Tet/Kan/ 0.02% arabinose+chloramphenicol (25, 35, 45 µg/mL) in the presence of 1 mM 5HTP for 36 hrs at 37° C.

Colonies from the 35 and 45 µg/mL chloramphenicol positive selection plates were harvested, and the pBK plasmids harboring mutant EcTrpRS were purified by miniprep and gel purification. These were co-transformed into ATMW1 harboring the negative selection plasmid pNegJ2-EcW (araBad-Barnase harboring two TGA codons at 3 and 45). 3×$10^7$ cfu were plated on LB+Amp/0.5×Kan/0.02% arabinose and incubated for 12 hrs at 37° C. Cells were harvested and library pBK plasmid was purified by miniprep/gel purification.

Isolated pBK plasmids from the negative selection were transformed again into ATMW1 pRepJI-EcW TGA, and $10^6$ cfu were plated on LB+0.5×Spec/Tet/Kan/0.02% arabinose+ chloramphenicol (30, 40, 50 µg/mL) in the presence or absence of 1 mM 5HTP for 18 hrs, 37° C., which revealed significantly higher number of colonies in the presence of the UAA. 96 colonies were picked into a 1 mL LB supplemented with Spec/Tet/Kan in deep 96 well polypropylene plates and grown overnight. The resulting cultures were diluted to ~0.01 $OD_{600}$ and 3 µL of each was spot plated on LB/Agar plates supplemented with Spec/Tet/Kan, and chloramphenicol (50, 60 µg/mL) in the presence or absence of 5HTP. Four clones exhibiting the most prominent UAA dependent growth were picked and sequenced.

Assessing activity of tRNA$^{EcTrp}_{CUA}$ and synthetase hits in HEK293T. Dulbecco's modified Eagle's medium (high glucose DMEM) supplemented with 10% fetal bovine serum (FBS) and Penicillin/Streptomycin (0.5×) was used to culture HEK293T Cells were incubated in a humidified incubator at 37° C. in the presence of 5% $CO_2$. HEK293T were seeded at a density of 600,000 per well for a 12-well plate one day prior to transfection and transfected at ~70% confluence. Polyethylenimine (PEI, Sigma) and DNA were mixed at a ratio of 4 µL PEI (1 mg/mL) to 1 µg DNA in DMEM. After 20 min incubation, 100 µL of this mixture was used to transfect one single well in a 12-well plate. For these transfections, 500 ng of pAcBac EGFP39*U6-EcWtR. TAG was transfected in the presence or absence of pAcBac-TrpRS (wt, h14, or h9) U6-EcWtR TAG. UAAs were added to the culture medium to a final concentration of 1 mM at the time of transfection. Fluorescence images were taken at 48 hrs post-transfection using a Zeiss Axio Observer fluorescence microscope.

To obtain EGFP39*-expression data, cells were harvested, washed once with PBS buffer (5000×g), and lysed with CelLytic-M lysis buffer (Sigma) supplemented with 1× Halt protease inhibitor and 0.01% Pierce universal nuclease. 50 µL lysis buffer was used for each well of a 12-well plate, and was allowed to incubate for 20 min. After incubation, the lysate was clarified by centrifuging at 22000×g for 5 minutes and was transferred to a clear bottom 96-well assay plate. Fluorescence was measured using a SpectraMAX M5 (Molecular Devices) (Ex. 488 nm; Em. 534 nm).

Isolation of EGFP-39-TAG reporters from HEK293T. HEK293T cells were cultured as previously described. One day prior to transfection, cells were seeded at a density of 8-million cells/10 cm dish. 50 μL PEI MAX (Polysciences) was mixed with 10 μg total DNA (5 μg reporter, 5 μg tRNA/aaRS plasmid) with 180 μL DMEM (no FBS), incubated for 20 min, and added evenly to the dish at 90% confluence. Desired UAAs were supplemented at a final concentration of 1 mM and cells were allowed to express the desired protein for 48 hours.

Cells from a 10 cm dish were harvested and lysed with 600 μL CelLytic M lysis buffer (Sigma, 1× Halt protease inhibitor, 0.01% Pierce universal nuclease). Lysate was clarified as described and purified via $Ni^{2+}$-NTA, following manufacturer's protocol. Purified protein was analyzed by SDS-PAGE and molecular weight was confirmed by ESI-MS (Agilent Technologies 1260 infinity ESI-170F).

Click-labeling of 5AzW and 5PrW residues. Purified proteins containing 5AzW were incubated with or without 20 μM DBCO-Cy5 (Sigma) for 1 hr in the dark at room temp. Proteins samples were resolved by SDS-PAGE gel and imaged using Cy5 specific settings on a Chemidoc MP Imaging System (Bio-Rad). The SDS-PAGE gels were then coomassie stained and imaged.

5PrW containing proteins were labeled using the Click-iT Plus Alexa Fluor Picolyl Azide kit (Life Technologies) with a modified protocol. The following were mixed in order; 1 μg protein (4 μL), 3 μL 10× buffer additive, 0.3 μL 100 mM $CuSO_4$, 0.3 μL copper protectant, 1.2 μL Alexa 488 PCA (50 μM, 2 μM final), 21.2 μL 1× Click-iT reaction buffer, to a final volume of 30 μL. Samples were incubated for 40 min in dark and subsequently resolved by SDS-PAGE and imaged using the Chemidoc MP Imaging System (Bio-Rad) with Alexa488 specific settings.

Tryptic Digestion and LC-MS/MS Analysis of reporter proteins. 12 μg purified reporter protein was treated with DMSO (0.2 μM) and precipitated with 5 μL 100% solution of trichloracetic acid. Sample was frozen at −80 C overnight. Thawed sample was centrifuged at 15000 rpm for 10 min, room temp. Supernatant was removed and pellets were vortexed to resuspend in 500 μL cold acetone. Samples were then centrifuged at 5000 rpm for 10 min. Acetone was then removed and pellet was allowed to air dry. Pellet was resuspended in 30 μL 8M urea in PBS followed by 70 μL 100 mM ammonium bicarbonate and then 1.5 μL 1 M DTT was added. Samples were incubated at 65° C. for 15 minutes. After incubation, 2.5 μL, of 500 mM iodoacetamide in PBS was added and the sample was left at room temperature for 30 minutes. Following incubation, 120 μL PBS was added to each sample and vortexed rapidly. 4 μL of trypsin was added to samples, followed by 2.5 μL 100 mM $CaCl_2$. Samples were then agitated for 37° C. overnight. Trypsin was then quenched with 10 μL formic acid and pelleted at 15,000 rpm for 20 min. Supernatants were stored at −20° C.

Samples were subsequently analyzed by LC MS/MS using a LTQ Orbitrap XL mass spectrometer (Thermo-Fisher) coupled to an EASY-nLC 1000 nanoLC (Thermo-Fisher). 10 μL samples were loaded onto 100 μm fused silica column with a 5 μm tip packed with 10 cm of Aqua C18 reverse phase resin (Phenomenex) using the EASY-nLC 1000 autosampler. The digests were eluted using a gradient 0-100% Buffer B in Buffer A (Buffer A: 95% water, 5% acetonitrile, 0.1% formic acid; Buffer B; 20% water, 80% acetonitrile, 0.1% formic acid). The flow rate through the column was set to 400 nL/min and the spray voltage was set to 3.5 kV. One fuLl MS scan (FTMS) (400-1800 MW) followed by 7 data dependent scans (ITMS) of the nth most intense ion from the imported mass list with dynamic exclusion. The tandem MS data were searched using the SEQUEST algorithm using a concatenated target/decoy variant of the human IPI databases. A static modification of +57.02146 on cysteine was specified to account for iodoacetamide alkylation. SEQUEST output files were filtered using DTASelect 2.0.

Construction of Various Plasmids:

Complementation plasmid pUltraG_ScW40$_{CCA}$. Previously reported pUltra Hit14, containing a tacI promoted wild type yeast tryptophanyl-tRNA synthetase and proK promoted evolved yeast tRNA amber suppressor,[14] was used to generate additional pUltra derivatives. To generate pUltra_ScW40$_{CUA}$, a previously evolved tRNA 40A was amplified from 40A gblock (IDT) using primers proK-F and TrpH NcoI-R.[15] The full-length prok-tRNA PCR product was cloned into pUltra. Hit14 via. SbfI/NcoI (NEB), producing pUltra ScW40$_{CUA}$.

To build pUltraG_ScW40$_{UCA}$, a complementation plasmid with a constitutively active synthetase, the tacI promoter region was removed by digesting the pUltra_ScW40$_{CUA}$ vector with XbaI/SbfI, and a glnS'-ScWRS cassette was amplified from an pEVOL[8] derived plasmid, pEvol ScW, using glnS-XbaI-F+glnS-SbfI-R and subsequently cloned using the same set of restriction sites. The 40A tRNA anticodon was then mutated to CCA using overlap extension PCR. The two PCR products were amplified with proK-F+Trp40CCA-iR and Trp40CCA-iF+SmR-R, overlap extended, and cloned into pUltraG_ScW40$_{CUA}$ using SbfI/NcoI, producing the final complementation plasmid pUltraG_ScW40$_{CCA}$.

Construction of selection plasmids. To generate the TAG positive selection plasmid, pRep-ScW14[14] was digested with SpeI/BglII. The lpp-promoted E. coli tRNA$^{Trp}_{CUA}$ was amplified from gblock I-EcWtR TAG with pNP-SpeI-F+pNP-BAB-R. The PCR product was digested with SpeI/BamHI, and cloned into the SpeI/BglII sites of the pRep vector creating pRepAC-EcWtR-TAG.

In order to create a selection plasmid based on TGA suppression, a smaller pRep-Cm3b[32] was used as a starting template. In order to delete the chloramphenicol-UPP fusion protein, chloramphenicol acetyl transferase was amplified from pEvol[33] with pEvol CmR SpeI-F+pEvol CmR PstI-R, digested with SpeI/PstI, and ligated into the same sites of pRep-Cm3b, creating pRep-Cm3J-wt. TGA sites were introduced into the CAT gene by replacing G7, I84, or Q98 via site-directed mutagenesis using primers CmR-TGA-7, CmR-TGA-84, or CmR-TGAT-98, building three different reporters. The lpp-promoted E. coli tRNA$^{Trp}_{CUA}$ was amplified from pRepAC-EcWtR-TAG with pRep-KpnI-tR-F and pRep-EcWtR-NdeI/AvrII-R and cloned via KpnI/AvrII into these pRep-Cm3J plasmids, creating three different pRep-Cm3J-# TGA-EcWtR TAG. The anti-codon of the tRNA was mutated to TGA using site-directed mutagenesis with primer EcWtR-TGA-MSDM. While all three reporter plasmids exhibited desired phenotypes upon TGA suppression, pRep-Cm3J-98TGA-EcWtR was used for the subsequent cloning steps.

To add the T7 RNA polymerase-GFPuv reporter system into pRep-Cm3J-98TGA-EcWtR, these elements were amplified from pRepAC-EcWtR-TAG using multiple overlap extension PCR reactions to change the two TAG nonsense codons in the T7RP gene to TGA: Three PCR products were first amplified using T7F1+T7R3, T7F3+T7R4b, T7F4+T7R5, which were overlapped to produce T7-araC PCR cassette. This cassette was first cloned back into pRepAC-EcWtR-TAG via KpnI/NsiI, and then the entire GFP-T7araC cassette was amplified from the resulting plasmid with T7_mut-SbfI-F+T7_mut-NotI/SbfI-R, digested with SbfI, and ligated into the PstI site of pRep-Cm3J-98TGA-ECWtR vector producing pRepJI-EcW.

The negative selection plasmid was built by modifying an existing pNeg plastnid.[3,4] The two barnase suppression sites (3TAG, 45TAG) were mutated to TGA with site-directed mutagenesis using primers Barnase MSDM 3 TGA and Barnase MSDM 45 TGA, creating plasmid pNegJ2. The *E. coli* tRNA$^{Trp}{}_{CUA}$ was amplified from pRep-Cm3J-98TGA-EcWtR with pRep_NegtR-EcoRI-R and pRep_KpnI-tR-F and then cloned into pNegJ2, replacing the preexisting tRNA, creating pNegJ2-EcW.

Construction of bacterial suppression plasmids. Since ATMW1 uses the pUltraG plasmid to express the yeast tryptophanyl pair, the suppression plasmids cannot use the CloDF13 origin of replication, or the spectinomycin marker. The previously described pEvoltac MjY plasmid,[8] which harbors a compatible p15a origin of replication and a chloramphenicol resistance marker, was used as the template to generate these plasmids. The plasmids pEvolT5 EcW sfGFP151 (TAG or TGA) were built to allow the rapid evaluation of various EcTrpRS mutants isolated from the selection scheme (encoded in pBK vector). Initially, a t5.lac-promoted sfGFP-151-TAG was amplified from pET22b-T5-sfGFP151TAG using GFPflip-NotI-F+sfGFP-T7+lam-PstI-R and subsequently cloned into pEvoltac MjY using EcoNI/PstI, to generate pEvolT5 MjY sfGFP151TAG.

A proK-promoted *E. coli* tRNA$^{Trp}{}_{CUA}$ was assembled by overlap extension as follows. The proK promoter was amplified from pUltraG ScW40 using EcWtR-PstI-F+EcWR proK-oR, which was overlapped with tRNA$^{EcTrp}{}_{CUA}$ amplified with EcWtR-proK-oF and EcWtR-KpnI-R. This PCR product was cloned into pEvoltac MjY sfGFP151TAG using PstI/KpnI, producing pEvottac MjY EcWtR sfGFP151TAG. The MjY tRNA was removed by using Polymerase Incomplete Primer Extension (PIPE) cloning with primers MjYtR-del-oF and MjYtR-del-oR, producing the final plasmid pEvolT5-EcW-sfGFP151TAG. Additionally, site-directed mutagenesis was used to build the TGA reporter pEvolT5-EcW-sfGFP151TGA with primers sfGFP(pEvol)TGA151 and EcWtR TGA MSDM.

For more efficient protein expression using evolved tRNA/aaRS pairs, plasmids containing the proK promoted tRNA$^{EcTrp}{}_{UCA}$ and loci promoted EcWRS-h14 or -h9 were assembled. The tRNA in pEvoltac MjY was first replaced by amplifying the EcTrp-tRNA$_{UCA}$ from pEvoltac-EcW-sfGFP151TGA with EcWtR PstI-F and pUltraII-tRsqR, and subsequently cloning into PstI/SphI to generate pEvoltac-EcW-MjYRS. EcWRS-h14 and -h9 were then amplified from their respective pBK plasmids using EcWRS-h14 FA.NotI-F and EcWRS-NotI-R, digested with NotI, and cloned into NotI-digested pEvoltac-EcW-MjYRS-pAcF, producing pEvoltac-EcW-TGA-h14 or -h9.

pBK MjYRS[4] was used as a template to introduce tryptophanyl-tRNA synthetase variants. Top10 genomic DNA was purified using previously described protocols,[34] and used as the template to amplify the EcTrpRS using EcTrpRS-NdeI-F and EcTrpRS-PstI-R. The PCR product was digested with NdeI/PstI, producing pBK EcWRS.

Construction of mammalian suppression plasmids. Previously reported pAcBac1 was used to generate mammalian reporter and suppression plasmids.[30] To build pAcBac1 TrpRS, EcTrpRS was amplified from Top10 genomic DNA with TrpRS-F-NheI+TrpRS-R-EcoRI and subsequently cloned into pAcBac1 via NheI/EcoRI. U6-EcWtR Gblock was used as a template and amplified with tRNAatrp*-NheI-R+tRNAtrp*Nhe-R to produce the human U6 promoted *E. coli* tRNA$^{EcTrp}{}_{CUA}$ PCR product. This PRC product was then digested with AvrII/NheI and cloned into the AvrII site in the pAcBac variants, resulting in pAcBac1-TrpRS-U6EcWtR-TAG and pAcBac1-EGFP39*-U6EcWtR-TAG. EcWRS-h14 and -h9 synthetase variants were cloned into the pAcBac1-TrpRS-U6EcWtR-TAG plasmid via NheI/EcoRI digestion after amplification with EcWRS_mamNheI-F+EcWRS_mamEcoRI-R to make pAcBac1-EcWRS-h14-U6EcWtR-TAG and pAcBac1-EcWRS-h9-U6EcWtR-TAG.

Unnatural amino acids 5HTP and 5MTP were purchased from Fisher Scientific, 5BrW and 5AmW were purchased from Chem-Impex International (Wood Dale, Ill.). AzK was purchased from Sirius Fine Chemicals. 5AzW was synthesized as previously described.[35]

Yield of sfGFP reporters incorporating various UAAs expressed in ATMW1 are shown in Table 3, below.

TABLE 3

| UAA | aaRS | Yield (mg/L) |
|---|---|---|
| 5HTP | h14 | 92 |
| 5MTP | h14 | 89 |
| 5BrW | h14 | 25 |
| 5AzW | h14 | 80 |
| 5PrW | h14 | 61 |
| 5AmW | h9 | 68 |
| sfGFPwt | N/A | 140 |

REFERENCES

1. Chin, J. W. Expanding and reprogramming the genetic code of cells and animals. *Amur. Rev. Biochem*, 83, 379-408 (2014).

2. Dumas, A., Lercher, L., Spicer, C. D. & Davis, B. G. Designing logical codon reassignment-Expanding the chemistry in biology. *Chem. Sci.* 6, 50-69 (2015).

3. Liu, C. C. & Schultz, P. G. Adding new chemistries to the genetic code. *Annu. Rev. Biochein.* 79, 413-444 (2010).

4. Wang, L., Brock, A., Herberich, B. &. Schultz, P. G. Expanding the genetic code of *Escherichia coli. Science* 292, 498-500 (2001).

5. Chin, J. W. et al. An expanded eukaryotic genetic code. *Science* 301, 964-967 (2003).

6. Wan, W., Tharp, J. M. & Liu, W. R. Pyrrolysyl-tRNA synthetase: an ordinary enzyme but an outstanding genetic code expansion tool. *Biochim. Biophys. Acta* 1844, 1059-1070 (2014).

7. Anderson, J. C. et al. An expanded genetic code with a functional quadruplet codon. *Proc. Natl. Acad. Sci. USA* 101, 7566-7571 (2004).

8. Chatteijee, A., Sun, S. B., Furman, J. L., Xiao, H. & Schultz, P. G. A versatile platform for single- and multiple-unnatural amino acid mutagenesis in *Escherichia coli. Biochemistry* 52, 1828-1837 (2013).

9. Neumann, H., Wang, K., Davis, L., Garcia-Alai, M. & Chin, J. W. Encoding multiple unnatural amino acids via evolution of a quadruplet-decoding ribosome. *Nature* 464, 441-444 (2010).

10. Wan, W. et al. A facile system for genetic incorporation of two different noncanonical amino acids into one protein in *Escherichia coli. Angew. Chem. Int. Ed.* 49, 3211-3214 (2010).

11. Xiao, et al. Genetic incorporation of multiple unnatural amino acids into proteins in mammalian cells. *Angew. Chem. Int. Ed.* 52, 14080-14083 (2013).

12. Iraha, F. et al. Functional replacement of the endogenous tyrosyl-tRNA synthetase-tRNATyr pair by the archaeal tyrosine pair in *Escherichia coli* for genetic code expansion. *Nucleic Acids Res.* 38, 3682-3691 (2010).

13. Chatterjee, A., Xiao, H. & Schultz, P. G. Evolution of multiple, mutually orthogonal prolyl-tRNA synthetase/tRNA pairs for unnatural amino acid mutagenesis in *Escherichia coli. Proc. Natl. Acad. Sci. USA* 109, 14841-14846 (2012).

14. Chatterjee, A., Xiao, H., Yang, P. Y., Soundararajan, G. & Schultz, P. G. A tryptophanyl-tRNA synthetase/tRNA pair for unnatural amino acid mutagenesis in *E. coli. Angew. Chem. Int. Ed.* 52, 5106-5109 (2013).

15. Ellefson, J. W. et al. Directed evolution of genetic parts and circuits by compartmentalized partnered replication. *Nat. Biotechnol.* 32, 97-101 (2014).

16. Wang, H. H. et al. Programming cells by multiplex genome engineering and accelerated evolution. *Nature* 460, 894-898 (2009).

17. Warming, S., Costantino, N., Court, D. L., Jenkins, N. A. & Copeland, N. G. Simple and highly efficient BAC recombineering using galK selection. *Nucleic Acids Res.* 33, e36 (2005).

18. Soll, L. & Berg, Recessive lethal nonsense suppressor in *Escherichia coli* which inserts glutamine. *Nature* 223, 1340-1342 (1969).

19. Jahn, M., Rogers, M. J. & Soil, D. Anticodon and acceptor stem nucleotides in tRNA(Gln) are major recognition elements for *E. coli* glutaminyl-tRNA synthetase. *Nature* 352, 258-260 (1991).

20. Rogers, M, J., Adachi, T., Inokuchi, H. & Soll, D. Switching tRNA(Gln) identity from glutamine to tryptophan. *Proc. Natl. Acari Sci. USA* 89, 3463-3467 (1992).

21. Kopelowitz, J., Hampe, C., Goldman, R., Reches, M. & Engelberg-Kulka, H. Influence of codon context on UGA suppression and readthrough. *Biol.* 225, 261-269 (1992).

22. O'Donoghue, P. et al. Near-cognate suppression of amber, opal and quadruplet codons competes with aminoacyl-tRNAPyl for genetic code expansion. *FEBS Lett.* 586, 3931-3937 (2012).

23. Santoro, S. W., Wang, L., Herberich, B., King, D. S. & Schultz, P. G. An efficient system for the evolution of aminoacyl-tRNA synthetase specificity. *Nat. Biotechnol.* 20, 1044-1048 (2002).

24. Zhang, Z. et al. Selective incorporation of 5-hydroxytryptophan into proteins in mammalian cells. *Proc. Natl. Acad. Sci. USA* 101, 8882-8887 (2004).

25. Antonczak A. K. et al. Importance of single molecular determinants in the fidelity of expanded genetic codes. *Proc. Natl. Acad. Sci. USA* 108, 1320-1325 (2011).

26. Cooley, R. B., Karplus, P. A. & Mehl, R. A. Gleaning unexpected fruits from hard-won synthetases: probing principles of permissivity in non-canonical amino acid-tRNA synthetases. *ChemBioChein* 15, 1810-1819 (2014).

27. Young, D. D. et al. An evolved aminoacyl-tRNA synthetase with atypical polysubstrate specificity. *Biochemisiry* 50, 1894-1900 (2011).

28. Prather, N. E., Murgola, E. J. & Mims, B. H. Primary structure of an unusual glycine tRNA UGA suppressor. *Nucleic Acids Res.* 9, 6421-6428 (1981).

29. Raftery, L. A., Egan, J. B., Cline, S. W. & Yarus, M. Defined set of cloned termination suppressors: in vivo activity of isogenetic UAG, UAA, and UGA suppressor tRNAs. *J. Bacteriol,* 158, 849-859 (1984).

30. Chatteijee, A., Mao, H., Bollong, M., Ai, H. W. & Schultz, P. G. Efficient viral delivery system for unnatural amino acid mutagenesis in mammalian cells. *Proc. Natl. Acad. Sci. USA* 110, 11803-11808 (2013).

31. Guo, J., Melancon, C. E., 3rd, Lee, H. S., Groff, D. & Schultz, P. G. Evolution of amber suppressor tRNAs for efficient bacterial production of proteins containing nonnatural amino acids. *Angew. Chem. Int. Ed.* 48, 9148-9151 (2009).

32. Melancon, C. E., 3rd & Schultz, P. G. One plasmid selection system for the rapid evolution of aminoacyl-tRNA synthetases. *Bioorg. Med. Chem. Lett.* 19, 3845-3847 (2009).

33. Young, T. S., Ahmad, I., Yin, J. A. & Schultz, P. G. An enhanced system for unnatural amino acid mutagenesis in *E. coli. J. Mol. Biol.* 395, 361-374 (2010).

34. Syn, C. K. & Swamp, S. A scalable protocol for the isolation of large-sized genomic DNA within an hour from several bacteria. *Anal. Biochem.* 278, 86-90 (2000).

35. Li, M. & Johnson, M. E. An efficient synthesis of 5-azidotryptophan. *Tetrahedron Lett.* 35, 6255-6258 (1994).

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising a variant *E. coli* tryptophanyl-tRNA synthetase (EcTrp-RS), wherein the variant EcTrp-RS preferentially aminoacylates an *E. coli* tryptophanyl tRNA (Ec-tRNA$^{Trp}$) with a tryptophan analog over the naturally-occurring tryptophan amino acid, wherein the variant EcTrp-RS comprises:
the amino acid sequence of SEQ ID NO: 91, or an amino acid sequence with at least 90% sequence identity with the full-length SEQ ID NO:91, wherein the variant EcTrp-RS is mutated, relative to SEQ ID NO:91, such that the serine at position 8 is replaced with alanine; the valine at position 144 is replaced with either serine, glycine or alanine; and the valine at position 146 is replaced with either alanine, isoleucine or cysteine.

2. The composition of claim 1, wherein the tryptophan analog is selected from the group consisting of: 5-azidotryptophan, 5-propargyloxytryptophan, 5-aminotryptophan, 5-methoxytryptophan, 5-O-allyltryptophan, 5-bromotryptophan or 5-hydroxytryptophan.

3. The composition of claim 1, wherein the variant EcTrp-RS comprises the amino acid sequence SEQ ID NO: 91 wherein the variant EcTrp-RS is is mutated to replace the serine at position 8 with alanine; the valine at position 144 with serine; and the valine at position 146 with alanine.

4. The composition of claim 1, wherein the variant EcTrp-RS comprises the amino acid sequence of SEQ ID NO: 91 wherein the variant EcTrp-RS is mutated to replace the serine at position 8 with alanine; the valine at position 144 glycine; and the valine at position 146 with isoleucine.

5. The composition of claim 1, wherein the variant EcTrp-RS comprises the amino acid sequence of SEQ ID NO: 91 wherein the variant EcTrp-RS to replace the serine at position 8 with alanine; the valine at position 144 with alanine; and the valine at position 146 with alanine.

6. The composition of claim 1, wherein the variant EcTrp-ES comprises the amino acid sequence of SEQ ID NO: 91 wherein the variant EcTrp-RS is mutated to replace the serine at position 8 alanine; the valine at position 144 with glycine; and the valine at position 146 with cysteine.

7. The composition of claim 1, comprising an *E. coli* tyrptophanyl tRNA, wherein the tRNA polynucleotide sequence comprises SEQ ID NO: 1 or SEQ ID NO: 3, or a homologous bacteria-derived tRNA comprising at least about 80% sequence identity with SEQ ID NO: 1 or 3, wherein the tRNA has an anti-codon loop comprising a sequence that specifically binds to a selector sequence of an mRNA selected from the group consisting of an amber codon or an opal codon.

8. The composition of claim 7, wherein the tRNA has the anti-codon loop sequence is UCA.

9. A cell comprising a variant *E. coli* tryptophanyl-tRNA synthetase (EcTrp-RS), wherein the variant EcTrp-RS preferentially aminoacylates an *E. coli* tryptophanyl tRNA (Ec-tRNA$^{Trp}$) with a tryptophan analog over the naturally-occurring tryptophan amino acid, wherein the variant EcTrp-RS comprises:

the amino acid sequence of SEQ ID NO: 91, or an amino acid sequence with at least 90% sequence identity with the full-length SEQ ID NO:91, wherein the variant *E. coli* EcTrp-RS is mutated, relative to SEQ ID NO:91, such that the serine at position 8 is replaced with alanine; the valine at position 144 is replaced with either serine, glycine or alanine; and the valine at position 146 is replaced with either alanine, isoleucine or cysteine.

10. The cell of claim 9, wherein the tryptophan analog is selected from the group consisting of: 5-azidotryptophan, 5-propargyloxytryptophan, 5-aminotryptophan, 5-methoxytryptophan, 5-O-allyltryptophan, 5-bromotryptophan or 5-hydroxytryptophan.

11. The cell of claim 9, wherein the Ec-tRNA$^{Trp}$ comprises the polynucleotide sequence SEQ ID NO: 1 or SEQ ID NO: 3, or a homologous bacteria-derived tRNA comprising at least about 80% sequence identity with SEQ ID NO: 1 or 3, wherein the tRNA has an anti-codon loop comprising a sequence that specifically binds to a selector sequence of an mRNA selected from the group consisting of an amber codon or an opal codon.

12. The cell of claim 9, wherein the cell is an *E. coli* cell or a eukaryotic cell.

13. The cell of claim 12, wherein the eukaryotic cell is a mammalian cell.

14. The *E. coli* cell of claim 12, wherein the *E. coli* is the BL21(DE3) strain of *E. coli* cell.

15. A method of producing a protein in a cell with one, or more, tryptophan analogs at specified positions in the protein, the method comprising:

a. culturing the cell of claim 9 in a culture medium under conditions suitable for growth, wherein the cell comprises a nucleic acid that encodes a protein with one, or more, amber or opal selector codons, wherein the cell further comprises an Ec-tRNA$^{Trp}$ that recognizes the selector codon(s), and b. contacting the cell culture medium with one, or more, tryptophan analogs under conditions suitable for incorporation of the one, or more, tryptophan analogs into the protein in response to the selector codon(s), thereby producing the protein with one, or more tryptophan analogs.

16. The method of claim 15, wherein the Ec-tRNA$^{Trp}$ polynucleotide sequence comprises SEQ ID NO: 1 or SEQ ID NO: 3, or a homologous bacteria-derived tRNA comprising at least about 80% sequence identity with SEQ ID NO: 1 or 3, wherein the tRNA has an anti-codon loop comprising a sequence that specifically binds to a selector sequence of an mRNA selected from the group consisting of an amber codon or an opal codon.

17. The method of claim 15, wherein the tryptophan analog is selected from the group consisting of: 5-azidotryptophan, 5-propargyloxytryptophan, 5-aminotryptophan, 5-methoxytryptophan, 5-O-allyltryptophan, 5-bromotryptophan or 5-hydroxytryptophan.

18. The method of claim 15, wherein the cell is an *E. coli* cell or a eukaryotic cell.

19. The method of claim 18 wherein the eukaryotic cell is a mammalian cell.

20. The method of claim 18, wherein the *E. coli* cell is the BL21(DE3) strain of *E. coli* cell.

21. The method of claim 18 wherein the cell further comprises a second tRNA/RS pair that is orthogonal to the cell, wherein the second pair does not cross-react with the EcTrp-RS/tRNA pair and that recognizes an amber selector codon in the protein, wherein the protein produced contains one, or more tryptophan analogs and one, or more, distinct unnatural amino acid other than a tryptophan analog.

22. A kit for producing a protein in a cell, wherein the protein comprises one, or more tryptophan analogs, the kit comprising:

a. a container containing a polynucleotide sequence encoding an Ec-tRNA$^{TRP}$) that recognizes an amber or opal selector codon(s) in a nucleic acid of interest in the cell; and;

b. a container containing an variant *E. coli* tryptophanyl-tRNA synthetase (EcTrp-RS) that preferentially amino-acylates the Ec-tRNA$^{Trp}$ with a tryptophan analog, wherein the variant EcTrp-RS comprises:

the amino acid sequence of SEQ ID NO: 91, or an amino acid sequence with at least 90% sequence identity with the full-length SEQ ID NO:91, wherein the variant *E. coli* EcTrp-RS is mutated, relative to SEQ ID NO:91, such that the serine at position 8 is replaced with alanine; the valine at position 144 is replaced with either serine, glycine or alanine; and the valine at position 146 is replaced with either alanine, isoleucine or cysteine.

23. The kit of claim 22, wherein the kit further comprises one, or more, tryptophan analogs.

24. The kit of claim 22, wherein the kit further comprises instructions for producing the protein.

\* \* \* \* \*

SEQUENCE LISTING

<160> NUMBER OF SEQ ID NOS: 91

<210> SEQ ID NO 1
<211> LENGTH: 73
<212> TYPE: RNA
<213> ORGANISM: Escherichia coli
<220> FEATURE:
<223> OTHER INFORMATION: strain K-12

<400> SEQUENCE: 1 agggggcguag uucaauuggu agagcaccgg ucuccaaaac cggguguugg gaguucgagu    60
cucuccgccc cug    73

<210> SEQ ID NO 2
<211> LENGTH: 72
<212> TYPE: RNA
<213> ORGANISM: Escherichia coli
<220> FEATURE:
<223> OTHER INFORMATION: strain K-12

<400> SEQUENCE: 2
ugggguaucg ccaagcggua aggcaccgga uucugauucc ggcauuccga gguucgaauc      60
cucguacccc ag                                                        72

<210> SEQ ID NO 3
<211> LENGTH: 76
<212> TYPE: DNA
<213> ORGANISM: Escherichia coli
<220> FEATURE:
<223> OTHER INFORMATION: strain K-12

<400> SEQUENCE: 3
aggggcgtag ttcaattggt agagcaccgg tctccaaaac cgggtgttgg gagttcgagt      60
ctctccgccc ctgcca                                                    76

<210> SEQ ID NO 4
<211> LENGTH: 75
<212> TYPE: DNA
<213> ORGANISM: Escherichia coli
<220> FEATURE:
<223> OTHER INFORMATION: strain K-12

<400> SEQUENCE: 4
tggggtatcg ccaagcggta aggcaccgga ttctgattcc ggcattccga ggttcgaatc      60
ctcgtacccc agcca                                                     75

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MISC_FEATURE
<222> LOCATION: (12)..(12)
<223> OTHER INFORMATION: May or may not be present

<400> SEQUENCE: 5
aggggcatag ctcaagcggt aaagcaccgg actccaaaac cggcagtccg aagttcgaat      60
cccccacccc cagcca                                                    76

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 6
atcagtctat aaatgacctt ctgcccgcat tagggcttcc gcatagcgaa aatcaggaat      60 cgaaaaggt gttgacaatt aatcatcggc                                      90

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 7
tgtaggccgg ataaggcgtt cacgccgcat ccggcatgaa caaagcgcaa tttgccagca      60
atagtgaaag cttgcaaatt aaagccttcg                                      90

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtcggcgact cacgcaatga tattcaggcg gc                                   32

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agcgagatgt ggaaacggcg aggcacttca c                                    31

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctggtcctgg accgcgctga tgaac                                           25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atcctggcgc acggtgatcg cgtgttg                                         27

<210> SEQ ID NO 12
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagtcggtta gaatacctgc ctgtcacgca gggggtcgcg ggttcgagtc ccgtccgttc      60
cgccacccta attacgcaca ccgtggaaac                                      90

<210> SEQ ID NO 13
<211> LENGTH: 90
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 13
cggtagaagg atttacttcg gagagggtta tttcagataa aaaaaatcct tagctttcgc    60
taaggatgat ttcccgggaa gccgatctcg                                     90

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggggtctccc catgcgagag tagggaac                                       28

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccgttgtcga tagcacaaca ctttcacggc c                                   31

<210> SEQ ID NO 16
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgcgcagtca gcgatatcca ttttcgcgaa tccggagtgt aagaacgcgc agtcagcgat    60
atccattttc gcgaatccgg agtgtaagaa                                     90

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggcagagac ccagcg                                                    16

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
accccagtcc atcagcg                                                   17

<210> SEQ ID NO 19
```

<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gctatgaaat agaaaaatga atccgttgaa gcctgctttt ttatactaac ttgagcgaaa    60
cgggaagcct gttgacaatt aatcatcggc                                    90

<210> SEQ ID NO 20
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gccgcgttga ttttctcctg ccagctcata atgctgccgc gttgtaatat tcagcactgt    60
cctgctcctt                                                          70

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtttgatca gaaggacgtt gatcgggcgg                                    30

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttcagatact ggcgatcatc cgccaccag                                     29

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agcccattga tagttttcat gtgcgacaat gggcg                              35

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a, c, t, g, unknown or other

```
<220> FEATURE:
<221> NAME/KEY: modified_base
<222> LOCATION: (34)..(34)
<223> OTHER INFORMATION: a, c, t, g, unknown or other

<400> SEQUENCE: 24
gaatcccata tgatgactaa gcccatcgtt nbtnstggcg cacagccctc aggtgaattg        60

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tacgctttga ggaatcccat atgatgacta agcccatcg                              39

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagattagtt tgatacagca ggatgtccgc tgccatc                                37

<210> SEQ ID NO 27
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 27
gatggcagcg gacatcctgc tgtatcaaac taatctgnnk nnknnkggtg aagaccagaa        60
acagcacctc gaactgagc                                                     79

<210> SEQ ID NO 28
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agcgtttgaa actgcagcca tggtaccttac ggcttcgcc acaaaaccaa tcgc              54

<210> SEQ ID NO 29
<211> LENGTH: 37
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 29
gttagcctgc aggtaattcc gcttcgcaac atgtgag                               37

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggccgccatg gcaaattcga ccctg                                           25

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcaaccaggc gctttggagg cgccagctct acccttgag                            39

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agctggcgcc tccaaagcgc ctggttgcag gttc                                 34

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgcgcgcaga tcagttggaa gaatttgtcc actacgtg                             38

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ataatggact agtgcgcttg tttcggc                                         27

<210> SEQ ID NO 35
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 35
ctccttagat cttcctaggt ggatccacca ttcc                                 34

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aataatacta gtgttgatac cgggaagccc tgg                                  33

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aataatctgc agcgaatttc tgccattcat ccgcttatta tcac                      44

<210> SEQ ID NO 38
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gctaaggaag ctaaaatgga gaaaaaaatc acttgatata ccaccgttga tatatcccaa     60
tggc                                                                  64

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcaatgaaag acggtgagct ggtgtgatgg gatagtgttc accttgtta cacc            54

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cccttgttac accgttttcc atgagtgatc tgaaacgttt tcatcgctct ggag           54

<210> SEQ ID NO 41
<211> LENGTH: 37
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 41
aataataggt accgttctgt tgcccgtctc actggtg                                37

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aataatacat atgcctaggt ggcaggggcg gagagactc                              39

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gttcaattgg tagagcaccg gtcttcaaaa ccgggtgttg ggagttcgag                  50

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
caggttcgca gcgtcagccg gaatggtacc g                                     31

<210> SEQ ID NO 45
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcgcccgaca gccttccagt tcctgtgaga aatcaagccg gaagccgtag cgtac           55

<210> SEQ ID NO 46
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtacgctacg gcttccggct tgatttctca caggaactgg aaggctgtcg ggcgc           55

<210> SEQ ID NO 47
<211> LENGTH: 51
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 47
ccatgaccat gattaccgtg cactgaaata ccattaacat tgctaagaac g                51

<210> SEQ ID NO 48
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
cgttcttagc aatgttaatg gtattucagt gcacggtaat catggtcatg g                51

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cgaaggcgaa gcggcatgca taatgtgcct gtcaaatgg                              39

<210> SEQ ID NO 50
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aataatcctg caggctactc aggagagcgt tcaccgac                               38

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aataatcctg cagggcggcc gctacgggag ggcttaccat ctgg                        44

<210> SEQ ID NO 52
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttaacttta agaaggagat atacatatgg catgagttat caacacgttt gacggggttg       60

<210> SEQ ID NO 53
<211> LENGTH: 48
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtggcatcaa aagggaacct tgcatgagtc gctccgggga aaagcatc                48

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttagcctgca gtgtgcttct caaatgcctg aggccagttt gctc                    44

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcgccccgca tttaggggcg tagttcaatt ggtagagcac cggtc                   45

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
actacgcccc taaatgcggg gcgcatctta ctgcgc                             36

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atatatggta ccaaaaaatg gcagggggcgg agagactcg                          39

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcgatcccgc gaaattaata cgactcacta tag                                33

<210> SEQ ID NO 59
<211> LENGTH: 48
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 59
atatactgca gcgccaagct agcttggatt ctcaccaata aaaaacgc                48

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tggcaggggc ggagagactc gaactcc                                        27

<210> SEQ ID NO 61
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cgagtctctc cgcccctgcc aaattcgaaa agcctgctca acgagcagg                49

<210> SEQ ID NO 62
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gttcaattgg tagagcaccg gtcttcaaaa ccgggtgttg ggagttcgag                50

<210> SEQ ID NO 63
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctcgagtaca actttaactc acacaatgta tgaatcacgg cagacaaaca aaagaatgg      59

<210> SEQ ID NO 64
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aataatagcg gccgcatgac taagcccatc gttttttgctg gcgcac                  46

<210> SEQ ID NO 65
<211> LENGTH: 42
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 65
aataatagcg ccgcttacg gcttcgccac aaaaccaatc gc                          42

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66 ggtgcccta aacgcctggt tgc                                               23

<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aataaacata tgatgactaa gcccatcgtt tttagtggcg cac                        43

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttattctgca gttacggctt cgccacaaaa ccaatcgc                              38

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
attattgaat tcttacggct tcgccacaa                                        29

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aataaatgct agcatgacta agcccatc                                         28

<210> SEQ ID NO 71
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 71
aattattgct agcaaaaaat ggcaggggcg                                          30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aattattgct agcaaaaaat ggcaggggcg                                          30

<210> SEQ ID NO 73
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aataatagct agcgccacca tgactaagcc catcgtt                                  37

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aataatagaa ttcttacggc ttcgccacaa aaccaatcgc                               40

<210> SEQ ID NO 75
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
atcagtctat aaatgacctt ctgcccgcat tagggcttcc gcatagcgaa atcaggaat          60 cgaaaaggt gttgacaatt aatcatcggc atagtatatt ggcatagtat aatacgacaa         120
ggtgaggaac taaaccatgg ccaagctgac cagtgccgtt ccggtgctca ccgcgcgcga        180
cgtcgccgga gcggtcgagt tctggaccga ccggctcggg ttctcccggg acttcgtgga       240
ggacgacttc gccggtgtgg tccgggacga cgtgaccctg ttcatcagcg cggtccagga      300
ccaggtggtg ccggacaaca ccctggcctg ggtgtgggtg cgcggcctgg acgagctgta     360
cgccgagtgg tcggaggtcg tgtccacgaa cttccgggac gcctccgggc cggccatgac    420
cgagatcggc gagcagccgt gggggcggga gttcgccctg cgcgacccgg ccggcaactg   480
cgtgcacttc gtggccgagg agcaggactg acacgtccga cggcggccca cgggtcccag  540
gcctcggaga tccgtccccc ttttcctttg tcgatatcat gtaattagtt atgtcacgct 600
tacattcacg ccctccccc acatccgctc taaccgaaaa ggaaggagtt agacaacctg  660
```

```
aagtctaggt ccctatttat tttttatag ttatgttagt attaagaacg ttatttatat      720
ttcaaatttt tcttttttt ctgtacagac gcgtgtacgc atgtaacatt atactgaaaa      780
ccttgcttga aaggttttg ggacgctcga aggctttaat ttgcaagctt tcactattgc      840
tggcaaattg cgctttgttc atgccggatg cggcgtgaac gccttatccg gcctaca       897
```

<210> SEQ ID NO 76
<211> LENGTH: 965
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
cagtcggtta gaatacctgc ctgtcacgca ggggtcgcg ggttcgagtc ccgtccgttc       60
cgccacccta attacgcaca ccgtggaaac ggatgaaggc acgaacccag ttgacataag     120
cctgttcggt tcgtaaactg taatgcaagt agcgtatgcg ctcacgcaac tggtccagaa     180
ccttgaccga acgcagcggt ggtaacggcg cagtggcggt tttcatggct tgttatgact     240
gtttttttgt acagtctatg cctcgggcat ccaagcagca agcgcgttac gccgtgggtc     300
gatgtttgat gttatggagc agcaacgatg ttacgcagca gcaacgatgt tacgcagcag    360
ggcagtcgcc ctaaaacaaa gttaggtggc tcaagtatgg catcattcg cacatgtagg     420 ctcggccctg accaagtcaa atccatgcgg gctgctcttg atcttttcgg tcgtgagttc     480
ggagacgtag ccacctactc ccaacatcag ccggactccg attacctcgg aacttgctc     540 cgtagtaaga cattcatcgc gcttgctgcc ttcgaccaag aagcggttgt tggcgctctc     600
gcggcttacg ttctgcccag gtttgagcag ccgcgtagtg agatctatat ctatgatctc    660
gcagtctccg gcgagcaccg gaggcagggc attgccaccg cgctcatcaa tctcctcaag    720
catgaggcca acgcgcttgg tgcttatgtg atctacgtgc aagcagatta cggtgacgat    780
cccgcagtgg ctctctatac aaagttgggc atacgggaag aagtgatgca ctttgatatc    840
gacccaagta ccgccaccta acaattcgtt caagccgaga tcggcttccc gggaaatcat    900
ccttagcgaa agctaaggat tttttttatc tgaaataacc ctctccgaag taaatccttc    960
taccg                                                                965
```

<210> SEQ ID NO 77
<211> LENGTH: 1348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
gctatgaaat agaaaaatga atccgttgaa gcctgctttt ttatactaac ttgagcgaaa      60
cgggaagcct gttgacaatt aatcatcggc atagtatatc ggcatagtat aatacgacaa     120
ggtgaggaac taaacccagg aggcagatca tgagtctgaa agaaaaaaca caatctctgt     180
ttgccaacgc atttggctac cctgccactc acaccattca ggcgcctggc cgcgtgaatt     240
tgattggtga acacaccgac tacaacgacg gtttcgttct gccctgcgcg attgattatc     300
aaaccgtgat cagttgtgca ccacgcgatg accgtaaagt tcgcgtgatg gcagccgatt     360
atgaaaatca gctcgacgag ttttccctcg atgcgcccat tgtcgcacat gaaaactatc     420
aatgggctaa ctacgttcgt ggcgtggtga acatctgca actgcgtaac aacagcttcg     480
```

```
gcggcgtgga catggtgatc agcggcaatg tgccgcaggg tgccgggtta agttcttccg    540
cttcactgga agtcgcggtc ggaaccgtat tgcagcagct ttatcatctg ccgctggacg    600
gcgcacaaat cgcgcttaac ggtcaggaag cagaaaacca gtttgtaggc tgtaactgcg    660
ggatcatgga tcagctaatt tccgcgctcg caagaaaga tcatgccttg ctgatcgatt    720
gccgctcact ggggaccaaa gcagtttcca tgcccaaagg tgtggctgtc gtcatcatca    780
acagtaactt caaacgtacc ctggttggca gcgaatacaa cacccgtcgt gaacagtgcg    840
aaaccggtgc gcgtttcttc agcagccag ccctgcgtga tgtcaccatt gaagagttca    900
acgctgttgc gcatgaactg acccgatcg tggcaaaacg cgtgcgtcat atactgactg    960
aaaacgcccg caccgttgaa gctgccagcg cgctggagca aggcgacctg aaacgtatgg   1020
gcgagttgat ggcggagtct catgcctcta tgcgcgatga tttcgaaatc accgtgccgc   1080
aaattgacac tctggtagaa atcgtcaaag ctgtgattgg cgacaaaggt ggcgtacgca   1140
tgaccggcgg cggatttggc ggctgtatcg tcgcgctgat cccggaagag ctggtgcctg   1200
ccgtacagca agctgtcgct gaacaatatg aagcaaaaac aggtattaaa gagactttt    1260 acgtttgtaa accatcacaa ggagcaggac agtgctgaat attacaacgc ggcagcatta   1320
tgagctggca ggagaaaatc aacgcggc                                      1348
```

<210> SEQ ID NO 78
<211> LENGTH: 3919
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
ggtaattccg cttcgcaaca tgtgagcacc ggtttattga ctacaggaag cagtgtgacc     60
gtgtgcttct caaatgcctg aggccagttt gctcaggctc tccccgtgga ggtaataatt    120
gacgatatga tcagtgcacg gctaactaag cggcctgctg actttctcgc cgatcaaaag    180
gcattttgct attaagggat tgacgagggc gtatctgcgc agtaagatgc gccccgcatt    240
gaagcggtgg ctcaagggta gagctggcgc ctccaaagcg cctggttgca ggttcaagtc    300
ctgcccgttt caccaaattc gaaaagcctg ctcaacgagc aggctttttt gcatgctcga    360
gcagctcagg gtcgaatttg ccatggcggc caccaggtac caccggcgcc tcaggcattt    420
gagaagcaca cggtcacact gcttccggta gtcaataaac cggtaaacca gcaatagaca    480
taagcggcta tttaacgacc ctgccctgaa ccgacgaccg ggtcatcgtg gccggatctt    540
gcggcccctc ggcttgaacg aattgttaga cattatttgc cgactacctt ggtgatctcg    600
cctttcacgt agtggacaaa ttcttccaac tgatctgcgc gcgaggccaa gcgatcttct    660
tcttgtccaa gataagcctg tctagcttca agtatgacgg gctgatactg gccggcagg    720 cgctccattg cccagtcggc agcgacatcc ttcggcgcga ttttgccggt tactgcgctg    780
taccaaatgc gggacaacgt aagcactaca tttcgctcat cgccagccca gtcgggcggc    840
gagttccata gcgttaaggt ttcatttagc gcctcaaata gatcctgttc aggaaccgga    900
tcaaagagtt cctccgccgc tggacctacc aaggcaacgc tatgttctct tgcttttgtc    960
agcaagatag ccagatcaat gtcgatcgtg gctggctcga agatacctgc aagaatgtca   1020
ttgcgctgcc attctccaaa ttgcagttcg cgcttagctg gataacgcca cggaatgatg   1080
tcgtcgtgca caacaatggt gacttctaca gcgcggagaa tctcgctctc tccagggga   1140
```

```
gccgaagttt ccaaaaggtc gttgatcaaa gctcgccgcg ttgtttcatc aagccttacg    1200
gtcaccgtaa ccagcaaatc aatatcactg tgtggcttca ggccgccatc cactgcggag    1260
ccgtacaaat gtacggccag caacgtcggt tcgagatggc gctcgatgac gccaactacc    1320
tctgatagtt gagtcgatac ttcggcgatc accgcttccc tcatactctt ccttttcaa     1380 tattattgaa gcatttatca gggttattgt ctcatgagcg gatacatatt tgaatgtatt    1440
tagaaaaata aacaaatagc tagctcactc ggtcgctacg ctccgggcgt gagactgcgg    1500
cgggcgctgc ggacacatac aaagttaccc acagattccg tggataagca ggggactaac    1560
atgtgaggca aaacagcagg gccgcgccgg tggcgttttt ccataggctc cgccctcctg    1620
ccagagttca cataaacaga cgcttttccg gtgcatctgt gggagccgtg aggctcaacc    1680
atgaatctga cagtacgggc gaaacccgac aggacttaaa gatccccacc gtttccggcg    1740
ggtcgctccc tcttgcgctc tcctgttccg accctgccgt ttaccggata cctgttccgc    1800
ctttctccct tacgggaagt gtggcgcttt ctcatagctc acacactggt atctcggctc    1860
ggtgtaggtc gttcgctcca agctgggctg taagcaagaa ctccccgttc agcccgactg    1920
ctgcgcctta tccggtaact gttcacttga gtccaacccg gaaaagcacg gtaaaacgcc    1980
actggcagca gccattggta actgggagtt cgcagaggat ttgtttagct aaacacgcgg    2040
ttgctcttga agtgtgcgcc aaagtccggc tacactggaa ggacagattt ggttgctgtg    2100
ctctgcgaaa gccagttacc acggttaagc agttccccaa ctgacttaac cttcgatcaa    2160
accacctccc caggtggttt tttcgtttac agggcaaaag attacgcgca gaaaaaaagg    2220
atctcaagaa gatcctttga tcttttctac tgaaccgctc tagagtcatc aatcatcccc    2280
ataatccttg ttagattatc aattttaaaa aactaacagt tgtcagcctg tcccgcttta    2340
atatcatacg ccgttatacg ttgtttacgc tttaaggagg cggccgcatg agcaacgacg    2400
aaactgtaga gaaagtcacc caacaagtgt cggaactaaa aagcacagat gttaaagagc    2460
aagtagttac accttgggat gtggaaggtg gggttgatga acaaggtaga gcccaaaata    2520
ttgattacga caaattgatc aaacaattcg gtactaagcc ggtcaacgaa gaaaccctga    2580
agagattcaa gcaagtgacg ggtcgtgaac cacatcattt tttgcgtaag ggattgtttt    2640
tcagtgagcg tgacttcact aaaatattag acctttacga acaaggcaaa ccatttttcc    2700
tatacactgg tagaggtcct tcgagcgatt ctatgcactt gggtcatatg atcccttttg    2760
tcttcaccaa atggttacag gaagtgtttg acgtaccatt agtcatagag ttgacagatg    2820
acgaaaaatt tttattcaaa cacaagttga ccatcaatga cgttaagaat tttgcccgtg    2880
aaaatgccaa ggatatcatt gctgttggct ttgacccaaa gaacacccttt atctttttctg   2940 atttgcaata catgggtggt gcattttacg aaactgtagt aagagtttcc agacaaatta    3000
caggatccac tgcaaaggct gttttcgggt ttaatgactc cgactgtatt ggtaagttcc    3060
attttgcctc cattcaaatt gctaccgcat tcccaagctc atttcctaat gtgttaggct    3120
tgcctgataa gacaccatgt ttgattccat gtgcaattga ccaagatcca tatttcagag    3180
tttgtagggg tgtcgcggat aaattgaagt actccaaacc tgctttgctt cattccagat    3240
tctttccagc tttgcaaggt tccacgacca aaatgtcagc tctgatgat accactgcca    3300 ttttcatgac cgatacacca aagcaaattc aaaagaaaat taacaagtac gcattcagcg    3360
gtggtcaagt gtccgccgac ctacatagag aattaggtgg taatcccgat gtcgatgttg    3420
cataccaata cttgtcattt ttcaaggatg acgatgtttt cttgaaggaa tgctatgaca    3480
```

| | |
|---|---:|
| aatataagtc cggtgaatta ctatcaggtg aaatgaagaa actgtgtatc gagactctgc | 3540 |
| aagaattcgt taaggcgttc caggaacgca gagctcaggt ggacgaagag accttggaca | 3600 |
| aattcatggt cccacataag ttggtttggg gcgaaaagga aagacttgtc gcacctaagc | 3660 |
| caaaaactaa gcaagaaaag aagtaagcgg ccgctttcaa acgctaaatt gcctgatgcg | 3720 |
| ctacgcttat caggcctaca tgatctctgc aatatattga gtttgcgtgc ttttgtaggc | 3780 |
| cggataaggc gttcacgccg catccggcaa gaaacagcaa acaatccaaa acgccgcgtt | 3840 |
| cagcggcgtt ttttctgctt ttcttcgcga attaattccg cttcgcaaca tgtgagcacc | 3900 |
| ggtttattga ctacctgca | 3919 |

<210> SEQ ID NO 79
<211> LENGTH: 10131
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

| | |
|---|---:|
| gcccttccgg ctggctggtt tattgctgat aaatctggag ccggtgagcg tgggtctcgc | 60 |
| ggtatcattg cagcactggg gccagatggt aagccctccc gtatcgtagt tatctacacg | 120 |
| acggggagtc aggcaactat ggatgaacga aatagacaga tcgctgagat aggtgcctca | 180 |
| ctgattaagc attggtaact gtcagaccaa gtttactcat atatacttta gattgattta | 240 |
| aaacttcatt tttaatttaa aaggatctag gtgaagatcc ttttttgataa tctcatgacc | 300 |
| aaaatccctt aacgtgagtt ttcgttccac tgagcgtcag accccttaat aagatgatct | 360 |
| tcttgagatc gttttggtct gcgcgtaatc tcttgctctg aaaacgaaaa aaccgccttg | 420 |
| cagggcggtt tttcgaaggt tctctgagct accaactctt tgaaccgagg taactggctt | 480 |
| ggaggagcgc agtcaccaaa acttgtcctt tcagtttagc cttaaccggc gcatgacttc | 540 |
| aagactaact cctctaaatc aattaccagt ggctgctgcc agtggtgctt ttgcatgtct | 600 |
| ttccggttg gactcaagac gatagttacc ggataaggcg cagcggtcgg actgaacggg | 660 |
| gggttcgtgc atacagtcca gcttggagcg aactgcctac ccggaactga gtgtcaggcg | 720 |
| tggaatgaga caaacgcggc cataacagcg gaatgacacc ggtaaaccga aaggcaggaa | 780 |
| caggagagcg cacgagggag ccgccagggg gaaacgcctg gtatctttat agtcctgtcg | 840 |
| ggtttcgcca ccactgattt gagcgtcaga tttcgtgatg cttgtcaggg gggcggagcc | 900 |
| tatgaaaaaa cggctttgcc gcggccctct cacttccctg ttaagtatct tcctggcatc | 960 |
| ttccaggaaa tctccgcccc gttcgtaagc catttccgct cgccgcagtc gaacgaccga | 1020 |
| gcgtagcgag tcagtgagcg aggaagcgga atatatcctg tatcacatat tctgctgacg | 1080 |
| caccggtgca gccttttttc tcctgccaca tgaagcactt cactgacacc ctcatcagtg | 1140 |
| ccaacatagt aagccagtat acactccgct agcgctgatg tccggcggtg cttttgccgt | 1200 |
| tacgcaccac cccgtcagta gctgaacagg agggacagct gatagaaaca gaagccactg | 1260 |
| gagcacctca aaaacaccat catacactaa atcagtaagt tggcagcatc acccgacgca | 1320 |
| cttttgcgccg aataaatacc tgtgacgaa gatcacttcg cagaataaat aaatcctggt | 1380 |
| gtccctgttg ataccgggaa gccctgggcc aacttttggc gaaaatgaga cgttgatcgg | 1440 |
| cacgtaagag gttccaactt tcaccataat gaaataagat cactaccggg cgtatttttt | 1500 |
| gagttatcga gattttcagg agctaaggaa gctaaaatgg agaaaaaaat cactggatat | 1560 |

-continued

```
accaccgttg atatatccca atggcatcgt aaagaacatt ttgaggcatt tcagtcagtt      1620
gctcaatgta cctataacca gaccgttcag ctggatatta cggccttttt aaagaccgta      1680
aagaaaaata agcacaagtt ttatccggcc tttattcaca ttcttgcccg cctgatgaat      1740
gctcatccgg aattccgtat ggcaatgaaa gacggtgagc tggtgatatg ggatagtgtt      1800 caccccttgtt acaccgtttt ccatgagcaa actgaaacgt tttcatcgct ctggagtgaa      1860
taccactagg atttccggca gtttctacac atatattcgc aagatgtggc gtgttacggt      1920
gaaaacctgg cctatttccc taaagggttt attgagaata tgttttcgt ctcagccaat      1980 ccctgggtga gtttcaccag ttttgattta aacgtggcca atatggacaa cttcttcgcc      2040
cccgttttca ccatgggcaa atattatacg caaggcgaca aggtgctgat gccgctggcg      2100
attcaggttc atcatgccgt ttgtgatggc ttccatgtcg gcagaatgct taatgaatta      2160
caacagtact gcgatgagtg gcagggcggg gcgtaatttt tttaaggcag ttattggtgc      2220
ccttaaacgc ctggttgcta cgcctgaata agtgataata agcggatgaa tggcagaaat      2280
tcgaaagcaa attcgacccg gtcgtcggtt caggcaggg tcgttaaata gccgcttatg      2340
tctattgctg gtttaccggt ttattgacta ccggaagcag tgtgaccgtg tgcttctcaa      2400
atgcctgagg ccagtttgct caggctctcc ccgtggaggt aataattgac gatatgatca      2460
tttattctgc ctcccagagc atgataaaaa cggttagcgc ttcgttaata cagatgtagg      2520
tgttccacag ggtagccagc agcatcctgc gatgcagatc cggaacataa tggactagtg      2580
cgcttgtttc ggcgggactg ttgtaactca gaataagaaa tgaggccgct catggcgttc      2640
tgttgcccgt ctcactggtg aaaagaaaaa caaccctggc gccgcttctt tgagcgaacg      2700
atcaaaaata agtggcgccc catcaaaaaa atattctcaa cataaaaaac tttgtgtaat      2760
acttgtaacg ctgaattcag gggcgtagtt caattggtag agcaccggtc tctaaaaccg      2820
ggtgttggga gttcgagtct ctccgccct gccactgcag atccttagcg aaagctaagg      2880
atttttttta agcttggcac tggccgtcgt tttacaacgt cgtgactggg aaaaccctgg      2940
cgttacccaa cttaatcgcc ttgcagcaca tcccccttc gccagttgag caccgccgcc      3000
gcaaggaatg gtgaattcag gatctaagga gcccgagatg cgccgcgtgc ggctgctgga      3060
gatggcggac gcgatggata tgttctgcca agggttggtt tgcgcattca cagttctccg      3120
caagaattga ttggctccaa ttcttggagt ggtgaatccg ttagcgaggt gccgccggct      3180
tccattcagg tcgaggtggc ccggctccat gcaccgcgac gcaacgcggg gaggcagaca      3240
aggtataggg cggcgcctac aatccatgcc aacccgttcc atgtgctcgc cgaggcggca      3300
taaatcgccg tgacgatcag cggtccaatg atcgaagtta ggctggtaag agccgcgagc      3360
gatccttgaa gctgtccctg atggtcgtca tctacctgcc tggacagcat ggcctgcaac      3420
gcgggcatcc cgatgccgcc ggaagcgaga agaatcataa tggggaaggc catccagcct      3480
cgcgtcgcga acgccagcaa gacgtagccc agcgcgtcgg ccgccatgcc ggcgataatg      3540
gcctgcttct cgccgaaacg tttggtggcg ggaccagtga cgaaggcttg agcgagggcg      3600
tgcaagattc cgaataccgc aagcgacagg ccgatcatcg tcgcgctcca gcgaaagcgg      3660
tcctcgccga aaatgaccca gagcgctgcc ggcacctgtc ctacgagttg catgataaag      3720
aagacagtca taagtgcggc gacgatagtc atgccccgcg cccaccggaa ggagctgact      3780
gggttgaagg ctctcaaggg catcggtcga cgctctccct tatgcgactc ctgcattagg      3840
aagcagccca gtagtaggtt gaggccgttg agcaccgccg ccgcaaggaa tggtgcatgc      3900
aaggagatgg cgcccaacag tccccccggcc acggggcctg ccaccatacc cacgccgaaa      3960
```

```
caagcgctca tgagcccgaa gtggcgagcc cgatcttccc catcggtgat gtcggcgata    4020
taggcgccag caaccgcacc tgtggcgccg gtgatgccgg ccacgatgcg tccggcgtag    4080
aggatccaca ggacgggtgt ggtcgccatg atcgcgtagt cgatagtggc tccaagtagc    4140
gaagcgagca ggactgggcg gcggccaaag cggtcggaca gtgctccgag aacgggtgcg    4200
catagaaatt gcatcaacgc atatagcgct agcagcacgc catagtgact ggcgatgctg    4260
tcggaatgga cgatatcccg caagaggccc ggcagtaccg gcataaccaa gcctatgcct    4320
acagcatcca gggtgacggt gccgaggatg acgatgagcg cattgttaga tttcatacac    4380
ggtgcctgac tgcgttagca atttaactgt gataaactac cgcattaaag cttatcgatg    4440
ataagctgtc aaacatgaga attacaactt atatcgtatg gggctgactt caggtgctac    4500
attgctcaaa gatgcagggg taaaagctaa ccgcatcttt accgacaagg catccggcag    4560
ttcaacagat cgggaagggc tggatttgct gaggatgaag gtggaggaag gtgatgtcat    4620
tctggtgaag aagctcgacc gtcttggccg cgacaccgcc gacatgatcc aactgataaa    4680
agagtttgat gctcagggtg tagcggttcg gtttattgac gacgggatca gtaccgacgg    4740
tgatatgggg caaatggtgg tcaccatcct gtcggctgtg gcacaggctg aacgccggag    4800
gatcctccgg gccgttgctt cgcaacgttc aaatccgctc ccggcggatt tgtcctactc    4860
aggagagcgt tcaccgacaa acaacagata aaacgaaagg cccagtcttt cgactgagcc    4920
tttcgtttta tttgatgcct ggcagttccc tactctcgca tggggagacc ccacactacc    4980
atcggcgcta cggcgtttca cttctgagtt cggcatgggg tcaggtggga ccaccgcgct    5040
actgccgcca ggcaaattct gttttatcag accgcttctg cgttctgatt taatctgtat    5100
caggctgaaa atcttctctc atccgacgtc ttaggcgaag gcgaagtccg actctaagat    5160
gtcacggagg ttcaagttac ctttagccgg aagtgctggc attttgtcca attgagactc    5220
gtgcaactgg tcagcgaact ggtcgtagaa atcagccagt acatcacaag actcatatgt    5280
gtcaaccata gtttcgcgca ctgctttgaa caggttcgca gcgtcagccg gaatggtacc    5340
gaaggagtcg tgaatcagtg caaaagattc gattccgtac ttctcgtgtg cccacactac    5400
agtcttacga aggtggctac cgtcttggct gtgtacaaag ttaggagcga taccagactc    5460
ctgtttgtgt gcatcaatct cgctatcttt gttggtgtta atggtaggct gtaagcggaa    5520
ctgaccgagg aacatcaggt tcaagcgcgt ctgaataggc ttcttgtatt cctgccacac    5580
agggaaacca tcaggagtta cccaatgcac agcgcaacgc ttgcgaagaa tctctccagt    5640
cttcttatct ttgacctcag cagccagcag cttagcagca gacttaagcc agttcattgc    5700
ttcaaccgca gctaccaccg tcacgctcac agattcccaa atcagcttag ccatgtatcc    5760
agcagcctga ttcggctgag tgaacatcag acccttgccg gaatcaatag ctggctgaat    5820
ggtatcttcc agcacttgtt gacggaagcc gaactctttg gacccgtaag ccagcgtcat    5880
gactgaacgt tagtcacac tgcgagtaac accgtaagcc agccattgac cagccagtgc    5940
cttagtgccc agcttgactt tctcagagat ttcaccagtg ttctcatcgg tcacggtaac    6000
tacttcgtta tcggtcccat tgattgcgtc tgcttgtaga atctcgttga ctttcttagc    6060
aacaatcccg tagatgtcct gaacggtttc actaggaagc aagttaaccg cgcgaccacc    6120
tacctcatct cggagcatcg cggagaagtg ctggatgcca gagcaagacc cgtcaaacgc    6180
cagcggaagg gagcagttat agctcaggcc gtggtgctgt accccagcgt actcaaagca    6240
gaacgcaagg aagcagaacg gagaatcttg ctcagcccac caagtgttct ccagtggaga    6300
```

```
cttagcgcaa gccatgatgt tctcgtggtt ttcctcaatg aacttgatgc gctcagggaa    6360
cggaacctta tcgacacccg cacagtttgc accgtggatt ttcagccagt agtaaccttc    6420
cttaccgatt ggtttacctt tcgccagcgt aagcagtcct ttggtcatat cgttaccttg    6480
cgggttgaac attgacacag cgtaaacacg accgcgccag tccatgttgt aagggaacca    6540
gatggcctta tggttagcaa acttattggc ttgctcaagc atgaactcaa ggctgatacg    6600
gcgagacttg cgagccttgt ccttgcggta cacagcagcg gcagcacgtt ccacgcggt     6660 gagagcctca ggattcatgt cgatgtcttc cggtttcatc gggagttctt cacgctcaat    6720
cgcagggatg tcctcgaccg gacaatgctt ccacttggtg attacgttgg cgaccgctag    6780
gactttcttg ttgattttcc atgcggtgtt ttgcgcaatg ttaatcgctt tgtacacctc    6840
aggcatgtaa acgtcttcgt agcgcatcag tgctttctta ctgtgagtac gcaccagcgc    6900
cagaggacga cgaccgttag cccaatagcc accaccagta atgccagtcc acggcttagg    6960
aggaactacg caaggttgga acatcggaga gatgccagcc agcgcacctg cacgggttgc    7020
gatagcctca gcgtattcag gtgcgagttc gatagtctca gagtcttgac ctactacgcc    7080
agcattttgg cggtgtaagc taaccattcc ggttgactca atgagcatct cgatgcagcg    7140
tactcctaca tgaatagagt cttccttatg ccacgaagac cacgcctcgc caccgagtag    7200
acccttagag agcatgtcag cctcgacaac ttgcataaat gctttcttgt agacgtgccc    7260
tacgcgcttg ttgagttgtt cctcaacgtt tttcttgaag tgcttagctt caaggtcacg    7320
gatacgaccg aagcgagcct cgtcctcaat ggcccgaccg attgcgcttg ctacagcctg    7380 aacgttgta ttgtcagcac tggttaggca agccagagtg gtcttaatgg tgatgtacgc    7440
tacggcttcc ggcttgattt cctacaggaa ctggaaggct gtcgggcgct tgccgcgctt    7500
agctttcact tcctcaaacc agtcgttgat gcgtgcaatc atcttaggga gtagggtagt    7560
gatgagaggc ttggcggcag cgttatccgc aacctcacca gctttaagtt gacgctcaaa    7620
catcttgcgg aagcgtgctt cacccatctc gtaagactca tgctcaaggg ccaactgttc    7680
gcgagctaaa cgctcaccgt aatggtcagc cagagtgttg aacgggatag cagccagttc    7740
gatgtcagag aagtcgttct tagcaatgtt aatggtattc tagtgcacgg taatcatggt    7800
catggttaat tcctcctgtt agcccaaaaa acgggtatgg agaaacagta gagagttgcg    7860
ataaaaagcg tcaggtagga tccgctaatc ttatggataa aaatgctatg gcatagcaaa    7920
gtgtgacgcc gtgcaaataa tcaatgtgga cttttctgcc gtgattatag acacttttgt    7980
tacgcgtttt tgtcatggct ttggtcccgc tttgttacag aatgctttta ataagcgggg    8040
ttaccggttt ggttagcgag aagagccagt aaaagacgca gtgacggcaa tgtctgatgc    8100 aatatgggaca attggtttct tctctgaatg gcgggagtat gaaaagtatg gctgaagcgc    8160
aaaatgatcc cctgctgccg ggatactcgt ttaatgccca tctggtggcg ggtttaacgc    8220
cgattgaggc caacggttat ctcgattttt ttatcgaccg accgctggga atgaaaggtt    8280
atattctcaa tctcaccatt cgcggtcagg gggtggtgaa aaatcaggga cgagaatttg    8340
tttgccgacc gggtgatatt ttgctgttcc cgccaggaga gattcatcac tacggtcgtc    8400
atccggaggc tcgcgaatgg tatcaccagt gggtttactt tcgtccgcgc gcctactggc    8460
atgaatggct taactggccg tcaatatttg ccaatacggg gttctttcgc ccggatgaag    8520
cgcaccagcc gcatttcagc gacctgtttg gcaaatcat taacgccggg caaggggaag    8580
ggcgctattc ggagctgctg gcgataaatc tgcttgagca attgttactg cggcgcatgg    8640
aagcgattaa cgagtcgctc catccaccga tggataatcg ggtacgcgag gcttgtcagt    8700
```

```
acatcagcga tcacctggca gacagcaatt ttgatatcgc cagcgtcgca cagcatgttt      8760
gcttgtcgcc gtcgcgtctg tcacatcttt tccgccagca gttagggatt agcgtcttaa      8820
gctggcgcga ggaccaacgt atcagccagg cgaagctgct tttgagcacc acccggatgc      8880
ctatcgccac cgtcggtcgc aatgttggtt ttgacgatca actctatttc tcgcgggtat      8940
ttaaaaaatg caccggggcc agcccgagcg agttccgtgc cggttgtgaa gaaaaagtga      9000
atgatgtagc cgtcaagttg tcataattgg taacgaatca gacaattgac ggcttgacgg      9060
agtagcatag ggtttgcaga atccctgctt cgtccatttg acaggcacat tatgcatgcc      9120
gcttcgcctt cgcgcgcgaa ttgatctgct gcctcgcgcg tttcggtgat gacggtgaaa      9180
acctctgaca catgcagctc ccggagacgg tcacagcctg cagcaaaaaa cccctcaaga      9240
cccgtttaga ggccccaagg ggttatgcta gttattgctc agcggtggca gcagccaact      9300
cagcttcctt tcgggctttg ttatttgtag agctcatcca tgccatgtgt aatcccagca      9360
gcagttacaa actcaagaag gaccatgtgg tcacgctttt cgttgggatc tttcgaaagg      9420
gcagattgtg tcgacaggta atggttgtct ggtaaaagga cagggccatc gccaattgga      9480
gtattttgtt gataatggtc tgctagttga acggatccat cttcaatgtt gtggcgaatt      9540
ttgaagttag ctttgattcc attcttttgt ttgtctgccg tgatgtatac attgtgtgag      9600
ttatagttgt actcgagttt gtgtccgaga atgtttccat cttctttaaa atcaatacct      9660
tttaactcga tacgattaac aagggtatca ccttcaaact tgacttcagc acgcgtcttg      9720
tagttcccgt catctttgaa agatatagtg cgttcctgta cataaccttc ggcatggca       9780 ctcttgaaaa agtcatgccg tttcatatga tccggataac gggaaaagca ttgaacacca      9840
taagagaaag tagtgacaag tgttggccat ggaacaggta gttttccagt agtgcaaata      9900
aatttaaggg taagttttcc gtatgttgca tcaccttcac cctctccact gacagaaaat      9960
ttgtgcccat taacatcacc atctaattca acaagaattg gacaactcc agtgaaaagt      10020 tcttctcctt tactcatatg tatatctcct tcttaaagtt aaacaaaatt atttctagag     10080
ggaaaccgtt gtggtctccc tatagtgagt cgtattaatt tcgcgggatc g               10131
```

<210> SEQ ID NO 80
<211> LENGTH: 4326
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

```
cgcgtccgcc atctccagca gccgcacgcg gcgcatcttg ggctccttgc atgcaccatt        60
ccttgcggcg gcggtgctca acggcctcaa cctactactg ggctgcttcc taatgcagga       120
gtcgcataag ggagagcgtc tggcgaaagg gggatgtgct gcaaggcgat taagttgggt       180
aacgccaggg ttttcccagt cacgacgttg taaaacgacg ccagtgccca agcttaaaaa       240
aaatccttag ctttcgctaa ggatcatatg cctaggtggc aggggcggag agactcgaac       300
tcccaacacc cggttttgaa gaccggtgct ctaccaattg aactacgccc ctgaattcag       360
cgttacaagt attacacaaa gttttttatg ttgagaatat ttttttgatg gggcgccact       420 tattttgat cgttcgctca agaagcggc gccaggggtg ttttctttt caccagtgag         480 acgggcaaca gaacggtacc tctagacaat tggtgcactt caaaaatcga tgagctgttg       540
acaattaatc atcgaactag tgttgatacc gggaagccct gggccaactt ttggcgaaaa       600
```

```
tgagacgttg atcggcacgt aagaggttcc aactttcacc ataatgaaat aagatcacta    660
ccgggcgtat tttttgagtt atcgagattt tcaggagcta aggaagctaa aatggagaaa    720
aaaatcactg atataccac cgttgatata tcccaatggc atcgtaaaga acattttgag     780
gcatttcagt cagttgctca atgtacctat aaccagaccg ttcagctgga tattacggcc    840
tttttaaaga ccgtaaagaa aaataagcac aagtttatc cggcctttat tcacattctt    900
gcccgcctga tgaatgctca tccggaattc cgtatggcaa tgaaagacgg tgagctggtg    960
atatgggata gtgttcaccc ttgttacacc gttttccatg agtgatctga acgttttca    1020 tcgctctgga gtgaatacca cgacgatttc cggcagtttc tacacatata ttcgcaagat   1080
gtggcgtgtt acggtgaaaa cctggcctat ttccctaaag ggtttattga atatgttt     1140 ttcgtctcag ccaatccctg ggtgagtttc accagttttg atttaaacgt ggccaatatg   1200
gacaacttct tcgcccccgt tttcaccatg ggcaaatatt atacgcaagg cgacaaggtg   1260
ctgatgccgc tggcgattca ggttcatcat gccgtttgtg atggcttcca tgtcggcaga   1320
atgcttaatg aattacaaca gtactgcgat gagtggcagg gcgggcgta atttttttaa    1380 ggcagttatt ggtgcccta aacgcctggt tgctacgcct gaataagtga taataagcgg    1440
atgaatggca gaaattcgct gcagcagcat caaagttctg gtgctggtag ctgcgccaga   1500
aggtatcgct gcgctggaaa aagcgcaccc ggacgtcgaa ctgtataccg catcgattga   1560
tcagggactg aacgagcacg gatacattat tccgggcctc ggcgatgccg gtgacaaaat   1620
ctttggtacg aaataaagaa ttcgaagctt gggcccgaac aaaaactcat ctcagaagag   1680
gatctgaata gcgccgtcga ccatcaccat catcatcatt gagtttaaac gacgtccagc   1740
ttggctgttt tggcggatga gagaagattt tcagcctgat acagattaaa tcagaacgca   1800
gaagcggtct gataaaacag aatttgcctg gcggcagtag cgcggtggtc ccacctgacc   1860
ccatgccgaa ctcagaagtg aaacgccgta gcgccgatgg tagtgtgagg cctcccatgc   1920
gagagtaggg aactgccagg catcaaataa aacgaaaggc tcagtcgaaa gactgggcct   1980
ttcgttttat ctgttgtttg tcggtgaacg atatctgctt ttcttcggat ccctcgagag   2040
atctccatgg gctagcggag tgtatactgg cttactatgt tggcactgat gagggtgtca   2100
gtgaagtgct tcatgtggca ggagaaaaaa ggctgcaccg gtgcgtcagc agaatatgtg   2160
atacaggata tattccgctt cctcgctcac tgactcgcta cgctcggtcg ttcgactgcg   2220
gcgagcggaa atggcttacg aacggggcgg agatttcctg gaagatgcca ggaagatact   2280 taacaggaa gtgagagggc gcggcaaag ccgttttttcc ataggctccg ccccctgac    2340 aagcatcacg aaatctgacg ctcaaatcag tggtggcgaa acccgacagg actataaaga   2400
taccaggcgt ttccccctgg cggctccctc gtgcgctctc ctgttcctgc ctttcggttt   2460
accggtgtca ttccgctgtt atggccgcgt ttgtctcatt ccacgcctga cactcagttc   2520
cgggtaggca gttcgctcca agctggactg tatgcacgaa ccccccgttc agtccgaccg   2580
ctgcgcctta tccggtaact atcgtcttga gtccaacccg gaagacatg caaaagcacc    2640 actggcagca gccactggta attgatttag aggagttagt cttgaagtca tgcgccggtt   2700
aaggctaaac tgaaaggaca gtttttggtg actgcgctcc tccaagccag ttacctcggt   2760
tcaaagagtt ggtagctcag agaaccttcg aaaaccgcc ctgcaaggcg ttttttttcgt   2820 tttcagagca agagattacg cgcagaccaa aacgatctca agaagatcat cttattaagg   2880
ggtctgacgc acatgtaatg tagcacctga agtcagcccc atacgatata agttgtaatt   2940
```

```
ctcatgtttg acagcttatc atcgataagc tttaatgcgg tagtttatca cagttaaatt    3000
gctaacgcag tcaggcaccg tgtatgaaat ctaacaatgc gctcatcgtc atcctcggca    3060
ccgtcaccct ggatgctgta ggcataggct tggttatgcc ggtactgccg ggcctcttgc    3120
gggatatcgt ccattccgac agcatcgcca gtcactatgg cgtgctgcta gcgctatatg    3180
cgttgatgca atttctatgc gcacccgttc tcggagcact gtccgaccgc tttggccgcc    3240
gcccagtcct gctcgcttcg ctacttggag ccactatcga ctacgcgatc atggcgacca    3300
cacccgtcct gtggattctc tacgccggac gcatcgtggc cggcatcacc ggcgccacag    3360
gtgcggttgc tggcgcctat atcgccgaca tcaccgatgg ggaagatcgg gctcgccact    3420
tcgggctcat gagcgcttgt ttcggcgtgg gtatggtggc aggccccgtg gccgggggac    3480
tgttgggcgc catctccttg catgcaccat tccttgcggc ggcggtgctc aacggcctca    3540
acctactact gggctgcttc ctaatgcagg agtcgcataa gggagagcgt cgaccgatgc    3600
ccttgagagc cttcaaccca gtcagctcct tccggtgggc gcggggcatg actatcgtcg    3660
ccgcacttat gactgtcttc tttatcatgc aactcgtagg acaggtgccg gcagcgctct    3720
gggtcatttt cggcgaggac cgcttcgct ggagcgcgac gatgatcggc ctgtcgcttg    3780
cggtattcgg aatcttgcac gccctcgctc aagccttcgt cactggtccc gccaccaaac    3840
gtttcggcga aagcaggcc attatcgccg gcatggcggc cgacgcgctg ggctacgtct    3900
tgctggcgtt cgcgacgcga ggctggatgg ccttccccat tatgattctt ctcgcttccg    3960
gcggcatcgg gatgcccgcg ttgcaggcca tgctgtccag gcaggtagat gacgaccatc    4020
agggacagct tcaaggatcg ctcgcggctc ttaccagcct aacttcgatc attggaccgc    4080
tgatcgtcac ggcgatttat gccgcctcgg cgagcacatg gaacgggttg catggattg     4140 taggcgccgc cctataccct tgtctgcctcc ccgcgttgcg tcgcggtgca tggagccggg    4200
ccacctcgac ctgaatggaa gccggcggca cctcgctaac ggattcacca ctccaagaat    4260
tggagccaat caattcttgc ggagaactgt gaatgcgcaa accaacccct tggcagaacat   4320 atccat                                                              4326
```

<210> SEQ ID NO 81
<211> LENGTH: 9722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
cgcgtccgcc atctccagca gccgcacgcg gcgcatcttg ggctccttgc atgcaccatt      60
ccttgcggcg gcggtgctca acggcctcaa cctactactg ggctgcttcc taatgcagga    120
gtcgcataag ggagagcgtc tggcgaaagg gggatgtgct gcaaggcgat taagttgggt    180
aacgccaggg ttttcccagt cacgacgttg taaaacgacg ccagtgcca agcttaaaaa     240 aaatccttag ctttcgctaa ggatcatatg cctaggtggc aggggcggag agactcgaac    300
tcccaacacc cggttttgaa gaccggtgct ctaccaattg aactacgccc ctgaattcag    360
cgttacaagt attacacaaa gttttttatg ttgagaatat tttttgatg gggcgccact     420 tattttgat cgttcgctca agaagcggc gccaggggttg ttttctttt caccagtgag      480 acgggcaaca gaacggtacc tctagacaat tggtgcactc caaaatcga tgagctgttg    540 acaattaatc atcgaactag tgttgatacc gggaagccct gggccaactt ttggcgaaaa    600
```

-continued

```
tgagacgttg atcggcacgt aagaggttcc aactttcacc ataatgaaat aagatcacta    660
ccgggcgtat tttttgagtt atcgagattt tcaggagcta aggaagctaa aatggagaaa    720
aaaatcactg gatataccac cgttgatata tcccaatggc atcgtaaaga acattttgag    780
gcatttcagt cagttgctca atgtacctat aaccagaccg ttcagctgga tattacggcc    840 ttttaaaga ccgtaaagaa aaataagcac aagttttatc cggcctttat tcacattctt    900
gcccgcctga tgaatgctca tccggaattc cgtatggcaa tgaaagacgg tgagctggtg    960
atatgggata gtgttcaccc ttgttacacc gttttccatg agtgatctga aacgttttca    1020
tcgctctgga gtgaatacca cgacgatttc cggcagtttc tacacatata ttcgcaagat    1080
gtggcgtgtt acggtgaaaa cctggcctat ttccctaaag ggtttattga gaatatgttt    1140
ttcgtctcag ccaatccctg ggtgagtttc accagttttg atttaaacgt ggccaatatg    1200
gacaacttct tcgccccgt tttcaccatg gcaaatatt atacgcaagg cgacaaggtg      1260
ctgatgccgc tggcgattca ggttcatcat gccgtttgtg atggcttcca tgtcggcaga    1320
atgcttaatg aattacaaca gtactgcgat gagtggcagg gcggggcgta attttttaa     1380 ggcagttatt ggtgcccta aacgcctggt tgctacgcct gaataagtga taataagcgg     1440
atgaatggca gaaattcgct gcaggctact caggagagcg ttcaccgaca aacaacagat    1500
aaaacgaaag gcccagtctt tcgactgagc ctttcgtttt atttgatgcc tggcagttcc    1560
ctactctcgc atgggagac cccacactac catcggcgct acggcgtttc acttctgagt     1620
tcggcatggg gtcaggtggg accaccgcgc tactgccgcc aggcaaattc tgttttatca    1680
gaccgcttct gcgttctgat ttaatctgta tcaggctgaa atcttctct catccgacgt     1740 cttaggcgaa ggcgaagtcc gactctaaga tgtcacggag gttcaagtta cctttagccg    1800
gaagtgctgg cattttgtcc aattgagact cgtgcaactg gtcagcgaac tggtcgtaga    1860
aatcagccag tacatcacaa gactcatatg tgtcaaccat agtttcgcgc actgctttga    1920
acaggttcgc agcgtcagcc ggaatggtac cgaaggagtc gtgaatcagt gcaaaagatt    1980
cgattccgta cttctcgtgt gcccacacta cagtcttacg aaggtggcta ccgtcttggc    2040
tgtgtacaaa gttaggagcg ataccagact cctgtttgtg tgcatcaatc tcgctatctt    2100
tgttggtgtt aatggtaggc tgtaagcgga actgaccgag gaacatcagg ttcaagcgcg    2160
tctgaatagg cttcttgtat tcctgccaca cagggaaacc atcaggagtt acccaatgca    2220
cagcgcaacg cttgcgaaga atctctccag tcttcttatc tttgacctca gcagccagca    2280
gcttagcagc agacttaagc cagttcattg cttcaaccgc agctaccacc gtcacgctca    2340
cagattccca aatcagctta gccatgtatc cagcagcctg attcggctga gtgaacatca    2400 gaccccttgcc ggaatcaata gctggctgaa tggtatcttc cagcacttgt tgacggaagc    2460
cgaactcttt ggaccccgtaa gccagcgtca tgactgaacg cttagtcaca ctgcgagtaa    2520
caccgtaagc cagccattga ccagccagtg ccttagtgcc cagcttgact ttctcagaga    2580
tttcaccagt gttctcatcg gtcacggtaa ctacttcgtt atcggtccca ttgattgcgt     2640
ctgcttgtag aatctcgttg acttttcttag caacaatccc gtagatgtcc tgaacggttt    2700
cactaggaag caagttaacc gcgcgaccac ctacctcatc tcggagcatc gcggagaagt    2760
gctggatgcc agagcaagac ccgtcaaacg ccagcggaag ggagcagtta tagctcaggc    2820
cgtggtgctg taccccagcg tactcaaagc agaacgcaag gaagcagaac ggagaatctt    2880
gctcagccca ccaagtgttc tccagtggag acttagcgca agccatgatg ttctcgtggt    2940
tttcctcaat gaacttgatg cgctcaggga acggaacctt atcgacaccc gcacagtttg    3000
```

```
caccgtggat tttcagccag tagtaacctt ccttaccgat tggtttacct ttcgccagcg   3060
taagcagtcc tttggtcata tcgttacctt gcgggttgaa cattgacaca gcgtaaacac   3120
gaccgcgcca gtccatgttg taagggaacc agatggcctt atggttagca aacttattgg   3180
cttgctcaag catgaactca aggctgatac ggcgagactt gcgagccttg tccttgcggt   3240
acacagcagc ggcagcacgt ttccacgcgg tgagagcctc aggattcatg tcgatgtctt   3300
ccggtttcat cgggagttct tcacgctcaa tcgcagggat gtcctcgacc ggacaatgct   3360
tccacttggt gattacgttg gcgaccgcaa ggactttctt gttgattttc catgcggtgt   3420
tttgcgcaat gttaatcgct ttgtacacct caggcatgta acgtcttcg tagcgcatca    3480 gtgctttctt actgtgagta cgcaccagcg ccagaggacg acgaccgtta gcccaatagc   3540
caccaccagt aatgccagtc cacggcttag gaggaactac gcaaggttgg aacatcggag   3600
agatgccagc cagcgcacct gcacgggttg cgatagcctc agcgtattca ggtgcgagtt   3660
cgatagtctc agagtcttga cctactacgc agcattttg gcggtgtaag ctaaccattc     3720
cggttgactc aatgagcatc tcgatgcagc gtactcctac atgaatagag tcttccttat   3780
gccacgaaga ccacgcctcg ccaccgagta gacccttaga gagcatgtca gcctcgacaa   3840
cttgcataaa tgctttcttg tagacgtgcc ctacgcgctt gttgagttgt tcctcaacgt   3900
ttttcttgaa gtgcttagct tcaaggtcac ggatacgacc gaagcgagcc tcgtcctcaa   3960
tggcccgacc gattgcgctt gctacagcct gaacggttgt attgtcagca ctggttaggc   4020
aagccagagt ggtcttaatg gtgatgtacg ctacggcttc cggcttgatt tctcacagga   4080
actggaaggc tgtcgggcgc ttgccgcgct tagctttcac ttcctcaaac cagtcgttga   4140
tgcgtgcaat catcttaggg agtagggtag tgatgagagg cttggcggca gcgttatccg   4200
caacctcacc agctttaagt tgacgctcaa acatcttgcg gaagcgtgct tcacccatct   4260
cgtaagactc atgctcaagg gccaactgtt cgcgagctaa acgctcaccg taatggtcag   4320
ccagagtgtt gaacgggata gcagccagtt cgatgtcaga gaagtcgttc ttagcaatgt   4380
taatggtatt tcagtgcacg gtaatcatgg tcatggttaa ttcctcctgt agcccaaaa    4440 aacgggtatg gagaaacagt agagagttgc gataaaaagc gtcaggtagg atccgctaat   4500
cttatggata aaaatgctat ggcatagcaa agtgtgacgc cgtgcaaata atcaatgtgg   4560
acttttctgc cgtgattata gacactttg ttacgcgttt ttgtcatggc tttggtcccg     4620
ctttgttaca gaatgctttt aataagcggg gttaccggtt tggttagcga gaagagccag   4680
taaaagacgc agtgacggca atgtctgatg caatatggaa aattggtttc ttctctgaat   4740
ggcgggagta tgaaaagtat ggctgaagcg caaaatgatc ccctgctgcc gggatactcg   4800
tttaatgccc atctggtggc gggtttaacg ccgattgagg ccaacggtta tctcgatttt   4860
tttatcgacc gaccgctggg aatgaaaggt tatattctca atctcaccat tcgcggtcag   4920
ggggtggtga aaaatcaggg acgagaattt gtttgccgac cgggtgatat tttgctgttc   4980
ccgccaggag agattcatca ctacggtcgt catccggagg ctcgcgaatg gtatcaccag   5040
tgggtttact ttcgtccgcg cgcctactgg catgaatggc ttaactggcc gtcaatattt   5100
gccaatacgg ggttctttcg cccggatgaa gcgcaccagc gcatttcag cgacctgttt     5160 gggcaaatca ttaacgccgg gcaaggggaa gggcgctatt cggagctgct ggcgataaat   5220
ctgcttgagc aattgttact gcggcgcatg gaagcgatta cgagtcgct ccatccaccg     5280 atggataatc gggtacgcga ggcttgtcag tacatcagcg atcacctggc agacagcaat   5340
```

```
tttgatatcg ccagcgtcgc acagcatgtt tgcttgtcgc cgtcgcgtct gtcacatctt    5400
ttccgccagc agttagggat tagcgtctta agctggcgcg aggaccaacg tatcagccag    5460
gcgaagctgc ttttgagcac cacccggatg cctatcgcca ccgtcggtcg caatgttggt    5520
tttgacgatc aactctattt ctcgcgggta tttaaaaaat gcaccggggc cagcccgagc    5580
gagttccgtg ccggttgtga agaaaaagtg aatgatgtag ccgtcaagtt gtcataattg    5640
gtaacgaatc agacaattga cggcttgacg gagtagcata gggtttgcag aatccctgct    5700
tcgtccattt gacaggcaca ttatgcatgc cgcttcgcct tcgcgcgcga attgatctgc    5760
tgcctcgcgc gtttcggtga tgacggtgaa aacctctgac acatgcagct cccggagacg    5820
gtcacagcct gcagcaaaaa acccctcaag acccgtttag aggccccaag gggttatgct    5880
agttattgct cagcggtggc agcagccaac tcagcttcct ttcgggcttt gttatttgta    5940
gagctcatcc atgccatgtg taatcccagc agcagttaca aactcaagaa ggaccatgtg    6000
gtcacgcttt tcgttgggat ctttcgaaag ggcagattgt gtcgacaggt aatggttgtc    6060
tggtaaaagg acagggccat cgccaattgg agtattttgt tgataatggt ctgctagttg    6120
aacggatcca tcttcaatgt tgtggcgaat tttgaagtta gctttgattc cattcttttg    6180
tttgtctgcc gtgatgtata cattgtgtga gttatagttg tactcgagtt tgtgtccgag    6240
aatgttttcca tcttctttaa aatcaatacc ttttaactcg atacgattaa caagggtatc    6300
accttcaaac ttgacttcag cacgcgtctt gtagttcccg tcatctttga aagatatagt    6360
gcgttcctgt acataacctt cgggcatggc actcttgaaa aagtcatgcc gtttcatatg    6420
atccggataa cgggaaaagc attgaacacc ataagagaaa gtagtgacaa gtgttggcca    6480
tggaacaggt agttttccag tagtgcaaat aaatttaagg gtaagttttc cgtatgttgc    6540
atcaccttca ccctctccac tgacagaaaa tttgtgccca ttaacatcac catctaattc    6600
aacaagaatt gggacaactc cagtgaaaag ttcttctcct ttactcatat gtatatctcc    6660
ttcttaaagt taaacaaaat tatttctaga gggaaaccgt tgtggtctcc ctatagtgag    6720
tcgtattaat ttcgcgggat cggcccttcc ggctggctgg tttattgctg ataaatctgg    6780
agccggtgag cgtgggtctc gcggtatcat tgcagcactg gggccagatg taagccctc    6840
ccgtagcggc cgccctgcag cagcatcaaa gttctggtgc tggtagctgc gccagaaggt    6900
atcgctgcgc tggaaaaagc gcacccggac gtcgaactgt ataccgcatc gattgatcag    6960
ggactgaacg agcacggata cattattccg ggcctcggcg atgccggtga caaaatcttt    7020
ggtacgaaat aaagaattcg aagcttgggc ccgaacaaaa actcatctca gaagaggatc    7080
tgaatagcgc cgtcgaccat caccatcatc atcattgagt ttaaacgacg tccagcttgg    7140
ctgtttggc ggatgagaga agattttcag cctgatacag attaaatcag aacgcagaag    7200
cggtctgata aaacagaatt tgcctggcgg cagtagcgcg gtggtccac ctgacccat    7260
gccgaactca gaagtgaaac gccgtagcgc cgatggtagt gtgaggcctc ccatgcgaga    7320
gtagggaact gccaggcatc aaataaaacg aaaggctcag tcgaaagact gggcctttcg    7380
ttttatctgt tgtttgtcgg tgaacgatat ctgcttttct tcggatccct cgagagatct    7440
ccatgggcta cgcgagtgta tactggctta ctatgttggc actgatgagg gtgtcagtga    7500
agtgcttcat gtggcaggag aaaaaaggct gcaccggtgc gtcagcagaa tatgtgatac    7560
aggatatatt ccgcttcctc gctcactgac tcgctacgct cggtcgttcg actgcggcga    7620
gcggaaatgg cttacgaacg gggcggagat tcctggaag atgccaggaa gatacttaac    7680
agggaagtga gagggccgcg gcaaagccgt ttttccatag gctccgcccc cctgacaagc    7740
```

```
atcacgaaat ctgacgctca aatcagtggt ggcgaaaccc gacaggacta taaagatacc    7800
aggcgtttcc ccctggcggc tccctcgtgc gctctcctgt tcctgccttt cggtttaccg    7860
gtgtcattcc gctgttatgg ccgcgtttgt ctcattccac gcctgacact cagttccggg    7920
taggcagttc gctccaagct ggactgtatg cacgaacccc ccgttcagtc cgaccgctgc    7980
gccttatccg gtaactatcg tcttgagtcc aacccggaaa gacatgcaaa agcaccactg    8040
gcagcagcca ctggtaattg atttagagga gttagtcttg aagtcatgcg ccggttaagg    8100
ctaaactgaa aggacaagtt ttggtgactg cgctcctcca agccagttac ctcggttcaa    8160
agagttggta gctcagagaa ccttcgaaaa accgccctgc aaggcggttt tttcgttttc    8220
agagcaagag attacgcgca gaccaaaacg atctcaagaa gatcatctta ttaaggggtc    8280
tgacgcacat gtaatgtagc acctgaagtc agccccatac gataaagtt gtaattctca    8340 tgtttgacag cttatcatcg ataagcttta atgcggtagt ttatcacagt taaattgcta    8400
acgcagtcag gcaccgtgta tgaaatctaa caatgcgctc atcgtcatcc tcggcaccgt    8460
caccctggat gctgtaggca taggcttggt tatgccggta ctgccgggcc tcttgcggga    8520
tatcgtccat tccgacagca tcgccagtca ctatggcgtg ctgctagcgc tatatgcgtt    8580
gatgcaattt ctatgcgcac ccgttctcgg agcactgtcc gaccgctttg ccgccgccc    8640 agtcctgctc gcttcgctac ttggagccac tatcgactac gcgatcatgg cgaccacacc    8700
cgtcctgtgg attctctacg ccggacgcat cgtggccggc atcaccggcg ccacaggtgc    8760
ggttgctggc gcctatatcg ccgacatcac cgatggggaa gatcgggctc gccacttcgg    8820
gctcatgagc gcttgtttcg gcgtgggtat ggtggcaggc cccgtggccg gggactgtt    8880 gggcgccatc tccttgcatg caccattcct tgcggcggcg gtgctcaacg gcctcaacct    8940
actactgggc tgcttcctaa tgcaggagtc gcataaggga gagcgtcgac cgatgccctt    9000
gagagccttc aacccagtca gctccttccg gtgggcgcgg ggcatgacta tcgtcgccgc    9060
acttatgact gtcttcttta tcatgcaact cgtaggacag gtgccggcag cgctctgggt    9120
cattttcggc gaggaccgct ttcgctggag cgcgacgatg atcggcctgt cgcttgcggt    9180
attcggaatc ttgcacgccc tcgctcaagc cttcgtcact ggtcccgcca ccaaacgttt    9240
cggcgagaag caggccatta tcgccggcat ggcggccgac gcgctgggct acgtcttgct    9300
ggcgttcgcg acgcgaggct ggatggcctt ccccattatg attcttctcg cttccggcgg    9360 catcggatg cccgcgttgc aggccatgct gtccaggcag gtagatgacg accatcaggg    9420
acagcttcaa ggatcgctcg cggctcttac cagcctaact tcgatcattg gaccgctgat    9480
cgtcacggcg atttatgccg cctcggcgag cacatggaac gggttggcat ggattgtagg    9540
cgccgcccta taccttgtct gcctccccgc gttgcgtcgc ggtgcatgga gccgggccac    9600
ctcgacctga atggaagccg gcggcacctc gctaacggat tcaccactcc aagaattgga    9660
gccaatcaat tcttgcggag aactgtgaat gcgcaaacca acccttggca gaacatatcc    9720
at                                                                  9722
```

<210> SEQ ID NO 82
<211> LENGTH: 4823
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
gggtggtgcg taacggcaaa agcaccgccg gacatcagcg ctagcggagt gtatactggc      60
ttactatgtt ggcactgatg agggtgtcag tgaagtgctt catgtggcag gagaaaaaag     120
gctgcaccgg tgcgtcagca gaatatgtga tacaggatat attccgcttc ctcgctcact     180
gactcgctac gctcggtcgt tcgactgcgg cgagcggaaa tggcttacga acggggcgga     240
gatttcctgg aagatgccag gaagatactt aacagggaag tgagagggcc gcggcaaagc     300
cgtttttcca taggctccgc cccctgaca agcatcacga aatctgacgc tcaaatcagt     360
ggtggcgaaa cccgacagga ctataaagat accaggcgtt tccccctggc ggctccctcg     420
tgcgctctcc tgttcctgcc tttcggttta ccggtgtcat tccgctgtta tggccgcgtt     480
tgtctcattc cacgcctgac actcagttcc gggtaggcag ttcgctccaa gctggactgt     540
atgcacgaac ccccgttca gtccgaccgc tgcgccttat ccggtaacta tcgtcttgag     600
tccaacccgg aaagacatgc aaaagcacca ctggcagcag ccactggtaa ttgatttaga     660
ggagttagtc ttgaagtcat gcgccggtta aggctaaact gaaaggacaa gttttggtga     720
ctgcgctcct ccaagccagt tacctcggtt caaagagttg gtagctcaga gaaccttcga     780
aaaaccgccc tgcaaggcgg ttttttcgtt ttcagagcaa gagattacgc gcagaccaaa     840
acgatctcaa gaagatcatc ttattaatca gataaaatat ttctagattt cagtgcaatt     900
tatctcttca aatgtagcac ctgaagtcag ccccatacga tataagttgt aattctcatg     960
tttgacagct tatcatcgat aagcttgcaa tttatctctt caaatgtagc acctgaagtc    1020
agccccatac gatataagtt gtaattctca tgttagtcat gccccgcgcc caccggaagg    1080
agctgactgg gttgaaggct ctcaagggca tcggtcgaga tcccggtgcc taatgagtga    1140
gctaacttac attaattgcg ttgcgctcac tgcccgcttt ccagtcggga aacctgtcgt    1200
gccagctgca ttaatgaatc ggccaacgcg cggggagagg cggtttgcgt attgggcgcc    1260
agggtggttt tcttttcac cagtgagacg ggcaacagct gattgccctt caccgcctgg    1320
ccctgagaga gttgcagcaa gcggtccacg ctggtttgcc ccagcaggcg aaaatcctgt    1380
ttgatggtgg ttaacggcgg gatataacat gagctgtctt cggtatcgtc gtatcccact    1440
accgagatgt ccgcaccaac gcgcagcccg gactcggtaa tggcgcgcat tgcgcccagc    1500
gccatctgat cgttggcaac cagcatcgca gtgggaacga tgccctcatt cagcatttgc    1560
atggtttgtt gaaaaccgga catggcactc cagtcgcctt cccgttccgc tatcggctga    1620
atttgattgc gagtgagata tttatgccag ccagccagac gcagacgcgc cgagacagaa    1680
cttaatgggc ccgctaacag cgcgatttgc tggtgaccca atgcgaccag atgctccacg    1740
cccagtcgcg taccgtcttc atgggagaaa ataatactgt tgatgggtgt ctggtcagag    1800
acatcaagaa ataacgccgg aacattagtg caggcagctt ccacagcaat ggcatcctgg    1860
tcatccagcg gatagttaat gatcagccca ctgacgcgtt gcgcgagaag attgtgcacc    1920
gccgctttac aggcttcgac gccgcttcgt tctaccatcg acaccaccac gctggcaccc    1980
agttgatcgg cgcgagattt aatcgccgcg acaatttgcg acggcgcgtg cagggccaga    2040
ctggaggtgg caacgccaat cagcaacgac tgtttgcccg ccagttgttg tgccacgcgg    2100
ttgggaatgt aattcagctc cgccatcgcc gcttccactt ttcccgcgt tttcgcagaa    2160 acgtggctgg cctggttcac cacgcgggaa acggtctgat aagagacacc ggcatactct    2220
gcgacatcgt ataacgttac tggtttcaca ttcaccaccc tgaattgact ctcttccggg    2280
cgctatcatg ccataccgcg aaaggttttg cgccattcga tggtgtccgg gatctcgacg    2340
```

```
ctctccctta tgcgactcct gcattaggct cactataggg gaattgtgag cggataacaa      2400 ttccctcta gagtttgaca gcattatcat cgatctcgag aaatcataaa aaatttattt       2460
gctttgtgag cggataacaa ttataataga ttcaattgtg agcggataac aatttcacac      2520
agaattcatt aaagaggaga aattacatat gagcaaagga gaagaacttt tcactggagt      2580
tgtcccaatt cttgttgaat tagatggtga tgttaatggg cacaaatttt ctgtccgtgg      2640
agagggtgaa ggtgatgcta caaacggaaa actcaccctt aaatttattt gcactactgg      2700
aaaactacct gttccgtggc caacacttgt cactactctg acctatggtg ttcaatgctt      2760
ttcccgttat ccggatcaca tgaaacggca tgactttttc aagagtgcca tgcccgaagg      2820
ttatgtacag gaacgcacta tatctttcaa agatgacggg acctacaaga cgcgtgctga      2880
agtcaagttt gaaggtgata cccttgttaa tcgtatcgag ttaaagggta ttgattttaa      2940
agaagatgga acattcttg gacacaaact cgagtacaac tttaactcac acaatgtata      3000
gatcacggca gacaaacaaa gaatggaat caaagctaac ttcaaaattc gccacaacgt       3060
tgaagatggt tccgttcaac tagcagacca ttatcaacaa aatactccaa ttggcgatgg      3120
ccctgtcctt ttaccagaca accattacct gtcgacacaa tctgtccttt cgaaagatcc      3180
caacgaaaag cgtgaccaca tggtccttct tgagtttgta actgctgctg ggattacaca      3240
tggcatggat gagctctaca aaggatccca ccaccaccac caccactaaa agcttaatta      3300
gctgagcttg gactcctgtt gatagatcca gtaatgacct cagaactcca tctggatttg      3360
ttcagaacgc tcggttgccg ccgggcgttt tttattggtg agaatccaag ctagcttggc      3420
gctgcagtgt gcttctcaaa tgcctgaggc cagtttgctc aggctctccc cgtggaggta      3480
ataattgacg atatgatcag tgcacggcta actaagcggc ctgctgactt tctcgccgat      3540
caaaaggcat tttgctatta agggattgac gagggcgtat ctgcgcagta agatgcgccc      3600
cgcatttagg ggcgtagttc aattggtaga gcaccggtct ctaaaaccgg tgttgggag      3660 ttcgagtctc tccgccctg ccaaattcga aaagcctgct caacgagcag cttttttgc       3720 atgctcgagc agctcagggt cgaatttgct ttcgaatttc tgccattcat ccgcttatta     3780
tcacttattc aggcgtagca accaggcgtt taagggcacc aataactgcc ttaaaaaaat     3840
tacgccccgc cctgccactc atcgcagtac tgttgtaatt cattaagcat tctgccgaca     3900
tggaagccat cacaaacggc atgatgaacc tgaatcgcca gcggcatcag caccttgtcg     3960
ccttgcgtat aatatttgcc catggtgaaa acggggggcga agaagttgtc catattggcc    4020
acgtttaaat caaaactggt gaaactcacc cagggattgg ctgagacgaa aaacatattc    4080
tcaataaacc ctttagggaa ataggccagg ttttcaccgt aacacgccac atcttgcgaa    4140
tatatgtgta gaaactgccg gaaatcgtcg tggtattcac tccagagcga tgaaaacgtt    4200
tcagtttgct catggaaaac ggtgtaacaa gggtgaacac tatcccatat caccagctca    4260
ccgtctttca ttgccatacg gaattccgga tgagcattca tcaggcgggc aagaatgtga    4320
ataaaggccg gataaaactt gtgcttattt ttctttacgg tctttaaaaa ggccgtaata    4380
tccagctgaa cggtctggtt ataggtacat tgagcaactg actgaaatgc ctcaaaatgt    4440
tctttacgat gccattggga tatatcaacg gtggtatatc cagtgatttt tttctccatt    4500
ttagcttcct tagctcctga aaatctcgat aactcaaaaa atacgcccgg tagtgatctt    4560
atttcattat ggtgaaagtt ggaacctctt acgtgccgat caacgtctca ttttcgccaa    4620
aagttggccc agggcttccc ggtatcaaca gggacaccag gatttattta ttctgcgaag    4680
tgatcttccg tcacaggtat ttattcggcg caaagtgcgt cgggtgatgc tgccaactta    4740
```

```
ctgatttagt gtatgatggt gttttgagg tgctccagtg gcttctgttt ctatcagctg    4800
tccctcctgt tcagctactg acg                                           4823

<210> SEQ ID NO 83
<211> LENGTH: 4823
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
gggtggtgcg taacggcaaa agcaccgccg gacatcagcg ctagcggagt gtatactggc     60
ttactatgtt ggcactgatg agggtgtcag tgaagtgctt catgtggcag gagaaaaaag    120
gctgcaccgg tgcgtcagca gaatatgtga tacaggatat attccgcttc ctcgctcact    180
gactcgctac gctcggtcgt tcgactgcgg cgagcggaaa tggcttacga acggggcgga    240
gatttcctgg aagatgccag gaagatactt aacaggaag tgagagggcc gcggcaaagc     300 cgttttcca taggctccgc ccccctgaca agcatcacga atctgacgc tcaaatcagt      360 ggtggcgaaa cccgacagga ctataaagat accaggcgtt tccccctggc ggctccctcg    420
tgcgctctcc tgttcctgcc tttcggttta ccggtgtcat tccgctgtta tggccgcgtt    480
tgtctcattc cacgcctgac actcagtcc gggtaggcag ttcgctccaa gctggactgt     540
atgcacgaac cccccgttca gtccgaccgc tgcgccttat ccggtaacta tcgtcttgag    600 tccaaccgg aaagacatgc aaaagcacca ctggcagcag ccactggtaa ttgatttaga    660
ggagttagtc ttgaagtcat gcgccggta aggctaaact gaaaggacaa gttttggtga    720
ctgcgctcct ccaagccagt tacctcggtt caaagagttg gtagctcaga gaaccttcga    780
aaaaccgccc tgcaaggcgg tttttcgtt ttcagagcaa gagattacgc gcagaccaaa    840
acgatctcaa gaagatcatc ttattaatca gataaaatat ttctagattt cagtgcaatt    900
tatctcttca aatgtagcac ctgaagtcag ccccatacga tataagttgt aattctcatg    960
tttgacagct tatcatcgat aagcttgcaa tttatctctt caaatgtagc acctgaagtc   1020
agccccatac gatataagtt gtaattctca tgttagtcat gccccgcgcc caccggaagg   1080
agctgactgg gttgaaggct ctcaagggca tcggtcgaga tcccggtgcc taatgagtga   1140
gctaacttac attaattgcg ttgcgctcac tgcccgcttt ccagtcggga aacctgtcgt   1200
gccagctgca ttaatgaatc ggccaacgcg cggggagagg cggtttgcgt attgggcgcc   1260
agggtggttt ttcttttcac cagtgagacg ggcaacagct gattgccctt caccgcctgg   1320
ccctgagaga gttgcagcaa gcggtccacg ctggtttgcc ccagcaggcg aaaatcctgt   1380
ttgatggtgg ttaacggcgg gatataacat gagctgtctt cggtatcgtc gtatcccact   1440
accgagatgt ccgcaccaac gcgcagcccg gactcggtaa tggcgcgcat tgcgcccagc   1500
gccatctgat cgttggcaac cagcatcgca gtgggaacga tgccctcatt cagcatttgc   1560
atggtttgtt gaaaaccgga catggcactc cagtcgcctt cccgttccgc tatcggctga   1620
atttgattgc gagtgagata tttatgccag ccagccagac gcagacgcgc cgagacagaa   1680
cttaatgggc ccgctaacag cgcgatttgc tggtgaccca atgcgaccag atgctccacg   1740
cccagtcgcg taccgtcttc atgggagaaa ataatactgt tgatgggtgt ctggtcagag   1800
acatcaagaa ataacgccgg aacattagtg caggcagctt ccacagcaat ggcatcctgg   1860
tcatccagcg gatagttaat gatcagccca ctgacgcgtt gcgcgagaag attgtgcacc   1920
```

```
gccgctttac aggcttcgac gccgcttcgt tctaccatcg acaccaccac gctggcaccc    1980
agttgatcgg cgcgagattt aatcgccgcg acaatttgcg acggcgcgtg cagggccaga    2040
ctggaggtgg caacgccaat cagcaacgac tgtttgcccg ccagttgttg tgccacgcgg    2100
ttgggaatgt aattcagctc cgccatcgcc gcttccactt tttcccgcgt tttcgcagaa    2160
acgtggctgg cctggttcac cacgcgggaa acggtctgat aagagacacc ggcatactct    2220
gcgacatcgt ataacgttac tggtttcaca ttcaccaccc tgaattgact ctcttccggg    2280
cgctatcatg ccataccgcg aaaggttttg cgccattcga tggtgtccgg gatctcgacg    2340
ctctccctta tgcgactcct gcattaggct cactataggg gaattgtgag cggataacaa    2400
ttcccctcta gagtttgaca gcattgtcat cgatctcgag aaatcataaa aaatttattt    2460
gctttgtgag cggataacaa ttataataga ttcaattgtg agcggataac aatttcacac    2520
agaattcatt aaagaggaga attacatat gagcaaagga gaagaacttt tcactggagt    2580
tgtcccaatt cttgttgaat tagatggtga tgttaatggg cacaaatttt ctgtccgtgg    2640
agagggtgaa ggtgatgcta caaacggaaa actcacccct aaatttattt gcactactgg    2700
aaaactacct gttccgtggc caacacttgt cactactctg acctatggtg ttcaatgctt    2760
ttcccgttat ccggatcaca tgaaacggca tgactttttc aagagtgcca tgcccgaagg    2820
ttatgtacag gaacgcacta tatctttcaa agatgacggg acctacaaga cgcgtgctga    2880
agtcaagttt gaaggtgata cccttgttaa tcgtatcgag ttaaagggta ttgattttaa    2940
agaagatgga acattcttg gacacaaact cgagtacaac tttaactcac acaatgtatg    3000
aatcacggca gacaaacaaa agaatggaat caaagctaac ttcaaaattc gccacaacgt    3060
tgaagatggt tccgttcaac tagcagacca ttatcaacaa atactccaa ttggcgatgg    3120 ccctgtcctt ttaccagaca accattacct gtcgacacaa tctgtccttt cgaaagatcc    3180
caacgaaaag cgtgaccaca tggtccttct tgagtttgta actgctgctg ggattacaca    3240
tggcatggat gagctctaca aggatcccca ccaccaccac caccactaaa gcttaatta    3300 gctgagcttg gactcctgtt gatagatcca gtaatgacct cagaactcca tctggatttg    3360
ttcagaacgc tcggttgccg ccgggcgttt tttattggtg agaatccaag ctagcttggc    3420
gctgcagtgt gcttctcaaa tgcctgaggc cagtttgctc aggctctccc cgtggaggta    3480
ataattgacg atatgatcag tgcacggcta actaagcggc ctgctgactt tctcgccgat    3540
caaaaggcat tttgctatta agggattgac gagggcgtat ctgcgcagta agatgcgccc    3600
cgcatttagg ggcgtagttc aattggtaga gcaccggtct tcaaaaccgg gtgttgggag    3660
ttcgagtctc tccgccctg ccaaattcga aaagcctgct caacgagcag gcttttttgc    3720
atgctcgagc agctcaggt cgaatttgct ttcgaatttc tgccattcat ccgcttatta    3780
tcacttattc aggcgtagca accaggcgtt taagggcacc aataactgcc ttaaaaaat    3840 tacgccccgc cctgccactc atcgcagtac tgttgtaatt cattaagcat tctgccgaca    3900
tggaagccat cacaaacggc atgatgaacc tgaatcgcca gcggcatcag caccttgtcg    3960
ccttgcgtat aatatttgcc catggtgaaa acggggcga agaagttgtc catattggcc    4020
acgtttaaat caaaactggt gaaactcacc cagggattgg ctgagacgaa aaacatattc    4080
tcaataaacc ctttagggaa ataggccagg ttttcaccgt aacacgccac atcttgcgaa    4140
tatatgtgta gaaactgccg gaaatcgtcg tggtattcac tccagagcga tgaaaacgtt    4200
tcagtttgct catggaaaac ggtgtaacaa gggtgaacac tatcccatat caccagctca    4260
```

-continued

```
ccgtctttca ttgccatacg gaattccgga tgagcattca tcaggcgggc aagaatgtga    4320
ataaaggccg gataaaactt gtgcttattt ttctttacgg tctttaaaaa ggccgtaata    4380
tccagctgaa cggtctggtt ataggtacat tgagcaactg actgaaatgc ctcaaaatgt    4440
tctttacgat gccattggga tatatcaacg gtggtatatc cagtgatttt tttctccatt    4500
ttagcttcct tagctcctga aaatctcgat aactcaaaaa atacgcccgg tagtgatctt    4560
atttcattat ggtgaaagtt ggaacctctt acgtgccgat caacgtctca ttttcgccaa    4620
aagttggccc agggcttccc ggtatcaaca gggacaccag gatttattta ttctgcgaag    4680
tgatcttccg tcacaggtat ttattcggcg caaagtgcgt cgggtgatgc tgccaactta    4740
ctgatttagt gtatgatggt gttttgagg tgctccagtg gcttctgttt ctatcagctg    4800
tccctcctgt tcagctactg acg                                            4823
```

<210> SEQ ID NO 84
<211> LENGTH: 5171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
gggtggtgcg taacggcaaa agcaccgccg gacatcagcg ctagcggagt gtatactggc      60
ttactatgtt ggcactgatg agggtgtcag tgaagtgctt catgtggcag gagaaaaaag     120
gctgcaccgg tgcgtcagca gaatatgtga tacaggatat attccgcttc ctcgctcact     180
gactcgctac gctcggtcgt tcgactgcgg cgagcggaaa tggcttacga acggggcgga     240
gatttcctgg aagatgccag gaagatactt aacaggaag tgagagggcc gcggcaaagc     300 cgttttttcca taggctccgc ccccctgaca agcatcacga aatctgacgc tcaaatcagt     360
ggtggcgaaa cccgacagga ctataaagat accaggcgtt tccccctggc ggctccctcg     420
tgcgctctcc tgttcctgcc tttcggttta ccggtgtcat tccgctgtta tggccgcgtt     480
tgtctcattc cacgcctgac actcagttcc gggtaggcag ttcgctccaa gctggactgt     540
atgcacgaac ccccgttca gtccgaccgc tgcgccttat ccggtaacta tcgtcttgag     600 tccaaccccgg aaagacatgc aaaagcacca ctggcagcag ccactggtaa ttgatttaga     660
ggagttagtc ttgaagtcat gcgccggtta aggctaaact gaaaggacaa gttttggtga     720
ctgcgctcct ccaagccagt tacctcggtt caaagagttg gtagctcaga gaaccttcga     780
aaaaccgccc tgcaaggcgg ttttttcgtt ttcagagcaa gagattacgc gcagaccaaa     840
acgatctcaa gaagatcatc ttattaatca gataaaatat ttctagattt cagtgcaatt     900
tatctcttca aatgtagcac ctgaagtcag ccccatacga tataagttgt aattctcatg     960
tttgacagct tatcatcgat aagcttgcaa tttatctctt caaatgtagc acctgaagtc    1020
agccccatac gatataagtt gtaattctca tgttagtcat gccccgcgcc caccggaagg    1080
agctgactgg gttgaaggct ctcaagggca tcggtcgaga tcccggtgcc taatgagtga    1140
gctaacttac attaattgcg ttgcgctcac tgcccgcttt ccagtcggga aacctgtcgt    1200
gccagctgca ttaatgaatc ggccaacgcg cggggagagg cggtttgcgt attgggcgcc    1260
agggtggttt ttcttttcac cagtgagacg ggcaacagct gattgcccct taccgcctgg    1320
ccctgagaga gttgcagcaa gcggtccacg ctggtttgcc ccagcaggcg aaaatcctgt    1380
ttgatggtgg ttaacggcgg gatataacat gagctgtctt cggtatcgtc gtatcccact    1440
```

```
accgagatgt ccgcaccaac gcgcagcccg gactcggtaa tggcgcgcat tgcgcccagc    1500
gccatctgat cgttggcaac cagcatcgca gtgggaacga tgccctcatt cagcatttgc    1560
atggtttgtt gaaaaccgga catggcactc cagtcgcctt cccgttccgc tatcggctga    1620
atttgattgc gagtgagata tttatgccag ccagccagac gcagacgcgc cgagacagaa    1680
cttaatgggc ccgctaacag cgcgatttgc tggtgaccca atgcgaccag atgctccacg    1740
cccagtcgcg taccgtcttc atgggagaaa ataatactgt tgatgggtgt ctggtcagag    1800
acatcaagaa ataacgccgg aacattagtg caggcagctt ccacagcaat ggcatcctgg    1860
tcatccagcg gatagttaat gatcagccca ctgacgcgtt gcgcgagaag attgtgcacc    1920
gccgctttac aggcttcgac gccgcttcgt tctaccatcg acaccaccac gctggcaccc    1980
agttgatcgg cgcgagattt aatcgccgcg acaatttgcg acggcgcgtg cagggccaga    2040
ctggaggtgg caacgccaat cagcaacgac tgtttgcccg ccagttgttg tgccacgcgg    2100
ttgggaatgt aattcagctc cgccatcgcc gcttccactt tttcccgcgt tttcgcagaa    2160
acgtggctgg cctggttcac cacgcgggaa acggtctgat aagagacacc ggcatactct    2220
gcgacatcgt ataacgttac tggttttcaca ttcaccaccc tgaattgact ctcttccggg    2280
cgctatcatg ccataccgcg aaaggttttg cgccattcga tggtgtccgg gatctcgacg    2340
ctctccctta tgcgactcct gcattaggga gctgttgaca attaatcatc ggctcgtata    2400
atgtgtggaa ttgtgagcgg ataacaattt cacaaggag gtgcggccgc atgactaagc    2460
ccatcgtttt tgctggcgca cagccctcag gtgaattgac cattggtaac tacatgggtg    2520
cgctgcgtca gtgggtaaac atgcaggatg actaccattg catttactgt atcgttgacc    2580
aacacgcgat caccgtgcgc caggatgcac agaagctgcg taaagcgacg ctggatacgc    2640
tggccttgta tctggcttgt ggtatcgatc ctgagaaaag caccatttt gttcagtccc    2700 acgtgccgga acatgcacag ttaggctggg cactgaactg ctatacctac ttcggcgaac    2760
tgagtcgcat gacgcagttt aaagataaat ctgcgcgtta tgccgagaac atcaacgctg    2820
gtctgtttga ctatccggtg ctgatggcag cggacatcct gctgtatcaa actaatctgg    2880
gtccttgtgg tgaagaccag aaacagcacc tcgaactgag ccgcgatatt gcccagcgtt    2940
tcaacgcgct gtatggcgag atcttttaagg tgccggagcc gtttattccg aaatctggcg    3000
cgcgcgtaat gtcgctgctg gagccgacca agaagatgtc caagtctgac gataatcgca    3060
ataacgttat cggcctgctg gaagatccga atcggtagt gaagaaaatc aaacgtgcgg    3120
tcactgactc cgacgagccg ccggtagttc gctacgatgt gcagaacaaa gcgggcgttt    3180
ccaacctgtt ggatatcctt tcagcggtaa cgggccagag catcccagaa ctggaaaaac    3240
agttcgaagg caagatgtat ggtcatctga aggtgaagt ggctgatgcc gtttccggta    3300
tgctgactga attgcaggaa cgctatcacc gtttccgcaa cgatgaagcc ttcctgcaac    3360
aggtgatgaa agatggcgcg gaaaaagcca gcgcgcacgc ttcccgtacg ctaaaagcgg    3420
tgtacgaagc gattggtttt gtggcgaagc cgtaagcggc gcgtttaaa cggtctccag    3480 cttggctgtt ttggcggatg agagaagatt ttcagcctga tacagattaa atcagaacgc    3540
agaagcggtc tgataaaaca gaatttgcct ggcggcagta gcgcggtggt cccacctgac    3600
cccatgccga actcagaagt gaaacgccgt agcgccgatg gtagtgtggg gtctccccat    3660
gcgagagtag ggaactgcca ggcatcaaat aaaacgaaag gctcagtcga aagactgggc    3720
cttgtttgtg agctcccggt catcaatcat ccccataatc cttgttagcc tgcagtgtgc    3780
ttctcaaatg cctgaggcca gtttgctcag gctctccccg tggaggtaat aattgacgat    3840
```

```
atgatcagtg cacggctaac taagcggcct gctgactttc tcgccgatca aaaggcattt    3900
tgctattaag ggattgacga gggcgtatct gcgcagtaag atgcgcccg catttagggg    3960
cgtagttcaa ttggtagagc accggtcttc aaaaccgggt gttgggagtt cgagtctctc    4020
cgccccctgcc aaattcgaaa agcctgctca acgagcaggc ttttttgcat gctcgagcag    4080
ctcagggtcg aatttgcttt cgaatttctg ccattcatcc gcttattatc acttattcag    4140
gcgtagcaac caggcgttta agggcaccaa taactgcctt aaaaaaatta cgccccgccc    4200
tgccactcat cgcagtactg ttgtaattca ttaagcattc tgccgacatg aagccatca    4260
caaacggcat gatgaacctg aatcgccagc ggcatcagca ccttgtcgcc ttgcgtataa    4320
tatttgccca tggtgaaaac gggggcgaag aagttgtcca tattggccac gtttaaatca    4380
aaactggtga aactcaccca gggattggct gagacgaaaa acatattctc aataaaccct    4440
ttagggaaat aggccaggtt ttcaccgtaa cacgccacat cttgcgaata tatgtgtaga    4500
aactgccgga atcgtcgtg gtattcactc cagagcgatg aaaacgtttc agtttgctca    4560
tggaaaacgg tgtaacaagg gtgaacacta tcccatatca ccagctcacc gtctttcatt    4620
gccatacgga attccggatg agcattcatc aggcgggcaa gaatgtgaat aaaggccgga    4680
taaaacttgt gcttattttt ctttacggtc tttaaaaagg ccgtaatatc cagctgaacg    4740
gtctggttat aggtacattg agcaactgac tgaaatgcct caaaatgttc tttacgatgc    4800
cattgggata tatcaacggt ggtatatcca gtgatttttt tctccatttt agcttcctta    4860
gctcctgaaa atctcgataa ctcaaaaaat acgcccggta gtgatcttat ttcattatgg    4920
tgaaagttgg aacctcttac gtgccgatca acgtctcatt ttcgccaaaa gttggcccag    4980
ggcttcccgg tatcaacagg gacaccagga tttatttatt ctgcgaagtg atcttccgtc    5040
acaggtattt attcggcgca aagtgcgtcg ggtgatgctg ccaacttact gatttagtgt    5100
atgatggtgt ttttgaggtg ctccagtggc ttctgtttct atcagctgtc cctcctgttc    5160
agctactgac g                                                         5171
```

<210> SEQ ID NO 85
<211> LENGTH: 1005
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atgactaagc ccatcgttttt tgctggcgca cagccctcag gtgaattgac cattggtaac      60
tacatgggtg cgctgcgtca gtgggtaaac atgcaggatg actaccattg catttactgt     120
atcgttgacc aacacgcgat caccgtgcgc caggatgcac agaagctgcg taaagcgacg     180
ctggatacgc tggccttgta tctggcttgt ggtatcgatc ctgagaaaag caccattttt     240
gttcagtccc acgtgccgga acatgcacag ttaggctggg cactgaactg ctataccta      300
ttcggcgaac tgagtcgcat gacgcagttt aaagataaat ctgcgcgtta tgccgagaac     360
atcaacgctg gtctgtttga ctatccggtg ctgatggcag cggacatcct gctgtatcaa     420
actaatctga gtcctgctgg tgaagaccag aaacagcacc tcgaactgag ccgcgatatt     480
gcccagcgtt tcaacgcgct gtatggcgag atctttaagg tgccggagcc gtttattccg     540
aaatctggcg cgcgcgtaat gtcgctgctg agccgaccca gaagatgtc caagtctgac     600
gataatcgca ataacgttat cggcctgctg gaagatccga atcggtagt gaagaaaatc     660
```

```
aaacgtgcgg tcactgactc cgacgagccg ccggtagttc gctacgatgt gcagaacaaa    720
gcgggcgttt ccaacctgtt ggatatcctt tcagcggtaa cgggccagag catcccagaa    780
ctggaaaaac agttcgaagg caagatgtat ggtcatctga aggtgaagt ggctgatgcc     840 gtttccggta tgctgactga attgcaggaa cgctatcacc gtttccgcaa cgatgaagcc    900
ttcctgcaac aggtgatgaa agatggcgcg gaaaaagcca gcgcgcacgc ttcccgtacg    960
ctaaaagcgg tgtacgaagc gattggtttt gtggcgaagc cgtaa                    1005
```

<210> SEQ ID NO 86
<211> LENGTH: 2976
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
cttttgctga gttgaaggat ccgcggccgc tcgggttgtc agcctgtccc gcttataaga     60
tcatacgccg ttatacgttg tttacgcttt gaggaatccc atatgatgac taagcccatc    120 gttttagtg gcgcacagcc ctcaggtgaa ttgaccattg gtaactacat gggtgcgctg     180
cgtcagtggg taaacatgca ggatgactac cattgcattt actgtatcgt tgaccaacac    240
gcgatcaccg tgcgccagga tgcacagaag ctgcgtaaag cgacgctgga tacgctggcc    300
ttgtatctgg cttgtggtat cgatcctgag aaaagcacca ttttttgttca gtcccacgtg   360 ccggaacatg cacagttagg ctgggcactg aactgctata cctacttcgg cgaactgagt    420
cgcatgacgc agtttaaaga taaatctgcg cgttatgccg agaacatcaa cgctggtctg    480
tttgactatc cggtgctgat ggcagcggac atcctgctgt atcaaactaa tctggtaccg    540
gtgggtgaag accagaaaca gcacctcgaa ctgagccgcg atattgccca gcgtttcaac    600
gcgctgtatg gcgagatctt taaggtgccg gagccgttta ttccgaaatc tggcgcgcgc    660
gtaatgtcgc tgctggagcc gaccaagaag atgtccaagt ctgacgataa tcgcaataac    720
gttatcggcc tgctggaaga tccgaaatcg gtagtgaaga aaatcaaacg tgcggtcact    780
gactccgacg agccgccggt agttcgctac gatgtgcaga acaaagcggg cgtttccaac    840
ctgttggata tcctttcagc ggtaacgggc cagagcatcc cagaactgga aaaacagttc    900
gaaggcaaga tgtatggtca tctgaaaggt gaagtggctg atgccgtttc cggtatgctg    960
actgaattgc aggaacgcta tcaccgtttc cgcaacgatg aagccttcct gcaacaggtg   1020
atgaaagatg gcgcggaaaa agccagcgcg cacgcttccc gtacgctaaa agcggtgtac   1080
gaagcgattg gttttgtggc gaagccgtaa ctgcagtttc aaacgctaaa ttgcctgatg   1140
cgctacgctt atcaggccta catgatctct gcaatatatt gagtttgcgt gcttttgtag   1200
gccggataag gcgttcacgc cgcatccggc aagaaacagc aaacaatcca aaacgccgcg   1260
ttcagcggcg ttttttctgc ttttcttcgc gaattaattc cgcttcgcac atgtgagcaa   1320
aaggccagca aaaggccagg aaccgtaaaa aggccgcgtt gctggcgttt ttccataggc   1380
tccgcccccc tgacgagcat cacaaaaatc gacgctcaag tcagaggtgg cgaaacccga   1440
caggactata aagataccag gcgtttcccc ctggaagctc cctcgtgcgc tctcctgttc   1500 cgacccctgcc gcttaccgga tacctgtccg ccttttctccc ttcgggaagc gtggcgcttt   1560
ctcatagctc acgctgtagg tatctcagtt cggtgtaggt cgttcgctcc aagctgggct   1620
gtgtgcacga accccccgtt cagcccgacc gctgcgcctt atccggtaac tatcgtcttg   1680
```

```
agtccaaccc ggtaagacac gacttatcgc cactggcagc agccactggt aacaggatta    1740
gcagagcgag gtatgtaggc ggtgctacag agttcttgaa gtggtggcct aactacggct    1800
acactagaag gacagtattt ggtatctgcg ctctgctgaa gccagttacc ttcggaaaaa    1860
gagttggtag ctcttgatcc ggcaaacaaa ccaccgctgg tagcggtggt ttttttgttt    1920
gcaagcagca gattacgcgc agaaaaaaag gatctcaaga agatcctttg atcttttcta    1980
cggggtctga cgctcagtgg aacgaaaact cacgttaagg gattttggtc atgaacaata    2040
aaactgtctg cttacataaa cagtaataca aggggtgtta tgagccatat tcaacgggaa    2100
acgtcttgct cgaggccgcg attaaattcc aacatggatg ctgatttata tgggtataaa    2160
tgggctcgcg ataatgtcgg gcaatcaggt gcgacaatct atcgattgta tgggaagccc    2220
gatgcgccag agttgtttct gaaacatggc aaaggtagcg ttgccaatga tgttacagat    2280
gagatggtca gactaaactg gctgacggaa tttatgcctc ttccgaccat caagcatttt    2340
atccgtactc ctgatgatgc atggttactc accactgcga tccccgggaa aacagcattc    2400
caggtattag aagaatatcc tgattcaggt gaaaatattg ttgatgcgct ggcagtgttc    2460
ctgcgccggt tgcattcgat tcctgttttgt aattgtcctt ttaacagcga tcgcgtattt    2520
cgtctcgctc aggcgcaatc acgaatgaat aacggtttgg ttgatgcgag tgattttgat    2580
gacgagcgta atggctggcc tgttgaacaa gtctggaaag aaatgcataa gcttttgcca    2640
ttctcaccgg attcagtcgt cactcatggt gatttctcac ttgataacct tatttttgac    2700
gaggggaaat taataggttg tattgatgtt ggacgagtcg gaatcgcaga ccgataccag    2760
gatcttgcca tcctatggaa ctgcctcggt gagttttctc cttcattaca gaaacggctt    2820
tttcaaaaat atggtattga taatcctgat atgaataaat tgcagtttca tttgatgctc    2880
gatgagtttt tctaatcaga attggttaat tggttgtaac actggcagag cattacgctg    2940
acttgacggg acggcggctt tgttgaataa atcgaa                              2976

<210> SEQ ID NO 87
<211> LENGTH: 1005
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
atgactaagc ccatcgtttt tgctggcgca cagccctcag gtgaattgac cattggtaac      60
tacatgggtg cgctgcgtca gtgggtaaac atgcaggatg actaccattg catttactgt     120
atcgttgacc aacacgcgat caccgtgcgc caggatgcac agaagctgcg taaagcgacg     180
ctggatacgc tggccttgta tctggcttgt ggtatcgatc ctgagaaaag caccattttt     240
gttcagtccc acgtgccgga acatgcacag ttaggctggg cactgaactg ctataccta c    300 ttcggcgaac tgagtcgcat gacgcagttt aaagataaat ctgcgcgtta tgccgagaac     360
atcaacgctg gtctgtttga ctatccggtg ctgatggcag cggacatcct gctgtatcaa     420
actaatctgg gtccttgtgg tgaagaccag aaacagcacc tcgaactgag ccgcgatatt     480
gcccagcgtt tcaacgcgct gtatggcgag atctttaagg tgccggagcc gtttattccg     540
aaatctggcg cgcgcgtaat gtcgctgctg agccgaccag agaagatgtc caagtctgac     600
gataatcgca ataacgttat cggcctgctg aagatccgaa atcggtagt gaagaaaatc     660 aaacgtgcgg tcactgactc cgacgagccg ccggtagttc gctacgatgt gcagaacaaa     720
```

```
gcgggcgttt ccaacctgtt ggatatcctt tcagcggtaa cgggccagag catcccagaa      780
ctggaaaaac agttcgaagg caagatgtat ggtcatctga aggtgaagt  ggctgatgcc      840 gtttccggta tgctgactga attgcaggaa cgctatcacc gtttccgcaa cgatgaagcc      900
ttcctgcaac aggtgatgaa agatggcgcg gaaaaagcca gcgcgcacgc ttcccgtacg      960
ctaaaagcgg tgtacgaagc gattggtttt gtggcgaagc cgtaa                     1005

<210> SEQ ID NO 88
<211> LENGTH: 1005
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atgactaagc ccatcgtttt tgctggcgca cagccctcag gtgaattgac cattggtaac      60
tacatgggtg cgctgcgtca gtgggtaaac atgcaggatg actaccattg catttactgt     120
atcgttgacc aacacgcgat caccgtgcgc caggatgcac agaagctgcg taaagcgacg     180
ctggatacgt ggccttgta  tctggcttgt ggtatcgatc ctgagaaaag caccattttt     240
gttcagtccc acgtgccgga acatgcacag ttaggctggg cactgaactg ctatacctac     300
ttcggcgaac tgagtcgcat gacgcagttt aaagataaat ctgcgcgtta tgccgagaac     360
atcaacgctg gtctgtttga ctatccggtg ctgatggcag cggacatcct gctgtatcaa     420
actaatctga gtcctgctgg tgaagaccag aaacagcacc tcgaactgag ccgcgatatt     480
gcccagcgtt tcaacgcgct gtatggcgag atctttaagg tgccggagcc gtttattccg     540
aaatctggcg cgcgcgtaat gtcgctgctg agccgaccag agaagatgtc caagtctgac     600
gataatcgca ataacgttat cggcctgctg gaagatccga atcggtagt  gaagaaaatc     660 aaacgtgcgc tcactgactc cgacgagccg ccggtagttc gctacgatgt gcagaacaaa     720
gcgggcgttt ccaacctgtt ggatatcctt tcagcggtaa cgggccagag catcccagaa     780
ctggaaaaac agttcgaagg caagatgtat ggtcatctga aggtgaagt  ggctgatgcc     840 gtttccggta tgctgactga attgcaggaa cgctatcacc gtttccgcaa cgatgaagcc     900
ttcctgcaac aggtgatgaa agatggcgcg gaaaaagcca gcgcgcacgc ttcccgtacg     960
ctaaaagcgg tgtacgaagc gattggtttt gtggcgaagc cgtaa                    1005

<210> SEQ ID NO 89
<211> LENGTH: 9147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
ttctctgtca cagaatgaaa atttttctgt catctcttcg ttattaatgt tgtaattga      60 ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcggggc  tcccctttagg gttccgattt agtgctttac ggcacctcga    300
ccccaaaaaa cttgattagg gtgatggttc acgtagtggg ccatcgccct gatagacggt    360
```

```
ttttcgccct tgacgttgg agtccacgtt ctttaatagt ggactcttgt tccaaactgg    420
aacaacactc aaccctatct cggtctattc ttttgattta taagggattt tgccgatttc    480
ggcctattgg ttaaaaaatg agctgattta acaaaaattt aacgcgaatt ttaacaaaat    540
attaacgttt acaatttcag gtggcacttt tcggggaaat gtgcgcggaa ccccctatttg   600 tttattttc taaatacatt caaatatgta tccgctcatg agacaataac cctgataaat    660
gcttcaataa tattgaaaaa ggaagagtat ggcgtagagt attcaacatt tccgtgtcgc   720
ccttattccc ttttttgcgg cattttgcct tcctgttttt gctcacccag aaacgctggt    780
gaaagtaaaa gatgctgaag atcagttggg tgcacgagtg ggttacatcg aactggatct   840
caacagcggt aagatccttg agagttttcg ccccgaagaa cgttttccaa tgatgagcac    900
ttttaaagtt ctgctatgtg gcgcggtatt atcccgtatt gacgccggc aagagcaact    960 cggtcgccgc atacactatt ctcagaatga cttggttgag tactcaccag tcacagaaaa   1020
gcatcttacg gatggcatga cagtaagaga attatgcagt gctgccataa ccatgagtga   1080
taacactgcg gccaacttac ttctgacaac gatcggagga ccgaaggagc taaccgcttt   1140
tttgcacaac atgggggatc atgtaactcg ccttgatcgt tgggaaccgg agctgaatga   1200
agccatacca aacgacgagc gtgacaccac gatgcctgta gcaatggcaa caacgttgcg   1260
caaactatta actggcgaac tacttactct agcttcccgg caacaattaa tagactggat   1320
ggaggcggat aaagttgcag gaccacttct gcgctcggcc cttccggctg gctggtttat   1380
tgctgataaa tctggagccg gtgagcgtgg gtctcgcggt atcattgcag cactggggcc   1440
agatggtaag ccctcccgta tcgtagttat ctacacgacg gggagtcagg caactatgga    1500
tgaacgaaat agacagatcg ctgagatagg tgcctcactg attaagcatt ggtaactgtc    1560
agaccaagtt tactcatata ctttagat tgatttaaaa cttcattttt aatttaaaag    1620
gatctaggtg aagatccttt ttgataatct catgaccaaa atcccttaac gtgagttttc    1680
gttccactga gcgtcagacc ccgtagaaaa gatcaaagga tcttcttgag atcctttttt   1740
tctgcgcgta atctgctgct tgcaaacaaa aaaaccaccg ctaccagcgg tggtttgttt    1800
gccggatcaa gagctaccaa ctcttttcc gaaggtaact ggcttcagca gagcgcagat    1860
accaaatact gtccttctag tgtagccgta gttaggccac cacttcaaga actctgtagc    1920
accgcctaca tacctcgctc tgctaatcct gttaccagtg gctgctgcca gtggcgataa    1980
gtcgtgtctt accgggttgg actcaagacg atagttaccg gataaggcgc agcggtcggg    2040
ctgaacgggg ggttcgtgca cacagcccag cttggagcga acgacctaca ccgaactgag    2100
atacctacag cgtgagcatt gagaaagcgc cacgcttccc gaagggagaa aggcggacag    2160
gtatccggta agcggcaggg tcggaacagg agagcgcacg agggagcttc caggggggaaa   2220 cgcctggtat ctttatagtc ctgtcgggtt tcgccacctc tgacttgagc gtcgattttt    2280
gtgatgctcg tcaggggggc ggagcctatg gaaaaacgcc agcaacgcgg cctttttacg    2340
gttcctggcc ttttgctggc cttttgctca catgttcttt cctgcgttat cccctgattc    2400
tgtggataac cgtattaccg cctttgagtg agctgatacc gctcgccgca gccgaacgac    2460
cgagcgcagc gagtcagtga gcgaggaagc ggaagagcgc ctgatgcggt attttctcct    2520
tacgcatctg tgcggtattt cacaccgcag accagccgcg taacctggca aaatcggtta    2580
cggttgagta taaatggat gccctgcgta agcgggtgtg gcggacaat aaagtcttaa     2640 actgaacaaa atagatctaa actatgacaa taaagtctta aactgacag aatagttgta    2700 aactgaaatc agtccagtta tgctgtgaaa aagcatactg gactttgtt atggctaaag    2760
```

```
caaactcttc attttctgaa gtgcaaattg cccgtcgtat taaagagggg cgtggccaag    2820
ggcatggtaa agactatatt cgcggcgttg tgacaattta ccgaacaact ccgcggccgg    2880
gaagccgatc tcggcttgaa cgaattgtta ggtggcggta cttgggtcga tatcaaagtg    2940
catcacttct tcccgtatgc ccaactttgt atagagagcc actgcgggat cgtcaccgta    3000
atctgcttgc acgtagatca cataagcacc aagcgcgttg gcctcatgct tgaggagatt    3060
gatgagcgcg gtggcaatgc cctgcctccg gtgctcgccg gagactgcga gatcatagat    3120
atagatctca ctacgcggct gctcaaacct gggcagaacg taagccgcga gagcgccaac    3180
aaccgcttct tggtcgaagg cagcaagcgc gatgaatgtc ttactacgga gcaagttccc    3240
gaggtaatcg gagtccggct gatgttggga gtaggtggct acgtctccga actcacgacc    3300
gaaaagatca agagcagccc gcatggattt gacttggtca gggccgagcc tacatgtgcg    3360
aatgatgccc atacttgagc cacctaactt tgttttaggg cgactgccct gctgcgtaac    3420
atcgttgctg ctgcgtaaca tcgttgctgc tccataacat caaacatcga cccacggcgt    3480
aacgcgcttg ctgcttggat gcccgaggca tagactgtac aaaaaaacag tcataacaag    3540
ccatgaaaac cgccactgcg ccgttaccac cgctgcgttc ggtcaaggtt ctggaccagt    3600
tgcgtgagcg catacgctac ttgcattaca gtttacgaac cgaacaggct tatgtcaact    3660
gggttcgtgc cttcatccgt ttccacggtg tgcgtcaccc ggcaaccttg ggcagcagcg    3720
aagtcgaggc atttctgtcc tggctggcga acgagcgcaa ggtttcggtc tccacgcatc    3780
gtcaggcatt ggcggccttg ctgttcttct acggcaaggt gctgtgcacg gatctgccct    3840
ggcttcagga gatcggtaga cctcggccgt cgcggcgctt gccggtggtg ctgaccccgg    3900
atgaagtggt tcgcatcctc ggttttctgg aaggcgagca tcgtttgttc gcccaggact    3960
ctagctatag ttctagtggt tggctacgta cccgtagtgg ctatggcagg gcttgcgctt    4020
aatgcgccgc tacagggcgc gtggggatac cccctagagc cccagctggt tctttccgcc    4080
tcagaagcca tagagcccac cgcatcccca gcatgcctgc tattgtcttc ccaatcctcc    4140
cccttgctgt cctgccccac cccacccccc agaatagaat gacacctact cagacaatgc    4200
gatgcaattt cctcattta ttaggaaagg acagtgggag tggcaccttc cagggtcaag    4260
gaaggcacgg gggaggggca acaacagat ggctggcaac tagaaggcac agtcgaggct    4320
gatcagcggg tttaaacggg ccctctagac tcgagttaaa gtcgacgcgg ggaggcggcc    4380
caaagggaga tccgactcgt ctgagggcga aggcgaagac gcggaagagg ccgcagagcc    4440
ggcagcaggc cgcgggaagg aaggtccgct ggattgaggg ccgaagggac gtagcagaag    4500
gacgtcccgc gcagaatcca ggtggcaaca caggcgagca gccaaggaaa ggacgatgat    4560
ttccccgaca acaccacgga attgtcagtg cccaacagcc gagcccctgt ccagcagcgg    4620
gcaaggcagg cggcgatgag ttccgccgtg gcaatagggg gggggaaagc gaaagtcccg    4680
gaaaggagct gacaggtggt ggcaatgccc caaccagtgg gggttgcgtc agcaaacaca    4740
gtgcacacca cgccacgttg cctgacaacg ggccacaact cctcataaag agacagcaac    4800
caggatttat acaaggagga gaaaatgaaa gccatacggg aagcaatagc atgatacaaa    4860
ggcattaaag cagcgtatcc acatagcgta aaaggagcaa catagttaag aataccagtc    4920
aatctttcac aaattttgta atccagaggt tgattgtcga cttaacgcgt tgaattctca    4980
atggtgatgg tgatgatgac cggtatgcat attcagatcc tcttctgaga tgagttttg    5040
ttcgaagggc cccttgtaca gctcgtccat gccgagagtg atcccggcgg cggtcacgaa    5100
```

```
ctccagcagg accatgtgat cgcgcttctc gttggggtct ttgctcaggg cggactgggt    5160
gctcaggtag tggttgtcgg gcagcagcac ggggccgtcg ccgatggggg tgttctgctg    5220
gtagtggtcg gcgagctgca cgctgccgtc ctcgatgttg tggcggatct tgaagttcac    5280
cttgatgccg ttcttctgct tgtcggccat gatatagacg ttgtggctgt tgtagttgta    5340
ctccagcttg tgcccagga tgttgccgtc ctccttgaag tcgatgccct tcagctcgat    5400
gcggttcacc agggtgtcgc cctcgaactt cacctcggcg cgggtcttgt agttgccgtc    5460
gtccttgaag aagatggtgc gctcctggac gtagccttcg ggcatggcgg acttgaagaa    5520
gtcgtgctgc ttcatgtggt cggggtagcg gctgaagcac tgcacgccgt aggtcagggt    5580
ggtcacgagg gtgggccagg gcacgggcag cttgccggtg gtgcagatga acttcagggt    5640
cagcttgccc taagtggcat cgccctcgcc ctcgccggac acgctgaact tgtggccgtt    5700
tacgtcgccg tccagctcga ccaggatggg caccaccccg gtgaacagct cctcgccctt    5760
gctcaccatg gtggcggcgc tagccagctt gggtctccct atagtgagtc gtattaattt    5820
cgataagcca gtaagccagt aagcagtggg ttctctagtt agccagagag ctctgcttat    5880
atagacctcc caccgtacac gcctaccgcc catttgcgtc aatggggcgg agttgttacg    5940
acattttgga aagtcccgtt gattttggtg ccaaaacaaa ctcccattga cgtcaatggg    6000
gtggagactt ggaaatcccc gtgagtcaaa ccgctatcca cgcccattga tgtactgcca    6060
aaaccgcatc accatggtaa tagcgatgac taatacgtag atgtactgcc aagtaggaaa    6120
gtcccataag gtcatgtact gggcataatg ccaggcgggc catttaccgt cattgacgtc    6180
aatggggggc gtacttggca tatgatacac ttgatgtact gccaagtggg cagtttaccg    6240
taaatagtcc acccattgac gtcaatggaa agtccctatt ggcgttacta tgggaacata    6300
cgtcattatt gacgtcaatg ggcggggtc gttgggcggt cagccaggcg ggccatttac    6360
cgtaagttat gtaacgcgga actccatata tgggctatga actaatgacc ccgtaattga    6420
ttactattaa taactagtca ataatcaatg tcaacgcgta tatctggccc gtacatcgcg    6480
aagcagcgca aaacggatcc tgcaggtatt tgcggccgcg gtccgtatac tccggaatat    6540
taatagatca tggagataat taaaatgata accatctcgc aaataaataa gtatttact     6600 gttttcgtaa cagttttgta ataaaaaaac ctataaatat tccggattat tcataccgtc    6660
ccaccatcgg gcgcgaactc ctaaaaaacc gccaccatga agtgcctttt gtacttagcc    6720
tttttattca ttggggtgaa ttgcaagttc accatagttt ttccacacaa ccaaaaagga    6780
aactggaaaa atgttccttc taattaccat tattgcccgt caagctcaga tttaaattgg    6840
cataatgact taataggcac agccttacaa gtcaaaatgc caagagtca caaggctatt     6900 caagcagacg gttggatgtg tcatgcttcc aaatgggtca ctacttgtga tttccgctgg    6960
tatggaccga agtatataac acattccatc cgatccttca ctccatctgt agaacaatgc    7020
aaggaaagca ttgaacaaac gaaacaagga acttggctga atccaggctt ccctcctcaa    7080
agttgtggat atgcaactgt gacggatgcc gaagcagtga ttgtccaggt gactcctcac    7140
catgtgctgg ttgatgaata cacaggagaa tgggttgatt cacagttcat caacggaaaa    7200
tgcagcaatt acatatgccc cactgtccat aactctacaa cctggcattc tgactataag    7260
gtcaaagggc tatgtgattc taacctcatt tccatggaca tcaccttctt ctcagaggac    7320
ggagagctat catccctggg aaaggagggc acagggttca gaagtaacta ctttgcttat    7380
gaaactggag gcaaggcctg caaaatgcaa tactgcaagc attggggagt cagactccca    7440
tcaggtgtct ggttcgagat ggctgataag gatctctttg ctgcagccag attccctgaa    7500
```

```
tgcccagaag ggtcaagtat ctctgctcca tctcagacct cagtggatgt aagtctaatt    7560
caggacgttg agaggatctt ggattattcc ctctgccaag aaacctggag caaaatcaga    7620
gcgggtcttc caatctctcc agtggatctc agctatcttg ctcctaaaaa cccaggaacc    7680
ggtcctgctt tcaccataat caatggtacc ctaaaatact ttgagaccag atacatcaga    7740
gtcgatattg ctgctccaat cctctcaaga atggtcggaa tgatcagtgg aactaccaca    7800
gaaagggaac tgtgggatga ctgggcacca tatgaagacg tggaaattgg acccaatgga    7860
gttctgagga ccagttcagg atataagttt cctttataca tgattggaca tggtatgttg    7920
gactccgatc ttcatcttag ctcaaaggct caggtgttcg aacatcctca cattcaagac    7980
gctgcttcgc aacttcctga tgatgagagt ttattttttg gtgatactgg gctatccaaa    8040
aatccaatcg agcttgtaga aggttggttc agtagttgga aaagctctat tgcctctttt    8100
ttctttatca tagggttaat cattggacta ttcttggttc tccgagttgg tatccatctt    8160
tgcattaaat taaagcacac caagaaaaga cagatttata cagacataga gatgaaccga    8220
cttggaaagt gataaggcca ggccggccaa gcttgtcgag aagtactaga ggatcataat    8280
cagccatacc acatttgtag aggttttact tgctttaaaa aacctcccac acctccccct    8340
gaacctgaaa cataaaatga atgcaattgt tgttgttaac ttgtttattg cagcttataa    8400
tggttacaaa taaagcaata gcatcacaaa tttcacaaat aaagcatttt ttcactgca    8460 ttctagttgt ggtttgtcca aactcatcaa tgtatcttat catgtctgga tctgatcact    8520
gcttgagcct aggtcgggca ggaagagggc ctatttccca tgattccttc atatttgcat    8580
atacgataca aggctgttag agagataatt agaattaatt tgactgtaaa cacaaagata    8640
ttagtacaaa atacgtgacg tagaaagtaa taatttcttg ggtagtttgc agttttaaaa    8700
ttatgtttta aaatggacta tcatatgctt accgtaactt gaaagtattt cgatttcttg    8760
gctttatata tcttgtggaa aggacgaaac accaggggcg tagttcaatt ggtagagcac    8820
cggtctctaa aaccgggtgt tgggagttcg agtctctccg cccctgccat tttttgctag    8880
gctcaagcag tgatctccga accagataag tgaaatctag ttccaaacta ttttgtcatt    8940
tttaattttc gtattagctt acgacgctac acccagttcc catctatttt gtcactcttc    9000
cctaaataat ccttaaaaac tccatttcca cccctcccag ttcccaacta ttttgtccgc    9060
ccacagcggg gcatttttct tcctgttatg tttttaatca acatcctgc caactccatg     9120 tgacaaaccg tcatcttcgg ctacttt                                        9147
```

<210> SEQ ID NO 90
<211> LENGTH: 9332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
ttctctgtca cagaatgaaa atttttctgt catctcttcg ttattaatgt tgtaattga     60 ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcggggc tcccctttaggg gttccgattt agtgctttac ggcacctcga    300
ccccaaaaaa cttgattagg gtgatggttc acgtagtggg ccatcgccct gatagacggt    360
```

```
tttcgccct tgacgttgg agtccacgtt ctttaatagt ggactcttgt tccaaactgg    420
aacaacactc aaccctatct cggtctattc ttttgattta taagggattt tgccgatttc    480
ggcctattgg ttaaaaaatg agctgattta acaaaaattt aacgcgaatt ttaacaaaat    540
attaacgttt acaatttcag gtggcacttt tcggggaaat gtgcgcggaa cccctatttg    600 tttattttc taaatacatt caaatatgta tccgctcatg agacaataac cctgataaat    660
gcttcaataa tattgaaaaa ggaagagtat gagtattcaa catttccgtg tcgcccttat    720 tcccttttt gcggcatttt gccttcctgt ttttgctcac ccagaaacgc tggtgaaagt    780
aaaagatgct gaagatcagt tgggtgcacg agtgggttac atcgaactgg atctcaacag    840
cggtaagatc cttgagagtt ttcgccccga agaacgtttt ccaatgatga gcacttttaa    900
agttctgcta tgtggcgcgg tattatcccg tattgacgcc gggcaagagc aactcggtcg    960
ccgcatacac tattctcaga atgacttggt tgagtactca ccagtcacag aaaagcatct   1020 tacgatggc atgacagtaa gagaattatg cagtgctgcc ataaccatga gtgataacac   1080
tgcggccaac ttacttctga acgatcgg aggaccgaag gagctaaccg cttttttgca   1140
caacatgggg gatcatgtaa ctcgccttga tcgttgggaa ccggagctga atgaagccat   1200
accaaacgac gagcgtgaca ccacgatgcc tgtagcaatg gcaacaacgt tgcgcaaact   1260
attaactggc gaactactta ctctagcttc ccggcaacaa ttaatagact ggatggaggc   1320
ggataaagtt gcaggaccac ttctgcgctc ggcccttccg gctggctggt ttattgctga   1380
taaatctgga gccggtgagc gtgggtctcg cggtatcatt gcagcactgg ggccagatgg   1440
taagccctcc cgtatcgtag ttatctacac gacggggagt caggcaacta tggatgaacg   1500
aaatagacag atcgctgaga taggtgcctc actgattaag cattggtaac tgtcagacca   1560
agtttactca tatatacttt agattgattt aaaacttcat ttttaattta aaaggatcta   1620
ggtgaagatc cttttgata atctcatgac caaaatccct taacgtgagt tttcgttcca   1680
ctgagcgtca gaccccgtag aaaagatcaa aggatcttct tgagatcctt ttttttctgcg   1740 cgtaatctgc tgcttgcaaa caaaaaaacc accgctacca gcggtggttt gtttgccgga   1800
tcaagagcta ccaactcttt ttccgaaggt aactggcttc agcagagcgc agataccaaa   1860
tactgtcctt ctagtgtagc cgtagttagg ccaccacttc aagaactctg tagcaccgcc   1920
tacatacctc gctctgctaa tcctgttacc agtggctgct gccagtggcg ataagtcgtg   1980
tcttaccggg ttggactcaa gacgatagtt accggataag gcgcagcggt cgggctgaac   2040
ggggggttcg tgcacacagc ccagcttgga gcgaacgacc tacaccgaac tgagatacct   2100
acagcgtgag cattgagaaa gcgccacgct tcccgaaggg agaaaggcgg acaggtatcc   2160 ggtaagcgg agggtcggaa caggagagcg cacgagggag cttccagggg gaaacgcctg   2220
gtatctttat agtcctgtcg ggtttcgcca cctctgactt gagcgtcgat ttttgtgatg   2280
ctcgtcaggg gggcggagcc tatggaaaaa cgccagcaac gcggcctttt tacgttcct   2340 ggccttttgc tggccttttg ctcacatgtt ctttcctgcg ttatcccctg attctgtgga   2400
taaccgtatt accgcctttg agtgagctga taccgctcgc cgcagccgaa cgaccgagcg   2460
cagcgagtca gtgagcgagg aagcggaaga gcgcctgatg cggtattttc tccttacgca   2520
tctgtgcggt atttcacacc gcagaccagc cgcgtaacct ggcaaaatcg gttacggttg   2580
agtaataaat ggatgccctg cgtaagcggg tgtgggcgga caataaagtc ttaaactgaa   2640
caaaatagat ctaaactatg acaataaagt cttaaactag acagaatagt tgtaaactga   2700
```

```
aatcagtcca gttatgctgt gaaaaagcat actggacttt tgttatggct aaagcaaact    2760
cttcattttc tgaagtgcaa attgcccgtc gtattaaaga ggggcgtggc caagggcatg    2820
gtaaagacta tattcgcggc gttgtgacaa tttaccgaac aactccgcgg ccgggaagcc    2880
gatctcggct tgaacgaatt gttaggtggc ggtacttggg tcgatatcaa agtgcatcac    2940
ttcttcccgt atgcccaact tgtatagag agccactgcg ggatcgtcac cgtaatctgc      3000
ttgcacgtag atcacataag caccaagcgc gttggcctca tgcttgagga gattgatgag    3060
cgcggtggca atgccctgcc tccggtgctc gccggagact gcgagatcat agatatagat    3120
ctcactacgc ggctgctcaa acctgggcag aacgtaagcc gcgagagcgc caacaaccgc    3180
ttcttggtcg aaggcagcaa gcgcgatgaa tgtcttacta cggagcaagt tcccgaggta    3240
atcggagtcc ggctgatgtt gggagtaggt ggctacgtct ccgaactcac gaccgaaaag    3300
atcaagagca gcccgcatgg atttgacttg gtcagggccg agcctacatg tgcgaatgat    3360
gcccatactt gagccaccta actttgtttt agggcgactg ccctgctgcg taacatcgtt    3420
gctgctgcgt aacatcgttg ctgctccata acatcaaaca tcgacccacg gcgtaacgcg    3480
cttgctgctt ggatgcccga ggcatagact gtacaaaaaa acagtcataa caagccatga    3540
aaaccgccac tgcgccgtta ccaccgctgc gttcggtcaa ggttctggac cagttgcgtg    3600
agcgcatacg ctacttgcat tacagtttac gaaccgaaca ggcttatgtc aactgggttc    3660
gtgccttcat ccgtttccac ggtgtgcgtc acccggcaac cttgggcagc agcgaagtcg    3720
aggcatttct gtcctggctg gcgaacgagc gcaaggtttc ggtctccacg catcgtcagg    3780
cattggcggc cttgctgttc ttctacggca aggtgctgtg cacggatctg ccctggcttc    3840
aggagatcgg tagacctcgg ccgtcgcggc gcttgccggt ggtgctgacc ccggatgaag    3900
tggttcgcat cctcggtttt ctggaaggcg agcatcgttt gttcgcccag gactctagct    3960
atagttctag tggttggcta cgtacccgta gtggctatgg cagggcttgc gcttaatgcg    4020
ccgctacagg gcgcgtgggg ataccccta gagccccagc tggttctttc cgcctcagaa     4080
gccatagagc ccaccgcatc cccagcatgc ctgctattgt cttcccaatc ctccccttg     4140
ctgtcctgcc ccaccccacc ccccagaata gaatgacacc tactcagaca atgcgatgca    4200
atttcctcat tttattagga aaggacagtg ggagtggcac cttccagggt caaggaaggc    4260
acggggagg ggcaaacaac agatggctgg caactagaag gcacagtcga ggctgatcag     4320
cgggtttaaa cgggccctct agactcgagt taaagtcgac gcggggaggc ggcccaaagg    4380
gagatccgac tcgtctgagg gcgaaggcga agacgcggaa gaggccgcag agccggcagc    4440
aggccgcggg aaggaaggtc cgctggattg agggccgaag ggacgtagca gaaggacgtc    4500
ccgcgcagaa tccaggtggc aacacaggcg agcagccaag gaaaggacga tgatttcccc    4560
gacaacacca cggaattgtc agtgcccaac agccgagccc ctgtccagca gcgggcaagg    4620
caggcggcga tgagttccgc cgtggcaata gggagggga agcgaaagt cccggaaagg      4680
agctgacagg tggtggcaat gccccaacca gtggggttg cgtcagcaaa cacagtgcac     4740
accacgccac gttgcctgac aacgggccac aactcctcat aaagagacag caaccaggat    4800
ttatacaagg aggagaaaat gaaagccata cggaagcaa tagcatgata caaaggcatt     4860
aaagcagcgt atccacatag cgtaaaagga gcaacatagt taagaatacc agtcaatctt    4920
tcacaaattt tgtaatccag aggttgattg tcgacttaac gcgttgaatt cttacggctt    4980
cgccacaaaa ccaatcgctt cgtacaccgc ttttagcgta cggaagcgt gcgcgctggc     5040
ttttccgcg ccatctttca tcacctgttg caggaaggct tcatcgttgc ggaaacggtg     5100
```

```
atagcgttcc tgcaattcag tcagcatacc ggaaacggca tcagccactt caccttttcag    5160
atgaccatac atcttgcctt cgaactgttt ttccagttct gggatgctct ggcccgttac    5220
cgctgaaagg atatccaaca ggttggaaac gcccgctttg ttctgcacat cgtagcgaac    5280
taccggcggc tcgtcggagt cagtgaccgc acgtttgatt ttcttcacta ccgatttcgg    5340
atcttccagc aggccgataa cgttattgcg attatcgtca gacttggaca tcttcttggt    5400
cggctccagc agcgacatta cgcgcgcgcc agatttcgga ataaacggct ccggcacctt    5460
aaagatctcg ccatacagcg cgttgaaacg ctgggcaata tcgcggctca gttcgaggtg    5520
ctgtttctgg tcttcaccca ccggtaccag attagtttga tacagcagga tgtccgctgc    5580
catcagcacc ggatagtcaa acagaccagc gttgatgttc tcggcataac gcgcagattt    5640
atctttaaac tgcgtcatgc gactcagttc gccgaagtag gtatagcagt tcagtgccca    5700
gcctaactgt gcatgttccg gcacgtggga ctgaacaaaa atggtgcttt tctcaggatc    5760
gataccacaa gccagataca aggccagcgt atccagcgtc gctttacgca gcttctgtgc    5820
atcctggcgc acggtgatcg cgtgttggtc aacgatacag taaatgcaat ggtagtcatc    5880
ctgcatgttt acccactgac gcagcgcacc catgtagtta ccaatggtca attcacctga    5940
gggctgtgcg ccactaaaaa cgatgggctt agtcatgcta gccagcttgg gtctccctat    6000
agtgagtcgt attaatttcg ataagccagt aagcagtggg ttctctagtt agccagagag    6060
ctctgcttat atagacctcc caccgtacac gcctaccgcc catttgcgtc aatggggcgg    6120
agttgttacg acattttgga aagtcccgtt gattttggtg ccaaaacaaa ctcccattga    6180
cgtcaatggg gtggagactt ggaaatcccc gtgagtcaaa ccgctatcca cgcccattga    6240
tgtactgcca aaaccgcatc accatggtaa tagcgatgac taatacgtag atgtactgcc    6300
aagtaggaaa gtcccataag gtcatgtact gggcataatg ccaggcgggc catttaccgt    6360
cattgacgtc aataggggc gtacttggca tatgatacac ttgatgtact gccaagtggg    6420
cagtttaccg taaatagtcc acccattgac gtcaatggaa agtccctatt ggcgttacta    6480
tgggaacata cgtcattatt gacgtcaatg ggcggggtc gttgggcggt cagccaggcg    6540
ggccatttac cgtaagttat gtaacgcgga actccatata tgggctatga actaatgacc    6600
ccgtaattga ttactattaa taactagtca ataatcaatg tcaacgcgta tatctggccc    6660
gtacatcgcg aagcagcgca aaacggatcc tgcaggtatt tgcggccgcg gtccgtatac    6720
tccggaatat aatagatcat ggagataat taaaatgata accatctcgc aaataaataa    6780
gtattttact gttttcgtaa cagttttgta ataaaaaaac ctataaatat tccgattatt    6840
tcataccgtc ccaccatcgg gcgcgaactc ctaaaaaacc gccaccatga agtgcctttt    6900
gtacttagcc tttttattca ttggggtgaa ttgcaagttc accatagttt ttccacacaa    6960
ccaaaaagga aactggaaaa atgttccttc taattaccat tattgcccgt caagctcaga    7020
tttaaattgg cataatgact aataggcac agccttacaa gtcaaaatgc caagagtca    7080
caaggctatt caagcagacg gttggatgtg tcatgcttcc aaatgggtca ctacttgtga    7140
tttccgctgg tatggaccga agtatataac acattccatc cgatccttca ctccatctgt    7200
agaacaatgc aaggaaagca ttgaacaaac gaaacaagga acttggctga atccaggctt    7260
ccctcctcaa agttgtggat atgcaactgt gacggatgcc gaagcagtga ttgtccaggt    7320
gactcctcac catgtgctgg ttgatgaata cacaggagaa tgggttgatt cacagttcat    7380
caacggaaaa tgcagcaatt acatatgccc cactgtccat aactctacaa cctggcattc    7440
```

```
tgactataag gtcaaagggc tatgtgattc taacctcatt tccatggaca tcaccttctt    7500
ctcagaggac ggagagctat catccctggg aaaggagggc acagggttca gaagtaacta    7560
ctttgcttat gaaactggag gcaaggcctg caaaatgcaa tactgcaagc attggggagt    7620
cagactccca tcaggtgtct ggttcgagat ggctgataag gatctctttg ctgcagccag    7680
attccctgaa tgcccagaag ggtcaagtat ctctgctcca tctcagacct cagtggatgt    7740
aagtctaatt caggacgttg agaggatctt ggattattcc ctctgccaag aaacctggag    7800
caaaatcaga gcgggtcttc caatctctcc agtggatctc agctatcttg ctcctaaaaa    7860
cccaggaacc ggtcctgctt tcaccataat caatggtacc ctaaaatact ttgagaccag    7920
atacatcaga gtcgatattg ctgctccaat cctctcaaga atggtcggaa tgatcagtgg    7980
aactaccaca gaaagggaac tgtgggatga ctgggcacca tatgaagacg tggaaattgg    8040
acccaatgga gttctgagga ccagttcagg atataagttt cctttataca tgattggaca    8100
tggtatgttg gactccgatc ttcatcttag ctcaaaggct caggtgttcg aacatcctca    8160
cattcaagac gctgcttcgc aacttcctga tgatgagagt ttattttttg gtgatactgg    8220
gctatccaaa aatccaatcg agcttgtaga aggttggttc agtagttgga aaagctctat    8280
tgcctctttt ttctttatca tagggttaat cattggacta ttcttggttc tccgagttgg    8340
tatccatctt tgcattaaat taaagcacac caagaaaaga cagatttata cagacataga    8400
gatgaaccga cttggaaagt gataaggcca ggccggccaa gcttgtcgag aagtactaga    8460
ggatcataat cagccatacc acatttgtag aggttttact tgctttaaaa aacctcccac    8520
acctccccct gaacctgaaa cataaaatga atgcaattgt tgttgttaac ttgtttattg    8580
cagcttataa tggttacaaa taaagcaata gcatcacaaa tttcacaaat aaagcatttt    8640
tttcactgca ttctagttgt ggtttgtcca aactcatcaa tgtatcttat catgtctgga    8700
tctgatcact gcttgagcct aggtcgggca ggaagagggc ctatttccca tgattccttc    8760
atatttgcat atacgataca aggctgttag agagataatt agaattaatt tgactgtaaa    8820
cacaaagata ttagtacaaa atacgtgacg tagaaagtaa taatttcttg ggtagtttgc    8880
agttttaaaa ttatgtttta aaatggacta tcatatgctt accgtaactt gaaagtattt    8940
cgatttcttg gctttatata tcttgtggaa aggacgaaac accaggggcg tagttcaatt    9000
ggtagagcac cggtctctaa aaccgggtgt tgggagttcg agtctctccg ccctgccat    9060 tttttgctag ggctaggaga tccgaaccag ataagtgaaa tctagttcca aactattttg    9120 tcattttaa ttttcgtatt agcttacgac gctacaccca gttccatct attttgtcac    9180 tcttccctaa ataatcctta aaactccat ttccacccct cccagttccc aactattttg    9240
tccgcccaca gcggggcatt tttcttcctg ttatgttttt aatcaaacat cctgccaact    9300
ccatgtgaca aaccgtcatc ttcggctact tt                                   9332
```

<210> SEQ ID NO 91
<211> LENGTH: 334
<212> TYPE: PRT
<213> ORGANISM: Escherichia coli
<220> FEATURE:
<223> OTHER INFORMATION: strain K-12

<400> SEQUENCE: 91

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
            20                  25                  30

```
Asp Asp Tyr His Cys Ile Tyr Cys Ile Val Asp Gln His Ala Ile Thr
        35              40              45
Val Arg Gln Asp Ala Gln Lys Leu Arg Lys Ala Thr Leu Asp Thr Leu
    50              55              60
Ala Leu Tyr Leu Ala Cys Gly Ile Asp Pro Glu Lys Ser Thr Ile Phe
65              70              75              80
Val Gln Ser His Val Pro Glu His Ala Gln Leu Gly Trp Ala Leu Asn
                85              90              95
Cys Tyr Thr Tyr Phe Gly Glu Leu Ser Arg Met Thr Gln Phe Lys Asp
            100             105             110
Lys Ser Ala Arg Tyr Ala Glu Asn Ile Asn Ala Gly Leu Phe Asp Tyr
            115             120             125
Pro Val Leu Met Ala Ala Asp Ile Leu Leu Tyr Gln Thr Asn Leu Val
    130             135             140
Pro Val Gly Glu Asp Gln Lys Gln His Leu Glu Leu Ser Arg Asp Ile
145             150             155             160
Ala Gln Arg Phe Asn Ala Leu Tyr Gly Glu Ile Phe Lys Val Pro Glu
            165             170             175
Pro Phe Ile Pro Lys Ser Gly Ala Arg Val Met Ser Leu Leu Glu Pro
            180             185             190
Thr Lys Lys Met Ser Lys Ser Asp Asp Asn Arg Asn Asn Val Ile Gly
            195             200             205
Leu Leu Glu Asp Pro Lys Ser Val Val Lys Lys Ile Lys Arg Ala Val
    210             215             220
Thr Asp Ser Asp Glu Pro Pro Val Val Arg Tyr Asp Val Gln Asn Lys
225             230             235             240
Ala Gly Val Ser Asn Leu Leu Asp Ile Leu Ser Ala Val Thr Gly Gln
            245             250             255
Ser Ile Pro Glu Leu Glu Lys Gln Phe Glu Gly Lys Met Tyr Gly His
            260             265             270
Leu Lys Gly Glu Val Ala Asp Ala Val Ser Gly Met Leu Thr Glu Leu
    275             280             285
Gln Glu Arg Tyr His Arg Phe Arg Asn Asp Glu Ala Phe Leu Gln Gln
    290             295             300
Val Met Lys Asp Gly Ala Glu Lys Ala Ser Ala His Ala Ser Arg Thr
305             310             315             320
Leu Lys Ala Val Tyr Glu Ala Ile Gly Phe Val Ala Lys Pro
            325             330
```